United States Patent [19]
Biller et al.

[11] Patent Number: 5,883,099
[45] Date of Patent: Mar. 16, 1999

[54] INHIBITORS OF MICROSOMAL TRIGLYCERIDE TRANSFER PROTEIN AND METHOD

[75] Inventors: Scott A. Biller, Hopewell; John K. Dickson, Eastampton, both of N.J.; R. Michael Lawrence, Yardley, Pa.; David R. Magnin, Hamilton, N.J.; Michael A. Poss, Lawrenceville, N.J.; Richard B. Sulsky, Franklin Park, N.J.; Joseph A. Tino, Lawrenceville, N.J.; John E. Lawson, Wallingford; Henry M. Holava, Meriden, both of Conn.; Richard A. Partyka, Neshanic, N.J.

[73] Assignee: Bristol-Myers Squibb Company, Princeton, N.J.

[21] Appl. No.: 896,872

[22] Filed: Jul. 21, 1997

Related U.S. Application Data

[60] Division of Ser. No. 472,067, Jun. 6, 1995, Pat. No. 5,739,135, which is a continuation-in-part of Ser. No. 391,901, Feb. 21, 1995, abandoned, which is a continuation-in-part of Ser. No. 284,808, Aug. 5, 1994, abandoned, which is a continuation-in-part of Ser. No. 117,362, Sep. 3, 1993, Pat. No. 5,595,872.

[51] Int. Cl.$^6$ ..................... A61K 31/495; C07D 241/04
[52] U.S. Cl. ..................... 514/255; 544/391; 544/392
[58] Field of Search ................... 544/391, 392; 514/255

[56] References Cited

U.S. PATENT DOCUMENTS

| | | | |
|---|---|---|---|
| 3,910,931 | 10/1975 | Cavalla et al. | 424/293.62 |
| 4,289,781 | 9/1981 | Bengtsson et al. | 424/267 |
| 4,367,232 | 1/1983 | Boix-Igleasias et al. | 424/267 |
| 4,576,940 | 3/1986 | Tahara et al. | 514/212 |
| 4,581,355 | 4/1986 | Tahara et al. | 514/212 |
| 4,607,042 | 8/1986 | Pierce | 514/323 |
| 4,826,975 | 5/1989 | Picciola et al. | 544/391 |
| 5,032,598 | 7/1991 | Baldwin et al. | 514/318 |
| 5,130,333 | 7/1992 | Pan et al. | 514/460 |
| 5,189,045 | 2/1993 | Peglion et al. | 514/319 |
| 5,215,989 | 6/1993 | Baldwin et al. | 514/252 |
| 5,527,801 | 6/1996 | Masuda et al. | 514/255 |
| 5,595,872 | 1/1997 | Wetterau | 435/6 |

FOREIGN PATENT DOCUMENTS

| | | |
|---|---|---|
| 0584446A2 | 3/1994 | European Pat. Off. . |
| 0643057A1 | 3/1995 | European Pat. Off. . |
| WO 9305778 | 9/1991 | WIPO . |
| WO96/40640 | 12/1996 | WIPO . |

OTHER PUBLICATIONS

Bulleid & Freedman, Nature 335, 649–651 (1988). "Defective co–translational formation of disulphide bonds in protein disulphideisomerase–deficient microsomes".

Koivu et al., J. Biol. Chem. 262, 6447–6449 (1987). "A Single Polypeptide Acts Both as the β–Subunit of Prolyl 4–Hydroxylase and as a Protein Disulfide–Isomerase".

Kane & Havel in the Metabolic Basis of Inherited Disease, Sixth Edition, 1139–1164 (1989). "Disorders of the Biogenesis and Secretion of Lipoproteins Containing the B Apolipoproteins".

Schaefer et al., Clin. Chem. 34, B9–B12 (1988). "Genetics and Abnormalties of Metabolism of Lipoproteins".

Drayna et al., Nature 327, 632–634 (1987). "Cloning and sequencing of human cholesteryl ester transfer protein cDNA".

Pihlajaniemi et al., EMBO J. 6, 643–649 (1987). "Molecular cloning of the β–subunit of human prolyl 4–hydroxylase. This subunit and protein disulphide isomerase are products of the same gene".

Yamaguchi et al., Biochem. Biophys. Res. Comm. 146, 1485–1492 (1987). "Sequence of Membrane–Associated Thyroid Hormone Binding Protein From Bovine Liver: Its Identity with Protein Disulphide Isomerase".

Edman et al., Nature 317, 267–270 (1985). Sequence of protein disulphide isomerase and implications of its relationship to thioredoxin.

(List continued on next page.)

*Primary Examiner*—Evelyn Huang
*Attorney, Agent, or Firm*—Burton Rodney

[57] ABSTRACT

Compounds are provided which inhibit microsomal triglyceride transfer protein and thus are useful for lowering serum lipids and treating atherosclerosis and related diseases. The compounds have the structure

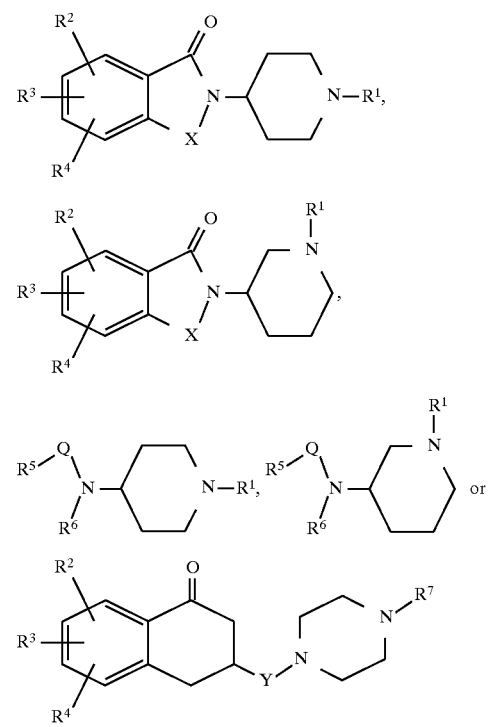

wherein $R^1$ to $R^7$, Q, X and Y are as defined herein.

9 Claims, No Drawings

OTHER PUBLICATIONS

Kao et al., Connective Tissue Research 18, 157–174 (1988). "Isolation of cDNA Clones and Genomic DNA Clones of β–Subunit of Chicken Prolyl 4–Hydroxylase*".

Wetterau, J. et al., Biochem 30, 9728–9735 (1991). "Protein Disulfide Isomerase Appears Necessary To Maintain the Catalytically Active Structure of the Microsomal Triglyceride Transfer Protein".

Morton, R.E. et al., J. Biol. Chem. 256, 1992–1995 (1981). "A Plasma Inhibitor of Triglyceride and Chloesteryl Ester Transfer Activities".

Wetterau, J. et al:, Biochem: 30, 4406–4412 (1991) : "Structural Properties of the Microsomal Triglyceride–Transfer Protein Complex".

Wetterau, J. et al., J. Biol. Chem. 265, 9800–9807 (1990). "Protein Disulfide Isomerase Is a Component of the Microsomal Triglyceride Transfer Protein Complex".

Wetterau, J. and Zilversmit, D.B., Chem. and Phys. of Lipids 38, 205–22 (1985). "Purification and Characterization of Microsomal Triglyceride and Cholesteryl Ester Transfer Protein From Bovine Liver Microsomes".

Wetterau, J. and Zilversmit, D.B., Biochimica et Biophysica Acta 875, 610–617 (1986). "Localization of intracellular triacylglycerol and cholesteryl ester transfer activity in rat tissues".

Wetterau, J. and Zilversmit, D.B., J. Biol. Chem. 259, 10863–10866 (1984), "A Triglyceride and Cholesteryl Ester Transfer Protein Associated with Liver Microsomes".

Wetterau, J., Grant Application entitled: "Intracellular Triglyceride Transport and Metabolism". Presentation Materials, Aspen Bile Acid/Cholesterol Conference, Aug. 15, 1992.

Wetterau, J. R., et al., Science, vol. 258, 999–1001, Nov. 6, 1992 "Absence of Microsomal Triglyceride Transfer Protein in Individuals with Abetalipoproteinemia".

Archibald, J. L., et al., Journal of Medicinal Chemistry, vol. 14, No. 11, pp. 1054–1059.

Cortizo, L. et al., J. Med. Chem., 34, pp. 2242–2247, 1991.

Hall, I. H. et al., Pharmaceutical Research, vol. 9, No. 10, pp. 1324–1329 1992.

Hall, I. H., et al., Pharmacological Research Communications, vol. 19, No. 12, pp. 839–858, 1987.

Murthy et al., Eur. J. Med. Chem.—Chim. Ther., vol. 20, No. 6, pp. 547–550, 1985.

INHIBITORS OF MICROSOMAL TRIGLYCERIDE TRANSFER PROTEIN AND METHOD

This is a division of application Ser. No. 08/472,067, filed Jun. 6, 1995, Pat. No. 5,739,135 which is a continuation-in-part of application Ser. No. 08/391,901, filed Feb. 21, 1995, now abandoned, which is a continuation-in-part of application Ser. No. 08/284,808, filed Aug. 5, 1994, now abandoned, which is a continuation-in-part of application Ser. No. 08/117,362, filed Sep. 3, 1993, now U.S. Pat. No. 5,595,872.

FIELD OF THE INVENTION

This invention relates to novel compounds which inhibit microsomal triglyceride transfer protein, and to methods for decreasing serum lipids and treating atherosclerosis employing such compounds.

BACKGROUND OF THE INVENTION

The microsomal triglyceride transfer protein (MTP) catalyzes the transport of triglyceride (TG), cholesteryl ester (CE), and phosphatidylcholine (PC) between small unilamellar vesicles (SUV). Wetterau & Zilversmit, *Chem. Phys. Lipids* 38, 205–22 (1985). When transfer rates are expressed as the percent of the donor lipid transferred per time, MTP expresses a distinct preference for neutral lipid transport (TG and CE), relative to phospholipid transport. The protein from bovine liver has been isolated and characterized. Wetterau & Zilversmit, *Chem. Phys. Lipids* 38, 205–22 (1985). Polyacrylamide gel electrophoresis (PAGE) analysis of the purified protein suggests that the transfer protein is a complex of two subunits of apparent molecular weights 58,000 and 88,000, since a single band was present when purified MTP was electrophoresed under nondenaturing condition, while two bands of apparent molecular weights 58,000 and 88,000 were identified when electrophoresis was performed in the presence of sodium dodecyl sulfate (SDS). These two polypeptides are hereinafter referred to as 58 kDa and 88 kDa, respectively, or the 58 kDa and the 88 kDa component of MTP, respectively, or the low molecular weight subunit and the high molecular weight subunit of MTP, respectively.

Characterization of the 58,000 molecular weight component of bovine MTP indicates that it is the previously characterized multifunctional protein, protein disulfide isomerase (PDI). Wetterau et al., *J. Biol. Chem.* 265, 9800–7 (1990). The presence of PDI in the transfer protein is supported by evidence showing that (1) the amino terminal 25 amino acids of the bovine 58,000 kDa component of MTP is identical to that of bovine PDI, and (2) disulfide isomerase activity was expressed by bovine MTP following the dissociation of the 58 kDa—88 kDa protein complex. In addition, antibodies raised against bovine PDI, a protein which by itself has no TG transfer activity, were able to immunoprecipitate bovine TG transfer activity from a solution containing purified bovine MTP.

PDI normally plays a role in the folding and assembly of newly synthesized disulfide bonded proteins within the lumen of the endoplasmic reticulum. Bulleid & Freedman, *Nature* 335, 649–51 (1988). It catalyzes the proper pairing of cysteine residues into disulfide bonds, thus catalyzing the proper folding of disulfide bonded proteins. In addition, PDI has been reported to be identical to the beta subunit of human prolyl 4-hydroxylase. Koivu et al., *J. Biol. Chem.* 26, 6447–9 (1987). The role of PDI in the bovine transfer protein is not clear. It does appear to be an essential component of the transfer protein as dissociation of PDI from the 88 kDa component of bovine MTP by either low concentrations of a denaturant (guanidine HCl), a chaotropic agent (sodium perchlorate), or a nondenaturing detergent (octyl glucoside) results in a loss of transfer activity. Wetterau et al., *Biochemistry* 30, 9728–35 (1991). Isolated bovine PDI has no apparent lipid transfer activity, suggesting that either the 88 kDa polypeptide is the transfer protein or that it confers transfer activity to the protein complex.

The tissue and subcellular distribution of MTP activity in rats has been investigated. Wetterau & Zilversmit, *Biochem. Biophys. Acta* 875, 610–7 (1986). Lipid transfer activity was found in liver and intestine. Little or no transfer activity was found in plasma, brain, heart, or kidney. Within the liver, MTP was a soluble protein located within the lumen of the microsomal fraction. Approximately equal concentrations were found in the smooth and rough microsomes.

Abetalipoproteinemia is an autosomal recessive disease characterized by a virtual absence of plasma lipoproteins which contain apolipoprotein B (apoB). Kane & Havel in *The Metabolic Basis of Inherited Disease*, Sixth edition, 1139–64 (1989). Plasma TG levels may be as low as a few mg/dL, and they fail to rise after fat ingestion. Plasma cholesterol levels are often only 20–45 mg/dL. These abnormalities are the result of a genetic defect in the assembly and/or secretion of very low density lipoproteins (VLDL) in the liver and chylomicrons in the intestine. The molecular basis for this defect has not been previously determined. In subjects examined, triglyceride, phospholipid, and cholesterol synthesis appear normal. At autopsy, subjects are free of atherosclerosis. Schaefer et al., *Clin. Chem.* 34, B9–12 (1988). A link between the apoB gene and abetalipoproteinemia has been excluded in several families. Talmud et al., *J. Clin. Invest.* 8 1803–6 (1988) and Huang et al., *Am. J. Hum. Genet.* 46, 1141–8 (1990).

Subjects with abetalipoproteinemia are afflicted with numerous maladies. Kane & Havel, supra. Subjects have fat malabsorption and TG accumulation in their enterocytes and hepatocytes. Due to the absence of TG-rich plasma lipoproteins, there is a defect in the transport of fat-soluble vitamins such as vitamin E. This results in acanthocytosis of erythrocytes, spinocerebellar ataxia with degeneration of the fasciculus cuneatus and gracilis, peripheral neuropathy, degenerative pigmentary retinopathy, and ceroid myopathy. Treatment of abetalipoproteinemic subjects includes dietary restriction of fat intake and dietary supplementation with vitamins A, E and K.

An vitro, MTP catalyzes the transport of lipid molecules between phospholipid membranes. Presumably, it plays a similar role in vivo, and thus plays some role in lipid metabolism. The subcellular (lumen of the microsomal fraction) and tissue distribution (liver and intestine) of MTP have led to speculation that it plays a role in the assembly of plasma lipoproteins, as these are the sites of plasma lipoprotein assembly. Wetterau & Zilversmit, *Biochem. Biophys. Acta* 8, 610–7 (1986). The ability of MTP to catalyze the transport of TG between membranes is consistent with this hypothesis, and suggests that MTP may catalyze the transport of TG from its site of synthesis in the endoplasmic reticulum (ER) membrane to nascent lipoprotein particles within the lumen of the ER.

Olofsson and colleagues have studied lipoprotein assembly in HepG2 cells. Bostrom at al., *J. Biol. Chem. A*, 4434–42 (1988). Their results suggest small precursor lipoproteins become larger with time. This would be consistent with the addition or transfer of lipid molecules to nascent lipoproteins as they are assembled. MTP may play a role in this process. In support of this hypothesis, Howell and Palade, *J. Cell Biol.* 92, 833–45 (1982), isolated nascent lipoproteins from the hepatic Golgi fraction of rat liver. There was a spectrum of sizes of particles present with varying lipid and protein compositions. Particles of high density lipoprotein (HDL) density, yet containing apoB, were found. Higgins and Hutson, *J. Lipid Res.* 25, 1295–1305 (1984), reported lipoproteins isolated from Golgi were consistently larger than those from the endoplasmic reticulum, again suggesting the assembly of lipoproteins is a progressive event.

Recent reports (Science, Vol. 258, page 999, 1992; D. Sharp et. al., Nature, Vol. 365, page 65, 1993) demonstrate that the defect causing abetalipoproteinemia is in the MTP gene, and as a result, the MTP protein. Individuals with abetalipoproteinemia have no MTP activity, as a result of mutations in the MTP gene, some of which have been characterized. These results indicate that MTP is required for the synthesis of apoB containing lipoproteins, such as VLDL, the precursor to LDL. It therefore follows that inhibitors of MTP would inhibit the synthesis of VLDL and LDL, thereby lowering VLDL levels, LDL levels, cholesterol levels, and triglyceride levels in animals and man.

Canadian Patent Application No. 2,091,102 published Mar. 2, 1994 (corresponding to U.S. application Ser. No. 117,362, filed Sep. 3, 1993 (file DC21b)), Pat. No. 5,595,872 reports MTP inhibitors which also block the production of apoB containing lipoproteins in a human hepatic cell line (HepG2 cells). This provides further support for the proposal that an MTP inhibitor would lower apoB containing lipoprotein and lipid levels in vivo. This Canadian patent application discloses a method for identifying the MTP inhibitors

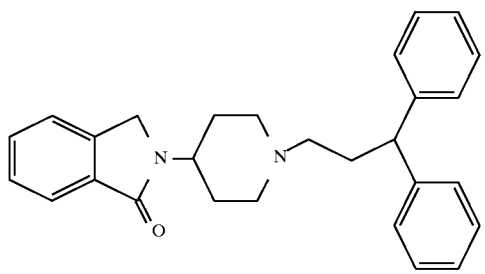

which has the name 2-[1-(3, 3-diphenylpropyl)-4-piperidinyl]-2, 3-dihydro-3-oxo-1H-isoindole hydrochloride and

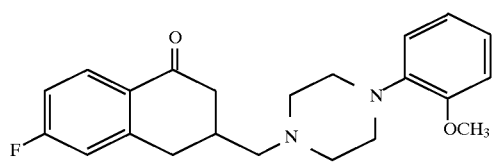

which has the name 1-[3-(6-fluoro-1-tetralanyl)methyl]-4-O-methoxyphenyl piperazine

SUMMARY OF THE INVENTION

In accordance with the present invention, novel compounds are provided which are inhibitors of MTP and have the structure

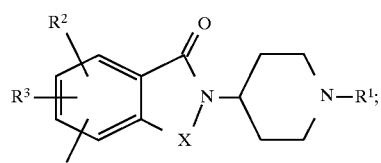

or

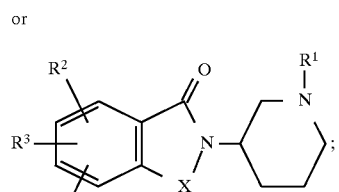

or

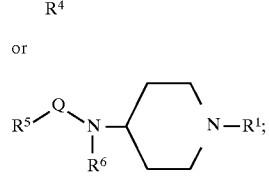

or

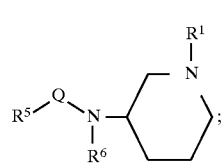

or

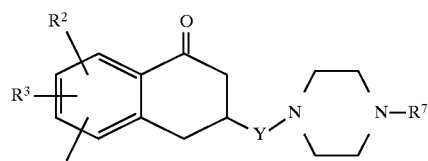

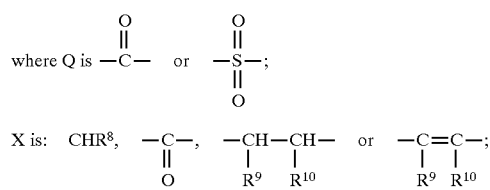

$R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

$$Y \text{ is } -(CH_2)_m- \quad \text{or} \quad -\underset{\underset{O}{\|}}{C}-$$

where m is 2 or 3;

$R_1$ is alkyl, alkenyl, alkynyl, aryl, heteroaryl, arylalkyl (wherein alkyl has at least 2 carbons, preferably at least 3 carbons), diarylalkyl, arylalkenyl, diarylalkenyl, arylalkynyl, diarylalkynyl, diarylalkylaryl, heteroarylalkyl (wherein alkyl has at least 2 carbons, preferably at least 3 carbons), cycloalkyl, or cycloalkylalkyl (wherein alkyl has at least 2 carbons, preferably at least 3 carbons); all of the aforementioned $R_1$ groups being optionally substituted through available carbon atoms with 1, 2, 3 or 4 groups selected from halo, haloalkyl, alkyl, alkenyl, alkoxy, aryloxy, aryl, arylalkyl, alkyl-mercapto, arylmercapto, cycloalkyl, cycloalkyl-alkyl, heteroaryl, fluorenyl, heteroarylalkyl, hydroxy or oxo; or $R^1$ is a fluorenyl-type group of the structure

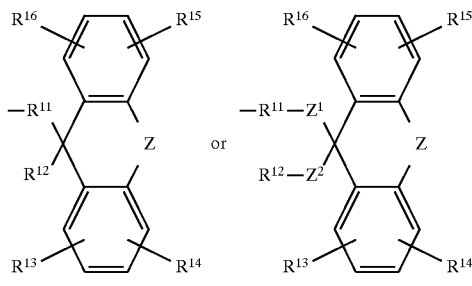

A      B

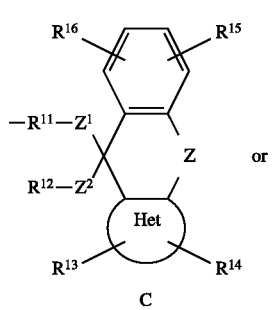

C

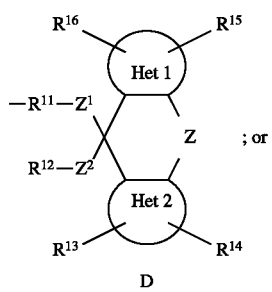

D $R^1$ is an indenyl-type group of the structure

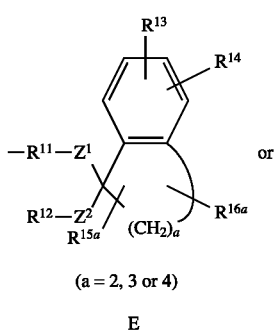

(a = 2, 3 or 4)

E

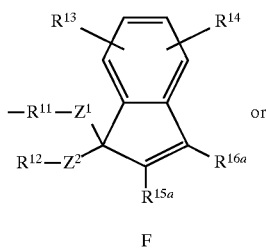

F

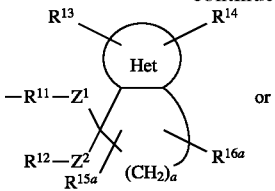

G

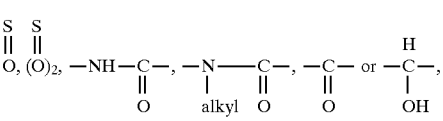

H $Z^1$ and $Z^2$ are the same or different and are independently a bond, O, S,

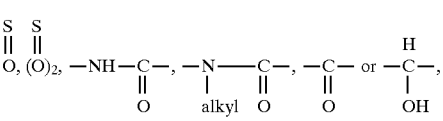

with the proviso that with respect to B, at least one of $Z^1$ and $Z^2$ will be other than a bond;

$R^{11}$ is a bond, alkylene, alkenylene or alkynylene of up to 10 carbon atoms, arylene (for example

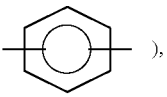

), or mixed arylene-alkylene (for example

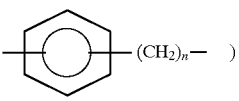

)

where n is 1 to 6;

$R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cycloalkyl, aryloxy, alkoxy, arylalkoxy or cycloalkylalkyl; with the provisos that (1) when $R^{12}$ is H, aryloxy, alkoxy or arylalkoxy, then $Z^2$ is

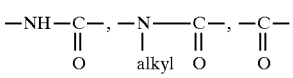

or a bond;

and (2) when $Z^2$ is a bond, $R^{12}$ cannot be heteroaryl or heteroarylalkyl;

Z is a bond, O, S, N-alkyl, N-aryl, or alkylene or alkenylene of from 1 to 5 carbon atoms;

$R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

$R^{15a}$ and $R^{16a}$ are independently any of the $R^{15}$ or $R^{16}$ groups except hydroxy, nitro, amino or thio;

or $R^1$ is

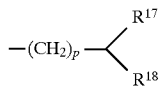

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl, at least one of $R^{17}$ and $R^{18}$ being other than H;

or $R^1$ is

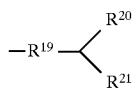

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is alkyl, alkenyl, alkynyl, aryl, alkoxy, aryloxy, arylalkoxy, heteroaryl, arylalkyl, heteroarylalkyl, cycloalkyl, cycloheteroalkyl, heteroaryloxy, cycloalkylalkyl, polycycloalkyl, polycycloalkylalkyl, cycloalkenyl, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all of the $R^5$ substituents and $R^6$ substituents (set out hereinafter) being optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino (wherein the amino includes 1 or 2 substituents which are alkyl, aryl or heteroaryl, or any of the other aryl compounds mentioned in the definitions), thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, or alkylsulfinyl. Where $R^5$ is phenyl, aryl, heteroaryl or cycloalkyl; this group preferably includes an ortho hydrophobic substituent such as alkyl, haloalkyl (with up to 5 halo groups), alkoxy, haloalkoxy (with up to 5 halo groups), aryl, aryloxy or arylalkyl;

$R^6$ is hydrogen or $C_1$–$C_4$ alkyl or $C_1$–$C_4$ alkenyl;

$R^7$ is alkyl, aryl or arylalkyl wherein alkyl or the alkyl portion is optionally substituted with oxo; and

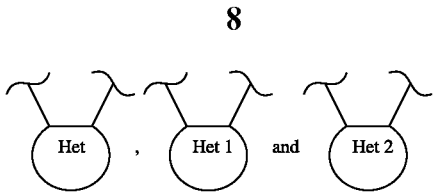

are the same or different and are independently selected from heteroaryl containing 5- or 6-ring members; and including N-oxides of the formulae I, Ii, II and II*i* compounds, that is

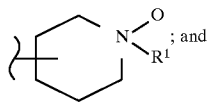

including pharmaceutically acceptable salts thereof such as alkali metal salts such as lithium sodium or potassium, alkaline earth metal salts such as calcium or magnesium, as well as zinc or aluminum and other cations such as ammonium, choline, diethanolamine, ethylenediamine, t-butylamine, t-octylamine, dehydroabietylamine, as well as pharmaceutically acceptable anions such as chloride, bromide, iodide, tartrate, acetate, methanesulfonate, maleate, succinate, glutarate, and salts of naturally occurring amino acids such as arginine, lysine, alanine and the like, and prodrug esters thereof.

In the formula I compounds, where X is $CH_2$ and $R^2$, $R^3$ and $R^4$ are each H, $R^1$ will be other than 3,3-diphenylpropyl.

In the formula III compounds, where one of $R^2$, $R^3$ and $R^4$ is 6-fluoro, and the others are H, $R^7$ will be other than 4-(2-methoxy)phenyl.

Thus, the compounds of formulae I and II of the invention encompass compounds of the structure

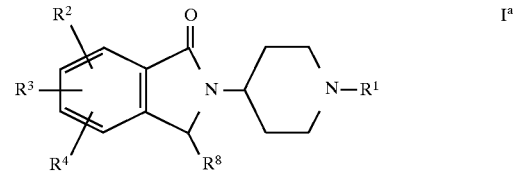

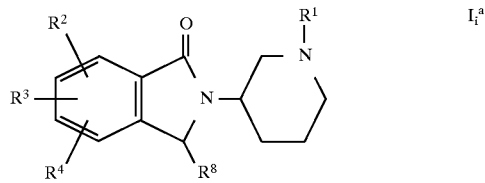

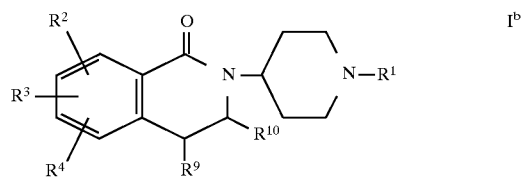

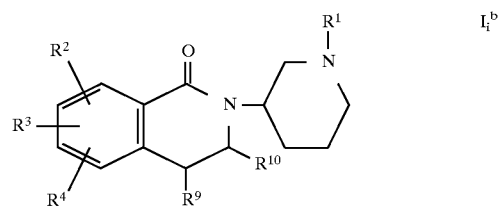

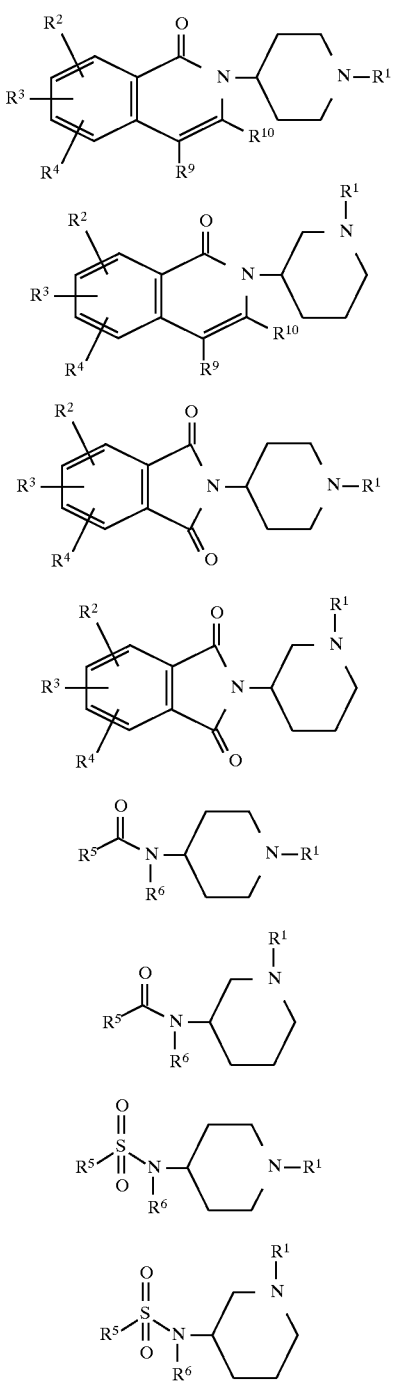

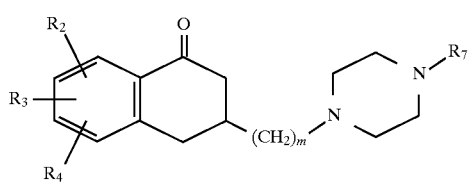

The compounds of formula III of the invention encompass compounds of the structure In addition, in accordance with the present invention, a method for preventing, inhibiting or treating atherosclerosis, pancreatitis or obesity is provided, wherein a compound of formula I, Ii, II, IIi or III as defined hereinbefore wherein $R^1$ also includes arylmethyl, heteroarylmethyl and cycloalkylmethyl and Y also includes —$CH_2$—, is administered in an amount which decreases the activity of microsomal triglyceride transfer protein.

Furthermore, in accordance with the present invention, a method is provided for lowering serum lipid levels, cholesterol and/or triglycerides, or inhibiting and/or treating hyperlipemia, hyperlipidemia, hyperlipoproteinemia, hypercholesterolemia and/or hypertriglyceridemia, wherein a compound of formula I, Ii, II, IIi or III as defined hereinbefore wherein $R^1$ also includes arylmethyl, heteroarylmethyl, and cycloalkylmethyl, and Y also includes —$CH_2$—, is administered in an amount which decreases the activity of microsomal triglyceride transfer protein.

DETAILED DESCRIPTION OF THE INVENTION

The following definitions apply to the terms as used throughout this specification, unless otherwise limited in specific instances.

The term "MTP" refers to a polypeptide or protein complex that (1) if obtained from an organism (e.g., cows, humans, etc.), can be isolated from the microsomal fraction of homogenized tissue; and (2) stimulates the transport of triglycerides, cholesterol esters, or phospholipids from synthetic phospholipid vesicles, membranes or lipoproteins to synthetic vesicles, membranes, or lipoproteins and which is distinct from the cholesterol ester transfer protein [Drayna et al., Nature 37, 632–634 (1987)] which may have similar catalytic properties. However, the MTP molecules of the present invention do not necessarily need to be catalytically active. For example, catalytically inactive MTP or fragments thereof may be useful in raising antibodies to the protein.

The phrase "stabilizing" atherosclerosis as used in the present application refers to slowing down the development of and/or inhibiting the formation of new atherosclerotic lesions.

The phrase "causing the regression of" atherosclerosis as used in the present application refers to reducing and/or eliminating atherosclerotic lesions.

Unless otherwise indicated, the term "lower alkyl", "alkyl" or "alk" as employed herein alone or as part of another group includes both straight and branched chain hydrocarbons, containing 1 to 40 carbons, preferably 1 to 20 carbons, more preferably 1 to 12 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, acyl, heteroaryl, heteroaryloxy, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio, as well as any of the other substituents as defined for $R^5$ and $R^6$.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

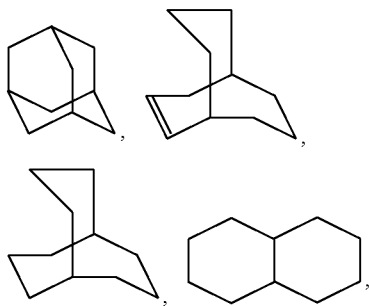

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio, as well as any of the other substituents as defined for $R^5$ or $R^6$.

The term "cycloalkenyl" as employed herein alone or as part of another group refers to cyclic hydrocarbons containing 5 to 20 carbons, preferably 6 to 12 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "polycycloalkyl" as employed herein alone or as part of another group refers to a bridged multicyclic group containing 5 to 20 carbons and containing 0 to 3 bridges, preferably 6 to 12 carbons and 1 or 2 bridges. Exemplary polycycloalkyl groups include [3.3.0]-bicyclooctanyl, adamantanyl, [2.2.1]-bicycloheptanyl, [2.2.2]-bicyclooctanyl and the like and may be optionally substituted as defined for cycloalkyl.

The term "polycycloalkenyl" as employed herein alone or as part of another group refers to a bridged multicyclic group containing 5 to 20 carbons and containing 0 to 3 bridges and containing 1 or 2 double bonds, preferably 6 to 12 carbons and 1 or 2 bridges. Exemplary polycycloalkyl groups include [3.3.0]-bicyclooctenyl, [2.2.1]-bicycloheptenyl, [2.2.2]-bicyclooctenyl and the like and may be optionally substituted as defined for cycloalkyl.

The term "aryl" or "Ar" as employed herein alone or as part of another group refers to monocyclic and bicyclic aromatic groups containing 6 to 10 carbons in the ring portion (such as phenyl or naphthyl) and may optionally include one to three additional rings fused to Ar (such as aryl, cycloalkyl, heteroaryl or cycloheteroalkyl rings) and may be optionally substituted through available carbon atoms with 1, 2, 3 or 4 groups selected from hydrogen, halo, haloalkyl, alkyl, haloalkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or any of the substituents as defined for the $R^5$ or $R^6$ groups set out above.

The term "aralkyl", "aryl-alkyl" or "aryllower alkyl" as used herein alone or as part of another group refers to alkyl groups as discussed above having an aryl substituent, such as benzyl or phenethyl, or naphthylpropyl, or an aryl as defined above.

The term "lower alkoxy", "alkoxy", "aryloxy" or "aralkoxy" as employed herein alone or as part of another group includes any of the above alkyl, aralkyl or aryl groups linked to an oxygen atom.

The term "amino" as employed herein alone or as part of another group may optionally be substituted with one or two substituents such as alkyl and/or aryl.

The term "lower alkylthio", alkylthio", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "acyl" as employed herein by itself or part of another group as defined herein, refers to an organic radical linked to a carbonyl

group, examples of acyl groups include alkanoyl, alkenoyl, aroyl, aralkanoyl, heteroaroyl, cycloalkanoyl and the like.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 3 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol and/or alkylthio, as well as any of the other substituents as defined for $R^5$ or $R^6$.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, as well as any of the other substituents as defined for $R^5$ or $R^6$.

The term "alkylene" as employed herein alone or as part of another group (which also encompasses "alkyl" as part of another group such as arylalkyl or heteroarylalkyl) refers to alkyl groups as defined above having single bonds for attachment to other groups at two different carbon atoms and may optionally be substituted as defined above for "alkyl". The definition of alkylene applies to an alkyl group which links one function to another, such as an arylalkyl substituent.

Ther terms "alkenylene" and "alkynylene" as employed herein alone or as part of another group (which also encompass "alkenyl" or "alkynyl" as part of another group such as arylalkenyl or arylalkynyl), refer to alkenyl groups as defined above and alkynyl groups as defined above, respectively, having single bonds for attachment at two different carbon atoms.

Suitable alkylene, alkenylene or alkynylene groups or $(CH_2)_m$, $(CH_2)_n$ or $(CH_2)_p$ (which may include alkylene, alkenylene or alkynylene groups) as defined herein, may optionally include 1,2, or 3 alkyl, alkoxy, aryl, heteroaryl, cycloheteroalkyl, alkenyl, alkynyl, oxo, aryloxy, hydroxy, halogen substituents as well as any of the substituents defined for $R^5$ or $R^6$, and in addition, may have one of the carbon atoms in the chain replaced with an oxygen atom, N—H, N-alkyl or N-aryl. Examples of alkylene, alkenylene, alkynylene, $(CH_2)_m$, $(CH_2)_n$ and $(CH_2)_p$ groups include

—CH=CH—CH₂—, —CH₂CH=CH—, —C≡C—CH₂—,

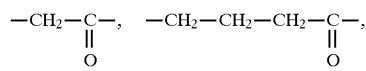

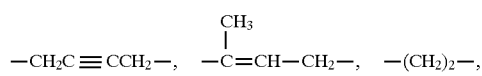

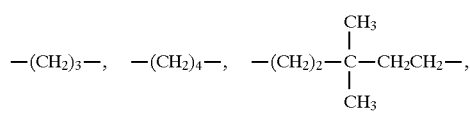

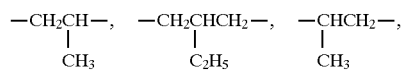

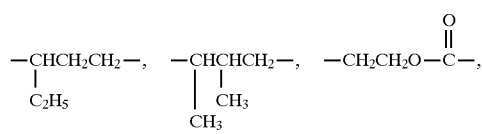

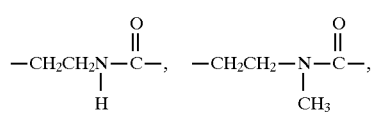

-continued

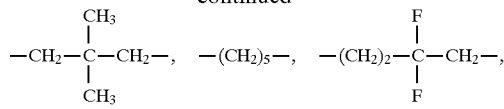

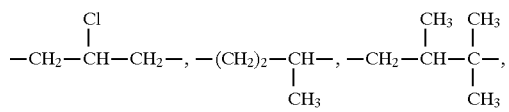

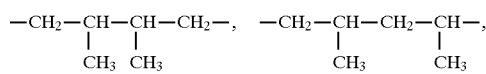

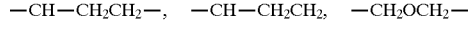

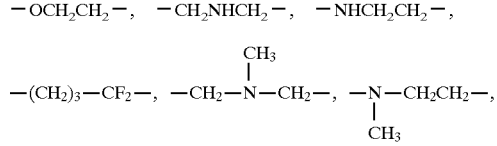

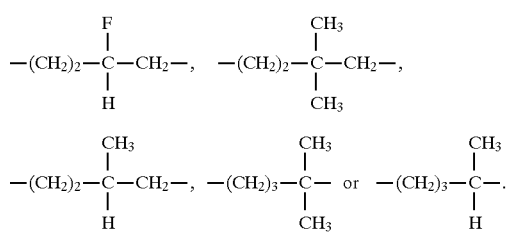

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

The term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (which is defined above), such as

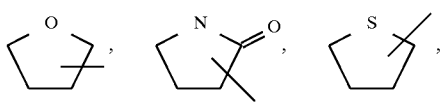

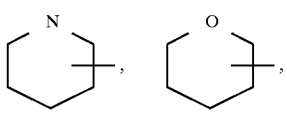

and the like. The above groups may include 1 to 3 substituents such as any of the $R^1$, $R^5$ or $R^6$ groups as defined above. In addition, any of the above rings can be fused to 1 or 2 cycloalkyl, aryl, heteroaryl or cycloheteroalkyl rings.

The term "heteroaryl" or

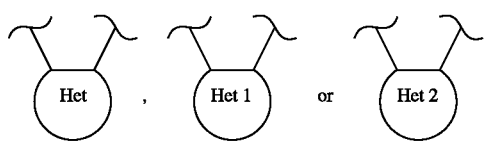

(also referred to as heteroaryl) as used herein alone or as part of another group refers to a 5- or 6- membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), linked through a carbon atom or a heteroatom, where possible, optionally via the linker $(CH_2)_p$ (which is defined above), such as

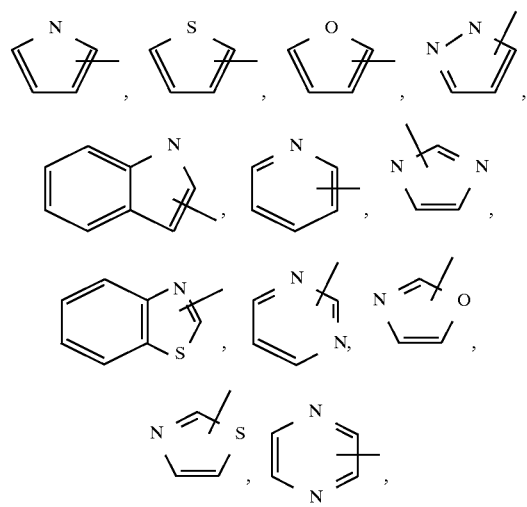

and the like, and includes all possible N-oxide derivatives.

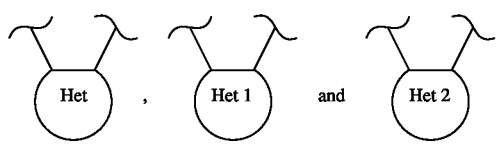

are the same or different as defined hereinbefore and are attached to the central ring of the indenyl or fluorenyl type group at adjacent positions (that is ortho or 1,2-positions). Examples of such groups include

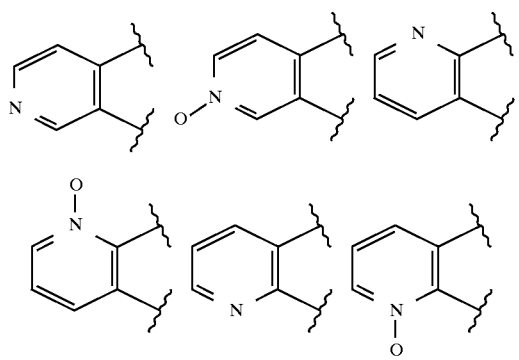

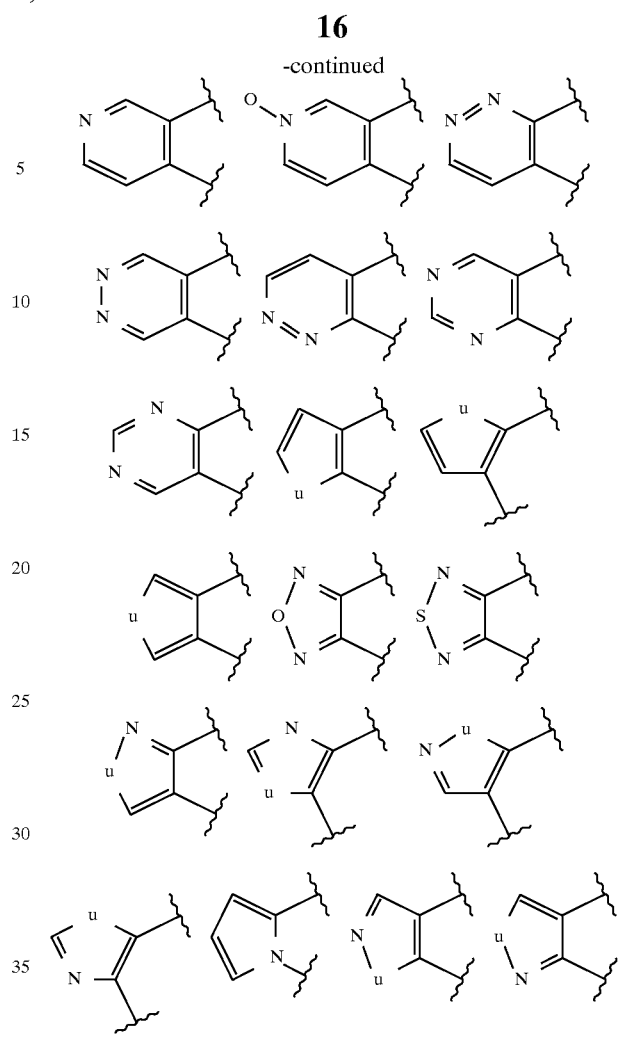

wherein u is selected from O, S, and $NR^{7a}$; $R^{7a}$ is H, lower alkyl, aryl, —$C(O)R^{7b}$, —$C(O)OR^{7b}$; $R^{7b}$ is alkyl or aryl, and includes all possible N-oxide derivatives.

The heteroaryl groups including the above groups may optionally include 1 to 4 substituents such as any of the substituents listed for aryl, or those substituents indicated for $R^5$ or $R^6$ groups as defined above. In addition, any of the above rings can be fused to a cycloalkyl, aryl, heteroaryl or cycloheteroalkyl ring.

The term "cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a —$(CH_2)_p$— chain, alkylene or alkenylene as defined above.

The term "fluorenyl" or "fluorenyl analog" or "fluorenyl-type group" as employed herein refers to a group of the structure:

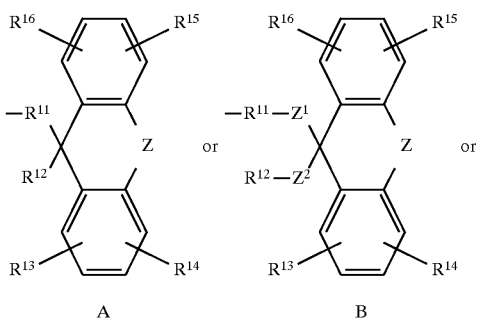

A                    B

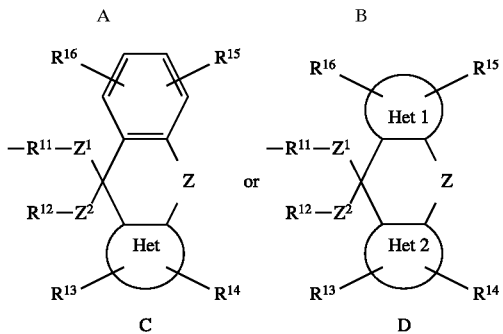

C                    D

The term "indenyl-type group" as emplyed herein refers to a group of the structure

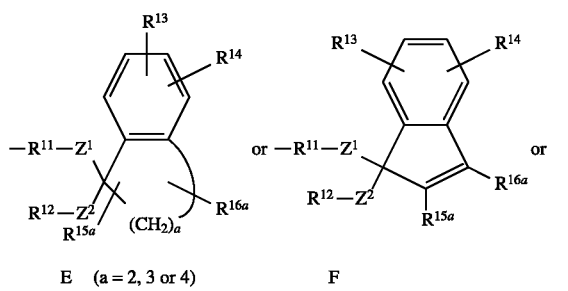

E (a = 2, 3 or 4)          F

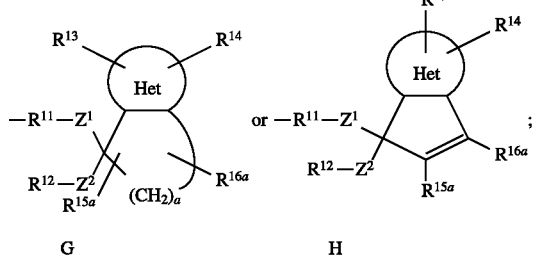

G                    H $Z, Z^1, Z^2, R^{11}, R^{12}, R^{13}, R^{14}, R^{15}, R^{16}, R^{15a}$ and $R^{16a}$ as used in the above groups A through H are as defined hereinbefore.

Preferred are compounds of formulae I and II wherein $R^1$ is arylalkyl, arylalkenyl, heteroarylalkyl, heteroarylalkenyl,

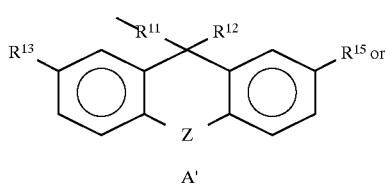

A'

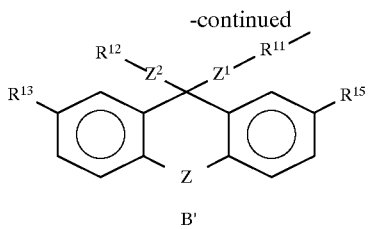

B'

(including where $Z^1$ is a bond and $R^{11}$ is alkylene or alkenylene and $Z^2$ is

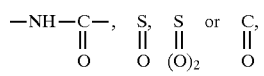

and $R^{12}$ is $C_1$–$C_3$ alkyl or 1,1,1-trifluoroethyl, $R^{13}$ is H or F and $R^{15}$ is H or F, and Z is a bond or O; and where $R^{11}$ is alkylene or alkenylene or alkylene substituted with oxo, $R^{12}$ is alkyl, alkenyl, aralkyl, aralkenyl, Z is O, S or a bond); or

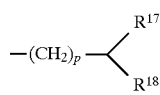

(wherein $R^{17}$ and $R^{18}$ are each independently alkyl, alkenyl, aryl, arylalkyl, heteroaryl, heteroarylalkyl, cycloalkyl or cycloalkylalkyl); or

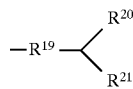

wherein $R^{19}$ is aryl or heteroaryl;

$R^{20}$ is aryl or heteroaryl;

$R^{21}$ is alkyl, aryl, alkylaryl, arylalkyl aryloxy, arylalkoxy, heteroaryl, heteroarylalkyl, heteroarylalkoxy, cycloalkyl, cycloalkylalkyl or cycloalkylalkoxy.

In structure I, it is preferred that $R^2$, $R^3$ and $R^4$ are each H and X is $CH_2$, $CH_2CH_2$, or CH=CH.

In structure II, it is preferred that $R^6$ is H or $CH_3$ and $R^5$ is cycloalkyl, phenyl, aryl or heteroaryl, or cycloalkyl, phenyl, aryl heteroaryl having an ortho hydrophobic substituent which is alkyl, alkoxy, haloalkyl (containing up to five halo groups), trifluoromethyl, aryl, aryloxy, arylalkyl, arylalkoxy, haloalkoxy (containing up to five halo groups).

In structure II, it is also preferred that $R^1$ is arylalkyl or heteroarylalkyl wherein alkyl of each has at least 2 carbons (preferably at least 3 carbons) and $R^5$ and $R^6$ may be as defined hereinbefore and may or may not be the preferred groups set out above.

In structure III, it is preferred that $R^2$, $R^3$ and $R^4$ are each H or halo and $R^7$ is aryl.

It is to be understood that combinations of substituents which lead to chemically unstable molecules are not included within the scope of the present invention; for example, compounds of the invention will not include —O—O—, —O—C—OH, N—C—OH and —S—C—OH linkages.

The compounds of formulae I, Ii, II, IIi and III may be prepared by the exemplary processes described in the following reaction schemes. Exemplary reagents and procedures for these reactions appear hereinafter and in the working Examples.

Scheme I
Routes to Isoindolinone Piperidines I
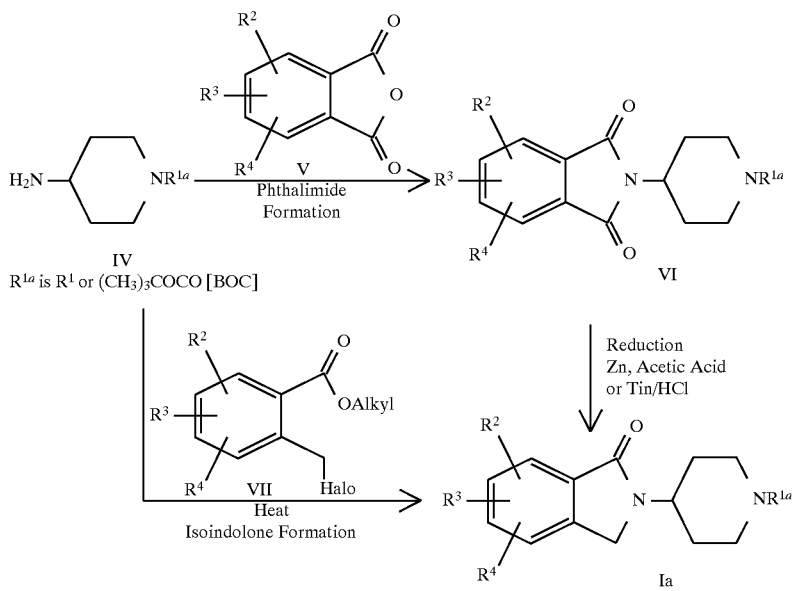
Scheme II
Additional Routes to Isoindolinone Piperidines I
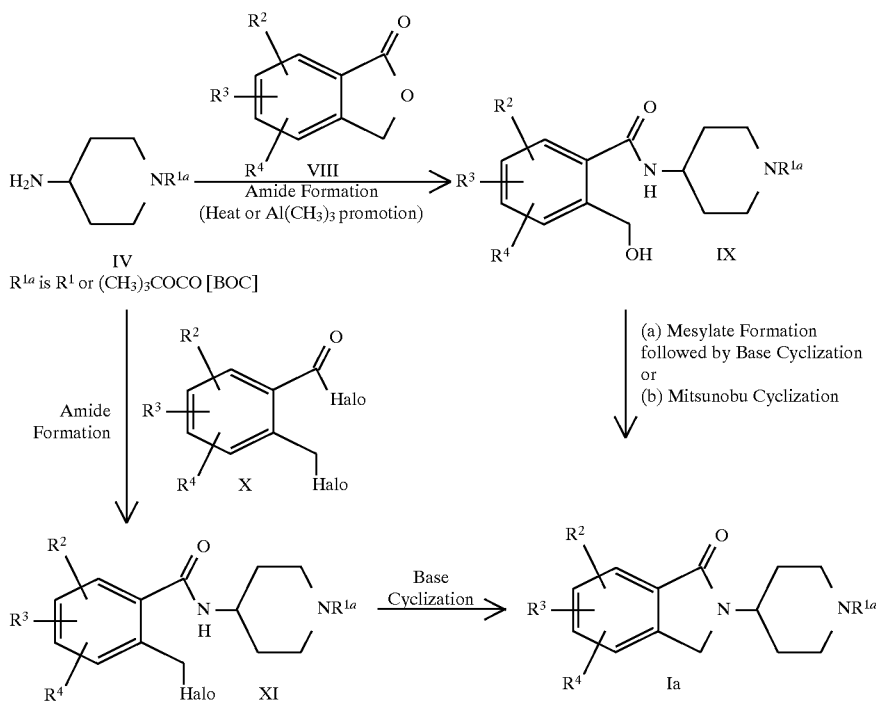

Scheme III
Introduction of R¹ by Alkylation or Arylation
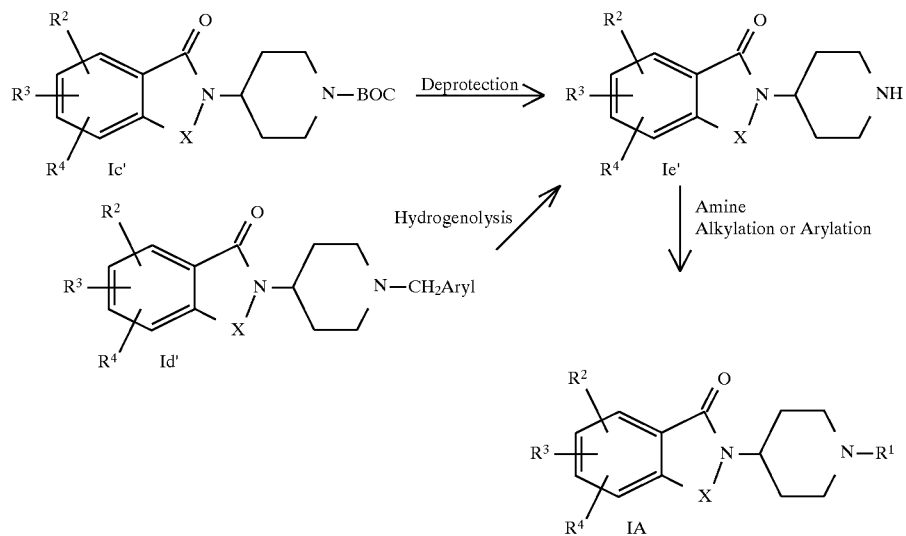
Scheme IV
Routes to Starting Materials IVb and IVc
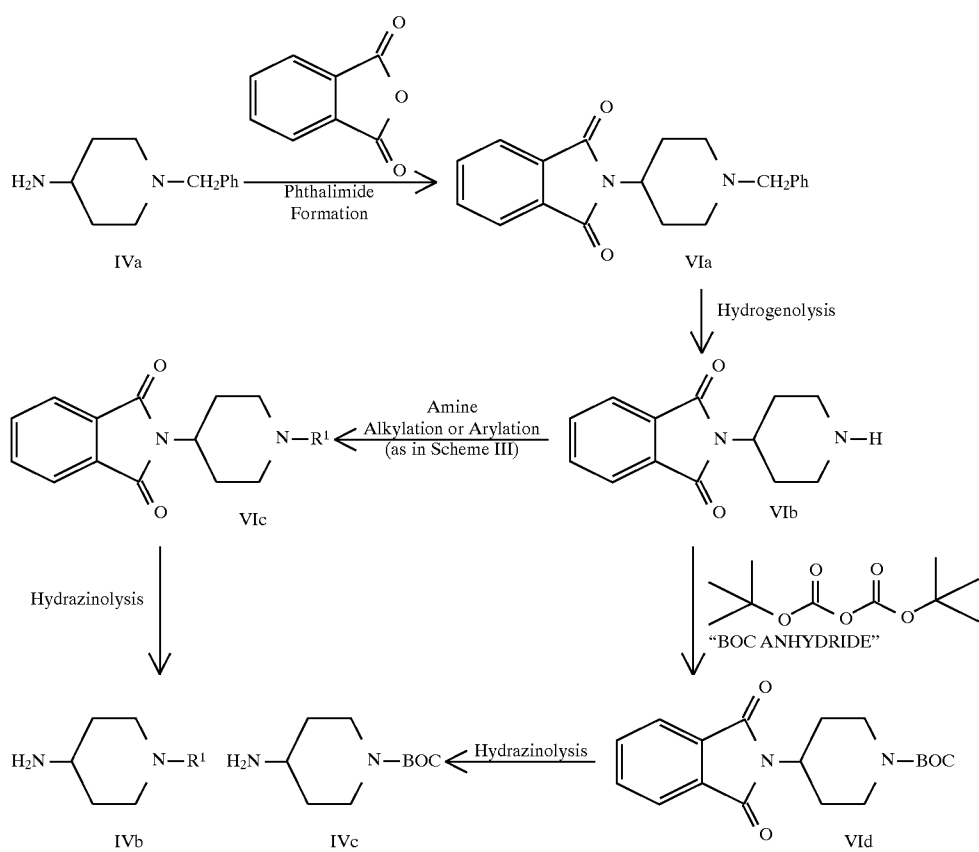

Scheme V
General Routes to Starting Materials IVb
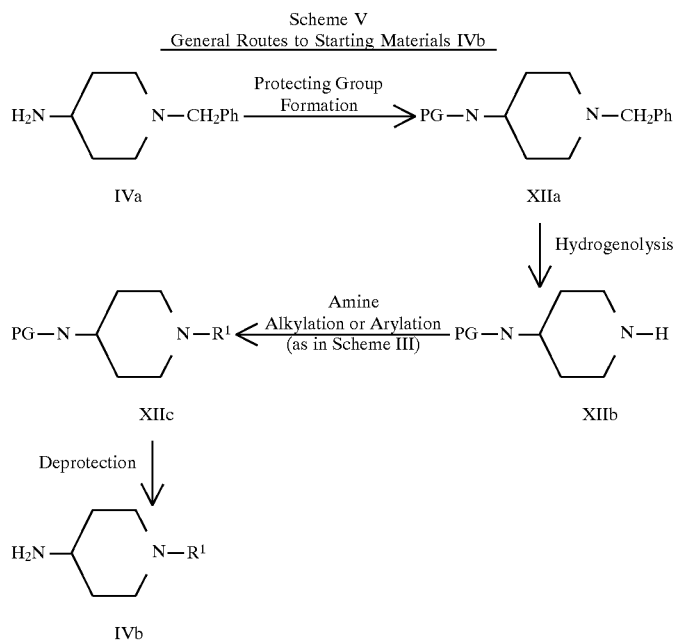
Scheme VI
General Routes to II
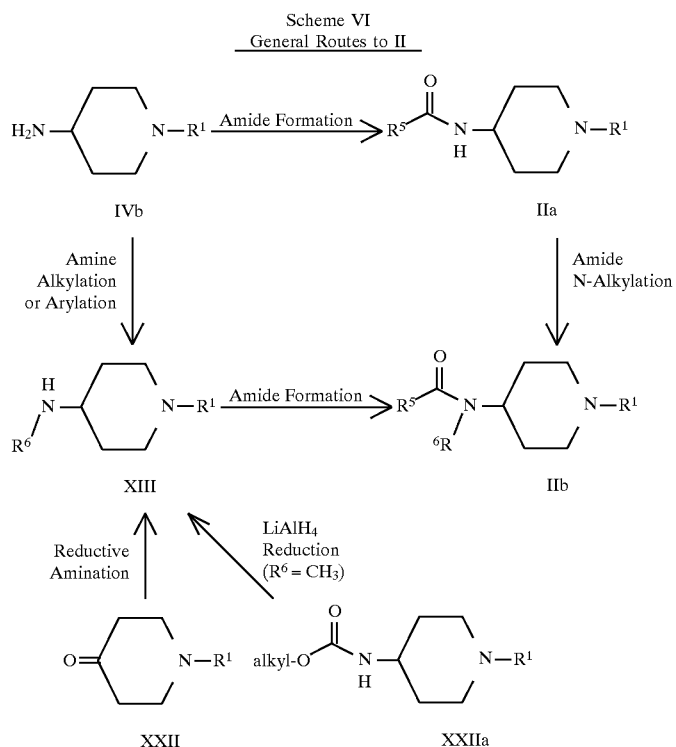

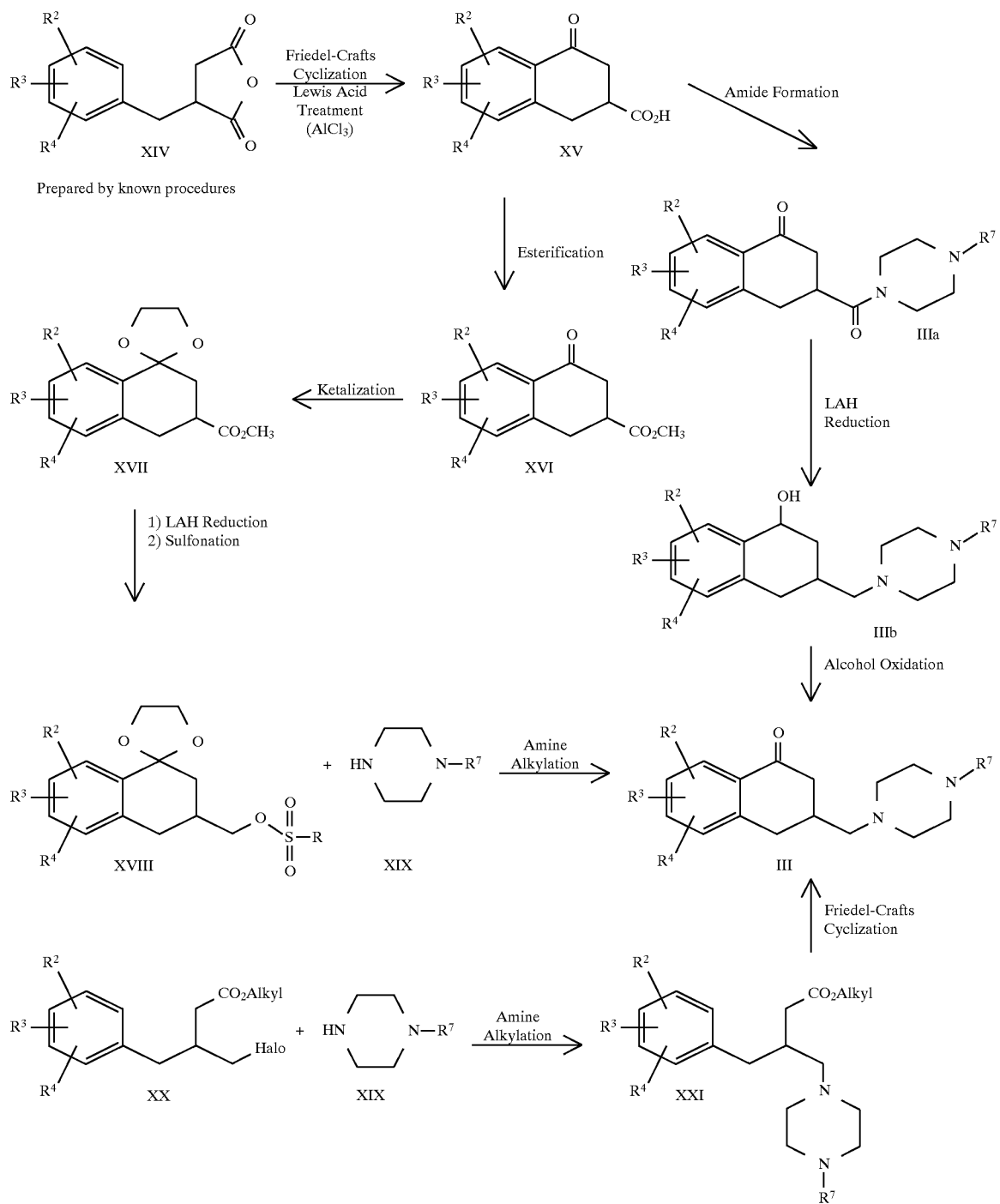

Scheme VIII
Preparation of Compounds IA¹, IA²
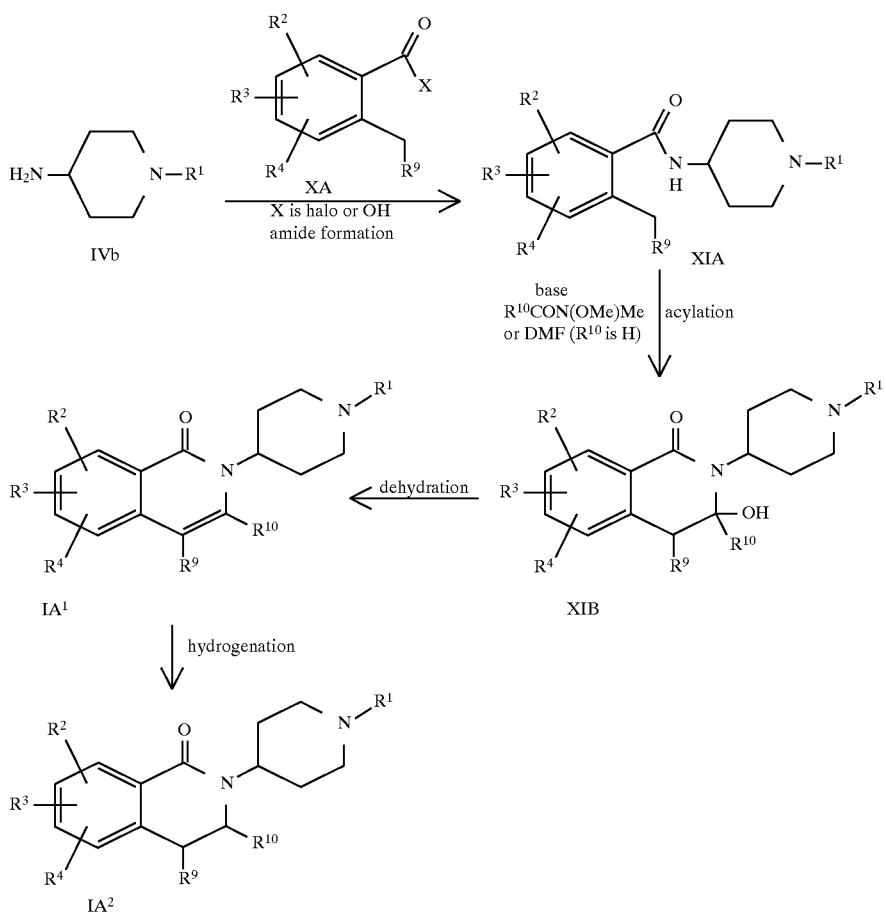
Scheme IX
Preparation of Compounds IA³–IA⁶
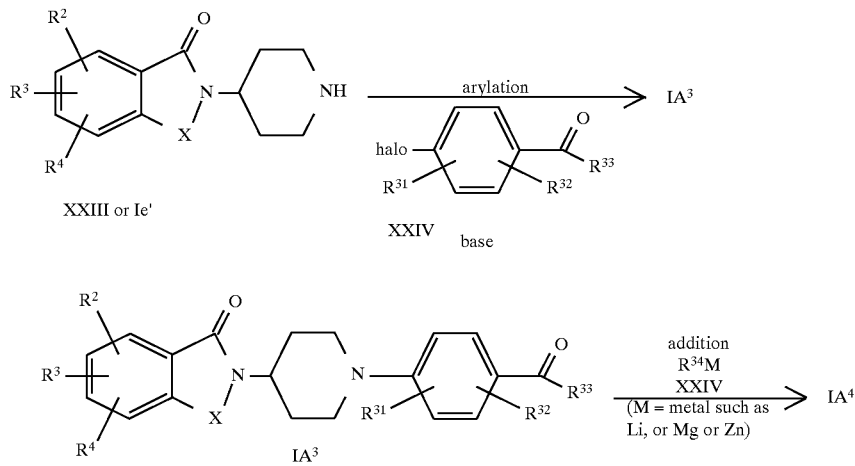

Scheme IX
Preparation of Compounds IA³–IA⁶
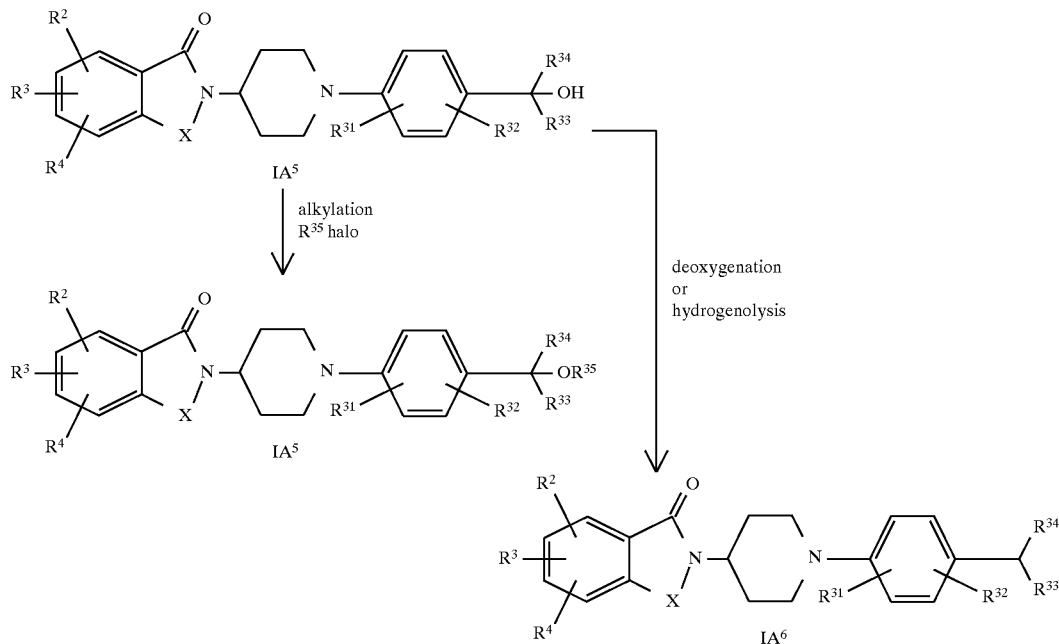
$R^{31}$ and $R^{32}$ are independently selected from any of the $R^2$, $R^3$, or $R^4$ radicals;
$R^{33}$ and $R^{34}$ are independently selected from any of the $R^1$ radicals as well as aryloxy, alkoxy, arylalkoxy, heteroarylalkoxy and heteroaryloxy;
$R^{35}$ can be any of the $R^1$ radicals.
Scheme X
Preparation of Compounds IA⁷
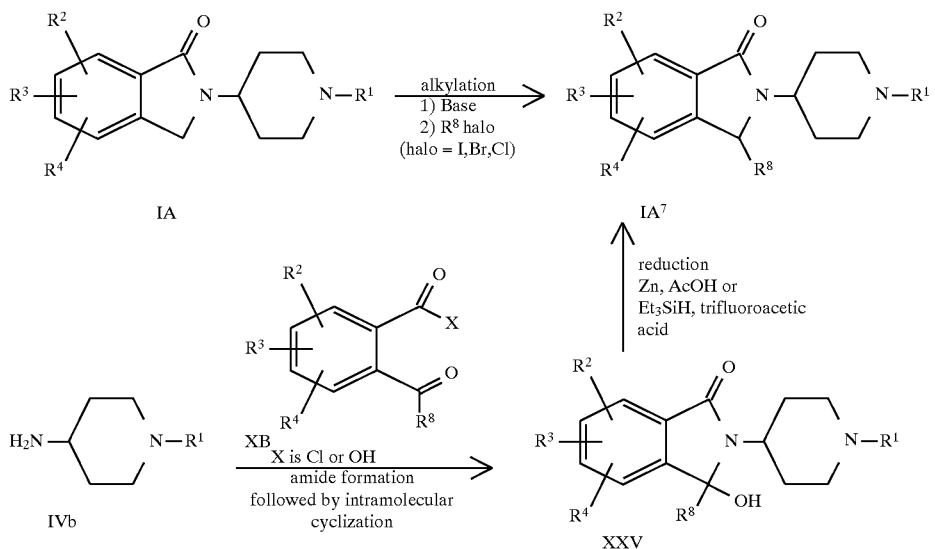

Scheme XI
Preparation of Compound II
(Robotic Amide Coupling)
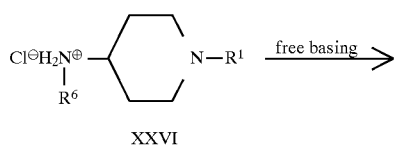
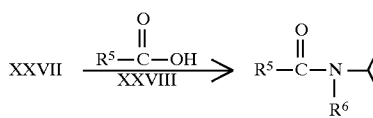
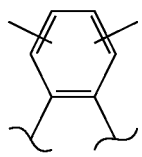
In the following Schemes XII et al, in the fluorenyl rings or fluorenyl analogs, the fused aryl groups:
may each optionally be replaced by a 5- or 6-membered heteroaryl ring as defined herein.
Scheme XII
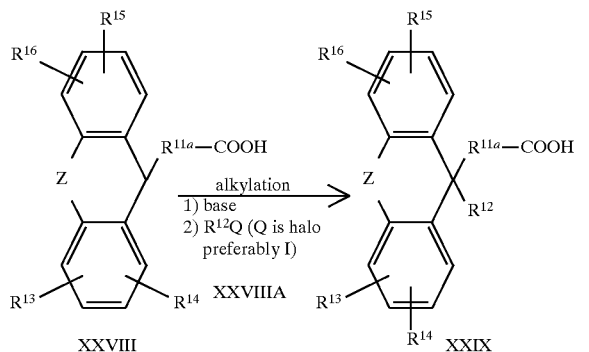
Scheme XII
-continued
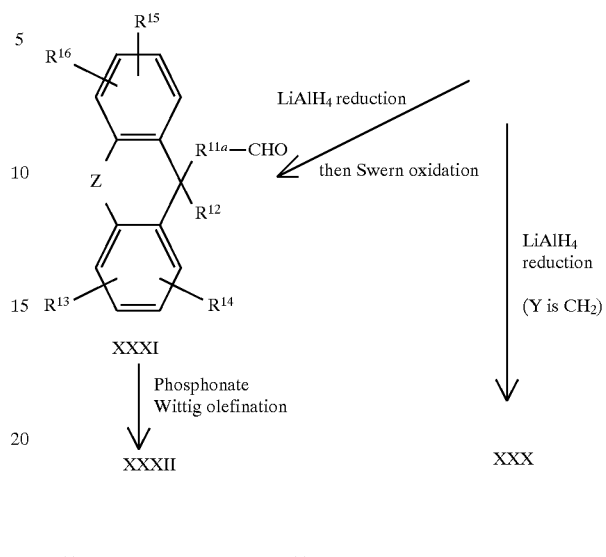
$R^{11a}$ can be any of the $R^{11}$ radicals.
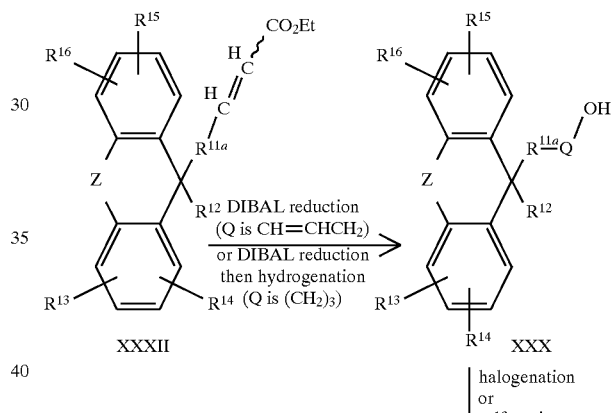
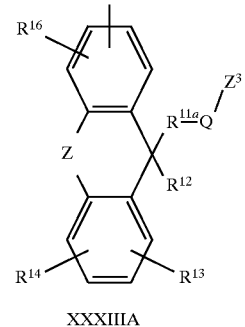
$Z^3$ is halo or Osulfonate

Scheme XIII
Preparation of Intermediates where $Z^2$ is S, SO or $SO_2$
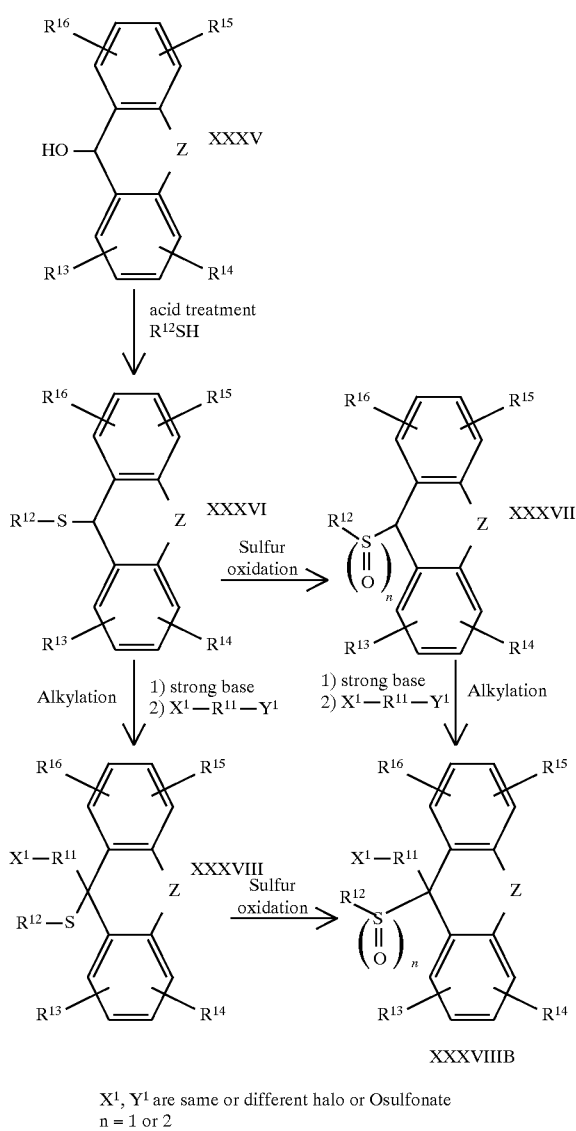
$X^1$, $Y^1$ are same or different halo or Osulfonate
n = 1 or 2
Scheme XIVA
Preparation of A
(Intermediates where $Z^2$ is NHCO)
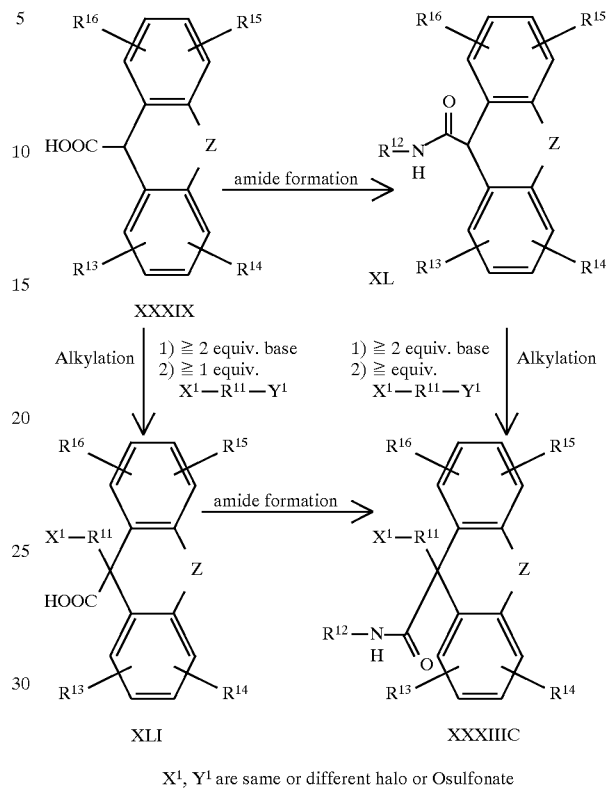
$X^1$, $Y^1$ are same or different halo or Osulfonate
Scheme XIVB
Alternative Procedure for Prepararing Intermediate XL
(Shown in Scheme XIVA)
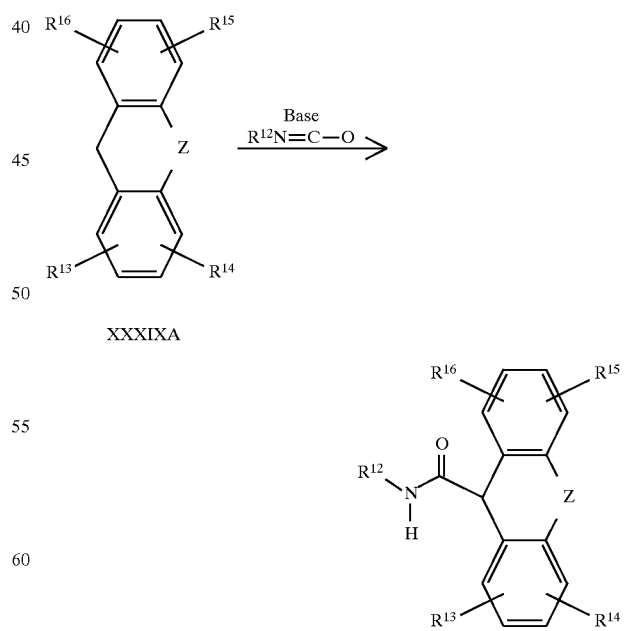

In carrying out the above reaction, bases such as n-butyllithiun, lithium bis(trimethylsilyl) amide and sodium bis(trimethylsilyl) amide may be employed in an aprotic solvent such as THF, at between −78° C. and 35° C.

It is preferable to have the starting material and isocyanate ($R^{12}N=C-O$) together in solvent, and then add the base, and optionally add further excess isocyanate subsequently.

Scheme XV

Preparation of Intermediate where $Z^1$ is $-N-C-$
                                              $|$   $\|$
                                              H    O

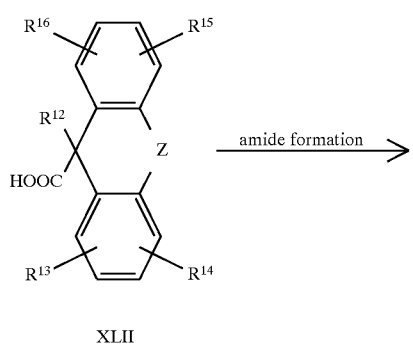

XLII

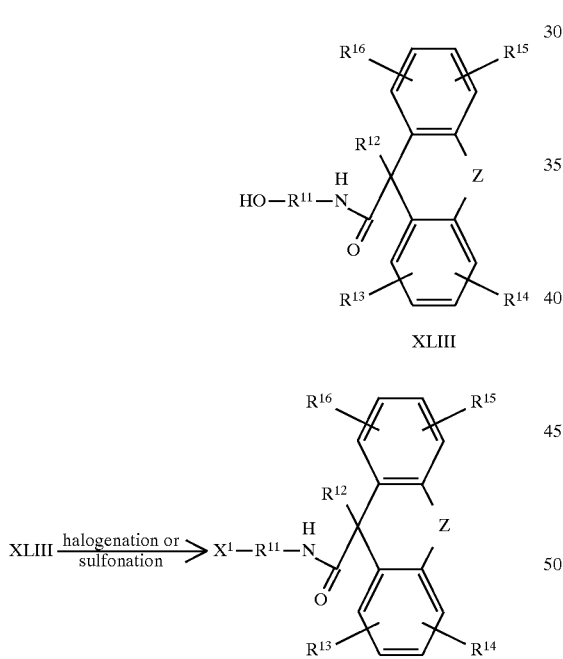

XLIII

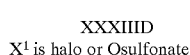

XXXIIID
$X^1$ is halo or Osulfonate

Scheme XVI

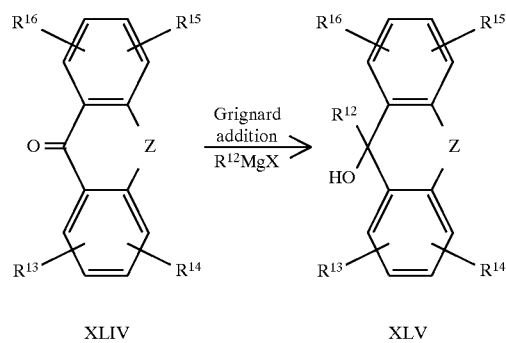

XLIV    XLV

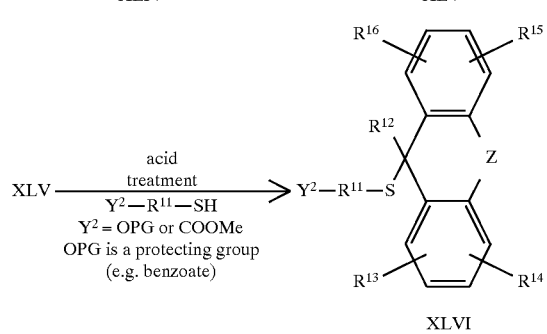

XLVI

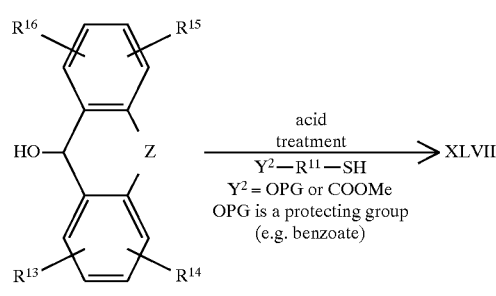

XXXV

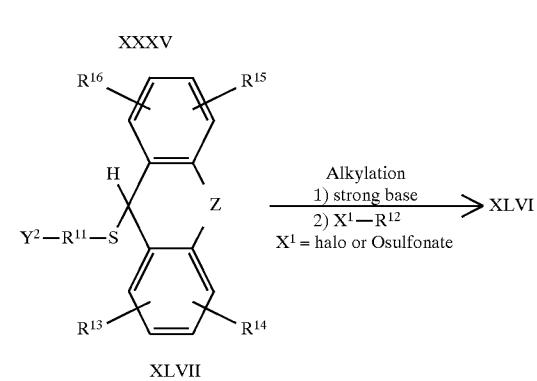

XLVII

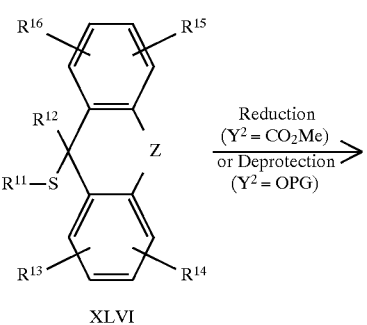

XLVI

-continued
Scheme XVI

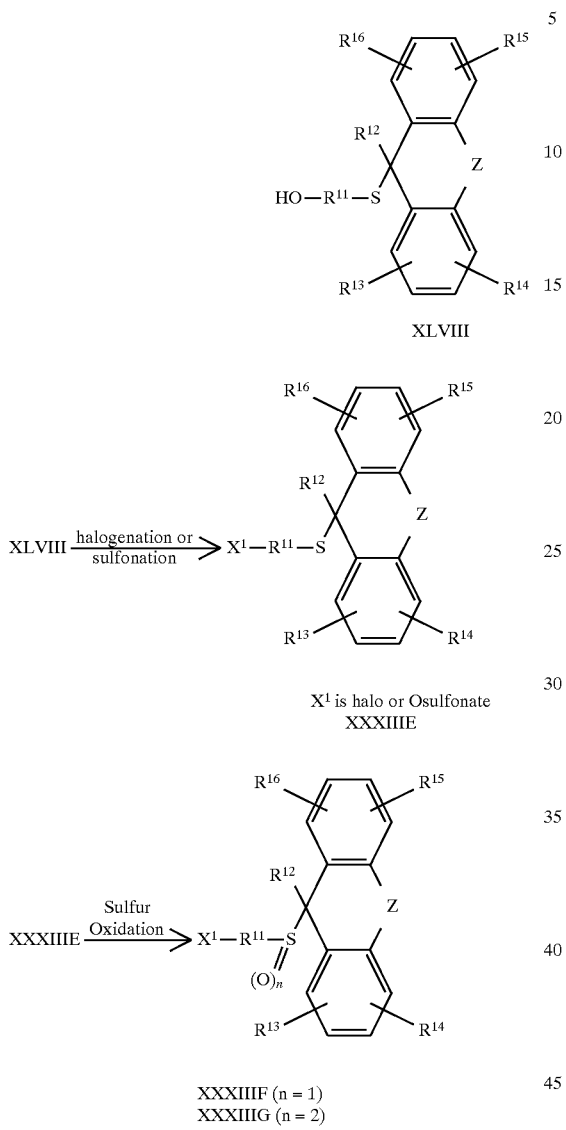

XLVIII

XLVIII —halogenation or sulfonation→ XXXIIIE $X^1$ is halo or Osulfonate
XXXIIIE XXXIIIE —Sulfur Oxidation→

XXXIIIF (n = 1)
XXXIIIG (n = 2)

Scheme XVIA
Preparation of Ketones

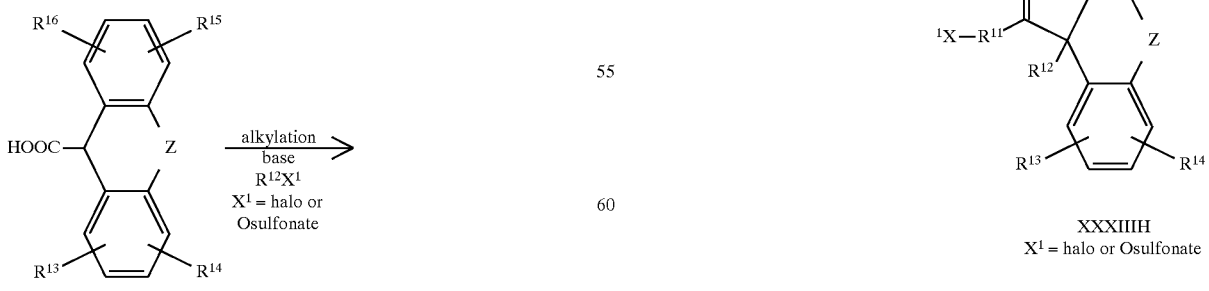

XXXIX

-continued
Scheme XVIA
Preparation of Ketones

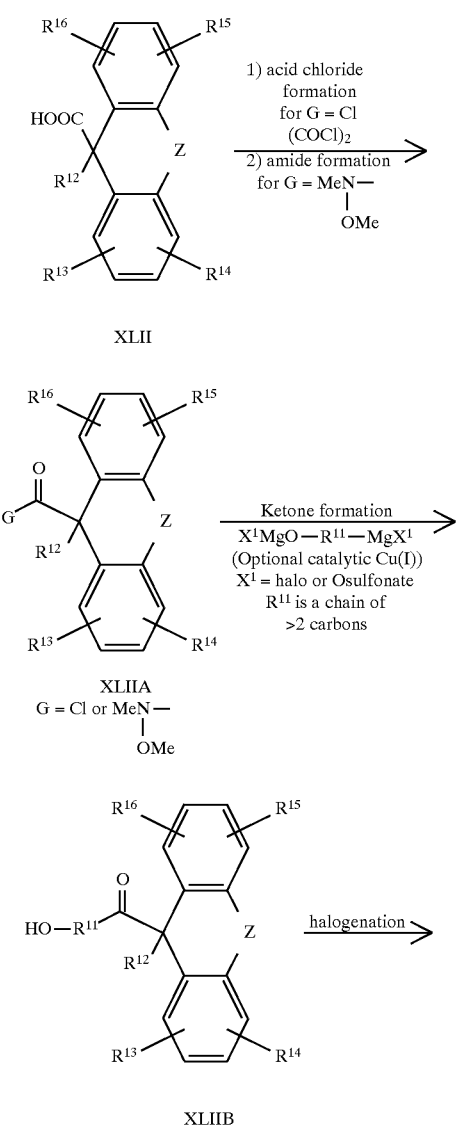

XLII 1) acid chloride formation for G = Cl (COCl)$_2$
2) amide formation for G = MeN—OMe XLIIA
G = Cl or MeN—OMe Ketone formation
$X^1MgO—R^{11}—MgX^1$
(Optional catalytic Cu(I))
$X^1$ = halo or Osulfonate
$R^{11}$ is a chain of >2 carbons XLIIB —halogenation→

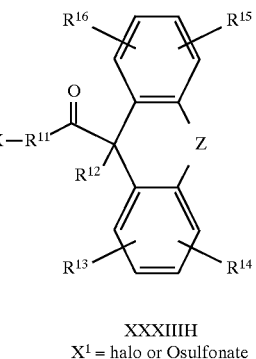

XXXIIIH
$X^1$ = halo or Osulfonate

Scheme XVIB.
Preparation of Ketones (Preferred Route)
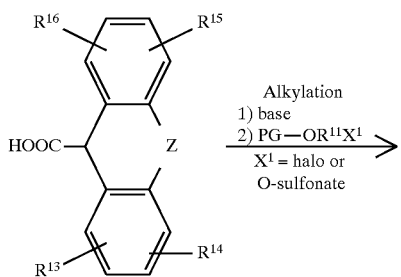
XXXIX
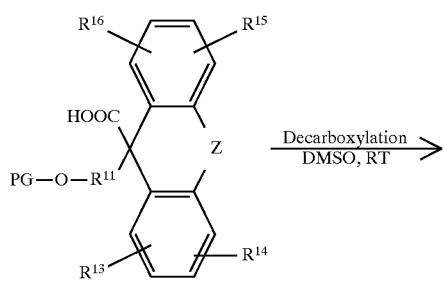
XLIIC
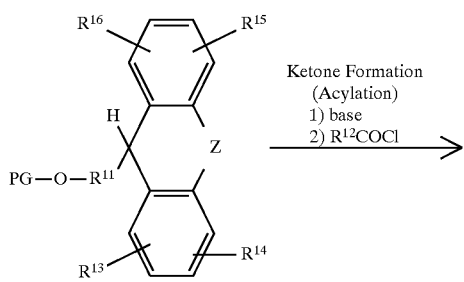
XLIID
-continued
Scheme XVIB.
Preparation of Ketones (Preferred Route)
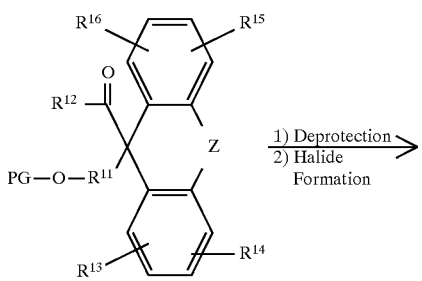
XLIIE
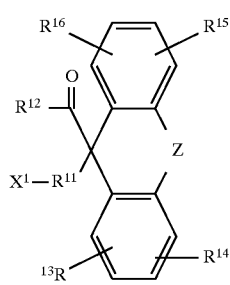
XXXIIII
PG is an appropiate protecting group: such as t-butyl(dimethyl)silyl or t-butyl(diphenyl)silyl, which can be deprotected with aqueous acid or n-Bu$_4$NF.

Scheme XVIIA
Preparation of Amide Linked Compounds
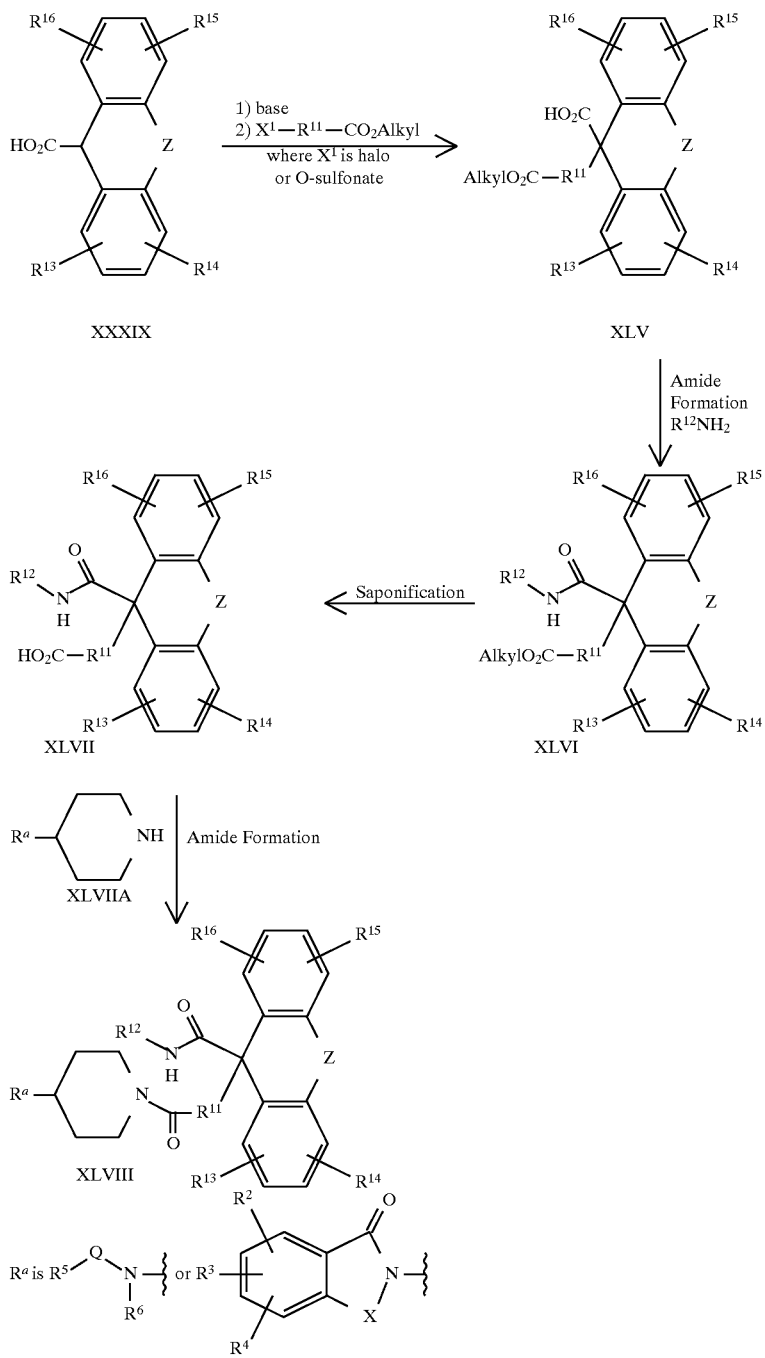

Scheme XVIIB
Preparation of Carbamate and Urea Linked Compounds
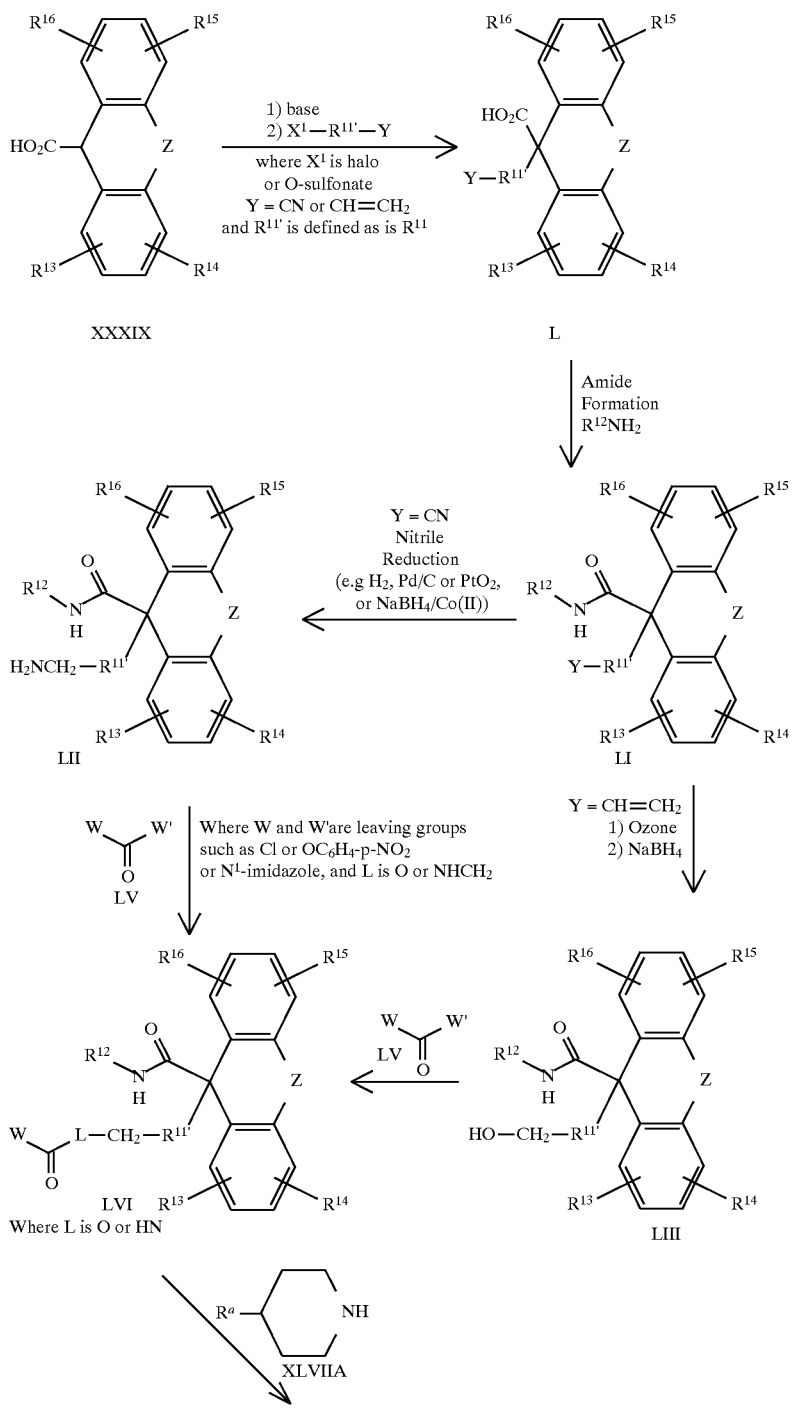

Scheme XVIIB
Preparation of Carbamate and Urea Linked Compounds

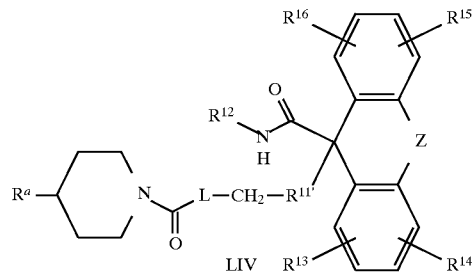
LIV

Scheme XVIIIA
Formation of Sulfonamides

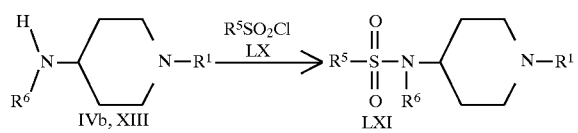

(Reaction in a variety of solvents (CH$_2$Cl$_2$, THF, pyridine) optionally in the presence of a tertiary amine base, such as pyridine or triethyl amine).

Scheme XVIIIB
Formation of Ureas (R$^5$ is Amino)

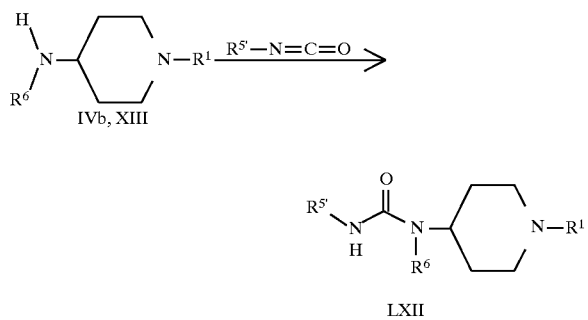
LXII (1 to 10 equiv of R—C=N=O, in aprotic solvent such as toluene, from 0° C. to 150° C.).
(R$^{5'}$ is alkyl, aryl, heteroaryl or arylalkyl).

Scheme XIXA
General Route to Final Product

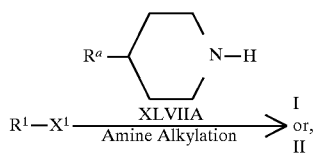

(where R$^1$ is as in XXXIII A-K or any other R$^1$ as defined herein)

Scheme XIXB
General Route to Final Products (I or II)

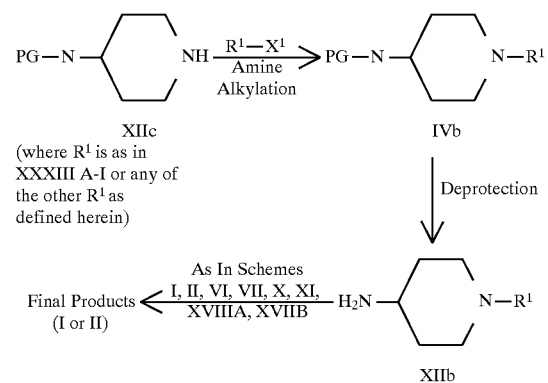

(where R$^1$ is as in XXXIII A-I or any of the other R$^1$ as defined herein)

(Example of a protected nitrogen (PG—N) is the t-BuOC=ONH (BOC amino) group, which can be deprotected under mild conditions, such as anhydrous HCl in dioxane or neat trifluoroacetic acid).

Scheme XX
Oxidation of sulfur at the end of the reaction sequence

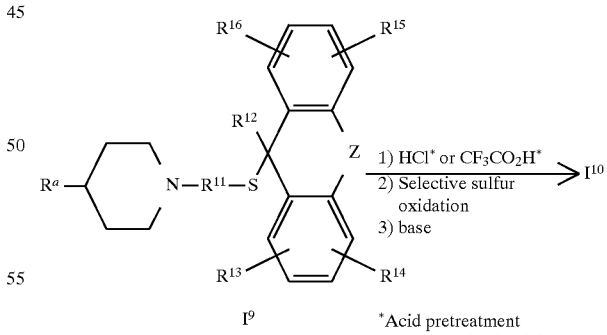

*Acid pretreatment protects basic piperidine from oxidation

Scheme XX

Oxidation of sulfur at the end of the reaction sequence

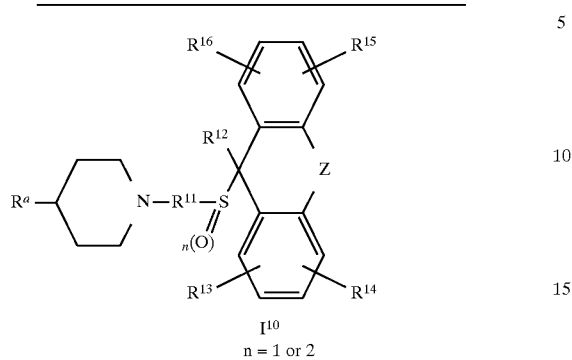

$I^{10}$
n = 1 or 2

($R^a$ is defined as in Scheme XVIIA)

Scheme XXI

Preparation of Halide Intermediates

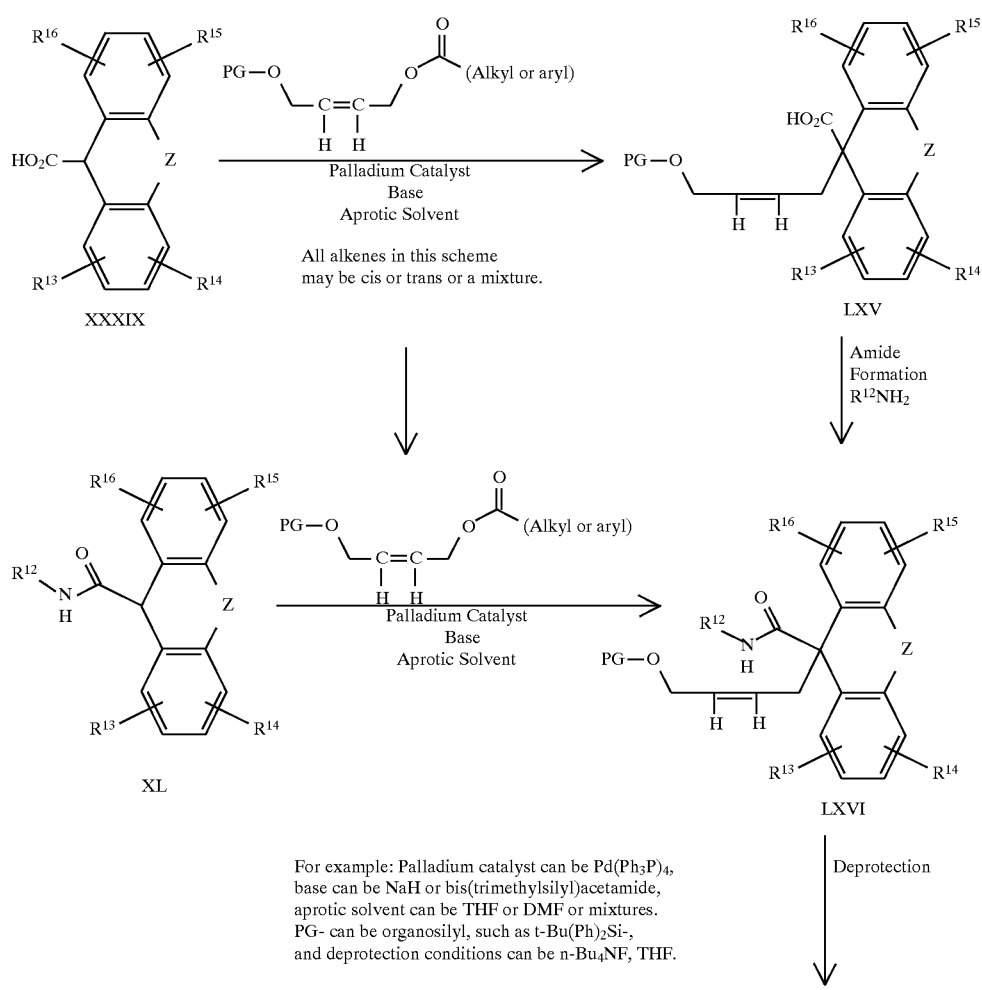

For example: Palladium catalyst can be $Pd(Ph_3P)_4$,
base can be NaH or bis(trimethylsilyl)acetamide,
aprotic solvent can be THF or DMF or mixtures.
PG- can be organosilyl, such as $t\text{-}Bu(Ph)_2Si\text{-}$,
and deprotection conditions can be $n\text{-}Bu_4NF$, THF.

Scheme XXI
Preparation of Halide Intermediates

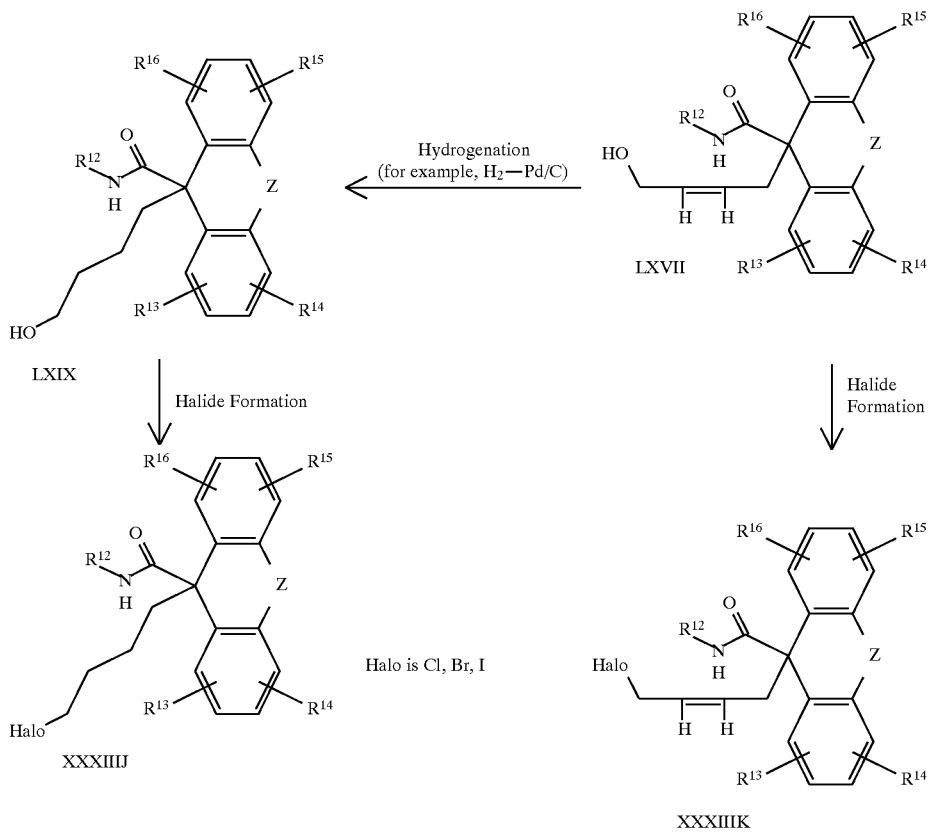

Halo is Cl, Br, I

Scheme XXII
Preparation of 3-Substituted Piperidine Starting Materials

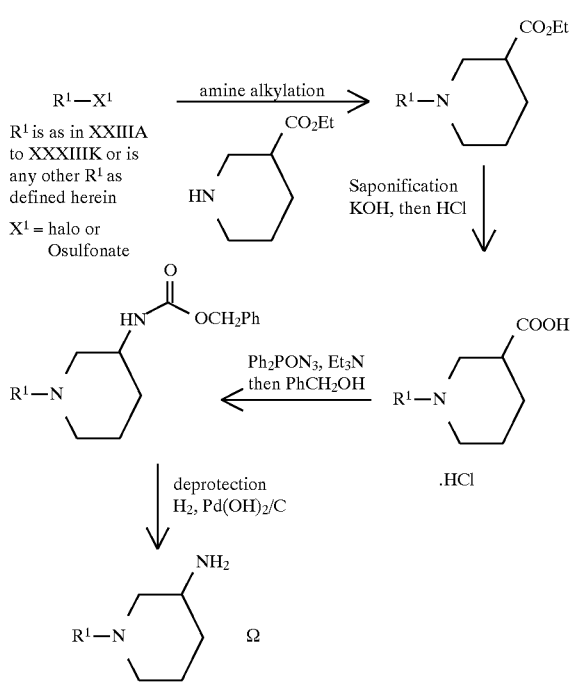

Intermediate Ω can be utilized as a starting material to prepare 3-substituted isomers Ii and IIi via the same methodology as outlined in the Schemes herein, specifically Schemes I, II, IV, V, VI, VIII, X, XI, XVIIIA, XVIIIB, XIXB, XX, XXIII.

Scheme XXIII
Preparation of N-Oxides of Formulae I and II compounds

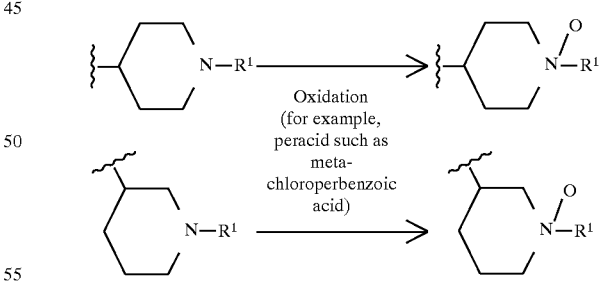

It is to be understood that in Schemes I to VI, VIII to XI, XVIIA, XVIIB, XVIIIA, XVIIIB, XIXA, XIXB, XX and XXI (which relate to preparation of compounds of the invention of formula I or II), the starting materials which are depicted as the 4-substituted piperidine isomers may be substituted with the corresponding 3-substituted piperidine isomers to afford the corresponding compounds of the invention Ii or IIi which include the 3-substituted piperidine isomer.

In the above Reaction Schemes XII through XXI, the starting fluorenyl-type acid XXVIII, alcohol XXXV, acids XXXIX and XLII, ketone XLIV, hydride XXXIXA, and amide XL groups may be substituted with corresponding acid, alcohol, ketone, hydride and amide containing fluorenyl type groups as set out in A, B, C and D or indenyl-type groups as set out in E, F, G and/or a to provide an intermediate compound for use in preparing a compound of formula I, I', II or II' of the invention as per Reaction Schemes I to XXIII.

Phthalimide formation (Reaction Schemes I, IV) may be carried out by heating to about 80° to 150° C. in an oil bath optionally in an inert solvent or by various other procedures known in the art. See, e.g., Example 13 hereinafter.

Reduction (Reaction Scheme I) may be carried out by treatment with such reducing agents as zinc in the presence of acetic acid or tin in the presence of hydrochloric acid under an inert atmoshphere (e.g., argon).

Isoindolone formation (Reaction Scheme I) may be carried out by heating in the range of about 50° to 150° C. in an organic solvent (e.g., toluene, ethanol, dimethylformamide) optionally in the presence of a salt (e.g., potassium carbonate) or a tertiary amine base (e.g., 2,6-di-t-butylpyridine or triethylamine).

Amide formation (Reaction Schemes II, VI, VII, VIII, X, XI, XIVA, XV, XVI, XVIA, XVIB, XVIIA, XVIIB), XXI may be carried out by a number of methods known in the art. For example, an amine substrate may be treated with (1) an acid halide $R^5C(O)$halo or compound X or XA in an aprotic solvent, optionally in the presence of a tertiary amine base (e.g., triethylamine); (2) the acid halide in the presence of an aqueous base under Schotten-Baumann conditions; (3) a free carboxylic acid ($R^5CO_2H$) in the presence of a coupling agent such as dicyclohexylcarbodiimide (DCC), diisopropyl carbodiimide (DIC) or 1-(3-dimethylamino-propyl)-3-ethylcarbodiimide hydrochloride (WSC), optionally in the presence of 1-hydroxybenzotriazole (HOBT); (4) the free acid in the presence of N, N-carbonyldiimidazole in an aprotic organic solvent followed by the amine substrate; (5) trialkylaluminum (e.g., $Al(CH_3)_3$) in an aprotic solvent, followed by an ester (e.g., $R^5CO_2$alkyl or compound VIII) or (6) mixed anhydride formation, by reacting the acid with an acid chloride (e.g., isobutyl chloroformate or bis-(2-oxo-3-oxazolidinyl)-phosphinic chloride (Bop—Cl)) in the presence of a tertiary amine base (e.g., triethylamine) followed by treatment with the amine substrate.

Mesylate formation (Reaction Scheme II) may be carried out by treatment of the amine-alcohol substrate with methanesulfonyl chloride and triethylamine or pyridine or in an aprotic solvent, such as dichloromethane.

Base cyclization (Reaction Schemes II, VIII) may be carried out by treatment with a base. (e.g., potassium 1-butoxide or sodium hydride) in an inert solvent (e.g., dimethylformamide, tetrahydrofuran, dimethoxymethane, or toluene). Mitsunobu cyclization (Reaction Scheme II) may be carried out by procedures generally known in the art. See, e.g., R. K. Olsen, *J. Org. Chem.*, 49, 3527 (1984); Genin, M. J., et al., *J. Org. Chem.*, 58, 2334–7 (1993).

Alternatively, a mixture of compounds IV and VIII can be converted to compound Ia in a single pot by heating the mixture in a protic solvent (e.g., water, methanol, ethenyl or isopropanol or mixtures thereof) at 100° to 200° C. See, e.g., European patent application 81 / 26,749, FR 2, 548,666 (1983).

Protection and deprotection (Reaction Schemes III, IV, V, XVI, XVIB, XIXB, XXI) may be carried out by procedures generally known in the art. See, for example, T. W. Greene, *Protecting Groups in Organic Synthesis,* Second edition, 1991. PG in Scheme V denotes a nitrogen-protecting group.

One particularly useful group is tert-butoxycarbonyl (BOC) which can be derived from the associated anhydride as shown in Scheme IV. BOC-protected amines may typically be deprotected by treatment with acid (e.g., trifluoroacetic acid or hydrochloric acid) in procedures well understood by those having ordinary skill in the art.

Hydrogenolysis (Reaction Schemes III, IV, V) may be carried out with $H_2$ using a balloon apparatus or a Parr Shaker in the presence of a catalyst (e.g., pallladium on activated carbon).

Amine alkylation and arylation (Reaction Schemes III, IV, V, VII, IX, XII, XIXA, XIXB) may be carried out by methods known in the art. Suitable procedures are described in Cortizo, L., *J. Med. Chem.* 3, 2242–2247 (1991). For example, the alkylation or arylation may be carried out by treating the amine substrate with a halide (e.g., $R^1$-halo) or an oxytosylate (e.g., $R^1$-O-tosylate) in an aprotic solvent (e.g., dimethylformamide), optionally in the presence of a tertiary amine (e.g., triethylamine) or an inorganic base (e.g., potassium carbonate).

Reductive amination may be employed as an alternative to the foregoing amine alkylation and arylation procedures when $R^1$, $R^6$ or $R^7$ is $R^9R^{10}CH$— and $R^9$ and $R^{10}$ are each independently hydrogen, alkyl, alkenyl, aryl, heteroaryl, arylalkyl, heteroarylalkyl, cycloalkyl, or cycloalkylalkyl, or $R^9$ and $R^{10}$ together are alkylene (i.e., $R^9R^{10}CH$— forms a cycloalkyl group). Such reductive amination may be carried out by treating the amine with (a) a ketone or aldehyde ($R^9$—C(O)—$R^{10}$), (b) $NaBH_4$, $NaBH_3CN$ or NaB(acetoxy)$_3$H, (c) a protic solvent (e.g., methanol) or a dipolar aprotic solvent (e.g., acetonitrile), and, optionally, (d) an acid (e.g., acetic acid, trifluoroacetic acid, hydrochloric acid, or titanium isopropoxide). When $R^1$ is aryl or heteroaryl, transition metals (e.g., palladium or copper salts or complexes) may be used to promote the arylation reaction.

Alkylation of the isoindolone (Reaction Scheme X) may be carried out by treatment of the isoindolone with a strong base (i.e. sodium bis(trimethylsilyl)amide or lithium diisopropylamide) followed by an alkyl halide (e.g. $R^8$-halo) or alkyl sulfonate (e.g. $R^8$-tosylate) in an inert solvent (e.g. tetrahydrofuran or dimethoxy-ethane). Alternatively, as seen in Scheme X, amine IVb can be treated under amide formation conditions with a ketone with the structure XB to provide a hydroxylactam XXV, which could be subjected to reduction conditions with such reducing agents as zinc in acetic acid or triethylsilane in trifluoroacetic acid to give $IA^7$.

Hydrazinolysis of phthalimides may be carried out by standard means known in the art. See, e.g., T. W. Greene, *Protecting Groups in Organic Synthesis,* Second edition, 1991.

Amide N-alkylation (Reaction Scheme VI) may be carried out by base treatment (e.g., NaH, KH, $KN[Si(CH_3)_3]_2$, $K_2CO_3$, P4-phosphazene base, or butyl lithium) in an aprotic organic solvent, followed by treatment with $R^6$-halo or $R^6$-O-tosylate. Use of P-phosphazene base is described in T. Pietzonka, D. Seebach, *Agnew. Chem. Int. Ed. Engl.* 31, 1481, 1992.

In Scheme VII, the Friedel-Crafts cyclization may be carried out with, for example, aluminum chloride, boron trifluoride or polyphosphoric acid and aprotic solvents such as nitrobenzene, nitromethane or carbon disulfide at about −20° C. to 80° C. The esterification may be carried out with a common esterifying agent (e.g., sulfuric acid in methanol) with heating to reflux. Ketalization may be carried out by treatment with such reagents as ethylene glycol in an organic solvent (e.g., benzene) in the presence of an acid catalyst (e.g., p-toluenesulfonic acid). Reduction with lithium aluminum hydride (LAH) may be carried out in an organic solvent (e.g., tetrahydrofuran) from 0° C. to 70° C. Oxidation of alcohols may be carried out by Oppenauer oxidation, such as treatment with potassium t-butoxide and benzophenone, or by other procedures known in the art. The sulfonation may be carried out with $RSO_2Cl$ wherein R is alkyl, haloalkyl or aryl in an organic solvent (e.g., pyridine, dichloromethine) in an inert atmosphere (e.g., nitrogen) optionally in the presence of a tertiary amine base (e.g., triethylamine).

Compound III can also be prepared from compound XX as described by Cortizo, L., J. Med. Chem. 34, 2242–2247 (1991).

Dehydration (Scheme VIII) may be carried out employing a strong acid such as hydrochloric acid, sulfuric acid or trifluoroacetic acid.

Hydrogenation (Scheme VIII) may be carried out in the presence of a conventional catalyst such as Pd/C or Pt or Rh under a $H_2$ atmosphere.

The addition reaction shown in Scheme IX may be carried out by treating $IA^3$ with an organometallic reagent XXIV, such as an organolithium or organic magnesium compound where organo is alkyl or aryl.

The deoxygenation or hydrogenation reaction (Scheme IX) is carried out in the presence of a strong acid such as trifluoroacetic acid or boron trifluoride etherate, in the presence of a hydride source such as triethyl silane or tris(trimethylsilyl)silane.

The alkylation in Schemes XII, XIII, XIV, XVI, XVIA, XVIB is carried out in the presence of base such as butyllithium or sodium bis(trimethylsilyl)amide. It will be appreciated that $R^{12}$ in $R^{12}Q$ may be any of the $R^{12}$ groups as defined hereinbefore.

Alternatively, the alkylation in the above Schemes can be performed where either or both $Z^1$ or $Z^2$ is a bond, using a palladium catalyzed allylic alkylation procedure. In this reaction, the fluorenyl-type or indenyl-type precursors (compounds XXVIII, XXXVI, XXXVII, XXXIX, XL, XLVII) are reacted with a base (sodium hydride, sodium bis(trimethylsilyl)amide or bis(trimethylsilyl)-acetamide), a palladium catalyst (for example $Pd(Ph_3)_4$) and an allylic acetate

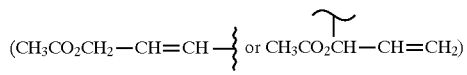

in an inert solvent (for example THF). This reaction is to introduce either —$R^{12}$ (Scheme XII) or —$R^{11}$—$X^1$ (Schemes XIII, XIV, XVI, XVIA) or —$R^{11}$—OPG (Scheme XVIB, Scheme XXI). The product of this reaction contains either an —$R^{12}$ group or an —$R^{11}$—$X^1$ group (or an —$R^{11}$—OPG group) which begins with

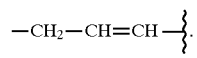

Saturation of the alkene in $R^{11}$ or $R^{12}$ can be accomplished by standard catalytic hydrogenation conditions.

With respect to Scheme XII, the $LiAlH_4$ reduction, Swern oxidation, Wittig olefination and halogenation/sulfonation reactions are conventional reactions well known to those skilled in the art.

The sulfur oxidation in Schemes XIII, XVI and XVIII is carried out as follows.

Sulfides of structures XXXVI, XXXVIII, XXXIIIE and $I^9$ can be selectively oxidized to sulfoxides by 1 molar equivalent of reagents known in the art, such as 30% $H_2O_2$, $NaIO_4$, and peracids (e.g., meta-chloroperbenzoic acid). The resulting sulfoxides can be further transformed to corresponding sulfones by another molar equivalent or excess of 30% $H_2O_2$, $KMnO_4$, $KHSO_5$, or peracids (e.g., meta-chloroperbenzoic acid). Alternatively, the sulfones can be directly prepared from sulfides with 2 molar equivalents or more of oxidizing agents, such as 30% $H_2O_2$ and peracids (e.g., meta-chloroperbenzoic acid). In cases where an amine (such as a piperidine in $I^9$) is present during the oxidation, the basic nitrogen may be protected by pretreatment with an acid such as HCl or $CF_3CO_2H$ (see Scheme XIX).

To prepare examples where $Z^1$ or $Z^2$ is —CHOH, the compounds I, Ii, II and IIi where $Z^1$ or $Z^2$ is C=O can be reduced with a hydride reagent, for example $NaBH_4$.

The compounds of the invention may be employed in preventing, stabilizing or causing regression of atherosclerosis in a mammalian species by administering a therapeutically effective amount of a compound to decrease the activity of MTP.

The compounds of the invention can be tested for MTP inhibitory activity employing the procedures set out in U.S. application Ser. No. 117,362 filed Sep. 3, 1993, Pat. No. 5,595,872, employing MTP isolated from one of the following sources:

(1) bovine liver microsomes,
(2) HepG2 cells (human hepatoma cells) or
(3) recombinant human MTP expressed in baculovirus.

The compounds of the invention may also be employed in lowering serum lipid levels, such as cholesterol or triglyceride (TG) levels, in a mammalian species, by administering a therapeutically effective amount of a compound to decrease the activity of MTP.

The compounds of the invention may be employed in the treatment of various other conditions or diseases using agents which decrease activity of MTP. For example, compounds of the invention decrease the amount or activity of MTP and therefore decrease serum cholesterol and TG levels, and TG, fatty acid and cholesterol absorption and thus are useful in treating hypercholesterolemia, hypertriglyceridemia, hyperlipidemia, pancreatitis, hyperglycemia and obesity.

The compounds of the present invention are agents that decrease the activity of MTP and can be administered to various mammalian species, such as monkeys, dogs, cats, rats, humans, etc., in need of such treatment. These agents can be administered systemically, such as orally or parenterally.

The agents that decrease the activity or amount of MTP can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), antioxidants (ascorbic acid or sodium bisulfite) or the like. Oral dosage forms are preferred, although parenteral forms are quite satisfactory as well.

The dose administered must be carefully adjusted according to the age, weight, and condition of the patient, as well as the route of administration, dosage form and regimen, and the desired result. In general, the dosage forms described above may be administered in amounts of from about 5 to about 500 mg per day in single or divided doses of one to four times daily.

The following Examples represent preferred embodiments of the invention. All temperatures are in °C. unless indicated otherwise.

EXAMPLE 1

N-[1-(3,3-Diphenylpropyl)-4-piperidinyl]benzamide monohydrochloride

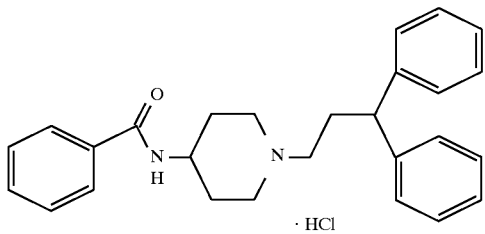

A. [1-(Phenylmethyl)-4-piperidinyl]carbamic acid, 1,1-dimethylethyl ester

To a solution of 4-amino-1-benzylpiperidine (20.0 g, 105 mmol) in dichloromethane (150 mL) was added dropwise a solution of di-tert-butyldicarbonate (25.2 g, 116 mmol) in dichloromethane (50 mL) at 0° C. After addition, the reaction was warmed to room temperature. The reaction was maintained at this temperature for 2 hours. The reaction was evaporated to dryness. The resulting residue was recrystallized from ethyl ether to give compound A (23.5 g, 76%) as a white solid (melting point 119°–121° C.).

B. 4-Piperidinylcarbamic acid, 1,1-dimethylethyl ester

A suspension of 64.94 g (0.224 mol) of compound A and 25.6 mL (0.447 mol) of acetic acid in 500 mL of absolute ethanol was warmed to dissolve all solids. After cooling, 6.5 g (1 wt. %) of 10% palladium on charcoal was added and the mixture was shaken on a Parr apparatus under initial hydrogen pressure of 40 psi for 23 hours. The catalyst was removed by filtration and the solution was concentrated to a clear oil which was dissolved in 1.5 L of chloroform. The organics were washed with a 3N KOH solution saturated with NaCl (2×75 mL). The aqueous layer was back extracted with chloroform (5×200 mL). The combined organics were dried (sodium sulfate) and concentrated to provide 65 g of a white solid which was redissolved in 1.5 L of chloroform and washed with brine (2×200) mL to remove residual acetate. The combined aqueous layers were back extracted and the combined organics were dried (sodium sulfate) and concentrated to provide 40.15 g (90%) of compound B as a white solid (melting point 156°–159° C.) .

C. g-Phenylbenzenepropanol, 4-methylbenzenesulfonate ester

To a solution of tosyl chloride (4.94 g, 25.9 mmol) in dichloromethane (10 mL) was added 3,3-diphenyl-1-propanol (5.00 g, 23.6 mmol) and pyridine (2.86 mL, 35.4 mmol) at room temperature. The reaction was stirred overnight at room temperature. Ethyl ether (200 mL) was added to dilute the reaction, and the organic layer was washed with 1N HCl (50 mL×2), saturated sodium carbonate (50 mL×2), brine (50 mL×2) and dried over $MgSO_4$. Purification was performed by flash chromatography, loaded and eluted with 25% ethyl acetate in hexane. Pure fractions were combined and evaporated to give compound C (5.2 g, 60%) as a colorless oil.

D. [1-(3,3-Diphenylpropyl)-4-piperidinyl]-carbamic acid, 1,1-dimethylethyl ester To a solution of compound C (1.83 g, 5.00 mmol) and compound B (1.00 g, 5.00 mmol) in isopropanol (25 mL) was added potassium carbonate (1.1 g, 8.00 mmol). The reaction was refluxed overnight. The reaction was cooled to room temperature and filtered, and the filtrate was evaporated to dryness. Purification was performed by flash chromatography, loaded and eluted with 2.5% methanol in dichloromethane. Pure fractions were combined and evaporated to give compound D (1.5 g, 76%) as a colorless oil.

E. 1-(3,3-Diphenylpropyl)-4-piperidinamine, hydrochloride

To a stirred solution of 9.21 g (23.34 mmol) of compound D in 60 mL of dioxane was added 58 mL (0.223 mol) of a 4.0M HCl in dioxane solution. The mixture was stirred for 15 hours then concentrated to provide 8.45 g (100%) of compound E as a white solid containing 10 wt. % of dioxane by $^1H$ NMR, melting point 123°–126° C. A dioxane-free sample of the hydrochloride salt has a melting point of 192°–194° C.

F. N-[1-(3,3-Diphenylpropyl)-4-piperidinyl]-benzamide

To solution of compound E (100 mg, 0.30 mmol) and triethylamine (152 mg, 0.33 mmol) in dichloromethane (2 mL) was added a solution of benzoyl chloride (46.8 mg, 0.33 mmol) in dichloromethane (0.5 mL) at 0° C. After addition, the reaction was stirred at 0° C. for 10 minutes. The reaction was diluted with dichloromethane (50 mL), the organic layer was washed with saturated sodium bicarbonate solution (10 mL), water (10 mL) and dried over sodium sulfate. The solution was evaporated to dryness. The resulting residue was recrystallized from isopropanol to give compound F (100 mg, 84%) as a white solid (melting point 151°–155° C.).

G. N-[1-(3,3-Diphenylpropyl)-4-piperidinyl]-benzamide, monohydrochloride

Compound F (100 mg, 0.25 mmol) was dissolved in ethanol (2 mL) and 1 E HCl in diethyl ether (0.5 mL) was added. The mixture was evaporated to give Example 1 (100 mg, 100%) as a white solid, melting point 246°–249° C.

Analysis for $C_{27}H_{31}ClN_2O \cdot 0.2H_2O$:
Calc'd C, 73.94; H, 7.22; N, 6.39; Cl, 8.08
Found: C, 73.90; H, 7.18; N, 6.40; Cl, 8.11

EXAMPLE 2

2-[1-(3,3-Diphenyl-2-propenyl)-4-piperidinyl]-2,3-dihydro-1H-isoindol-1-one, monohydrochloride

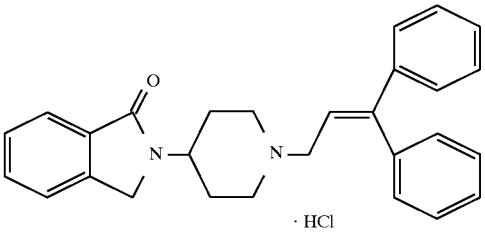

A. 2-(4-piperidinyl)-2,3-dihydro-1H-isoindol-1-one

To a solution of compound B from Example 3 (8.5 g, 26.4 mmol) in ethanol (65 mL) was added acetic acid (3.5 mL, 52.8 mmol), followed by 10% palladium on activated carbon (0.7 g) under argon. The slurry was purged with nitrogen and agitated under a pressure of 45 psi of hydrogen gas for 48 hours. The reaction mixture was filtered through Celite® and washed with ethanol. The filtrate was evaporated to dryness. The resulting residue was dissolved in chloroform (100 mL) and washed with 1N KOH saturated with sodium chloride (2×30 mL) and dried over $MgSO_4$. The resulting clear solution was evaporated to dryness and azeotroped with toluene (2×30 mL) to give compound A (5.0 g, 77%) as a white solid, melting point 137°–140° C.;

B. 3,3-Diphenyl-2-propen-1-ol

To a solution of b-phenylcinnamaldehyde (5.0 g, 24.0 mmol) in toluene (100 mL) was added 1M diisobutylaluminum hydride (26.4 mL, 26.4 mmol) at 0° C. The reaction was stirred at 0° C. for 15 minutes, and methanol (5 mL) was added slowly to quench the reaction. 1M potassium sodium tartrate solution (150 mL) was added and the mixture was stirred at room temperature overnight. The reaction was diluted with ethyl ether (100 mL), and the organic layer was washed with brine (30 mL) and dried over $Na_2SO_4$. Evaporation gave compound B (3.95 g, 80%) as a pale yellow oil.

C. 1-Chloro-3,3-diphenyl-2-propene

To a solution of N-chlorosuccinimide (1.52 g, 11.4 mmol) in dichloromethane (40 mL) was added dimethyl sulfide (1.1 mL, 14.5 mmol) at −40° C. under argon. The reaction was stirred at −40° C. for 10 minutes then warmed to room temperature for 30 minutes. The white cloudy solution was recooled to −40° C., and a solution of compound B (2.17 g, 10.3 mmol) in dichloromethane (3 mL) was added dropwise. The reaction was stirred at −40° C. for 2 hours and then diluted with hexane (100 mL). The organic layer was washed with water (50 mL), brine (50 mL×2) and dried over $Na_2SO_4$. Evaporation gave compound C (1.9 g, 81%) as a colorless oil.

D. 2-[1-(3,3-Diphenyl-2-propenyl)-4-piperidinyl]-2,3-dihydro-1H-isoindol-1-one

To a solution of compound A (1.63 g, 7.56 mmol) and compound C (1.90 g, 8.32 mmol) in dimethylformamide (35 mL), potassium carbonate (1.10 g, 7.94 mmol) was added at room temperature. The reaction was stirred at 50° C. overnight. The reaction was evaporated to dryness. The resulting residue was dissolved in dichloromethane (150 mL) and washed with water (50 mL×2), brine (50 mL×2) and dried over $MgSO_4$. Evaporation gave a crude solid. Purification was performed by flash chromatography, loaded and eluted with 3% methanol in dichloromethane. Pure fractions were combined and evaporated to give compound D (1.95 g, 63%) as a white solid, melting point 164°–167° C.

Analysis for $C_{28}H_{28}N_2O \cdot 0.3\ H_2O$:
Calc'd: C, 81.24; H, 6.96; N, 6.77;
Found: C, 81.29; H, 6.88; N, 6.79.

E. 2-[1-(3,3-Diphenyl-2-propenyl)-4-piperidinyl]-2,3-dihydro-1H-isoindol-1-one, monohydrochloride To a solution of compound D (200 mg, 0.49 mmol) in methanol (2 mL) was added 1 E HCl in ethyl ether (0.5 mL) at room temperature. The resulting salt was filtered and washed with cold methanol (2×0.5 mL). After drying under high vacuum, Example 2 was obtained (160 mg, 80%) as a white solid, melting point 231°–235° C.

Analysis for $C_{28}H_{29}ClN_2O \cdot 0.9\ H_2O$:
Calc'd: C, 72.92; H, 6.73; Cl, 7.69; N, 6.07;
Found: C, 72.99; H, 6.91; Cl, 7.36; N, 6.06.

EXAMPLE 3

2,3-Dihydro-2-[1-(phenylmethyl)-4-piperidinyl]-1H-isoindol-1-one, monohydrochloride

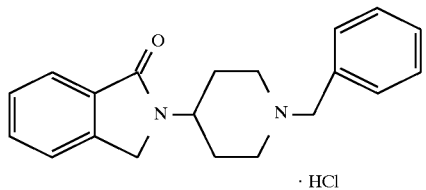

· HCl

A. 2-[1-(Phenylmethyl)-4-piperidinyl]-1H-isoindol-1,3 (2H)-dione

A mixture of phthalic anhydride (15.0 g, 101 mmol) and 4-amino-1-benzylpiperidine (19.3 g, 101 mmol) was heated with stirring in an oil bath until the mixture melted (about 125° C.). The reaction was kept at this temperature until the mixture solidified again (about 30 minutes). The reaction was cooled to room temperature. Purification was performed by flash chromatography on 1 kg silica gel, loaded and eluted with 30% ethyl acetate in hexane. Pure fractions were combined and evaporated to give compound A (25 g, 77%) as a white solid, melting point 151°–154° C.

B. 2,3-Dihydro-2-[1-(phenylmethyl)-4-piperidinyl]-1H-isoindol-1-one

To a solution of compound A (20.0 g, 62.5 mmol) in acetic acid (248 mL) was added zinc dust (28.6 g, 438 mmol) under argon. With mechanical stirring, the reaction was refluxed overnight. The reaction was filtered through Celite, then evaporated to dryness. Dichloromethane (500 mL) was added, and the organic layer was washed with saturated sodium bicarbonate (2×100 mL), brine (100 mL) and dried over $MgSO_4$. Evaporation gave a crude oil. The resulting residue was azeotroped with toluene (2×30 mL) to afford a white solid. The product was recrystallized from isopropanol to give compound B (16 g, 80%) as a white solid (melting point 130°–133° C.).

C. 2,3-Dihydro-2-[1-(phenylmethyl)-4-piperidinyl]-1H-isoindol-1-one, monohydrochloride Compound B (200 mg, 0.62 mmol) was dissolved in ethanol (3 mL) and 4N HCl in dioxane (1 mL) was added. After 2 minutes at room temperature, a white solid precipitated. The solid was filtered and pumped under high vaccum to give Example 3 (120 mg, 60%) as a white solid, melting point 271°–274° C.

Analysis for $C_{20}H_{23}N_2OCl \cdot 0.8\ H_2O$:
Calc'd. C, 67.22; H, 6.94; N, 7.84;
Found: C, 66.99; H, 7.05; N, 8.07.

EXAMPLE 4

2,3-Dihydro-2-[1-(3-phenylpropyl)-4-piperidinyl]-1H-isoindol-1-one, monohydrochloride

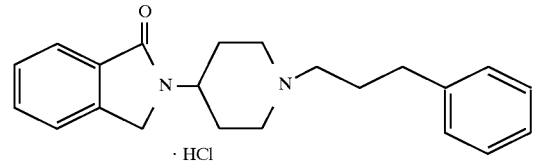

· HCl

A. 2,3-Dihydro-2-[1-(3-phenylpropyl)-4-piperidinyl]-1H-isoindol-1-one

To a solution of compound A from Example 2 (300 mg, 1.39 mmol) in dimethylformamide (8 mL) was added 1-bromo-3-phenylpropane (276 mg, 1.39 mmol, Aldrich) and potassium carbonate (201 mg, 1.46 mmol) at room temperature. The reaction was stirred at room temperature for 30 minutes, then the reaction was heated to 50° C. for 4 hours. The reaction was cooled to room temperature. Dichloromethane (100 mL) was added to dilute the reaction, and the organic layer was washed with water (50 mL×2), brine (50 mL×2) and dried over magnesium sulfate. Evaporation under reduced pressure gave a crude oil. Purification was performed by flash chromatography on silica gel (50 g), loaded and eluted with.0.5% methanol in dichloromethane (1.5 L) then 1.2% methanol in dichloromethane (1.0 L). Pure fractions were combined and evaporated to give compound A (400 mg, 84%) as a colorless oil.

B. 2,3-Dihydro-2-[1-(3-phenylpropyl)-4-piperidinyl]-1H-isoindol-1-one, monohydrochloride Compound A (400 mg, 1.20 mmol) was dissolved in 20% methanol in ethyl ether (2 mL). A solution of 1M HCl in ethyl ether (4 mL, 4.0 mmol) was added. The HCl salt precipitated and was filtered and washed with ethyl ether. The resulting solid was dried under high vacuum at 60° C. overnight to give Example 4 (320 mg, 80%) as a white solid, melting point 229°–231° C.

Analysis for $C_{22}H_{27}ClN_2O$:
Calc'd: C, 71.24; H, 7.34; N, 7.55; Cl, 9.56;

Found: C, 70.96; H, 7.42; N, 7.60; Cl, 9.63.

EXAMPLE 5

2-[1-(5,5-Diphenylpentyl)-4-piperidinyl]-2,3-dihydro-1H-isoindol-1-one, monohydrochloride

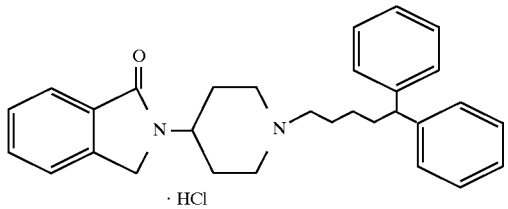

· HCl

A. b-Phenylbenzenepropanal

To a solution of oxalyl chloride (2.0M in dichloromethane, 1.53 mL, 30.7 mmol) in dichloromethane (100 mL) was added dropwise a solution of dimethyl sulfoxide (4.35 mL, 61.4 mmol) in dichloromethane (9 mL) at −70° C. After addition, the reaction was stirred at −70° C. for 30 minutes, then a solution of 3,3-diphenyl-1-propanol (5.0 g, 23.6 mmol) in dichloromethane (10 mL) was added dropwise. The reaction was stirred at −70° C. for 1 hour. Triethylamine (27 mL, 141 mmol) was added and the reaction mixture was warmed to room temperature. Ethyl ether (300 mL) was added to dilute the reaction, the organic layer was washed with water (2×100 mL), 1N HCl (2×100 mL), saturated sodium bicarbonate solution (2×100 mL), brine (2×100 mL) and dried over MgSO$_4$. Evaporation gave compound A (5.0 g, 100%) as a yellowish oil.

B. (E)-5,5-Diphenyl-2-pentenoic acid, ethyl ester

To a suspension of sodium hydride (1.14 g, 28.6 mmol) in tetrahydrofuran (50 mL) was added dropwise a solution of triethyl phosphonoacetate (6.13 mL, 30.9 mmol) in tetrahydrofuran (5 mL) at 0° C. The reaction was stirred at room temperature for 20 minutes (the solution is clear) then recooled to −78° C. A solution of compound A (5.0 g, 23.8 mmol) in tetrahydrofuran (5 mL) was added dropwise. The reaction was warmed to room temperature and quenched with saturated ammonium chloride solution (5 mL). Ethyl ether (200 mL) was added to dilute the reaction, and the organic layer was washed with water (2×50 mL), brine (2×50 mL) and dried over MgSO$_4$. Evaporation gave a crude oil. Purification was performed by flash chromatography on 250 g silica gel, loaded and eluted with 6% ethyl acetate in hexane. Pure fractions were combined and evaporated to give compound B (5.0 g, 75%) as a colorless oil.

C. (E)-5,5-Diphenyl-2-penten-1-ol

To a solution of compound B (4.97 g, 17.8 mmol) in toluene (30 mL) at 0° C. was added dropwise diisobutyl aluminum hydride (1.0N in toluene) (39.1 mL, 39.1 mmol). The reaction was stirred at 0° C. for 1 hour. The reaction was quenched with methanol (5 mL). Potassium sodium tartrate solution (1M, 200 mL) was added, and the reaction mixture was stirred for 3.5 hours. Ethyl ether (200 mL) was added, and the organic layer was washed with water (2×50 mL), brine (2×50 mL) and dried over MgSO$_4$. Evaporation gave a crude oil. Purification was performed by flash chromatography on 300 g silica gel, loaded and eluted with 20% ethyl acetate in hexane. Pure fractions were combined and evaporated to give compound C as a colorless oil (3.6 g, 85%).

D. (E)-1-Chloro-5,5-diphenyl-2-pentene

To a solution of N-chlorosuccinimide (2.22 g, 16.6 mmol) in dichloromethane (50 mL) at −40° C. was added dropwise methyl sulfide (1.55 mL, 21.1 mmol). The reaction was stirred at −40° C. for 10 minutes then warmed to room temperature for 30 minutes. The reaction was recooled to −40° C., and a solution of compound C (3.6 g, 15.1 mmol) in dichloromethane (5 mL) was added dropwise. The reaction was stirred at −40° C. for 2 hours then warmed to room temperature for 30 minutes. Hexane (300 mL) was added to dilute the reaction and the organic layer was washed with water (2×50 mL), brine (2×50 mL) and dried over MgSO$_4$. Evaporation gave compound D (3.4 g, 87%) as a colorless oil.

E. (E)-2-[1-(5,5-Diphenyl-2-pentenyl)-4-piperidinyl]-2,3-dihydro-1H-isoindol-1-one To a solution of compound A from Example 2 (800 mg, 3.70 mmol) in dimethylformamide (20 mL) was added compound D (952 mg, 3.70 mmol) followed by anhydrous potassium carbonate (536 mg, 3.89 mmol). The reaction was stirred at 50° C. for 3 hours. The reaction was cooled to room temperature. Ethyl acetate (100 mL) was added to dilute the reaction, and the organic layer was washed with water (2×50 mL), brine (2×50 mL) and dried over Na$_2$SO$_4$. Evaporation gave a crude oil. Purification was performed by flash chromatography on 100 g of silica gel, loaded and eluted with 2% methanol in dichloromethane. Pure fractions were combined and evaporated to give compound E (1.0 g, 62%) as a white solid (melting point 136°–141° C.).

F. 2-[1-(5,5-Diphenylpentyl)-4-piperidinyl]-2,3-dihydro-1H-isoindol-1-one

To a solution of compound E (500 mg, 1.36 mmol) in ethanol (10 mL) was added 10% palladium on activated carbon (50 mg) under argon at room temperature. A hydrogen balloon was connected to the solution. Hydrogenation was maintained overnight. The reaction was filtered through Celite, and the filtrate was evaporated to dryness. Purification was performed by flash chromatography on 100 g silica gel, loaded and eluted with 2.5% methanol in dichloromethane. Pure fractions were combined and evaporated to give compound F (400 mg, 80%) as a white solid, melting point 121°–124° C.

G. 2-[1-(5,5-Diphenylpentyl)-4-piperidinyl]-2,3-dihydro-1H-isoindol-1-one, monohydrochloride Compound F (400 mg, 0.91 mmol) was dissolved in 20% methanol in ethyl ether (2 mL). A solution of 1M HCl in ethyl ether (4 mL, 4.0 mmol) was added. The HCl salt precipitated and was filtered and washed with ethyl ether. The resulting solid was dried under high vacuum at 60° C. overnight to give Example 5 (320 mg, 80%) as a white solid (melting point 208°–211° C.).

Analysis for C$_{30}$H$_{35}$ClN$_2$O:
Calc'd: C, 75.85; H, 7.43; N, 7.90; Cl, 7.46;
Found: C, 75.54; H, 7.54; N, 7.82; Cl, 7.56.

EXAMPLE 6

N-[1-(3,3-Diphenylpropyl)-4-piperidinyl]cyclohexane-carboxamide, monohydrochloride

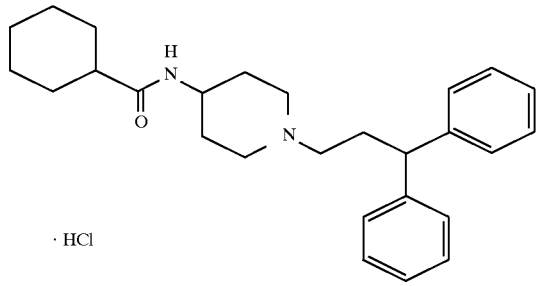

· HCl

A. N-[1-(3,3-Diphenylpropyl)-4-piperidinyl]-cyclohexanecarboxamide

To a stirred solution of 405 mg (1.22 mmol) of compound E from Example 1 and 7 mg (5 mol %) of 4-dimethylaminopyridine in 8 mL of methylene chloride at 0° C. under argon were added 296 mL (3.67 mmol) of pyridine and 171 mL (1.28 mmol) of cyclohexylcarbonyl chloride. After warming to room temperature, the mixture was stirred for one hour and diluted with methylene chloride and water. The organics were separated, and the aqueous layer was basified with 1M KOH and extracted with methylene chloride. The combined organics were dried (sodium sulfate) and concentrated to provide a yellow solid which was dried under high vacuum. The crude product was purified by flash chromatograghy on silica gel (80 g) eluted with 9:1 methylene chloride/methanol. Pure fractions were combined and concentrated to yield 438 mg (88%) of compound A as a clear, glassy solid.

B. N-[1-(3,3-Diphenylpropyl)-4-piperidinyl] cyclohexane-carboxamide, monohydrochloride To a solution of 430 mg (1.06 mmol) of compound A in 4 mL of methylene chloride was added 2.12 mL (2.12 mmol) of a 1.0M solution of hydrogen chloride in diethyl ether. The opaque white solution was concentrated and dried under vacuum to provide 375 mg (76%) of Example 6 as a white solid, melting point greater than 250° C.

Analysis for $C_{27}H_{37}N_2OCl$:
Calcd.: C, 73.53; H, 8.46; N, 6.35; Cl, 8.04;
Found: C, 73.38; H, 8.52; N, 6.16; Cl, 7.97.

EXAMPLE 7

2-[1-(3-Butylheptyl)-4-piperidinyl]-2,3-dihydro-1H-isoindol-1- one, monohydrochloride

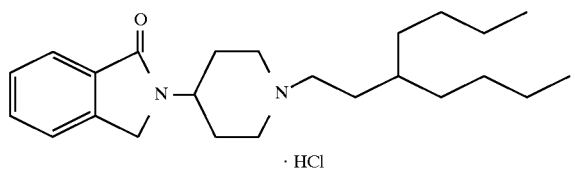

· HCl

A. 3-Butyl-2-heptenoic acid, ethyl ester

To a suspension of sodium hydride (60% in mineral oil) (1.01 g, 25.3 mmol) in tetrahydrofuran (40 mL) was added dropwise a solution of triethyl phosphonoacetate (5.44 mL, 27.4 mmol) in tetrahydrofuran (5 mL) at 0° C. The reaction was warmed to room temperature and stirring was continued until the solution was clear. The reaction was recooled to −78° C., a solution of 5-nonanone (3.0 g, 21.1 mmol) in tetrahydrofuran (5 mL) was added dropwise. The reaction was stirred at −78° C. for 1 hour. The reaction was warmed to room temperature and quenched with saturated ammonium chloride (5 mL). Ethyl ether (200 mL) was added to dilute the reaction, and the organic layer was washed with water (2×50 mL), brine (2×50 mL) and dried over magnesium sulfate. Purification was performed by flash chromatography on 400 g silica gel, loaded and eluted with 15% ethyl acetate in hexane. Pure fractions were combined and evaporated to give compound A (1.63 g, 37%) as a colorless oil.

B. 3-Butyl-2-hepten-1-ol

To a solution of compound A (1.63 g, 7.69 mmol) in toluene (20 mL) at 0° C. was added a solution of diisobutylaluminum hydride (1M solution in toluene, 16.9 mL, 16.9 mmol). The reaction was stirred at room temperature for 10 minutes and quenched with methanol (5 mL). Potassium sodium tartrate solution (1M, 100 mL) was added, the mixture was stirred overnight. Ethyl ether (100 mL) was added, and the organic layer was washed with water (2×50 mL), brine (2×50 mL) and dried over magnesium sulfate. Evaporation gave compound B (1.30 g, 99%) as a colorless oil.

C. 3-Butyl-2-hepten-1-yl chloride

To a suspension of N-chlorosuccinimide (1.12 g, 8.42 mmol) in dichloromethane (20 mL) at −40° C. was added dropwise a solution of methyl sulfide (0.79 mL, 10.7 mmol) in dichloromethane (1 mL). After addition, the reaction was warmed to room temperature for 30 minutes. The reaction was recooled to −40° C., and a solution of 3 (1.3 g, 7.65 mmol) in dichloromethane (2 mL) was added. The reaction was stirred at −40° C. for 2 hours and warmed to room temperature. Hexane (150 mL) was added to dilute the reaction, and the organic layer was washed with water (2×50 mL), brine (2×50 mL) and dried over magnesium sulfate. Evaporation gave compound C (860 mg, 60%) as a cololess oil.

D. 2-[1-(3-Butyl-2-heptenyl)-4-piperidinyl]-2,3-dihydro-1H-isoindol-1-one

To a solution of compound A from Example 2 (974 mg, 4.51 mmol) in dimethylformamide (14 mL) was added a solution of compound C (850 mg, 4.51 mmol) in dimethylformamide (2 mL) followed by anhydrous potassium carbonate (653 mg, 4.74 mmol). The reaction was stirred at 50° C. for 3 hours. The reaction was cooled to room temperature. Ethyl acetate (100 mL) was added to dilute the reaction, and the organic layer was washed with water (2×50 mL), brine (2×50 mL) and dried over magnesium sulfate. Evaporation gave a crude oil. Purification was performed by flash chromatography on 100 g of silica gel, loaded and eluted with 2% methanol in dichloromethane. Pure fractions were combined and evaporated to give compound D (1.13 g, 68%) as a cololess oil.

E. 2-[1-(3-Butylheptyl)-4-piperidinyl]-2,3-dihydro-1H-isoindol-1-one

To a solution of compound D (500 mg, 1.36 mmol) in ethanol (10 mL) was added 10% palladium on activated carbon (50 mg) under argon at room temperature. Argon on the reaction was replaced by hydrogen. A hydrogen balloon was connected to the solution. Hydrogenation was maintained overnight. The reaction was filtered through Celite, and the filtrate was evaporated to dryness. Purification was performed by flash chromatography on 100 g silica gel, loaded and eluted with 2.5% methanol in dichloromethane. Pure fractions were combined and evaporated to give compound F (480 mg, 95%) as a waxy solid.

F. 2-[1-(3-Butylheptyl)-4-piperidinyl]-2,3-dihydro-1H-isoindol-1-one, monohydrochloride Compound E (480 mg, 1.30 mmol) was dissolved in 20% methanol in ethyl ether (2 mL). A solution of 1M HCl in ethyl ether (4 mL, 4.0 mmol) was added. The HCl salt precipitated and was filtered and washed with ethyl ether. The resulting solid was dried under high vacuum at 60° C. overnight to give Example 7 (300 mg, 62%) as a white solid (melting point 185°–187° C.).

Analysis for $C_{24}H_{39}ClN_2O·0.5 H_2O$:
Calc'd: C, 69.29; H, 9.69; N, 6.73; Cl, 8.52;
Found: C, 69.17; H, 9.75; N, 6.88; Cl, 8.91.

EXAMPLE 8

N-[1-(3,3-Diphenylpropyl)-4-piperidinyl]pentamide, monohydrochloride

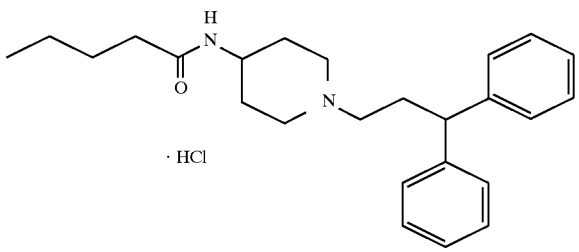

A. N-[1-(3,3-Diphenylpropyl)-4-piperidinyl]-pentamide

To a stirred solution of 385 mg (1.16 mmol) of compound E from Example 1 and 7 mg (5 mol %) of 4-dimethylaminopyridine in 8 mL of methylene chloride at 0° C. under argon were added 282 mL (3.49 mmol) of pyridine and 147 mL (1.22 mmol) of valeryl chloride. After warming to room temperature, the mixture was stirred for one hour and diluted with methylene chloride and water. The organic layers were separated, and the aqueous layer was basified with 1M KOH and extracted with methylene chloride. The combined organic layers were dried (sodium sulfate) and concentrated to provide a yellow solid which was dried under high vacuum. The crude product was purified by flash chromatography on silica gel (75 g) eluted with 95:5 methylene chloride/methanol. Pure fractions were combined and concentrated to yield 334 mg (76%) of compound A as a clear, glassy solid, melting point 126°–128° C.

B. N-[1-(3,3-Diphenylpropyl)-4-piperidinyl]-pentamide, monohydrochloride

To a solution of 319 mg (0.84 mmol) of compound A in 4 mL of methylene chloride was added 1.68 mL (1.68 mmol) of a 1.0M solution of hydrogen chloride in diethyl ether and the heterogeneous mixture was stirred for thirty minutes. The resulting precipitate was filtered, washed with ether, and dried under vacuum to provide 327 mg (72%) of Example 8 as a yellow solid, melting point 189°–191° C.

Analysis for $C_{25}H_{35}N_2OCl+0.3\ H_2O$:
Calc'd: C, 71.41; H, 8.54; N, 6.66; Cl, 8.43;
Found: C, 71.56; H, 8.46; N, 6.51; Cl, 8.66.

EXAMPLE 9

(E)-2,3-Dihydro-2-[1-[3-(2-phenoxyphenyl)-2-propenyl]-4-piperidinyl]-1H-isoindol-1-one, monohydrochloride

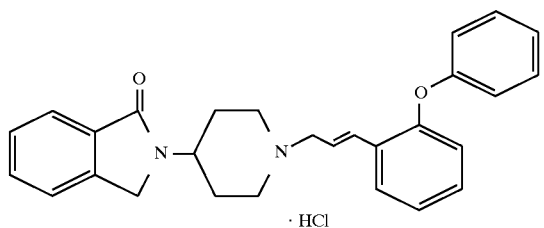

A. 2-Phenoxybenzenemethanol

To a solution of 2-phenoxybenzoic acid (5.0 g, 23.3 mmol) in tetrahydrofuran (50 mL) was added dropwise at 0° C. lithium aluminum hydride solution (1M in tetrahydrofuran, 23.3 mL, 23.3 mmol). The reaction was warmed to room temperature and stirring was continued for 8 hours. The reaction was quenched with methanol (5 mL), and 1M potassium sodium tartrate solution (100 mL) was added. The mixture was stirred at room temperature overnight. Ethyl ether (200 mL) was added, and the organic layer was washed with water (2×50 mL), brine (2×50 mL) and dried over magnesium sulfate. Evaporation gave compound A (4.65 g, 99%) as a colorless oil.

B. 2-Phenoxybenzaldehyde

To a solution of oxalyl chloride (2.0M in dichloromethane, 15.1 mL, 30.3 mmol) in dichloromethane (100 mL) at −70° C. was added dropwise a solution of dimethyl sulfoxide (4.25 mL, 60.6 mmol) in dichloromethane (5 mL). After addition, the reaction was stirred at −70° C. for 30 minutes, then a solution of compound A (4.65 g, 23.3 mmol) in dichloromethane (10 mL) was added dropwise. The reaction was stirred at −70° C. for 1 hour. Triethylamine (27 mL) was added and the reaction mixture was warmed to room temperature. Ethyl ether (300 mL) was added to dilute the reaction, and the organic layer was washed with water (2×100 mL), 1N HCl (2×100 mL), saturated sodium bicarbonate solution (2×100 mL) and brine (2×100 mL) and dried over $MgSO_4$. Evaporation gave compound B as a yellowish oil (4.63 g, 100%).

C. (E)-3-(2-Phenoxyphenyl)-2-propenoic acid, ethyl ester

To suspension of sodium hydride (1.12 g, 28.1 mmol) in tetrahydrofuran (50 mL) was added dropwise a solution of triethyl phosphonoacetate (6.04 mL, 30.4 mmol) in tetrahydrofuran (5 mL) at 0° C. Then the reaction was stirred at room temperature for 20 minutes (the solution was clear). The reaction was recooled to −78° C., and a solution of compound A (4.63 g, 23.4 mmol) in tetrahydrofuran (5 mL) was added dropwise. The reaction was warmed to room temperature and quenched with saturated ammonium chloride solution (5 mL). Ethyl ether (200 mL) was added to dilute the reaction, and the organic layer was washed with water (2×50 mL), brine (2×50 mL) and dried over $MgSO_4$. Evaporation gave a crude oil. Purification was performed by flash chromatography on 500 g silica gel, loaded and eluted with 10% ethyl acetate in hexane. Pure fractions were combined and evaporated to give compound C (6.0 g, 96%) as a colorless oil.

D. (E)-3-(2-Phenoxyphenyl)-2-propenol

To a solution of compound C (2.5 g, 9.33 mmol) in toluene at 0° C. was added dropwise a diisobutyl aluminum hydride (1.0M in toluene) (20.5 mL, 20.5 mmol) solution. The reaction was stirred at 0° C. for 1 hour. The reaction was quenched with methanol (5 mL). 1M potassium sodium tartrate solution (100 mL) was added, and the reaction mixture was stirred for 3.5 hours. Ethyl ether (200 mL) was added, and the organic layer was washed with water (2×50 mL), brine (2×50 mL) and dried over $MgSO_4$. Evaporation gave a crude oil. Purification was performed by flash chromatography on 300 g silica gel, loaded and eluted with 20% ethyl acetate in hexane. Pure fractions were combined and evaporated to give compound D (1.85 g, 88%) as a colorless oil.

E. (E)-1-(3-Chloro-1-propenyl)-2-phenoxybenzene

To a solution of N-chlorosuccinimide (1.11 g, 8.33 mmol) in dichloromethane (20 mL) was added dropwise methyl sulfide (0.78 mL, 10.6 mmol) at −40° C. The reaction was stirred at −40° C. for 10 minutes then warmed to room temperature for 30 minutes. The reaction was recooled to −40° C., and a solution of compound D (1.71 g, 7.57 mmol) in dichloromethane was added dropwise. The reaction was stirred at −40° C. for 3 hours, then warmed to room temperature for 30 minutes. Hexane (100 mL) was added to dilute the reaction, and the organic layer was washed with water (2×50 mL), brine (2×50 mL) and dried over MgSO$_4$. Evaporation gave compound E (1.72 g, 93%) as a colorless oil.

F. (E)-2,3-Dihydro-2-[1-[3-(2-phenoxyphenyl)-2-propenyl]-4-piperidinyl]-1H-isoindol-1-one To a solution of compound A from Example 2 (0.88 g, 4.09 mmol) in dimethylformamide (10 mL) was added a solution of compound E (1.0 g, 4.09 mmol)in dimethylformamide (2 mL) followed by potassium carbonate (592 mg, 4.29 mmol). The reaction was stirred at 50° C. for 14 hours. The reaction was cooled to room temperature. Ethyl ether (100 mL) was added to dilute the reaction, and the organic layer was washed with water (2×50 mL), brine (2×50 mL) and dried over MgSO$_4$. Evaporation gave a crude oil. Purification was performed by flash chromatography on 150 g silica gel, loaded and eluted with 2% methanol in dichloromethane. Pure fractions were combined and evaporated to give compound F (1.1 g, 63%) as a colorless oil.

G. (E)-2,3-Dihydro-2-[1-[3-(2-phenoxyphenyl)-2-propenyl]-4-piperidinyl]-1H-isoindol-1-one, monohydrochloride To a solution of compound F (500 mg, 1.15 mmol) in ethyl ether: methanol (2 mL, 5:1) was added 1M HCl in ethyl ether (1.5 mL, 1.5 mmol). The HCl salt precipitated from the solution. The salt was filtered and dried at 60° C. under vacuum to give Example 9 (300 mg, 55%) as a white solid, melting point 215°–218° C.

Analysis for $C_{28}H_{29}ClN_2O_2$:
Calc'd: C, 72.95; H, 6.34; N, 6.08; Cl, 7.69;
Found: C, 72.49; H, 6.39; N, 6.04; Cl, 7.37.

EXAMPLE 10

2,3-Dihydro-2-[1-[3-(2-methoxyphenyl)-propyl]-4-piperidinyl]-1H-isoindol-1-one, monohydrochloride

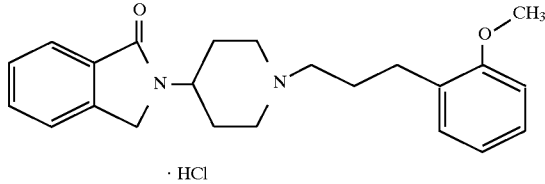

· HCl

A. 2-Methoxybenzenepropanol

To a solution of 3-(2-methoxyphenyl)-propionic acid (2.0 g, 11.1 mmol) in tetrahydrofuran (25 mL) was added dropwise at 0° C. lithium aluminum hydride solution (1M in tetrahydrofuran, 11.1 mL, 11.1 mmol). The reaction was warmed to room temperature and stirring was continued overnight. The reaction was quenched with methanol (5 mL), and 1 potassium sodium tartrate solution (100 mL) was added. The mixture was stirred at room temperature overnight. Ethyl ether (200 mL) was added, and the organic layer was washed with water (2×50 mL), brine (2×50 mL) and dried over magnesium sulfate. Evaporation gave compound A (1.5 g, 81%) as a colorless oil.

B. 1-(3-Bromopropyl)-2-methoxybenzene

To a solution of compound A (620 mg, 3.73 mmol) and triphenyaphosphine (1.08 g, 4.11 mmol) in dichloromethane (10 mL) was added N-bromosuccinimide (731 mg, 4.11 mmol) at 0° C. The reaction was stirred at 0° C. for 2 hours. Dichloromethane (100 mL) was added to dilute the reaction, and the organic layer was washed with water (2×50 mL), brine (2×50 mL) and dried over MgSO$_4$. Purification was performed by flash chromatography on 100 g silica gel, loaded and eluted with 10% dichloromethane in hexane. Pure fractions were combined and evaporation to give compound B (582 mg, 68%) as a colorless oil.

C. 2,3-Dihydro-2-[1-[3-(methoxyphenyl)propyl]-4-piperidinyl]-1H-isoindol-1-one

To a solution of compound A from Example 2 (549 mg, 2.54 mmol) in dimethylformamide (10 mL) was added a solution of compound B (582 mg, 2.54 mmol) in dimethylformamide (1 mL) followed by potassium carbonate (386 mg, 2.80 mmol). The reaction was stirred at 50° C. for 14 hours. The reaction was cooled to room temperature. Ethyl ether (100 mL) was added to dilute the reaction, and the organic layer was washed with water (2×50 mL), brine (2×50 mL) and dried over MgSO$_4$. Evaporation gave a crude oil. Purification was performed by flash chromatography on 150 g silica gel, loaded and eluted with 2% methanol in dichloromethane. Pure fractions were combined and evaporated to give compound C (560 mg, 61%) as a colorless oil.

D. 2,3-Dihydro-2-[1-[3-(2-methoxyphenyl)propyl]-4-piperidinyl]-1H-isoindol-1-one, monohydrochloride To a solution of compound C (500 mg, 1.37 mmol) in methanol (2 mL) was added 1N HCl in ethyl ether (1.5 mL, 1.5 mmol). The mixture was evaporated and dried at 70° C. under vacuum to give Example 10 (300 mg, 60%) as a yellowish solid, melting point 191°–195° C.

Analysis for $C_{23}H_{29}ClN_2O_2$+0.3 mol $H_2O$:
Calc'd: C, 67.98; H, 7.34; N, 6.89; Cl, 8.72;
Found: C, 67.92; H, 7.63; N, 6.75; Cl, 8.54

EXAMPLE 11

6-Fluoro-3,4-dihydro-3-[[4-(2-methoxyphenyl)-1-piperazinyl]-methyl]-1(2H)-naphthalenone

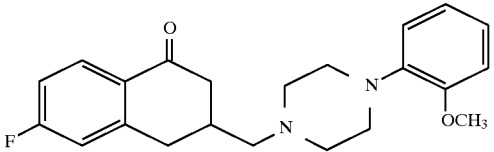

A. a-Acetyl-3-fluorobenzenepropanoic acid, ethyl ester

To a solution of 500 mL of 10% dimethylformamide in benzene was added 58.6% NaH (41 g, 1.0 mol) cooled in an ice bath was added ethyl acetoacetate (130 g, 1.0 mol) was added. The reaction was stirred at room temperature for 30 minutes, and m-fluorobenzyl chloride (145 g, 1.0 mol) was added. The reaction was heated to reflux for 3 hours and gave an NaCl precipitate which was then removed by filtration. The filtrated was poured into $H_2O$, acidified with concentrated HCl and was extracted with a mixture of ether and benzene. The organic layer was washed with $H_2O$, brine, dried over $Na_2SO_4$ and concentrated in vacuo. The crude product was purified by distillation (112°–119° C./25 mmHg) to give compound A (133 g, 56%).

Analysis for $C_{13}H_{15}FO_3$:
Calc'd: C, 65.53; H, 6.35;
Found: C, 65.56; H 6.12.

B. 2-Acetyl-2-[(3-fluorophenyl)methyl]-butanedioic acid, diethyl ester

This reaction procedure was followed as described above for the preparation of compound A. The reaction scale is as follows: Compound A (130 g, 0.546 mol), ethyl chloroacetate (67 g, 0.546 mol), 58.6% NaH (22.36 g, 0.546 mol) and 400 mL of 20% dimethylformamide in benzene. The reflux time in this reaction was 21 hours and the crude product was purified by distillation at 135°–158° C./0.2 mmHg to give compound B (119 g, 67%).

C. 2-[(3-Fluorophenyl)methyl]butanedioic acid, diethyl ester

To a solution of compound B (119.3 g, 0.368 mol) in 550 mL H$_2$O was added NaOH (45 g, 1.10 mol) and the reaction was reflux for 23 hours. The reaction was cooled to room temperature, and the reaction mixture was washed with ether. The aqueous layer was placed in the ice bath, acidified with concentrated HCl and gave a precipitate. The crude product was removed by filtration and recrystallized in hot benzene to give compound C (57.8 g, 69%), melting point 120.5°–121.5° C.

Analysis for C$_{11}$H$_{11}$FO$_4$:
Calc'd: C, 58.41; H, 4.90;
Found: C, 58.91; H, 5.10.

D. 3-[(3-Fluorophenyl)methyl]-3,4-dihydro-2,5-furandione

To a solution of compound C (43.0 g, 0.19 mol) in 100 mL acetic anhydride was added 8 mL acetic acid. The reaction was heated to reflux for 20 minutes and concentrated in vacuo with dry benzene. The crude product was dissolved in 10 mL benzene, 70 mL skelly B was added and upon cooling in an ice bath, a crystalline solid formed. The crystals were collected by filtration and recrystallized in isopropanol/skelly B to give compound D (24.0 g, 61%), melting point 55°–57° C.

Analysis for C$_{11}$H$_9$FO$_3$:
Calc'd: C, 63.46; H, 4.36;
Found: C, 63.92; H, 5.25.

E. 7-Fluoro-1,2,3,4-tetrahydro-4-oxo-2-naphthalene-carboxylic acid

To 500 mL of nitrobenzene was slowly added AlCl$_3$ (30.66 g, 0.23 mol) and compound D (23.85 g, 0.115 mol) keeping the temperature between 20°–25° C. The reaction was stirred at room temperature for 67 hours and was poured into a mixture of 360 g ice and 170 mL concentrated HCl. The nitrobenzene was then removed by distillation. The crude product was crystallized in the ice bath and was recrystallized from benzene/skelly B to give compound E (20.0 g, 84%), melting point 146°–147° C.

Analysis for C$_{11}$H$_9$FO$_3$:
Calc'd: C, 63.46; H, 4.36
Found: C, 63.54; H, 4.48.

F. 7-Fluoro-1,2,3,4-tetrahydro-4-oxo-2-naphthalene-carboxylic acid, methyl ester To a solution of compound E (5.0 g, 0.024 mol) in 25 mL methanol was added 1 mL concentrated H$_2$SO$_4$. The reaction mixture heated to reflux for 40 hours. The reaction mixture was concentrated in vacuo and was partitioned between ethyl acetate and 5% NaHCO$_3$. The organic layer was washed further with H$_2$O, brine, dried over Na$_2$SO$_4$ and was concentrated in vacuo. The crude product was crystallized in a mixture of ethyl acetate and skelly B and was recrystallized in hot skelly B to give compound F (4.9 g, 92%), melting point 90°–92° C.

Analysis for C$_{12}$H$_{11}$FO$_3$:
Calc'd: C, 64.86; H, 4.99;
Found: C, 65.21; H, 5.21.

G. 6-Fluoro-3',4'-dihydrospiro[1,3-dioxolane-2,1'(2'H)-naphthalene]-3'-carboxylic acid, methyl ester To a solution of compound F (103.4 g, 0.465 mol) in 700 mL of dry benzene was added ethylene glycol (78.5 mL, 1.395 mol), followed by a catalytic amount of p-toluenesulfonic acid. The reaction was heated to reflux for 66 hours. The reaction mixture was concentrated in vacuo, and the crude product was crystallized in methanol to give compound G (82 g, 66%), melting point 79°–81° C.

Analysis for C$_{14}$H$_{15}$FO$_4$:
Calc'd: C, 63.15; H, 5.67;
Found: C, 63.13; H, 5.82.

H. 6-Fluoro-3',4'-dihydrospiro[1,3-dioxolane-2,1'(2'H)-naphthalene]-3'-methanol

To a suspension of lithium aluminum hydride (11.25 g, 0.296 mol) in 700 mL of dry tetrahydrofuran was added a solution of compound G (78.8 g, 0.296 mol) in 300 mL tetrahydrofuran. The reaction was heated to reflux for 17 hours and 22.5 mL H$_2$O and 18 mL 10% NaOH was added with cooling. The reaction was stirred at room temperature for 2 hours. The reaction mixture was filtered and the filtrate was concentrated in vacuo to give compound H (69.4 g, 78%).

Analysis for C$_{13}$H$_{15}$FO$_3$
Calc'd: C, 65.53; H, 6.35
Found: C, 65.82; H, 6.72.

I. 6-Fluoro-3',4'-dihydrospiro[1,3-dioxolane-2,1'(2'H)-naphthalene]-3'-methanol, methanesulfonate ester To a solution of compound H (61.1 g, 0.256 mol) in 175 mL dry pyridine under nitrogen was added methanesulfonyl chloride (27.15 mL, 0.358 mol) maintaining the temperature between 10° and 15° C. The reaction was stirred between 5°–10° C. for 30 minutes and room temperature for 2.5 hours. The reaction mixture was poured into ice-water and extracted with CH$_2$Cl$_2$. The organic layer was further washed with H$_2$O, brine, dried over Na$_2$SO$_4$ and was concentrated in vacuo. The crude product was further evaporated with toluene at 35° C. under water pressure to give compound I (83.7 g, quant.).

J. 6-Fluoro-3,4-dihydro-3-[[4-(2-methoxyphenyl)-1-piperazinyl]-methyl]-1(2H)-naphthalenone To a solution of compound I (10.0 g, 0.0316 mmol) in 150 mL of 25% methyl isobutyl ketone in absolute ethanol was added Na$_2$CO$_3$ (2.7 g, 0.0316 mol) and 1-(2-methoxyphenyl)piperazine followed by a catalytic amount of KI. The reaction was heated to reflux for 25 hours and the mixture was filtered. The filtrate was concentrated in vacuo and dissolved in CH$_2$Cl$_2$. The organic layer was washed with H$_2$O, NaHCO$_3$, brine, dried over Na$_2$SO$_4$ and was concentrated in vacuo. 15% HCl (100 mL) was added to the crude and stirred at room temperature for 4 hours. The solution was filtered and was extracted with ethyl ether. The aqueous solution was then basified and extracted with ethyl ether. The final ethyl ether layer was washed with H$_2$O, brine, dried over Na$_2$SO$_4$ and was concentrated in vacuo. The crude product was recrystallized from methanol twice to give Example 11 (6.57 g, 56%), melting point 111°–113° C.

Analysis for C$_{22}$H$_{25}$N$_2$O$_2$F:
Calc'd: C, 71.72; H, 6.84; N, 7.60;
Found: C, 70.11; H, 7.06, N, 7.83.

EXAMPLE 12

3,4-Dihydro-3-[(4-phenyl-1-piperazinyl)-methyl]-1-(2H)-naphthalenone, monohydrochloride

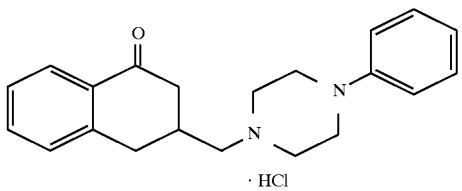

A. 2-Acetyl-2-(phenylmethyl)butanedioic acid, diethyl ester

This reaction procedure followed the procedure described in the preparation of compound B of Example 11. The reaction scale is as follows: Benzyl acetoacetate (180 g, 0.86 mol), ethyl chloroacetate (105 g, .0.86 mol), 58.6% NaH (35.2 g, 0.86 mol) and 300 mL of 10% dimethylformamide in dry benzene. The reflux time in this reaction was 3 hours and the crude product was purified by distillation at 148°–159° C./0.3 mmHg to give compound A (164.7 g, 63%).

B. 2-(Phenylmethyl)butanedioic acid

This reaction procedure followed the procedure described in the preparation of compound C of Example 11. The reaction scale is as follows: compound A (164.7 g, 0.54 mol) and 1.5 L of 2N NaOH. The reaction was reflux for 20 hours and gave compound B (95.8 g, 85%), melting point 152°–156° C.

C. 3,4-Dihydro-3-(phenylmethyl)-2,5-furandione

This reaction procedure was followed as described in the preparation of compound D of Example 11. 95.8 g of compound B gave 72 g (82%) of compound C, boiling point 156° C. (0.4 mm), and the resulting solid was recrystallzed from hot benzene, melting point 94°–96° C.

D. 1,2,3,4-Tetrahydro-4-oxo-2-naphthalenecarboxylic acid

This reaction procedure was followed as described in the preparation of compound E of Example 11. The reaction scale is as follows: compound C (55.7 g, 0.29 mol), $AlCl_3$ (80 g, 0.6 mol) and 280 mL nitrobenzene. The nitrobenzene was removed by distillation and the aqueous was crystallized to give compound D (50.8 g, 91%), melting point 145°–148° C.

E. 1,2,3,4-Tetrahydro-4-oxo-2-naphthalenecarboxylic acid, methyl ester

To a solution of N-nitro-N-methyl urea in 500 mL ether was added 135 mL of 40% KOH, followed by compound D (50.8 g, 0.27 mol), while cooling in an ice bath. The reaction was stirred at room temperature for 1 hour and acetic acid was added to react with excess diazomethane. The ethyl ether layer was washed with 200 mL of 5% NaOH, 200 mL of dilute acetic acid, 200 mL of dilute $NaHCO_3$, brine, dried over $Na_2SO_4$ and was concentrated in vacuo. The crude product was isolated by distillation at 124° C./0.15 mmHg to give compound E (50.3 g, 91%).

F. 3',4'-Dihydrospiro[1,3-dioxolane-2,1'(2'H)-naphthalene]-3'-carboxylic acid, methyl ester This reaction procedure was followed as described in the preparation of compound G of Example 11. The reaction scale is as follows: compound E (5.0 g, 0.025 mol), ethylene glycol (4.8 Ml, 0.075 mol), 40 mL dry benzene and a catatalytic amount p-toluenesulfonic acid. The reaction was reflux for 64 hours and was concentrated in vacuo to give compound F (6.0 g, 95%).

G. 3',4'-Dihydrospiro[1,3-dioxolane-2,1'(2'H)-naphthalene]-3'-methanol

This reaction procedure was followed as described in the preparation of compound H of Example 11. The reaction scale is as follows: compound F (7.3 g, 0.028 mol), lithium aluminum hydride (1.06 g, 0.028 mol) and 50 mL dry tetrahydrofuran. The crude product was isolated by distillation at 152°–153° C./0.15 mmHg to give compound G (4.0 g, 62%).

Analysis for $C_{13}H_{16}O_3$:
Calc'd: C, 70.89; H, 7.32;
Found: C, 70.73; H 7.33.

H. 3',4'-Dihydrospiro[1,3-dioxolane-2,1'(2'H)-naphthalene]-3'-methanol, methanesulfonate ester This reaction procedure was followed as described in the preparation of compound I of Example 11. The reaction scale is as follows: compound G (3.16 g, 0.144 mol), methanesulfonyl chloride (1.6 mL, 0.202 mol) and 30 mL pyridine. The reaction was stirred at room temperature for 2 hours and the crude product was precipitated by pouring onto ice to give compound H (3.35 g, 78%), melting point 75°–79° C.

I. 3,4-Dihydro-3-[(4-phenyl-1-piperazinyl)methyl]-1-(2H)-naphthalenone, monohydrochloride To a solution of compound H (1.43 g, 0.048 mmol) in 50 mL of a mixture of methyl isobutyl ketone and absolute ethanol was added $Na_2CO_3$ (0.71 g, 0.048 mol) and 1-phenylpiperazine (1.77 g, 0.011 mol). The reaction was heated to reflux for 20 hours and the particles was removed by filtration. The filtrate was concentrated in vacuo and dissolved in ethyl acetate. The organic layer was washed with $H_2O$, 5% $NaHCO_3$ and was concentrated in vacuo to dryness. 100 mL of 10% HCl was added to the crude and stirred at room temperature for 4 hours. The mixture was extracted with ethyl ether and the aqueous solution was then basified with concentrated $NH_4OH$ to pH 9 and extracted with ethyl ether. The ethyl ether layer was combined, washed with $H_2O$, brine, dried over $Na_2SO_4$ and concentrated in vacuo. The crude product was redissolved in 200 mL ethyl ether, saturated with HCl, and the solid precipitate was recrystallized from hot ethanol to give Example 12 (0.43 g, 23%), melting point 243°–246° C.

Analysis for $C_{21}H_{24}N_2O \cdot HCl$:
Calc'd: C, 64.09; H, 6.67; N, 7.13; Cl, 9.95;
Found: C, 70.77; H, 7.10; N, 7.69; Cl, 10.69.

EXAMPLE 13

3,4-Dihydro-3-[[4-(2-methoxyphenyl)-1-piperazinyl]-carbonyl]-1(2H)-naphthalenone, monohydrochloride

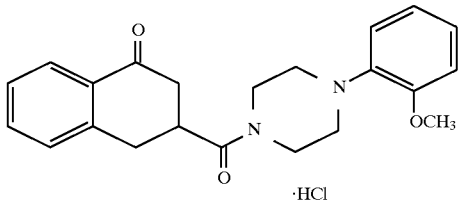

A. 1,2,3,4-Tetrahydro-4-oxo-2-naphthalene-carboxylic acid

To a solution of KOH (6.7 g, 0.12 mol) in 60 mL $H_2O$ was added compound E from Example 12 (10.0 g, 0.049 mol). The reaction was warmed gently for 30 minutes and was then cooled to room temperature and was acidified with 1N HCl. The crude product was filtered, washed with cold $H_2O$ and dried over $P_2O_5$ to give compound A (8.68 g, 93%), melting point 148°–150° C.

B. 3,4-Dihydro-3-[[4-(2-methoxyphenyl)-1-piperazinyl]-carbonyl]-1(2H)-naphthalenone, monohydrochloride To a solution of compound A (9.5 g, 0.05 mmol) and triethylamine (8.38 mL, 0.05 mol) in 125 mL $CH_2Cl_2$ was added isobutyl chloroformate (6.58 mL, 0.05 mol) at −10° C. The reaction was stirred at −5° to −10° C. for 10 minutes and was followed by 1-(2-methoxyphenyl)piperazine (9.61 g, 0.05 mol) in 25 mL $CH_2Cl_2$. The ice bath was removed and the reaction was stirred at room temperature for 17 hours. The reaction mixture was washed with 5% $NaHCO_3$, $H_2O$, brine, dried over $Na_2SO_4$ and concentrated in vacuo. The crude product was dissolved in ethyl ether, bubbled with HCl and was filtered to give Example 13 (15.45 g, 85%), melting point 197°–199° C.

Analysis for $C_{22}H_{24}N_2O_3 \cdot HCl$:
Calc'd: C, 65.89; H, 6.28; N, 6.99; Cl, 8.85;
Found: C, 66.27; H, 6.41; N, 7.35; Cl, 9.58.

EXAMPLE 14

3,4-Dihydro-3-[[4-(2-methoxyphenyl)-1-piperazinyl]-methyl]-1(2H)-naphthalenone, dihydrochloride

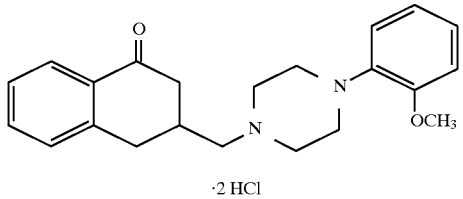

·2 HCl

A. 1,2,3,4-Tetrahydro-3-[[4-(2-methoxyphenyl)-1-piperazinyl]methyl]-1-naphthalenol To a solution of the free base of compound B of Example 13 (11.74 g, 0.0322 mol) in 50 mL of dry tetrahydrofuran was added lithium aluminum hydride (2.45 g, 0.0644 mol) in 50 mL of dry tetrahydrofuran. The reaction was heated to reflux for 22 hours. The reaction was mixed with 5 mL $H_2O$, 4 mL of 10% NaOH and was stirred at room temperature for 2 hours. The solids were removed by filtration, washed with tetrahydrofuran and concentrated in vacuo to give compound A (10.1 g, 89%).

Analysis for $C_{22}H_{28}N_2O_2 \cdot 2$ HCl·$H_2O$:
Calc'd: C, 59.59; H, 7.27; N, 6.32; Cl, 15.99; KF, 4.06;
Found: C, 59.45; H, 7.10; N, 6.50; Cl, 16.49; KF, 4.36.

B. 3,4-Dihydro-3-[[4-(2-methoxyphenyl)-1-piperazinyl]methyl]-1(2H)-naphthalenone, dihydrochloride To a solution of compound A (4.91 g, 0.014 mmol) in 120 mL benzene was added potassium tert-butoxide (3.93 g, 0.035 mol) and benzophenone (11.8 g, 0.065 mol). The reaction was refluxed for 16 hours and washed with $H_2O$. The organic layer was washed further with brine, dried over $Na_2SO_4$ and concentrated in vacuo to dryness. The crude product was dissolved in ethyl ether, bubbled with HCl salt, recrystallized from methanol/ethyl ether to give Example 14 (5.2 g, 87%), melting point 218°–219° C.

Analysis for $C_{22}H_{26}N_2O_2 \cdot 2$ HCl
Calc'd: C, 62.41; H, 6.67; N, 6.62; Cl, 16.75;
Found: C, 62.61; H, 6.87; N, 6.37.

EXAMPLE 15

5-Chloro-2,3-dihydro-2-[1-(phenylmethyl)-4-piperidinyl]-1H-isoindol-1-one, monohydrochloride

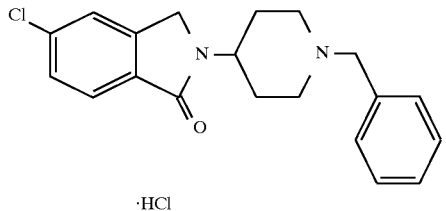

·HCl

A. 5-Chloro-1,3-isobenzofurandione

4-Chlorophthalic acid (446.5 g, 2.23 mol) was heated neat until $H_2O$ was no longer released to give compound A (415.9 g, quantitative), melting point 138°–140° C.

B. 5-Chloro-1H-isoindole-1,3(2H)-dione

A solution of compound A (415.9 g, 2.28 mol) and 1000 mL of 28% ammonium hydroxide was heated at 300° C. until $H_2O$ was no longer released to give compound B (361.0 g, 8%).

C. 5-Chloro-2-[1-(phenylmethyl)-4-piperidinyl]-1H-isoindole-1,3(2H)-dione

To a solution of compound B (10.0 g, 55.2 mmol) in 100 mL amyl alcohol was added 4-amino-1-benzylpiperidine (10.5 g, 55.2 mmol). The reaction was heated to reflux for 16 hours. The reaction mixture was concentrated in vacuo and dissolved in 250 mL $CHCl_3$. The $CHCl_3$ layer was washed with $H_2O$, dried over $Mg_2SO_4$ and was concentrated in vacuo. The crude product was dissolved in 400 mL isopropyl ether, treated with charcoal and filtered. The filtrate was acidified with 4N HCl in dioxane to give compound C (19.0 g, 97%) as a white solid, melting point 233°–234.5° C.

Analysis for $C_{20}H_{19}ClN_2O_2 \cdot HCl$:
Calc'd: C, 61.40; H, 5.16; N, 7.16;
Found: C, 62.04; H, 5.64; N, 7.31.

D. 5-Chloro-2,3-dihydro-2-[1-(phenylmethyl)-4-piperidinyl]-1H-isoindol-1-one, monohydrochloride To a solution of compound C (5.5 g, 14.1 mmol) in 40 mL acetic acid and 8.25 mL concentrated HCl was added tin (4.2 g, 35.3 mmol). The reaction was heated at 95°–100° C. for 16 hours, treated with 5% NaOH to pH greater than 9, and extracted with $CHCl_3$. The organic layer was dried over $Mg_2SO_4$ and was concentrated in vacuo to the dryness. The crude product was dissolved in 200 mL $H_2O$ and treated with HCl in dioxane to give Example 15 (4.64 g, 87%), melting point 269°–271° C.

Analysis for $C_{20}H_{21}ClN_2O+0.8$ HCl+0.2 $H_2O$:
Calc'd: C, 64.29; H, 5.99; N, 7.50; Cl, 17.08; $H_2O$, 0.96;
Found: C, 64.19; H, 6.05; N, 7.54; Cl, 16.96; $H_2O$, 0.95.

EXAMPLE 16

2,3-Dihydro-2-[1-[3-(2-phenoxyphenyl)propyl]-4-piperidinyl]-1H-isoindol-1-one, monohydrochloride

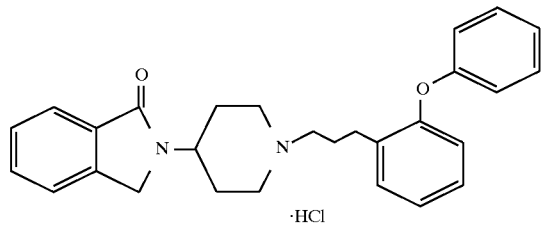

·HCl

A. 2,3-Dihydro-2-[1-[3-(2-phenoxyphenyl)-propyl]-4-piperidinyl]-1H-isoindol-1-one To a solution of compound F from Example 9 (450 mg, 1.06 mmol) in ethanol (10 mL) was added 10% palladium on activated carbon (45 mg) under argon at room temperature. Argon on the reaction was replaced by hydrogen. A hydrogen balloon was connected to the solution. Hydrogenation was maintained overnight. The reaction was filtered through Celite, and the filtrate was evaporated to dryness. Purification was performed by flash chromatography on 100 g silica gel, loaded and eluted with 1.5% methanol in dichloromethane. Pure fractions were combined and evaporated to give compound A (450 mg, 100%) as a colorless oil.

B. 2,3-Dihydro-2-[1-[3-(2-phenoxyphenyl)-propyl]-4-piperidinyl]-1H-isoindol-1-one, monohydrochloride Compound A (450 mg, 1.06 mmol) was dissolved in 20% methanol in ethyl ether (2 mL). A solution of 1M HCl in ethyl ether (2 mL, 2.0 mmol) was added. The HCl salt precipitated and was filtered and washed with ethyl ether. Dichloromethane (80 mL) was added to dissolve the solid, and the organic layer was washed with saturated sodium bicarbonate solution (2×30 mL). Evaporation gave a colorless oil. Purification was performed by flash chromatography, loaded and eluted with 1.5% methanol in dichloromethane. Pure fractions were combined and evaporated to give a colorless oil. The resulting oil was dissolved in 20% methanol in hexane. A solution of 1M HCl in ethyl ether (1 mL, 1.0 mmol) was added. The HCl salt precipitated and was filtered and washed ethyl ether. The resulting solid was dried under high vacuum at 60° C. overnight to give Example 16 (160 mg, 35%) as a white solid, melting point 199°–202° C.

Analysis. for $C_{28}H_{31}ClN_2O_2 \cdot 0.5\ H_2O$:
Calc'd: C, 71.25; H, 6.83; N, 5.93;
Found: C, 71.13; H, 6.78; N, 5.93.

EXAMPLE 17

(z)-2,3-Dihydro-2-[1-(5,5-diphenyl-2-pentenyl)-4-piperidinyl]-1H-isoindol-1-one, monohydrochloride

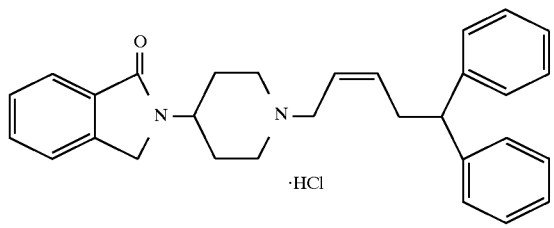

A. (Z)-5,5-Diphenyl-2-pentenoic acid, methyl ester

To a suspension of bis(2,2,2-trifluoroethyl)-(methoxycarbonylmethyl)phosphonate (4.16 g, 13.1 mmol) and 18-crown-6 (3.46 g, 13.1 mmol) in tetrahydrofuran (65 mL) at 0° C. was added dropwise 0.5M potassium bis(trimethylsilyl)amide in toluene (26.2 mL, 13.1 mmol). The reaction was stirred at 0° C. for 15 minutes, then cooled to −78° C. A solution of compound A from Example 5 (5.0 g, 23.8 mmol) in tetrahydrofuran (5 mL) was added dropwise. The reaction was stirred at −78° C. for 1 hour, then warmed to room temperature and quenched with saturated ammonium chloride solution (5 mL). Ethyl ether (200 mL) was added to dilute the reaction, and the organic layer was washed with water (2×50 mL), brine (2×50 mL) and dried over MgSO$_4$. Evaporation gave a crude oil. Purification was performed by flash chromatography on 250 g silica gel, loaded and eluted with 6% ethyl acetate in hexane. Pure fractions were combined and evaporated to give compound A (2.2 g, 70%) as a colorless oil.

B. (Z)-5,5-Diphenyl-2-penten-1-ol

To a solution of compound A (2.2 g, 8.27 mmol) in toluene (20 mL) at 0° C. was added dropwise diisobutylaluminum hydride (1.0M in toluene, 18.2 mL, 18.2 mmol). The reaction was stirred at 0° C. for 1 hour. The reaction was quenched with methanol (5 mL). Potassium sodium tartrate solution (1M, 200 mL) was added, and the reaction mixture was stirred for 3.5 hours. Ethyl ether (200 mL) was added, and the organic layer was washed with water (2×50 mL), brine (2×50 mL) and dried over MgSO$_4$. Evaporation gave a crude oil. Purification was performed by flash chromatography on 300 g silica gel, loaded and eluted with 20% ethyl acetate in hexane. Pure fractions were combined and evaporated to give compound B as a colorless oil (1.9 g, 97%).

C. (Z)-1-Chloro-5,5-diphenyl-2-pentene

To a solution of N-chlorosuccinimide (0.56 g, 4.16 mmol) in dichloromethane (12 mL) at −40° C. was added dropwise methyl sulfide (0.4 mL, 5.29 mmol). The reaction was stirred at −40° C. for 10 minutes then warmed to room temperature for 30 minutes. The reaction was recooled to −40° C., and a solution of compound B (0.9 g, 3.78 mmol) in dichloromethane (5 mL) was added dropwise. The reaction was stirred at −40° C. for 2 hours then warmed to room temperature for 30 minutes. Hexane (300 mL) was added to dilute the reaction and the organic layer was washed with water (2×50 mL), brine (2×50 mL) and dried over MgSO$_4$. Evaporation gave compound C (0.9 g, 93%) as a colorless oil.

D. (Z)-2,3-Dihydro-2-[1-(5,5-diphenyl-2-pentenyl)-4-piperidinyl]-1H-isoindol-1-one To a solution of compound A from Example 2 (756 mg, 3.50 mmol) in dimethylformamide (12 mL) was added compound C (900 mg, 3.50 mmol) followed by anhydrous potassium carbonate (531 mg, 3.85 mmol). The reaction was stirred at 50° C. overnight. The reaction was cooled to room temperature. Ethyl ether (100 mL) was added to dilute the reaction, and the organic layer was washed with water (2×50 mL), brine (2×50 mL) and dried over Na$_2$SO$_4$. Evaporation gave a crude oil. Purification was performed by flash chromatography on 100 g of silica gel, loaded and eluted with 2% methanol in dichloromethane. Pure fractions were combined and evaporated to give compound D (950 mg, 62%) as a white solid, melting point 138°–140° C.

E. (Z)-2,3-Dihydro-2-[1-(5,5-diphenyl-2-pentenyl)-4-piperidinyl]-1H-isoindol-1-one, monohydrochloride To a solution of compound D (500 mg, 1.15 mmol) in methanol (2 mL) was added 1M HCl in ethyl ether (1.5 mL, 1.5 mmol). The mixture was evaporated to dryness. The resulting white solid was dried at 60° C. under vacuum to give Example 17 (300 mg, 80%) as a white solid, melting point 174°–177° C.

Analysis for $C_{30}H_{33}ClN_2O+1.2\ H_2O$:
Calc'd: C, 72.84; H, 7.21; N, 5.66; Cl, 7.17;
Found: C, 72.74; H, 6.88; N, 5.70; Cl, 7.42.

EXAMPLE 18

N-[1-(3,3-Diphenylpropyl)-4-piperidinyl]-2-methoxybenzamide, monohydrochloride

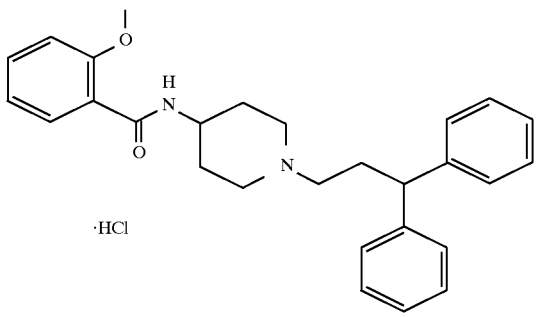

A. N-[1-(3,3-Diphenylpropyl)-4-piperidinyl]-2-methoxybenzamide

To a stirred solution of 503 mg (1.52 mmol) of compound E from Example 1 in 8 mL of methylene chloride at 0° C. were added 370 μL (4.52 mmol) of pyridine and 238 μL (1.59 mmol) of o-anisoyl chloride. After warming to room temperature, the mixture was stirred for 1 h then diluted with methylene chloride and water. The organics were separated and the aqueous layer basified with 1N KOH and extracted with methylene chloride. The combined organics were dried (sodium sulfate) and concentrated to provide a yellow oil which was dried under high vacuum. Flash chromatography on silica gel (180 g) eluted with 2% methanol in ethyl acetate afforded 336 mg (56%) of title compound A as a yellow solid, melting point 96°–98° C.

B. N-[1-(3,3-Diphenylpropyl)-4-piperidinyl]-2-methoxybenzamide, monohydrochloride To a solution of 364 mg (0.85 mmol) of compound A in 4 mL of methylene chloride was added a freshly prepared saturated solution of hydrogen chloride in diethyl ether. The opaque white mixture was concentrated and dried to provide 329 mg (83%) of Example 18 as an off-white solid, melting point 170°–172° C.

Analysis for $C_{28}H_{33}N_2O_2Cl+1.11\ H_2O$:
Calcd. C, 69.34; H, 7.32; N, 5.78;
Found C, 69.41; H, 7.31; N, 5.71.

EXAMPLE 19

N-[1-(3,3-Diphenylpropyl)-4-piperidinyl]-2-methylbenzamide, monohydrochloride

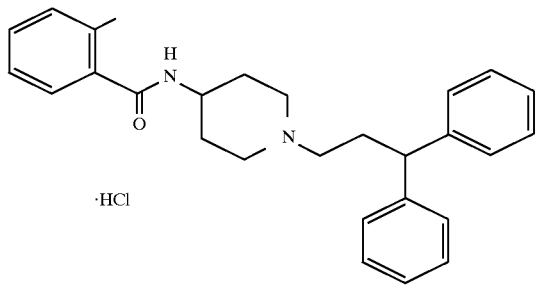

A. N-[1-(3,3-Diphenylpropyl)-4-piperidinyl]-2-methylbenzamide

Compound A was prepared as described for compound A in Example 18, using 485 mg (1.46 mmol) of compound E from Example 18, 336 mL (4.38 mmol) of pyridine, and 200 mL (1.54 mmol) of o-toluoyl chloride. The crude product was purified by flash chromatography on silica gel eluted with 98:2 ethyl acetate/methanol to provide 345 mg (67%) of compound A as a yellow solid.

B. N-[1-(3,3-Diphenylpropyl)-4-piperidinyl]-2-methylbenzamide, monohydrochloride To a solution of 342 mg (0.83 mmol) of compound A in 2 mL of methylene chloride was added a freshly prepared saturated solution of hydrogen chloride in diethyl ether. The opaque white mixture was concentrated, evaporated from methylene chloride to remove residual ether, and dried under vacuum to provide 348 mg (94%) of Example 19 as a white solid, melting point 237°–239° C.

Analysis for $C_{28}H_{33}N_2OCl\cdot1.15\ H_2O$:
Calc'd: C, 71.60; H, 7.57; N, 5.96, Cl, 7.55;
Found: C, 71.59; H, 7.31; N, 5.97, Cl, 7.86.

EXAMPLE 20

N-[1-(3,3-Diphenylpropyl)-4-piperidinyl]-2-pyridine-amide, monohydrochloride

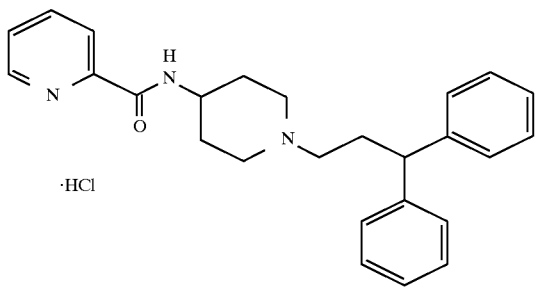

A. N-[1-(3,3-Diphenylpropyl)-4-piperidinyl]-2-pyridine-amide

To a stirred suspension of 199 mg (1.62 mmol) of picolinic acid in 2.5 mL of methylene chloride at 0° C. was added 225 mL (1.62 mmol) of triethylamine. After all the solids had dissolved, the solution was treated with 412 mg (1.62 mmol) of bis(2-oxo-3-oxazolidinyl)phosphinic chloride, and stirred for 30 minutes. A methylene chloride solution of 535 mg (1.62 mmol) of compound E from Example 1 was converted to the free amine by washing with sodium bicarbonate and concentrating the organic layer to a brown oil which was redissolved in 1 mL of dry methylene chloride and added to the reaction mixture. After stirring at room temperature for 16 hours, the reaction was quenched with water and 4M HCl and diluted with methylene chloride. The aqueous layer was basified with 1N KOH and extracted two times. The combined organics were dried (sodium sulfate) and concentrated to provide 554 mg of a brown oil. The crude product was purified by flash chromatography on silica gel eluted with 98:2 ethyl acetate/methanol to provide 316 mg (58%) of compound A as a brown glass.

B. N-[1-(3,3-Diphenylpropyl)-4-piperidinyl]-2-pyridin-amide, monohydrochloride

The hydrochloride salt of compound A was prepared by the procedure used for compound B in Example 18, using 316 mg (0.83 mmol) of compound A, to afford 336 mg (83%) of Example 20 as a yellow solid, melting point 109°–116° C.

Analysis for $C_{26}H_{30}N_3OCl+1.42\ H_2O$
Calc'd: C 67.65, H 7.17, N 9.10;
Found: C 67.53, H 7.10, N 9.22.

EXAMPLE 21

N-[1-(3,3-Diphenylpropyl)-4-piperidinyl]-N-methyl-benzamide, monohydrochloride

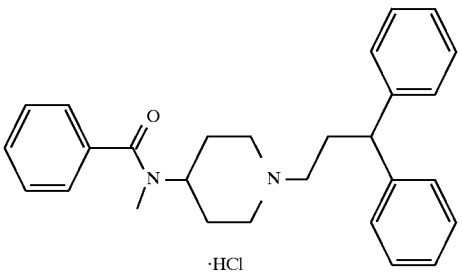

A. N-[1-(3,3-Diphenylpropyl)-4-piperidinyl]-N-methyl-amine

To a solution of 550 mg (1.4 mmol, 1 eq) of compound D from Example 1 in 5 mL of tetrahydrofuran at 0° C. was added 8.4 mL (8.4 mmol, 6 eq) of a 1M solution of lithium aluminum hydride in tetrahydrofuran and the reaction was allowed to warm to room temperature. After 15 hours, the reaction was heated at 60° C. for 4 hours, then quenched by slow addition of a saturated aqueous solution of $Na_2SO_4$. To the resulting heterogeneous mixture was added solid $Na_2SO_4$ and the mixture was stirred for 30 minutes. The solids were removed by filtration and rinsed well with ethyl acetate. Concentration of the organic filtrate afforded 400 mg (93%) of compound A as a viscous pale yellow oil which was used without further purification.

B. N-[1-(3,3-Diphenylpropyl)-4-piperidinyl]-N-methyl-benzamide

Compound B was prepared from 390 mg (1.3 mmol) of compound A, 158 μL (1.4 mmol) of pyridine and 166 μL (1.4 mmol) of benzoyl chloride as described for compound A in Example 18. Flash chromatography on silica gel (75 g) eluted with 1.5% methanol in t-butylmethylether afforded 472 mg (88%) of compound B as a pale yellow oil.

C. N-[1-(3,3-Diphenylpropyl)-4-piperidinyl]-N-methyl-benzamide, monohydrochloride To a solution of 460 mg (1.1 mmol, 1 eq) of compound B in 5 mL of ether and 1 mL of $CH_2Cl_2$ was added an excess of HCl as a saturated solution in ether and the resulting heterogeneous mixture was stirred for 20 min. The solid was isolated by filtration, rinsed well with ether, concentrated and the solvent remnants were removed in a vacuum oven at 52° C. and full vacuum to afford 540 mg (82%) of Example 21 as a white solid; melting point 216°–217° C.

Analysis for $C_{34}H_{37}N_2OCl$:

Calc'd: C 74.90, H 7.41, N 6.24, Cl 7.90

Found: C 74.64, H 7.38, N 6.35, Cl 7.75

Additional compounds falling within the scope of the present invention are described by the following structures. Substituents for each example are identified in the table following each structure.

EXAMPLES 22 to 204

TABLE A

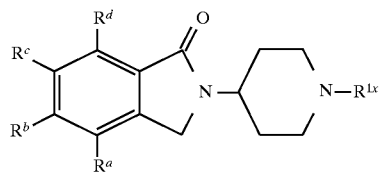

where $R^{lx}$ is

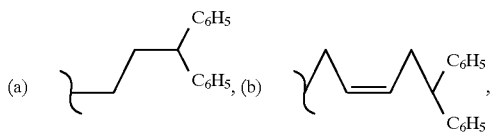

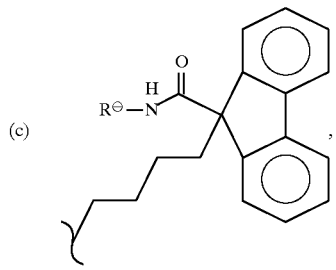

($R^{\ominus}$ = $C_3H_7$ or $CF_3CH_2$)

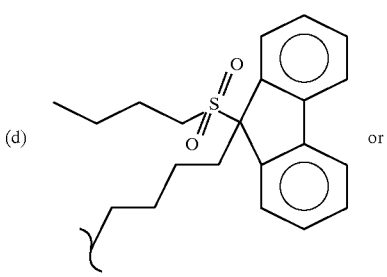

or

TABLE A-continued (e) [Structure: fluorene with -CH2-CH=CH- chain and -C(=O)-NH-R⊖ substituent]

| Rᵃ | Rᵇ | Rᶜ | Rᵈ |
|---|---|---|---|
| H | H | H | F |
| H | H | H | -O-CH2CH2CH3 |
| H | H | F | Cl |
| H | H | CF3 | H |
| H | OCH3 | H | H |
| H | H | H | -CH2-C6H5 |
| -OCH2-C6H5 | H | H | H |
| H | H | -C6H5 | H |
| F | Cl | H | H |
| H | H | H | -S-C6H5 |
| H | H | Cl | H |
| H | H | H | -C6H4-Cl (para) |
| H | H | H | H |
| H | H | H | Cl |
| H | H | CH3 | H |
| H | CH3 | H | -(2-thienyl) |
| SCH3 | H | H | H |
| H | H | OCH3 | H |
| H | H | H | SCH3 |
| H | H | H | H |
| H | H | H | -CH2-C≡CH |
| H | -cyclopropyl | H | H |
| H | H | H | -CH2-cyclopropyl |

EXAMPLE 205

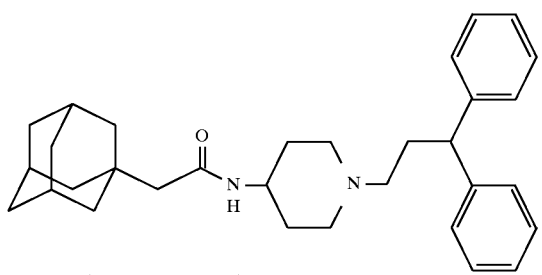

A. 1-(3,3-Diphenylpropyl)-4-piperidinamine hydrochloride

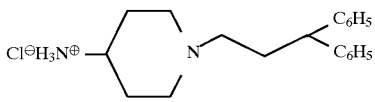

The title compound was prepared as described in Example 1, Part E.

B. 1-(3.3-Diphenylpropyl)-4-piperidinamine

A 2.2 g sample of Part A compound was suspended in $CH_2Cl_2$ (25 mL) and washed with 1N KOH (15 mL). The organic solution was filtered through cotton and concentrated to afford 1.68 g (95%) of Part B amine as a clear oil which was used without further purification or characterization.

C.

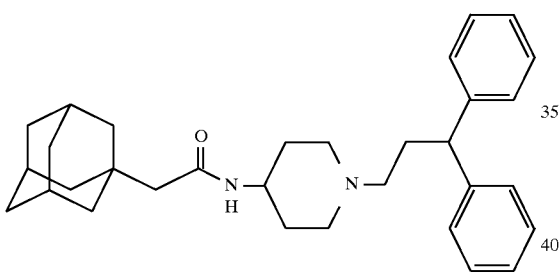

The coupling of carboxylic acid to the Part B amine was carried out using a standard carbodiimide mediated coupling. The process was automated by using a Zymark Benchmate® robotic workstation to carry out the acid-amine coupling and the purification of the resulting amide products. An IBM PC was used to run the Zymark Benchmate® workstation operating program and to write the Benchmate® procedures. The standard protocol for preparation of amides from the Part B free diamine and a carboxylic acid was as follows:

A 16 mm×100 mm tube was charged with 47 mg (0.24 mmol, 4 eq) of adamantane acetic acid and capped loosely with a plastic cap/column holder. The Benchmate® then carried out the following steps on the tube:

1) Added 500 μL (12.5 mg, 0.092 mmol, 1.5 eq) of a 25 mg/mL solution of 1-hydroxybenzotriazole in DMF
2) Added 500 μL (11.5 mg, 0.092 mmol, 1.5 eq) of a 23 mg/mL solution of diisopropylcarbodiimide in $CH_2Cl_2$
3) Added 500 μL (18 mg, 0.061 mmol, 1 eq) of a 36 mg/mL solution of Part B diamine in $CH_2Cl_2$
4) Washed syringe with 3mL of $CH_2Cl_2$
5) Mixed tube contents by vortexing at speed 3 for 15 sec.

After 19 h, the reaction was complete (no starting Part B diamine remained as determined by TLC; 10% MeOH+1% $NH_4OH$ in $CH_2Cl_2$, $I_2$; $R_f$[diamine]=0.13).

The reaction mixture contents were then purified by ion exchange chromatography on a solid phase extraction cartridge mediated by the Benchmate® robotic workstation using the following protocol:

1) Condition a Varian solid phase extraction column (500 mg, SCX cation exchange) with 10 mL of MeOH at 0.25 mL/sec
2) Load reaction contents onto column at 0.05 mL/sec
3) Wash column with 2×10 mL of MeOH at 0.1 mL/sec
4) Wash column with 2 mL of 0.1M ammonia in MeOH at 0.1 mL/sec
5) Elute column with 2 mL of 1M ammonia in MeOH and collect into a tared receiving tube at 0.1 mL/sec.

All solution/solvent deliveries were followed by 1.8 mL of air and a 10 sec push delay was used after loading reaction contents onto the ion exchange column.

The product solution was concentrated on a Savant Speed Vac (approx. 2 mm Hg for 5 h) and final solvent remnants were removed by further exposure to high vac (0.015 mm Hg, 14 h) to afford 22 mg (77% yield) of title compound. Products were characterized by HPLC and MS.

M.S. (electrospray, pos. ions) 471 (M+H).

EXAMPLES 206 to 276

Following the procedure of Example 205, the following compounds of the invention were prepared.

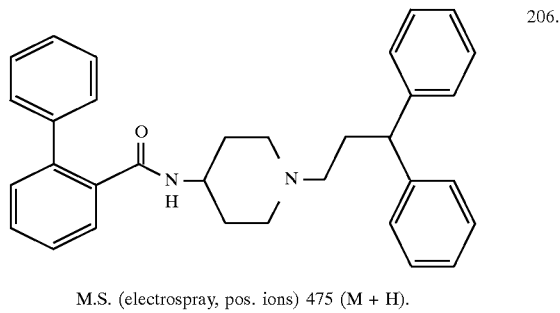

206.

M.S. (electrospray, pos. ions) 475 (M + H).

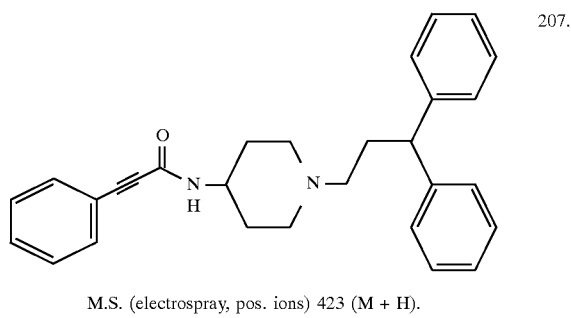

207.

M.S. (electrospray, pos. ions) 423 (M + H).

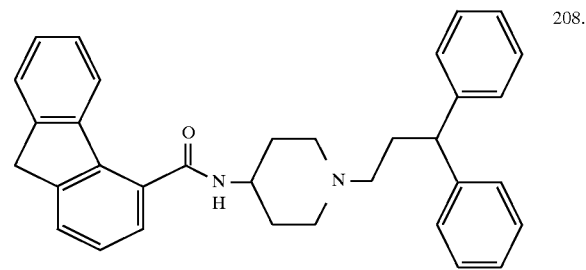

208.

M.S. (electrospray, pos. ions) 487 (M + H).

209.
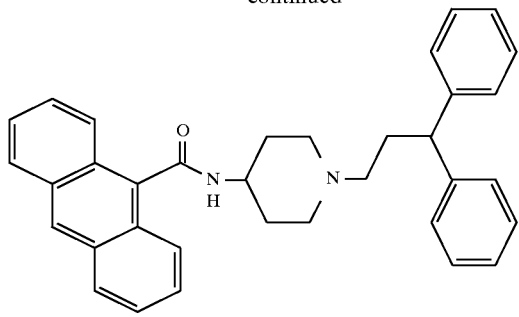
M.S. (electrospray, pos. ions) 499 (M + H).
210.
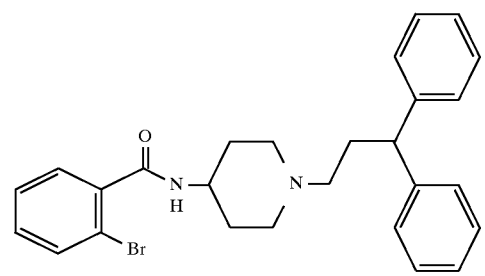
M.S. (electrospray, pos. ions)
477 (M + H + 2).
211.
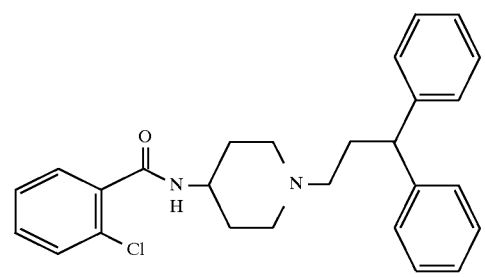
M.S. (electrospray, pos. ions) 433 (M + H).
212.
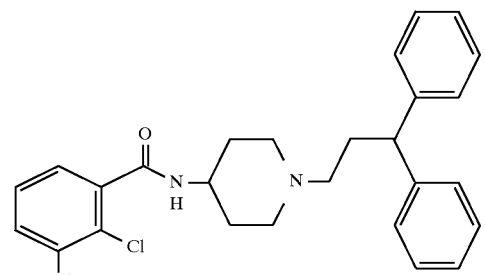
M.S. (electrospray, pos. ions)
467 (M + H + 2).
213.
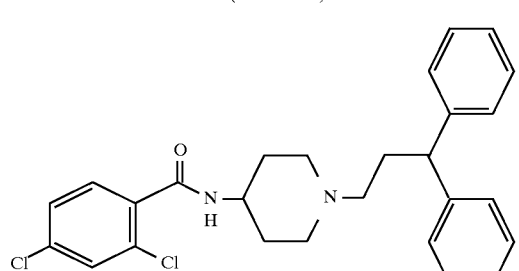
M.S. (electrospray, pos. ions)
467 (M + H + 2).
214.
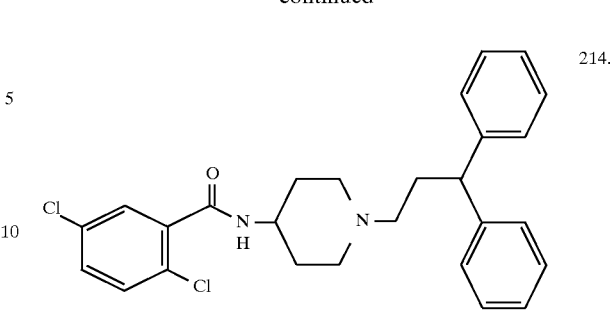
M.S. (electrospray, pos. ions)
467 (M + H + 2).
215.
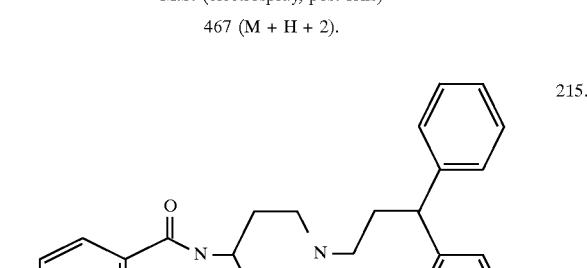
M.S. (electrospray, pos. ions) 467 (M + H).
216.
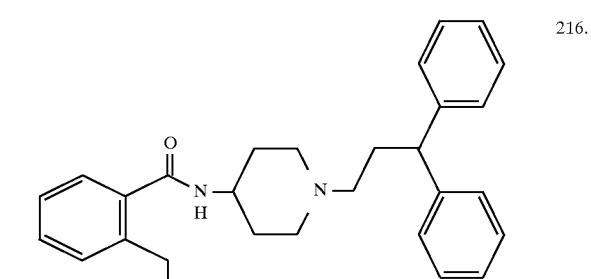
M.S. (electrospray, pos. ions) 489 (M + H).
217.
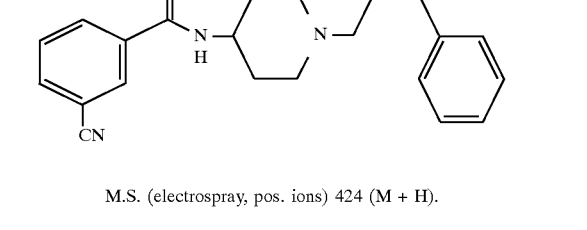
M.S. (electrospray, pos. ions) 424 (M + H).

218.
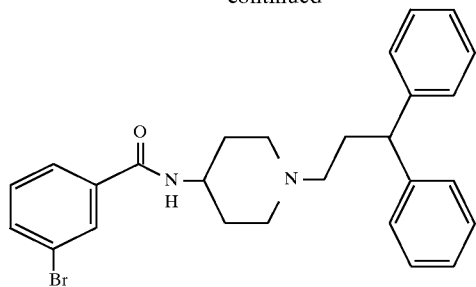
M.S. (electrospray, pos. ions)
477 (M + H + 2).
219.
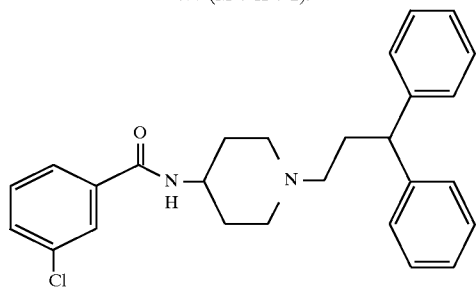
M.S. (electrospray, pos. ions) 433 (M + H).
220.
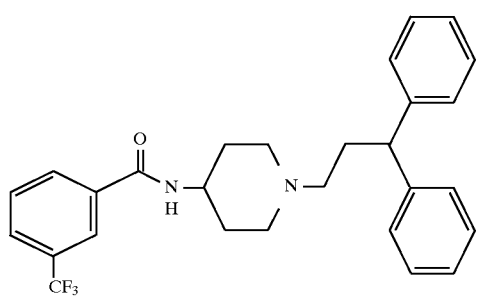
M.S. (electrospray, pos. ions) 467 (M + H).
221.
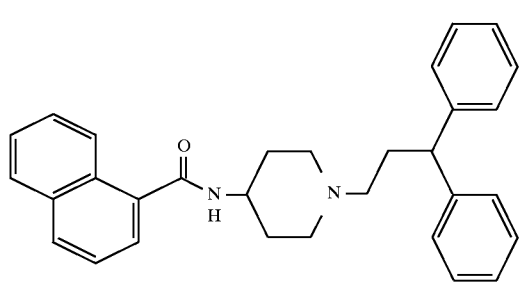
M.S. (electrospray, pos. ions) 449 (M + H).
222.
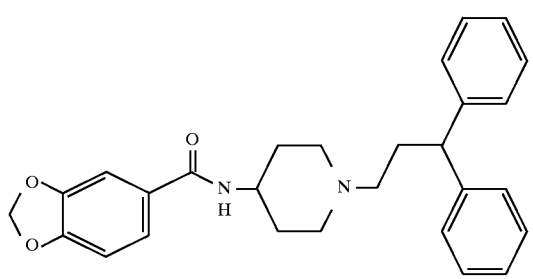
M.S. (electrospray, pos. ions) 443 (M + H).
223.
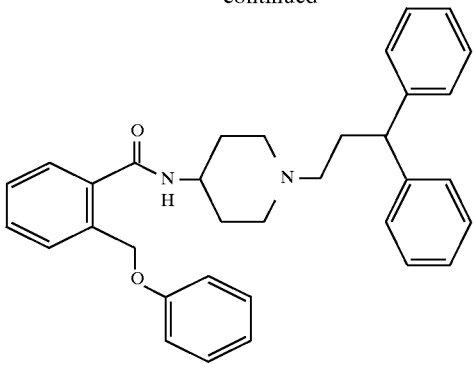
M.S. (electrospray, pos. ions) 505 (M + H).
224.
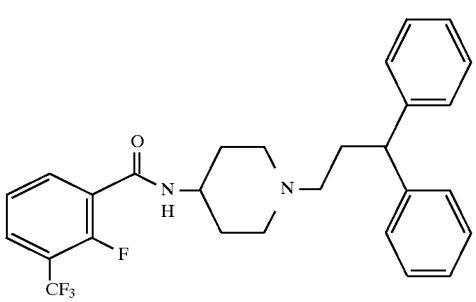
M.S. (electrospray, pos. ions) 485 (M + H).
225.
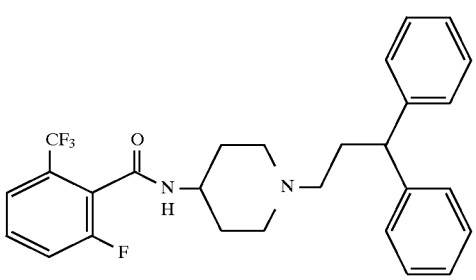
M.S. (electrospray, pos. ions) 485 (M + H).
226.
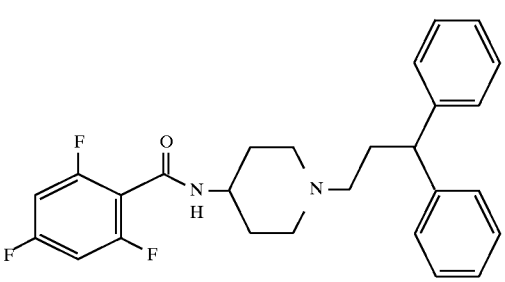
M.S. (electrospray, pos. ions) 453 (M + H).
227.
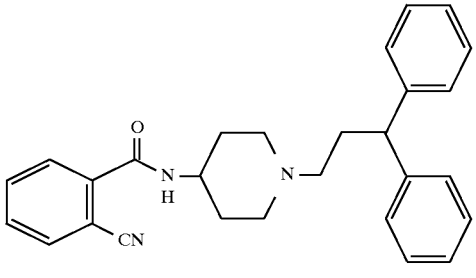
M.S. (electrospray, pos. ions) 424 (M + H).

228.
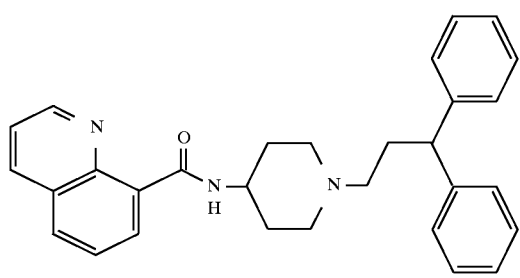
M.S. (electrospray, pos. ions) 450 (M + H).
229.
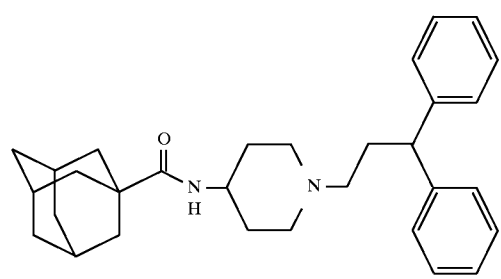
M.S. (electrospray, pos. ions) 457 (M + H).
230.
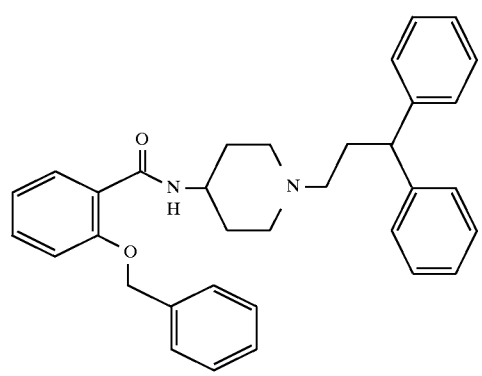
M.S. (electrospray, pos. ions) 505 (M + H).
231.
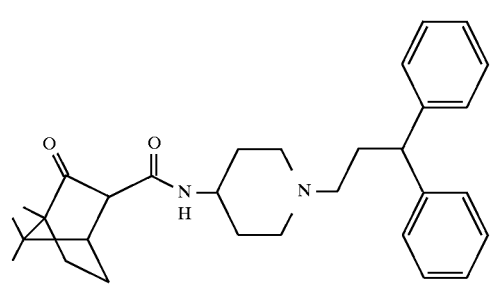
M.S. (electrospray, pos. ions) 473 (M + H).
232.
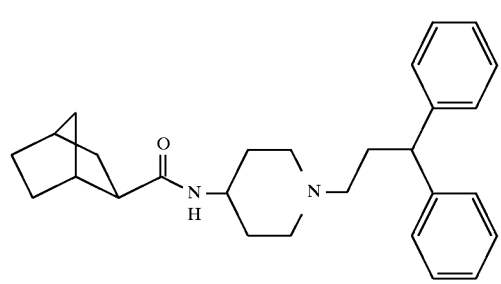
M.S. (electrospray, pos. ions) 417 (M + H).
233.
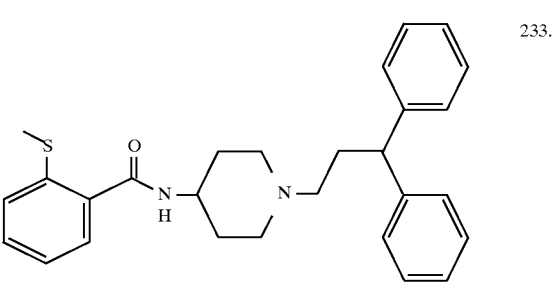
M.S. (electrospray, pos. ions) 445 (M + H).
234.
M.S. (electrospray, pos. ions) 441 (M + H).
235.
M.S. (electrospray, pos. ions) 456 (M + H).
236.
M.S. (electrospray, pos. ions) 455 (M + H).
237.
M.S. (electrospray, pos. ions) 537 (M + H).

238.
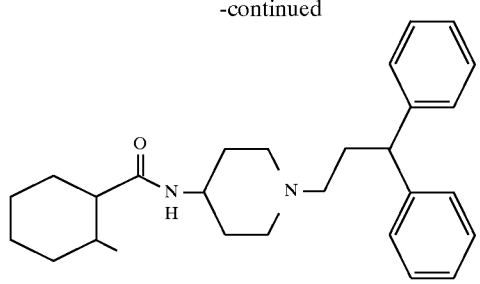
mixture of cis and trans
M.S. (electrospray, pos. ions) 419 (M + H).
239.
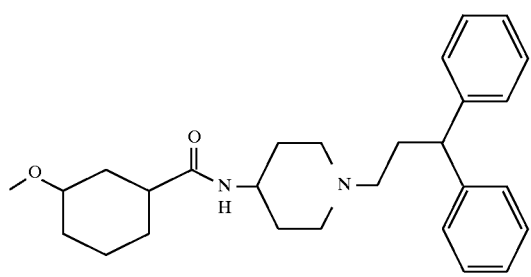
mixture of cis and trans
M.S. (electrospray, pos. ions) 435 (M + H).
240.
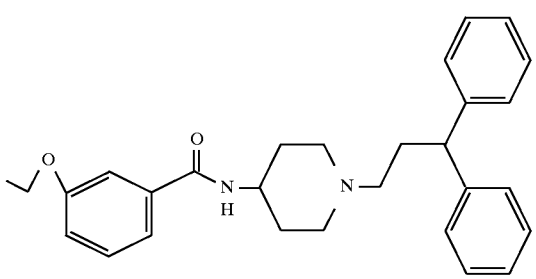
M.S. (electrospray, pos. ions) 443 (M + H).
241.
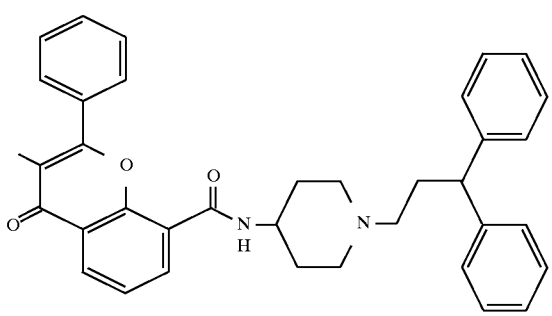
M.S. (electrospray, pos. ions) 557 (M + H).
242.
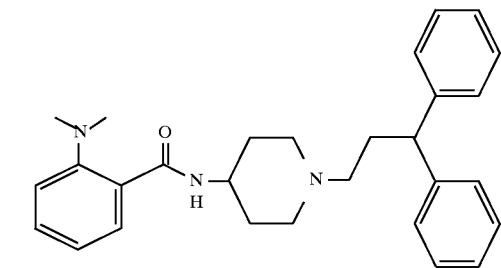
M.S. (electrospray, pos. ions) 442 (M + H).
243.
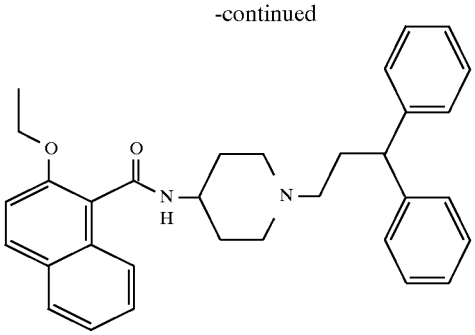
M.S. (electrospray, pos. ions) 493 (M + H).
244.
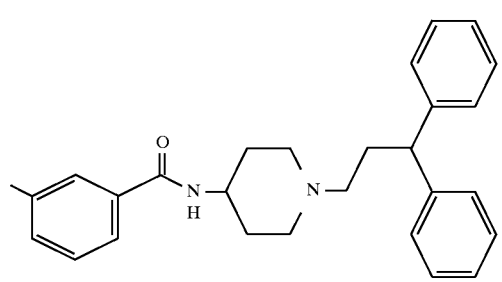
M.S. (electrospray, pos. ions) 427 (M + H).
245.
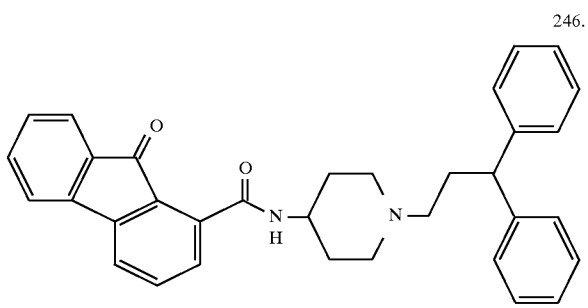
M.S. (electrospray, pos. ions) 413 (M + H).
246.
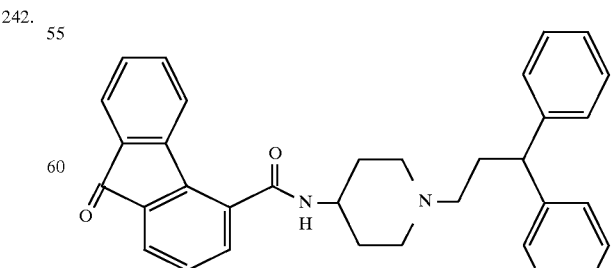
M.S. (electrospray, pos. ions) 501 (M + H).
247.
M.S. (electrospray, pos. ions) 501 (M + H).

248.
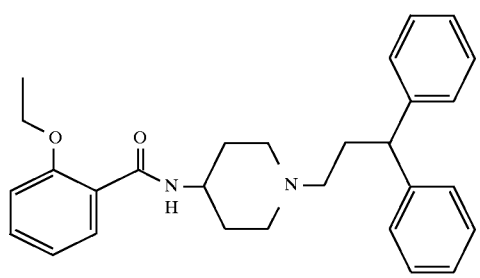
M.S. (electrospray, pos. ions) 443 (M + H).
249.
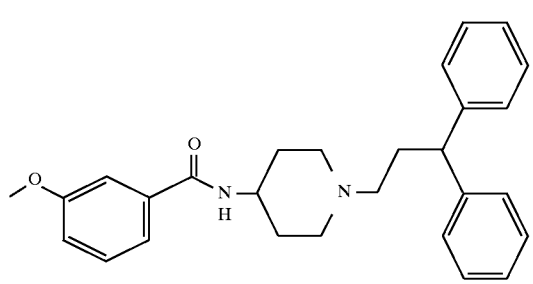
M.S. (electrospray, pos. ions) 429 (M + H).
250.
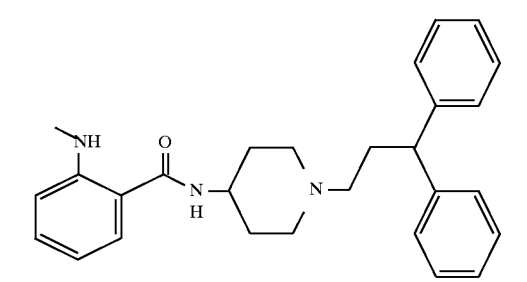
M.S. (electrospray, pos. ions) 428 (M + H).
251.
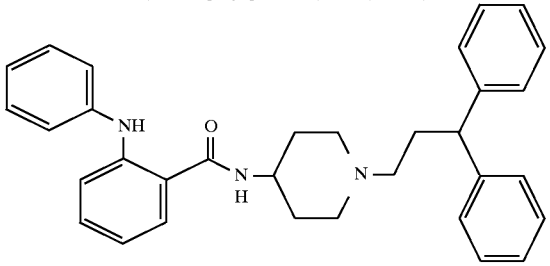
M.S. (electrospray, pos. ions) 490 (M + H).
252.
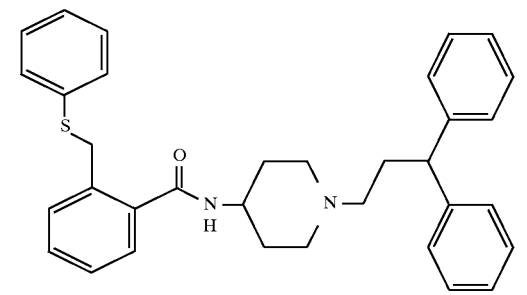
M.S. (electrospray, pos. ions) 521 (M + H).
253.
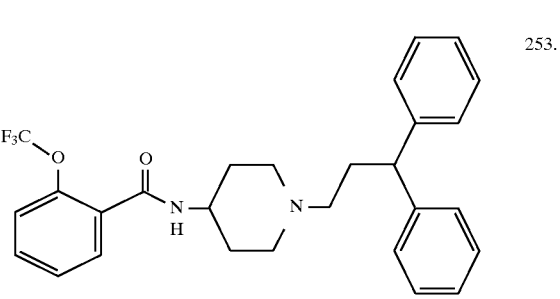
M.S. (electrospray, pos. ions) 483 (M + H).
254.
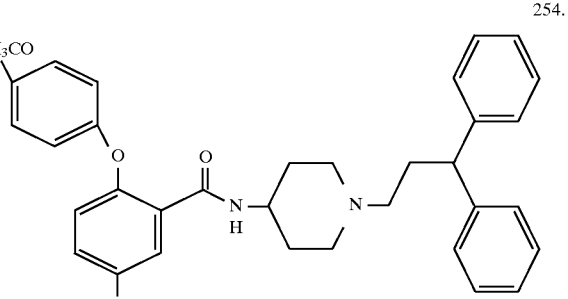
M.S. (electrospray, pos. ions) 566 (M + H).
255.
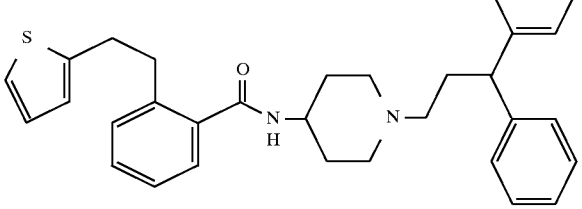
M.S. (electrospray, pos. ions) 509 (M + H).
256.
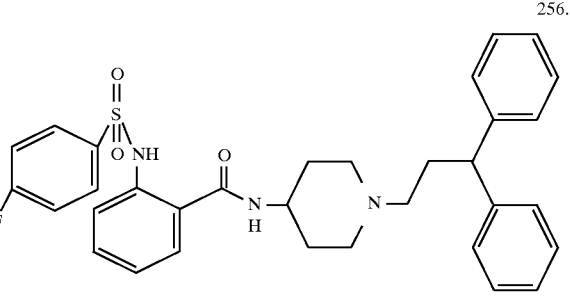
M.S. (electrospray, pos. ions) 572 (M + H).

257.
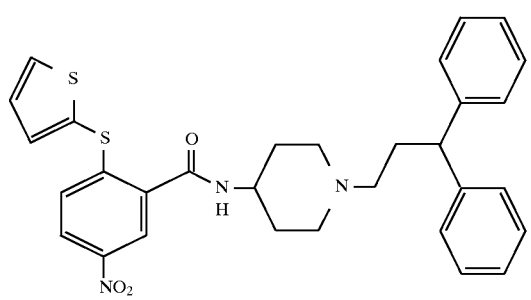
M.S. (electrospray, pos. ions) 558 (M + H).
258.
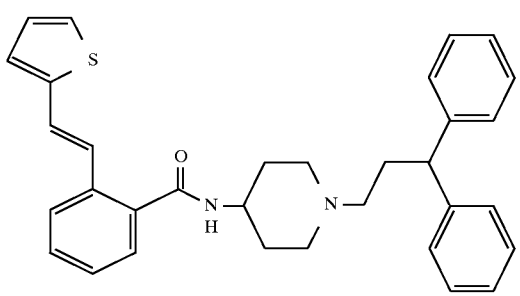
M.S. (electrospray, pos. ions) 507 (M + H).
259.
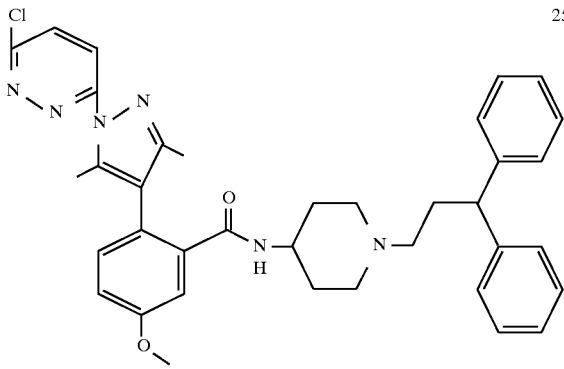
M.S. (electrospray, pos. ions) 635 (M + H).
260.
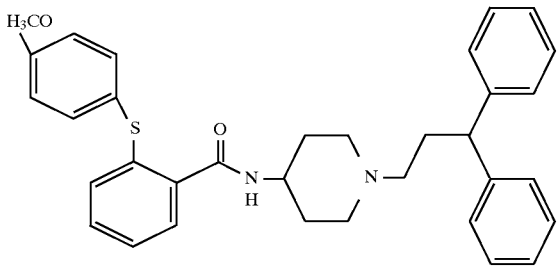
M.S. (electrospray, pos. ions) 537 (M + H).
261.
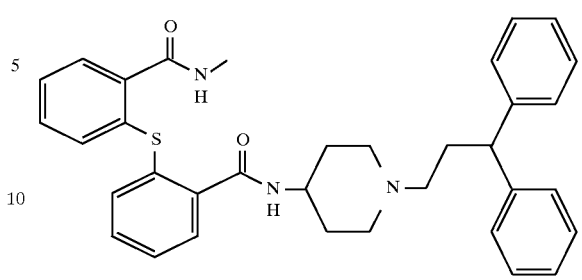
M.S. (electrospray, pos. ions) 564 (M + H).
262.
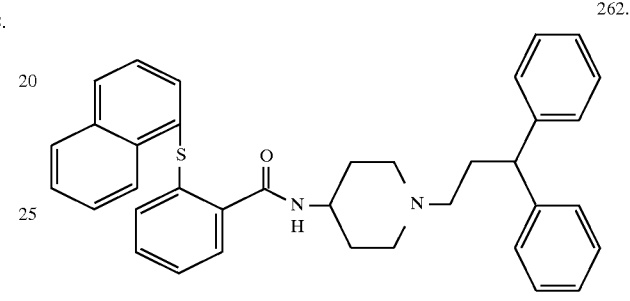
M.S. (electrospray, pos. ions) 557 (M + H).
263.
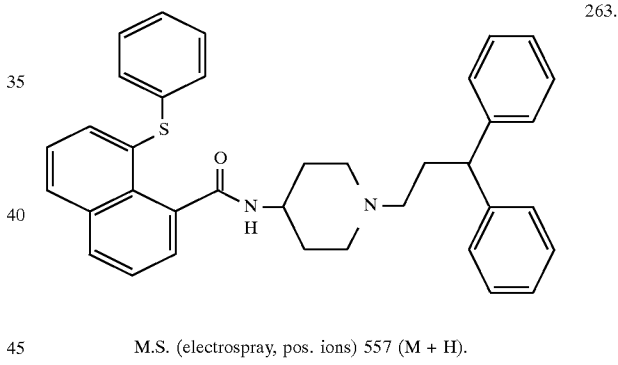
M.S. (electrospray, pos. ions) 557 (M + H).
264.
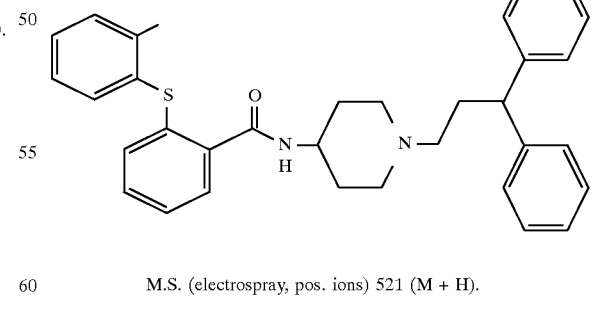
M.S. (electrospray, pos. ions) 521 (M + H).

265.
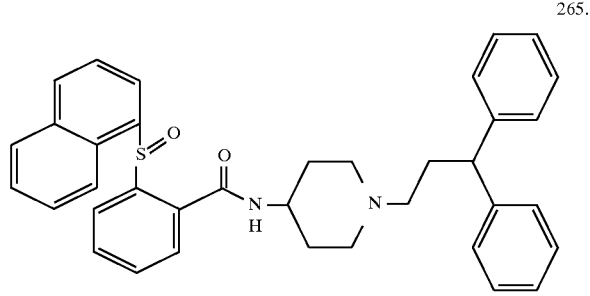
M.S. (electrospray, pos. ions) 573 (M + H).
266.
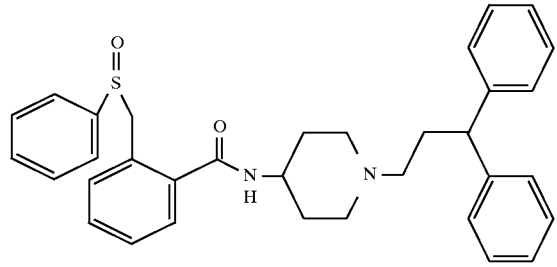
M.S. (electrospray, pos. ions) 537 (M + H).
267.
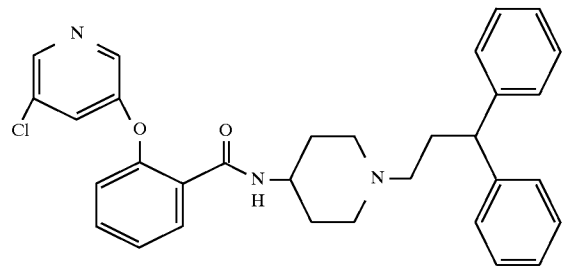
M.S. (electrospray, pos. ions) 571 (M + H).
268.
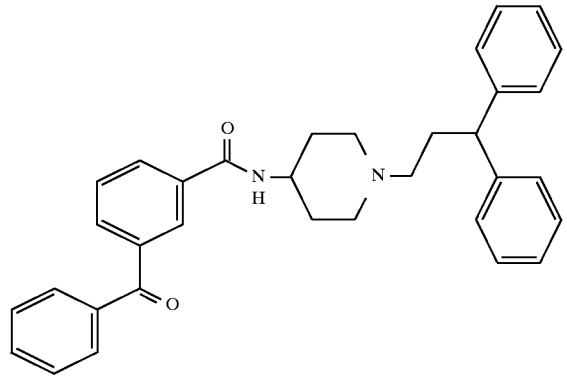
M.S. (electrospray, pos. ions) 503 (M + H).
269.
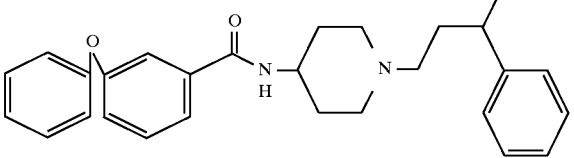
M.S. (electrospray, pos. ions) 491 (M + H).
270.
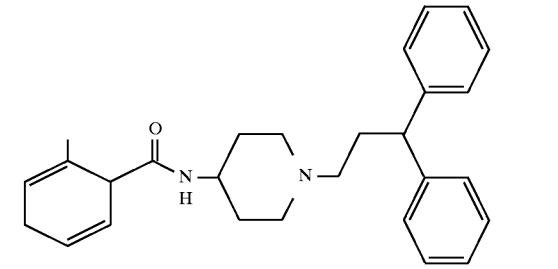
M.S. (electrospray, pos. ions) 415 (M + H).
271.
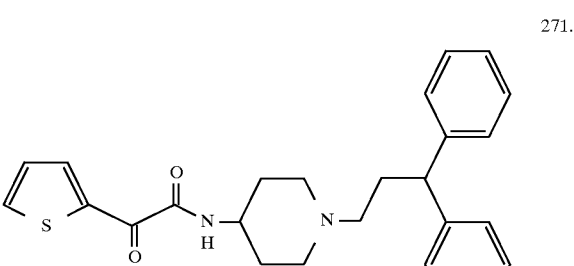
M.S. (electrospray, pos. ions) 433 (M + H).
272.
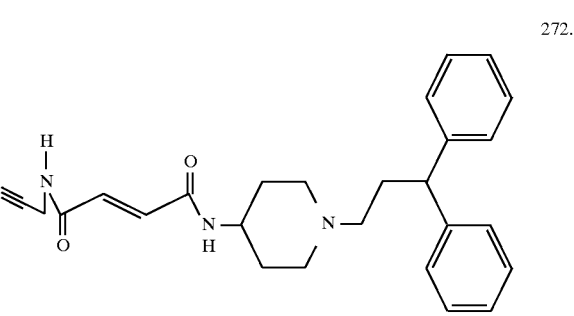
M.S. (electrospray, pos. ions) 430 (M + H).

273.

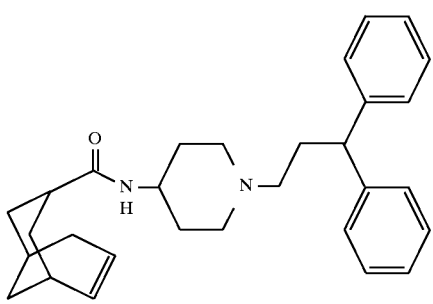

M.S. (electrospray, pos. ions) 443 (M + H).

274.

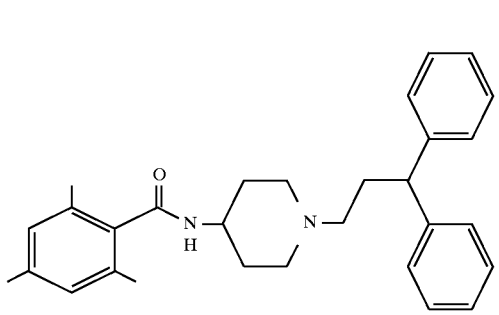

M.S. (electrospray, pos. ions) 441 (M + H).

275.

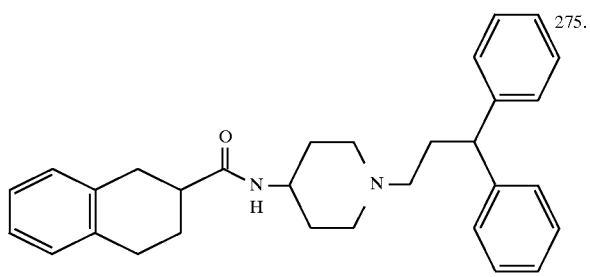

M.S. (electrospray, pos. ions) 453 (M + H).

276.

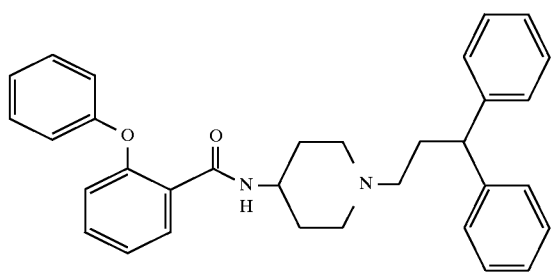

M.S. (electrospray, pos. ions) 491 (M + H).

EXAMPLE 277

(Z)-2,3-Dihydro-2-[1-[3-(2-phenoxyphenyl)-2-propenyl]-4-piperidin-yl]-1H-isoindol-1-one, monohydrochloride

A.

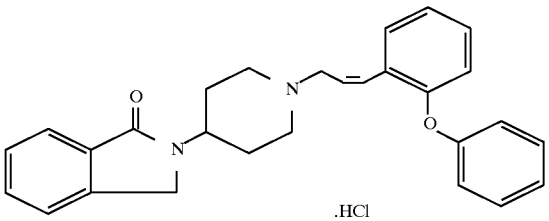

.HCl

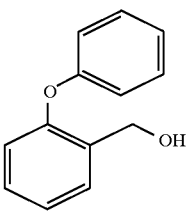

To a solution of 2-phenoxybenzoic acid (Aldrich) (2.5 g, 11.7 mmol) in THF (20 mL) at 0° C. was added dropwise a solution of boranetetrahydrofuran complex in THF (1.0M, 17.5 mL, 17.5 mmol). The reaction was stirred at RT for 3 h. The reaction was quenched with water/THF (1:1, 2 mL) followed by potassium carbonate unitil solution was basic. Ethyl ether (200 mL) was added and the organic layer was washed with water (2×50 mL), saturated sodium bicarbonate solution (2×50 mL), brine (2×50 mL) and dried over MgSO$_4$. Evaporation gave title compound (2.3 g, 95%) as a crude oil.

B.

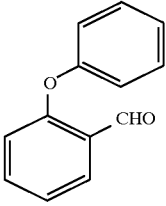

To a solution of oxalyl chloride (2.0M, 4.23 mL, 8.45 mL) in dichloromethane (20 mL) at −74° C. was added dropwise a solution of DMSO (1.2 mL, 16.9 mmol) in dichloromethane (1 mL). The reaction was stirred at −74° C. for 1 h. A solution of Part A compound (1.3 g, 6.50 mmol) in dichloromethane (4 mL) was added dropwise. The reaction was stirred at −74° C. for 1.5 h. Triethylamine (5.4 mL, 39 mmol) was added and the reaction was warmed to RT over 1 h. Ethyl ether (100 mL) was added and the organic layer was washed with 1N HCl solution (2×30 mL), water (2×30 mL), saturated sodium bicarbonate solution (2×30 mL), brine (2×30 mL) and dried over MgSO$_4$. Evaporation gave title compound (1.29 g, 100%) as a crude oil.

C.

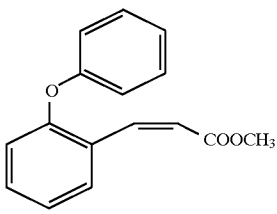

To a solution of bis(2,2,2-trifluoroethyl)-(methoxycarbonylmethyl)phosphonate (3.04 g, 9.56 mmol), 18-crown-6 (2.53 g, 9.56 mmol) in THF (60 mL) at 0° C. was added a solution of potassium bis(trimethylsilyl)amide in toluene (0.5M, 19.1 mL, 9.56 mmol). The reaction was stirred at 0° C. for 30 min then cooled to −78° C. A solution of Part B compound (1.72 g, 8.79 mmol) in THF (2 mL) was added. The reaction was stirred at −78° C. for 1 h. The reaction was quenched with saturated ammonium chloride solution (5 mL). Ethyl ether (200 mL) was added to the reaction, and the organic layer was washed with water (2×50 mL), brine (2×50 mL) and dried over MgSO$_4$. Purification was performed by flash chromatography on silica gel (200 g), loaded and eluted with 5% ethyl acetate in hexane. Pure fractions were combined and evaporated to give title compound (1.38 g, 58%) as a colorless oil.

D.

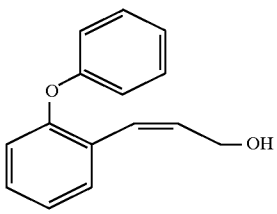

To a solution of Part C compound (1.38 g, 5.15 mmol) in THF (20 mL) at 0° C. was added dropwise a solution of diisobutylaluminum hydride in hexane (1.0M, 11.3 mL, 11.3 mmol). The ice bath was removed and the reaction was stirred at RT for 15 min. The reaction was quenched by methanol (2 mL) followed by potassium sodium tartrate solution (1M, 100 mL). The mixture was stirred at RT overnight. Ethyl ether (200 mL) was added and the organic layer was washed with water (2×50 mL), brine (2×50 mL) and dried over MgSO$_4$. Purification was performed by flash chromatography on silica gel (150 g), loaded and eluted with 20% ethyl acetate in hexane. Pure fractions were combined and evaporated to give title compound (1.24 g, 100%) as a colorless oil.

E.

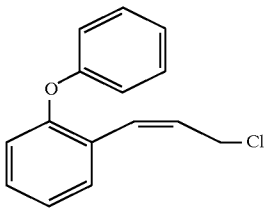

To a solution of N-chlorosuccinimide (802 mg, 6.01 mmol) in dichloromethane (15 mL) at −40° C. was added dropwise methyl sulfide (0.56 mL, 7.64 mmol). The reaction was stirred at −40° C. for 10 min then warmed to RT for 30 min. The reaction was recooled to −40° C., and a solution of Part D compound(1.24 g, 5.46 mmol) in dichloromethane (2 mL) was added dropwise. The reaction was stirred at −40° C. for 2 h then warmed to RT for 30 min. Hexane (300 mL) was added to dilute the reaction and the organic layer was washed with water (2×50 mL), brine (2×50 mL) and dried over MgSO$_4$. Evaporation gave title compound (1.12 g, 84%) as a colorless oil.

F. (Z)-2,3-Dihydro-2-[1-[3-(2-phenoxyphenyl)-2-propenyl]-4-piperidinyl]-1H-isoindol-1-one, monohydrochloride To a solution of Part E compound (600 mg, 2.45 mmol) in DMF (20 mL) was added Example 2 Part A compound (2-(4-piperidinyl)-2,3-dihydro-1H-isoindol-1-one) (530 mg, 2.45 mmol) followed by anhydrous potassium carbonate (372 mg, 2.69 mmol). The reaction was stirred at 55° C. overnight. The reaction was cooled to RT. Ethyl ether (200 mL) was added to dilute the reaction, and the organic layer was washed with water (2×50 mL), brine (2×50 mL) and dried over MgSO$_4$. Evaporation gave a crude oil. Purification was performed by flash chromatography on 100 g of silica gel, loaded and eluted with 2% methanol in dichloromethane. Pure fractions were combined and evaporated to give a colorless oil. The resulting oil was dissolved in methanol (2 mL) and HCl in ethyl ether solution (1.0M, 3.0 mL, 3.0 mmol) was added. The HCl salt precipitated from the solution. The salt was filtered and dried at 60° C. under vacuum to give title compound (490 mg, 80%) as a white solid.

m.p. 196°–198° C.

Anal. Calc. for $C_{28}H_{28}N_2O_2 \cdot HCl$: C, 72.95; H, 6.34; N, 6.08; Cl, 7.69

Found: C, 72.48; H, 6.42; N, 5.98; Cl, 7.70.

EXAMPLE 278

2,3-Dihydro-2-[1-[4-(hydroxyphenylmethyl)phenyl]-4-piperidinyl]-1H-isoindol-1one

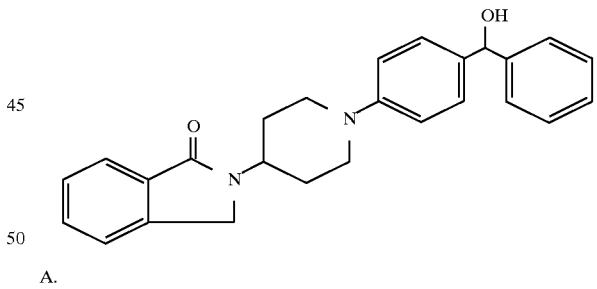

A.

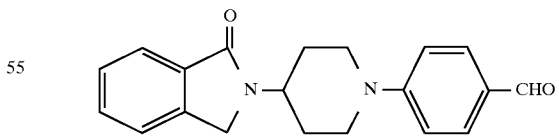

Potassium carbonate (10.6 g, 76.5 mmol) was added to a solution of Example 2 Part A compound (15.0 g, 69.6 mmol) and 4-fluorobenzaldehyde (Aldrich) (8.61 g, 69.6 mmol) in N,N-dimethylacetamide (100 mL) and the reaction was stirred at 125° C. for 24 h, then cooled to RT. The reaction was dissolved in CH$_2$Cl$_2$ (500 mL) and washed with water (4×180 mL) and brine (2×200 mL), then dried over MgSO$_4$. Evaporation gave a solid mass. The crude product was triturated with EtOAc (10 mL), then washed with EtOAc (10 mL) and filtered to give title compound (17.8 g, 80%) as a white solid (mp 211°–214° C.).

B. 2,3-Dihydro-2-[1-[4-(hydroxyphenylmethyl)phenyl]-4-piperidinyl]-1H-isoindol-1-one To a solution of Part A compound (2.30 g, 7.19 mmol) in THF (30 mL) at 0° C. was added dropwise phenyl magnesium bromide solution (1.0M, 7.91 mL, 7.91 mmol). The reaction was stirred at RT for 4 h over which time the reaction became clear. Saturated ammonium chloride solution (5 mL) was added to quench the reaction. Ethyl ether (200 mL) was added and the organic layer was washed with water (2×50 mL), brine (2×50 mL) and dried over $MgSO_4$. Purification was performed by flash chromatography on silica gel (200 g), loaded and eluted with 10% acetone in dichloromethane. Pure fractions were combined and evaporated to give title compound (1.5 g, 52%) as a white solid. m.p. 164°–166° C.

Anal. Calc. for $C_{26}H_{26}N_2O_2 \cdot 0.2H_2O$: C, 77.66; H, 6.62; N, 6.97

Found: C, 77.77; H, 6.44; N, 6.94

EXAMPLE 279

2,3-Dihydro-2-[1-[4-(phenylmethyl)phenyl]-4-piperidinyl]-1H-isoindol-1-one

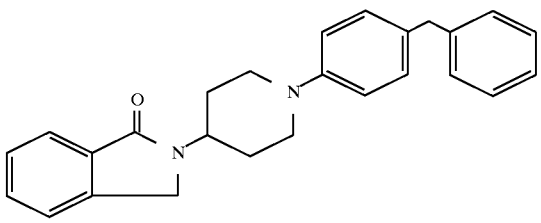

To a solution of Example 278 compound (300 mg, 0.75 mmol) and triethylsilane (0.24 mL, 1.50 mmol) in dichloromethane (5 mL) at 0° C. was added dropwise a solution of boron trifluoride etherate (0.18 mL, 1.50 mmol). The reaction was stirred at RT overnight. Saturated ammonium chloride solution (2 mL) was added to quench the reaction. Ethyl ether (100 mL) was added and the organic layer was washed with water (2×30 mL), brine (2×30 mL) and dried over $MgSO_4$. Purification was performed by flash chromatography on silica gel (50 g), loaded and eluted with 30% acetone in hexane. Pure fractions were combined and evaporated to give title compound (96 mg, 34%) as a white solid.

m.p. 151°–155° C.

Anal. Calc. for $C_{26}H_{26}N_2O \cdot 0.5H_2O$: C, 79.76; H, 6.95; N, 7.16

Found: C, 79.88; H, 6.78; N, 7.12.

EXAMPLE 280

2-[1-(4-Benzoylphenyl)-4-piperidinyl]-2,3-dihydro-1H-isoindol-1-one

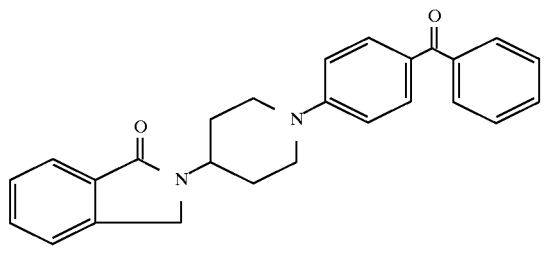

To a solution of 4-fluorobenzophenone (Aldrich) (3.0 g, 15.0 mmol) and Example 2, Part A compound (3.24 g, 15.0 mmol) in N,N-dimethylacetamide (30 mL) was added potassium carbonate (2.28 g, 16.5 mmol). The reaction was refluxed 15 h then cooled to RT. Ethyl ether (300 mL) was added and the solution was washed with water (2×70 mL), brine (2×70 mL) and dried over $MgSO_4$. Evaporation gave a crude solid. Purification was performed by flash chromatography on silica gel (300 g), loaded and eluted with 4% acetone in dichloromethane. Pure fractions were combined and evaporated to give title compound (3.5 g, 59%) as a yellowish solid.

m.p. 173°–175° C.

Anal. Calc. for $C_{26}H_{24}N_2O_2$: C, 78.76; H, 6.10; N, 7.07

Found: C, 78.34; H, 6.12; N, 7.00.

EXAMPLE 281

2-[1-(4-Diphenylmethyl)phenyl]-4-piperidinyl]-2,3-dihydro-1H-isoindol-1-one

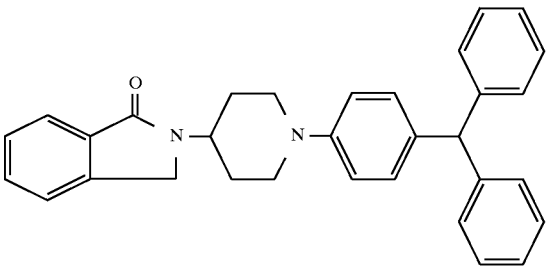

A.

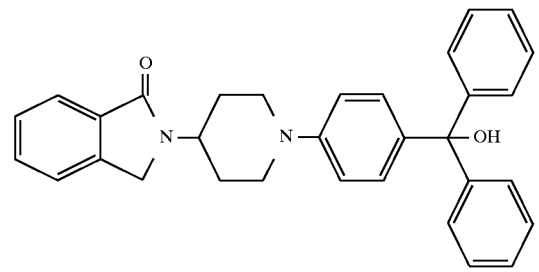

To a solution of Example 280 compound (2.0 g, 5.05 mmol) in THF (40 mL) at 0° C. was added dropwise a solution of phenylmagnesium bromide (1.0M, 5.55 mL, 5.55 mmol) in THF. The reaction was stirred at RT for 2 days. Saturated ammonium chloride solution (2 mL) was added to quench the reaction. Ethyl ether (200 mL) was added and the organic layer was washed with water (2×50 mL), brine (2×50 mL) and dried over MgSO$_4$. Purification was performed by flash chromatography on silica gel (200 g), loaded and eluted with 2% methanol in dichloromethane. Pure fractions were combined and evaporated to give title compound (400 mg, 17%) as a white solid (m.p. 163°–166° C.).

B. 2-[1-(4-Diphenylmethyl)phenyl]-4-piperidinyl]-2.3-dihydro-1H-isoindol-1-one

To a solution of Part A compound (150 mg, 0.32 mmol) in TFA (1 mL) at 0° C. was added triethylsilane (0.06 mL, 0.35 mmol). The reaction was stirred at RT for 30 min. Saturated sodium bicarbonate solution (20 mL) was added to quench the reaction. Ethyl ether (50 mL) was added and the organic layer was washed with water (2×20 mL), brine (2×20 mL) and dried over MgSO$_4$. Purification was performed by flash chromatography on silica gel (50 g), loaded and eluted with 10% acetone in dichloromethane. Pure fractions were combined and evaporated to give title compound (120 mg, 77%) as a white solid.

m.p. 162°–165° C.

Anal. Calc. for $C_{32}H_{30}N_2O$: C, 83.81; H, 6.59; N, 6.11
Found: C, 83.65; H, 6.69; N, 5.97.

EXAMPLE 282

(Z)-N-[1-(5,5-Diphenyl-2-pentenyl)-4-piperidinyl]-2-phenoxybenz-amide

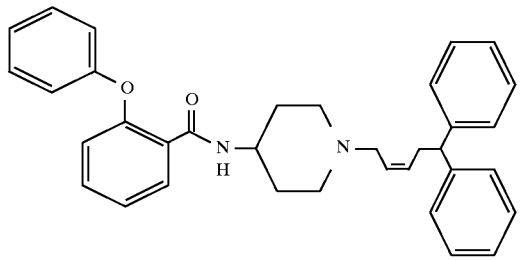

A.

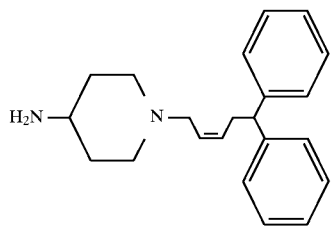

A(1). (Z)-[1-(5,5-Diphenyl-2-pentenyl)-4-piperidinyl]-carbamic acid, 1,1-dimethylethyl ester A stirred suspension of 1.16 g (5.78 mmol) of 4-piperidinylcarbamic acid, 1,1-dimethylethyl ester (Example 1 Part B), 1.35 g (5.26 mmol) of (Z)-1-chloro-5,5-diphenyl-2-pentene, and 799 mg (5.78 mmol) of potassium carbonate in 15 mL of N,N-dimethylformamide was heated to 60° C. for eighteen hours, cooled, filtered and concentrated to a dark oil which was chromatographed on silica gel (150 g) eluted with 95:5 methylene chloride/methanol to provide 1.82 g (82%) of title compound, as an off-white solid.

m.p. 105°–108° C.

Analysis Calcd. for $C_{27}H_{36}N_2O_2 \cdot 0.35\ H_2O$: C, 75.97; H, 8.66; N, 6.56

Found C, 75.81; H, 8.79; N, 6.72.

A(2).

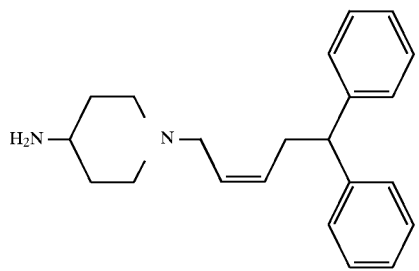

Part A(1) compound 1.44 g (34.31 mmol) was treated with 8.5 mL (34.31 mmol) of 4M HCl in dioxane. The crude product was twice evaporated from methylene chloride and dried under high vacuum to provide 1.42 mg (100%) of di-HCl salt of the title A compound as an off-white solid.

The free amine was obtained by suspending/dissolving the di-HCl salt in CH$_2$Cl$_2$ and washing with 1N KOH. The CH$_2$Cl$_2$ solution was filtered through cotton and concentrated and the diamine was used without characterization.

B. (Z)-N-[1-(5,5-Diphenyl-2-pentenyl)-4-piperidinyl]-2-phenoxybenzamide

To a solution of 197 mg (0.9 mmol, 1.5 eq) of ortho-phenoxybenzoic acid (Aldrich) and 124 mg (0.9 mmol, 1.5 eq) of 1-hydroxybenzotriazole (HOBt) in 10 mL of CH$_2$Cl$_2$ and 0.5 mL of DMF was added 144 µL (0.9 mmol, 1.5 eq) of diisopropyl-carbodiimide (DIC) followed by a solution of 196 mg (0.6 mmol, 1 eq) of Part A compound in 2.5 mL of CH$_2$Cl$_2$. After 17 h, the reaction was diluted with CH$_2$Cl$_2$ and washed with 1N KOH. The organic solution was filtered through cotton and concentrated to afford a viscous heterogeneous mixture which was chromatographed on silica gel (75 g) eluted with 4% methanol in CH$_2$Cl$_2$. The material obtained from this column was contaminated with a significant amount of urea by-product. The mixture was dissolved in EtOAc from which most of the urea precipitated. After filtration of the precipitated urea and concentration of the EtOAc solution, the resulting oil was chromatographed on silica gel (75 g) eluted with EtOAc to afford 192 mg of title compound as a pale yellow waxy solid which was recrystallized from ether/hexanes to provide 138 mg (44%) of title compound as a white crystalline solid;

m.p. 91°–94° C.

Anal. Calcd. for $C_{35}H_{36}N_2 \cdot 0.4\ H_2O$: C, 80.24; H, 7.08; N, 5.35

Found: C, 79.85; H, 6.87; N, 5.13.

EXAMPLE 283

(Z)-N-[1-(5,5-Diphenyl-2-pentenyl)-4-piperidinyl]-3-phenoxybenzamide

To a solution of 197 mg (0.9 mmol, 1.5 eq) of meta-phenoxybenzoic acid (Aldrich) and 124 mg (0.9 mmol, 1.5 eq) of 1-hydroxybenzotriazole (HOBt) in 10 mL of CH$_2$Cl$_2$ and 0.5 mL of DMF was added 144 µL (0.9 mmol, 1.5 eq) of diisopropylcarbo-diimide (DIC) followed by a solution of 196 mg (0.6 mmol, 1 eq) of Example 282 Part A compound in 2.5 mL of CH$_2$Cl$_2$. After 17 h, the reaction was diluted with CH$_2$Cl$_2$ and washed with 1N KOH. The organic solution was filtered through cotton and concentrated to afford a viscous heterogeneous mixture which was taken up in EtOAc. The resulting precipitated urea was removed by filtration and the filtrate was concentrated to afford an oil which was chromatographed on silica gel (70 g) eluted with 4% methanol in CH$_2$Cl$_2$. The product containing fractions still contaminated with urea by-product were concentrated and the resulting oil was rechromatographed on silica gel (50 g) eluted with EtOAc to afford 226 mg of a pale yellow oil. The oil was dissolved in ether and treated with excess HCl in ether. The resulting HCl salt was isolated by filtration and solvent remnants were removed by heating in a vacuum oven at 80° C. under full vacuum for 13 h to afford 231 mg (70%) of title compound as an off-white solid; m.p. 181°–184° C.

Anal. Calcd. for C$_{35}$H$_{37}$N$_2$O$_2$Cl: C, 76.00; H, 6.74; N, 5.06; Cl, 6.41

Found: C, 75.68; H, 6.81; N, 5.03; Cl, 6.11.

EXAMPLE 284

2,3-Dihydro-2-[1-(3-oxo-3-phenylpropyl)-4-piperidinyl]-1H-isoindol-1-one (intermediate)

A.

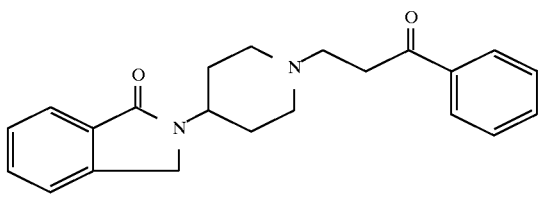

To a solution of benzaldehyde (Aldrich) (4.0 g, 37.7 mmol) in THF (100 mL) at 0° C. was added dropwise a solution of vinylmagnesium bromide (1.0M, 41.5 mL, 41.5 mmol) in THF (100 mL). The reaction was stirred at 0° C. for 1 h then warmed to RT for 2 h. Saturated ammonium chloride solution (10 mL) was added to quench the reaction. Ethyl ether (200 mL) was added and the organic layer was washed with water (2×50 mL), brine (2×50 mL) and dried over MgSO$_4$. Purification was performed by flash chromatography on silica gel (200 g), loaded and eluted with 10% ethyl acetate in hexane. Pure fractions were combined and evaporated to give title compound (1.3g, 23%) as a colorless oil.

B.

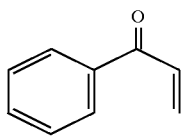

To a solution of oxalyl chloride (5.2 mL, 10.4 mmol) in dichloromethane (40 mL) at −60° C. was added dropwise DMSO (1.5 mL, 20.8 mmol). The reaction was stirred at −60° C. for 1 h. A solution of Part A compound (1.2 g, 8.0 mmol) in dichloromethane (3 mL) was added dropwise. Stirring was continued at −60° C. for 1 h. Triethylamine (6.7 mL, 48 mmol) was added and the reaction was warmed to RT over 1 h. Ethyl ether (200 mL) was added and the organic layer was washed with water (2×50 mL), brine (2×50 mL) and dried over MgSO$_4$. Evaporation gave title compound (1.1 g, 100%) as a crude oil.

C. 2,3-Dihydro-2-[1-(3-oxo-3-phenylpropyl)-4-piperidinyl]-1H-isoindol-1-one

To a solution of Example 2 Part A compound (1.93 g, 8.92 mmol) in dry ethanol (15 mL) at RT was added a solution of Part B compound (1.1 g, 7.43 mmol) in dry ethanol (2 mL). The reaction was stirred at RT for 4 h. The reaction was evaporated to dryness. Ethyl ether (150 mL) was added, and the solution was washed water (2×30 mL), brine (2×30 mL) and dried over MgSO$_4$. Purification was performed by flash chromatography on silica gel (150 g), loaded and eluted with 4% methanol in dichloromethane. Pure fractions were combined and evaporated to give title compound (1.0 g, 37%) as a yellowish solid.

m.p. 87°–90° C.

Anal. Calc. for C$_{22}$H$_{24}$N$_2$O$_2$: C, 75.83; H, 6.94; N, 8.04

Found: C, 75.40; H, 6.97; N, 7.96.

EXAMPLE 285

2,3-Dihydro-2-[1-[3-phenyl-3-(4-propylphenyl)-propyl]-4-piperidinyl]-1H-isoindol-1-one, monohydrochloride

A.

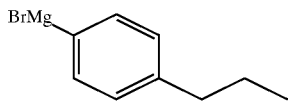

To a suspension of magnesium turnings (1.0 g, 41.2 mmol) in THF (8.2 mL) was added a solution of 1-bromo-4-propylbenzene (Aldrich) (1.64 g, 8.20 mmol) in THF (8.2 mL). The reaction was refluxed for 1.5 h, then cooled to RT. The Grignard solution was cannulated then titrated against 1.0M isopropanol in toluene using 2,2-biquinoline as an indicator to give title compound (0.35M, 70%) as a black solution.

B.

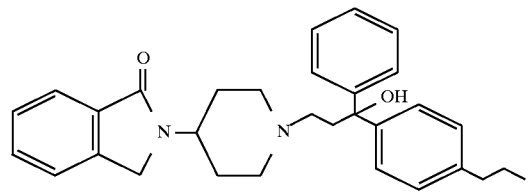

To a solution of Example 284 compound (500 mg, 1.37 mmol) in THF (8 mL) was added dropwise at 0° C. a solution of Part A compound (4.3 mL, 1.51 mmol). The reaction was stirred at 0° C. for 3 h then warmed to RT for 3 h. The reaction was quenched with saturated ammonium chloride solution (3 mL). Ethyl ether (200 mL) was added and the organic was washed with water (2×50 mL), brine (2×50 mL) and dried over MgSO$_4$. Evaporation gave title compound (400 mg, 63%) as a crude oil.

C. 2,3-Dihydro-2-[1-[3-phenyl-3-(4-propylphenyl)propyl]-4-piperidinyl]-1H-isoindol-1-one, monohydrochloride Triethylsilane (0.15 mL, 0.94 mmol) was added dropwise at 0° C. to a solution of Part B compound (360 mg, 0.78 mmol) in trifluoroacetic acid (4 mL). After addition, the reaction was stirred for 1 h then evaporated to dryness. The resulting residue was pumped under high vacuum for 2 h. Purification was performed by flash chromatography on silica gel (100 g), loaded and eluted with 2.5% methanol in dichloromethane. Pure fractions were combined and evaporated to give a colorless oil consisting of a mixture of desired deoxygenated product and olefin elimination products.

The resulting residue was dissolved in EtOAc (3 mL) and palladium (10%) on active carbon (40 mg) was added under nitrogen. The slurry was purge with nitrogen twice. A hydrogen balloon was connected to the reaction. Hydrogenation was maintained overnight. The reaction was filtered through Celite and the filtrate was evaporated to give a crude oil. Purification was performed by flash chromatography on silica gel (50 g), loaded and eluted with 5% methanol in dichloromethane. Pure fractions were combined and evaporated to give a colorless oil. The resulting oil was dissolved in methanol (1 mL), and HCl in ethyl ether solution(1M, 1 mL, 1 mmol) was added at RT. The mixture was evaporated to give title compound (85 mg, 22%) as a white solid.

m.p. 125°–130° C.

Anal. Calc. for $C_{31}H_{37}ClN_2O \cdot 1.4H_2O$: C, 72.39; H, 7.80; N, 5.45

Found: C, 72.11; H, 7.26; N, 5.22.

EXAMPLE 286

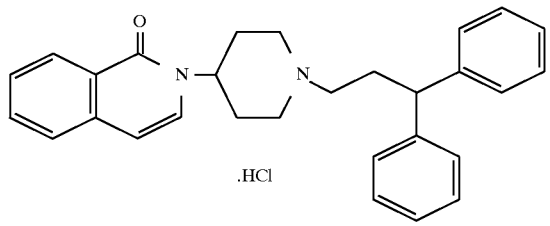

A. N-[1-(3,3-Diphenylpropyl)-4-piperidinyl]-2-methylbenzamide

To a stirred solution of 485 mg (1.46 mmol) of Example 1 Part E compound in 8 mL of methylene chloride at 0° C. under argon was added 336 mL (4.38 mmol) of pyridine and 200 mL (1.54 mmol) of o-toluoyl chloride. After warming to room temperature, the mixture was stirred for one hour and diluted with methylene chloride and water. The organics were separated, and the aqueous layer was basified with 1M KOH and extracted with methylene chloride. The combined organics were dried (sodium sulfate) and concentrated to provide a yellow oil which was dried under high vacuum. The crude product was purified by flash chromatography on silica gel (80 g) eluted with 98:2 ethyl acetate/methanol. Pure product fractions were combined and concentrated to provide 345 mg (67%) of title compound as a yellow solid.

B.

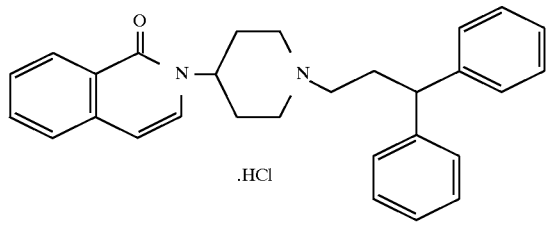

A solution of Part A compound (865mg, 2.1 mmol) in 8.6 ml of dry tetrahydrofuran was cooled to −22° C. under an argon atmosphere and 2 equiv. of 1.6M n-butyl lithium (2.63 ml) in hexanes was added keeping the temperature below −20° C. The reaction was stirred at −20° C. for 30 minutes and then dimethylformamide (0.186 ml, 2.4 mmol) was added keeping the temperature below −15° C. When the addition of the DMF was completed the reacton was stirred at −20° C. for 30 minutes and then quenched with 6N HCl (1.66 ml). After stirring for 30 minutes the reaction was made basic by adding 1N NaOH and extracted with ether (3×15 ml). The ether extracts were combined, washed with water (30ml), brine (30ml) and dried over sodium sulfate. The solvents were evaporated and the crude product was purified on a Merck silica column eluting with 5 to 10% MeOH/EtOAc yielding 293 mg (36%) of the "free base" as a colorless solid. The purified product was dissolved in 8 ml of ether and 0.5 ml of a 1N HCl solution in ether was added. The colorless precipitated HCl salt was collected, washed with additional ether and dried under vacuum at 80° C. yielding 320 mg (36%) of title compound as a colorless solid, m.p. 188°–194° C. (dec).

Analysis Calcd for $C_{29}H_{31}N_2ClO_2 \cdot 0.25\ H_2O$: C, 75.15; H, 6.85; N, 6.04; Cl, 7.65

Found: C, 74.98; H, 7.07; N, 6.21; Cl, 7.91.

EXAMPLE 287

2-[1-(3,3-Diphenylpropyl)-4-piperidinyl]-3,4-dihydro-1(2H)-isoquinolinone, monohydrochloride

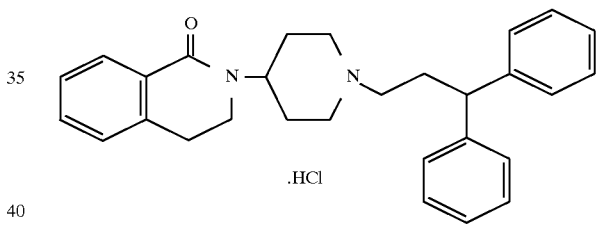

A quantity of Example 286 compound (95 mg, 0.225 mmol) was dissolved in 3 ml of absolute ethanol containing 0.5 ml of 0.1N HCl. 50 mg of 10% Pd/C was suspended in the reaction and the mixture was stirred under a hydrogen atmosphere (balloon). After stirring for 6 days starting material still remained. The reaction was filtered, fresh catalyst (50 mg) was added and the mixture stirred under 50 psi of hydrogen for 24 hrs. Tlc, silica 5% MeOH/CH$_2$Cl$_2$ showed some starting material present. The reaction was filtered, and the solvents evaporated yielding the crude product as a colorless oil. Purification by flash chromatography on silica eluting with 1 to 3% MeOH/CH$_2$Cl$_2$ yielded 22 mg of pure free base as a colorless oil. The oily free base was dissolved in ether and 0.5 ml of 1N HCl in ether was added forming the product as a white precipitate which was collected, washed with ether and dried under vacuum yielding 22 mg (24%) of title compound as a colorless solid, m.p. 180°–184° C.

Anal. Calc'd for $C_{29}H_{33}N_2ClO+0.75\ H_2O$: C, 73.40; H, 7.32; N, 5.43; Cl, 7.47

Found: C, 73.69; H, 7.67; N, 5.13; Cl, 7.35.

EXAMPLE 288

2-[1-[2-(9H-Fluoren-9-yl)ethyl]-4-piperidinyl]-2,3-dihydro-1H-isoindol-1-one

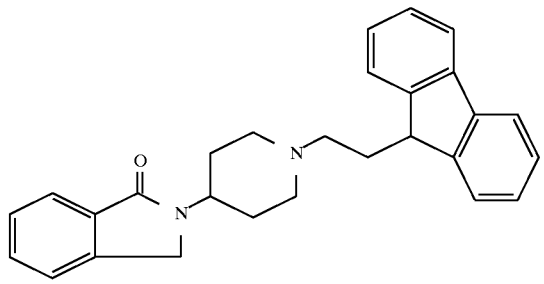

A.

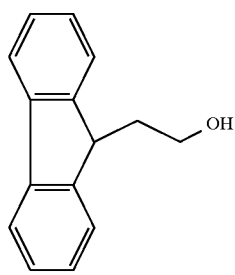

To a solution of 9-fluoreneacetic acid (Aldrich) (2.0 g, 8.92 mmol) in THF (20 mL) at 0° C. was added a solution of borane-tetrahydrofuran complex (1.0M in THF)(13.4 mL, 13.4 mmol). The reaction was stirred at 0° C. for 4 h. Saturated ammonium chloride solution (5 mL) was added to quench the reaction. Ethyl ether (200 mL) was added and the organic layer was washed with water (2×50 mL), saturated sodium bicarbonate solution (2×50 mL), brine (2×50 mL) and dried over MgSO$_4$. Evaporation gave a crude oil. Purification was performed by flash chromatography on silica gel (200 g), loaded and eluted with 20% ethyl acetate in hexane. Pure fractions were combined and evaporated to give title compound (1.82 g, 90%) as a colorless oil.

B.

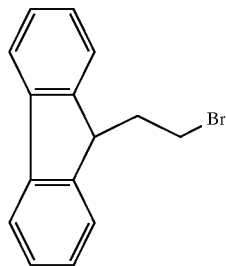

To a solution of Part A alcohol (800 mg, 3.81 mmol) and triphenylphosphine (1.1 g, 4.19 mmol) in dichloromethane (10 mL) at 0° C. was added N-bromosuccinimide (746 mg, 4.19 mmol). The reaction was stirred at 0° C. for 4 h. Hexane (150 mL) was added to dilute the reaction and the organic layer was washed with 10% sodium bisulfite solution (2×30 mL), brine (2×50 mL) and dried over MgSO$_4$. Purification was performed by flash chromatography on silica gel (100 g), loaded and eluted with 10% dichloromethane in hexane. Pure fractions were combined and evaporated to give title compound (1.02 g, 98%) as a colorless oil.

C.

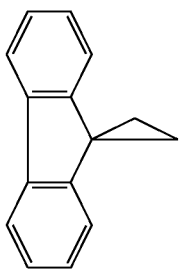

To a solution of Part B compound (680 mg, 2.50 mmol) and Example 2 Part A compound (540 mg, 2.50 mmol) in DMF (10 mL) was added potassium carbonate (380 mg, 2.75 mmol) at RT. The reaction was stirred at 70° C. overnight. Saturated ammonium chloride solution (5 mL) was added to quench the reaction. Ethyl ether (150 mL) was added and the organic layer was washed with water (2×30 mL), brine (2×30 mL) and dried over MgSO$_4$. Purification was performed by flash chromatography on silica gel (100 g), loaded eluted with 10% ethyl acetate in hexane. Pure fractions were combined and evaporated to give title compound (450 mg, 94%) as a white solid (m.p. 65°–68° C.).

D. 2-[1-[2-(9H-Fluoren-9-yl)ethyl]-4-piperidinyl]-2.3-dihydro-1H-isoindol-1-one

A mixture of Part C compound (650 mg, 3.29 mmol) and Example 2 Part A compound (750 mg, 3.47 mmol) was heated until the mixture melted (155° C.). The reaction was maintained at 155° C. for 4.5 h then cooled to RT. Purification was performed by flash chromatography on silica gel (100 g), loaded and eluted with 1% methanol in dichloromethane. Pure fractions were combined and evaporated to give title compound (220 mg, 16%) as a white solid.

m.p. 159°–162° C.

Anal. Calc. for $C_{28}H_{28}N_2O \cdot 0.6\ H_2O$: C, 80.20; H, 7.02; N, 6.68

Found: C, 80.35; H, 6.83; N, 6.57.

EXAMPLE 289

2-[1-(3,3-Diphenylpropyl)-4-piperidinyl]-2,3-dihydro-3-(phenylmethyl)-1H-isoindol-1-one, monohydrochloride

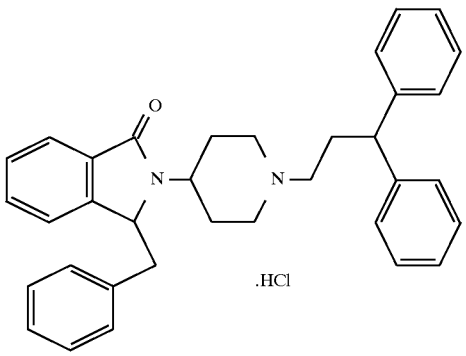

A. 2-[1-(3, 3-Diphenylpropyl)-4-piperidinyl]-2, 3-dihydro-1H-isoindol-1-one

To a solution of compound A from Example 2 (2.0 g, 9.26 mmol) and compound C from Example 1 (3.40 g, 9.26 mmol) in isopropanol (25 mL) was added potassium carbonate (2.05 g, 14.8 mmol). The reaction was refluxed overnight. The reaction was cooled to room temperature and filtered, and the filtrate was evaporated to dryness. Purification was performed by flash chromatography, loaded and eluted with 2.5% methanol in dichloromethane. Pure fractions were combined and evaporated to give compound A (2.82 g, 74 %) as a colorless oil.

B. 2-[1-(3,3-Diphenylpropyl)-4-piperidinyl]-2,3-dihydro-3-(phenylmethyl)-1H-isoindol-1-one, monohydrochloride Sodium bis(trimethylsilyl)amide (775 μL, 1.0M in .THF, 0.775 mmol) was added dropwise to a solution of Part A compound (265 mg, 0.646 mmol) in THF (4 mL) at −78° C. under argon. Upon addition the reaction color went from yellow to orange. The reaction was stirred at −78° C. for 20 min, then benzyl bromide (92 μL, 0.775 mmol) was added dropwise. The dark yellow reaction was stirred at −78° C. for 30 min, then quenched with saturated $NH_4Cl$ (1 mL). Water (1 mL) was added and the reaction mixture was extracted with $Et_2O$ (2×10 mL). The combined organic layers were washed with water (4 mL) and brine (4 mL), then dried over $MgSO_4$. Evaporation gave a yellow oil, which was purified by flash chromatography on silica (50 g) eluting with 50:50 EtOAc/hexane to give 205 mg of a yellow oil.

The free amine prepared above was dissolved in $Et_2O$ (3 mL) and treated with 1N HCl in $Et_2O$ (1 mL, 1 mmol). The resultant white precipitate was filtered, washed with Et2O (3×3 mL), and dried under high vacuum (0.4 torr) at 65° C. for 48 h to give title compound (169 mg, 49%) as a white solid.

mp 130°–131° C.

Anal. Calcd. for $C_{35}H_{36}N_2O \cdot HCl$: C, 78.26; H; 6.94; N, 5.22; Cl, 6.60.

Found: C, 78.05; H, 6.92; N, 5.18; Cl, 6.77.

EXAMPLE 290

2-[1-(3,3-Diphenylpropyl)-4-piperidinyl]-2,3-dihydro-3-methyl-1H-isoindol-1-one, monohydrochloride

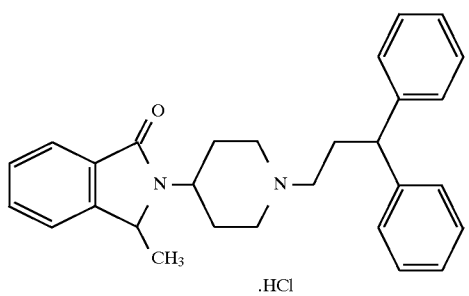

Utilizing the procedure for preparation of the Example 289 compound, the Example 289 Part A compound (276 mg, 0.673 mmol) was reacted with methyl iodide (50 μL, 0.808 mmol) instead of benzyl bromide then subjected to chromatography in 3:97 iPrOH/hexane to provide title compound (91 mg, 29%) as a white solid.

mp 129°–131° C.

Anal. Calcd. for $C_{29}H_{32}N_2O \cdot HCl$: C, 75.55; H, 7.21; N, 6.08; Cl, 7.69

Found: C, 75.10; H, 7.22; N, 6.06; Cl, 7.49.

EXAMPLE 291

2,3-Dihydro-2-[1-[2-[9-(2-propylenyl)-9H-fluoren-9-yl]ethyl]-4-piperidinyl]-1H-isoindol-1-one

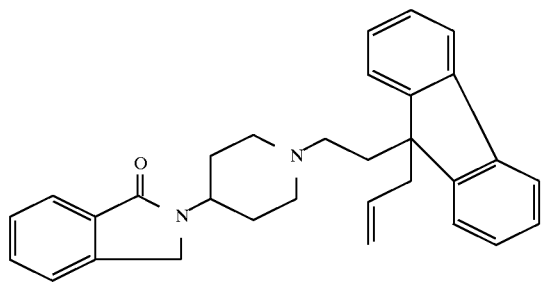

A.

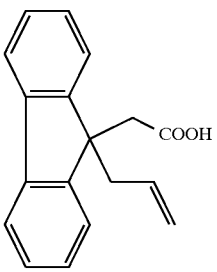

To a solution of 9-fluoreneacetic acid (Aldrich) (500 mg, 2.23 mmol) in THF (8 mL) at −78° C. was added dropwise a solution of butyllithium in hexane (2.5M, 1.78 mL, 4.46 mmol) followed by a solution of allylbromide (0.21 mL, 2.45 mL) in THF (1 mL). The reaction was stirred at −78° C. for 1 h. The reaction was quenched with saturatd ammonium chloride solution (2 mL) and warmed to RT. Ethyl ether (200 mL) was added and the organic layer was washed with water (2×50 mL), brine (2×50 mL) and dried over $MgSO_4$. Purification was performed by flash chromatography on silica gel (100 g), loaded and eluted with 15% acetone in hexane (4 L), then 25% acetone in hexane (4 L). Pure fractions were combined and evaporated to give title compound (420 mg, 71%) as a white solid (m.p. 121°–124° C.).

B.

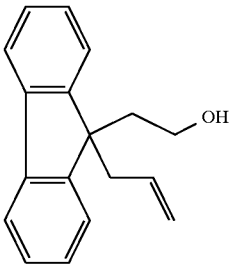

To a solution of Part A compound (420 mg, 1.59 mmol) in THF (10 mL) at 0° C. was added dropwise a solution of lithium aluminum hydride (1.0M in THF)(1.59 mL, 1.59 mmol). The reaction was stirred at 0° C. for 4 h. Methanol (2 mL) was added to quench the reaction. Potassium sodium tartrate solution (1M, 100 mL) was added and the mixture was stirred at RT for 4 h. Ethyl ether (200 mL) was added and the organic layer was washed with water (2×50 mL), saturated sodium bicarbonate solution (2×50 mL), brine (2×50 mL) and dried over MgSO$_4$. Evaporation gave title compound (350 mg, 88%) as a white solid (m.p. 89°–92° C.).

C.

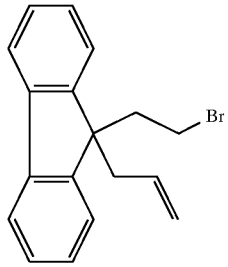

To a solution of Part B compound (350 mg, 1.40 mmol) and triphenylphosphine (403 mg, 1.54 mmol) in dichloromethane (10 mL) at 0° C. was added N-bromosuccinimide (274 mg, 1.54 mmol). The reaction was stirred at 0° C. for 1 h then warmed to RT for 2 h. Hexane (150 mL) was added to dilute the reaction and the organic layer was washed with 10% sodium bisulfite solution (2×30 mL), brine (2×50 mL) and dried over MgSO$_4$. Purification was performed by flash chromatography on silica gel (100 g), loaded and eluted with 10% dichloromethane in hexane. Pure fractions were combined and evaporated to give title compound (270 mg, 65%) as a colorless oil.

D. 2,3-Dihydro-2-[1-[2-[9-(2-propylenyl)-9H-fluoren-9-yl]ethyl]-4-piperidinyl]-1H-isoindol-1-one To a solution of Part C compound (270 mg, 0.86 mmol) and Example 2 Part A compound (224 mg, 1.04 mmol) in DMF (5 mL) was added potassium carbonate (144 mg, 1.04 mmol) at RT. The reaction was stirred at 60° C. overnight. Saturated ammonium chloride solution (2 mL) was added to quench the reaction. Ethyl ether (200 mL) was added and the organic layer was washed with water (2×50 mL), brine (2×50 mL) and dried over MgSO$_4$. Purification was performed by flash chromatography on silica gel (30 g), loaded eluted with 2% methanol in dichloromethane. Pure fractions were combined and evaporated to give title compound (250 mg, 65%) as a white solid.

m.p. 117°–120° C.

Anal. Calc. for $C_{31}H_{32}N_2O \cdot 0.5\ H_2O$: C, 81.37; H, 7.27; N, 6.12

Found: C, 81.25; H, 7.31; N, 6.02.

EXAMPLE 292

2-[1-(3,3-Diphenylpropyl)-4-piperidinyl]-2,3-dihydro-3-phenyl-1H-isoindol-1-one

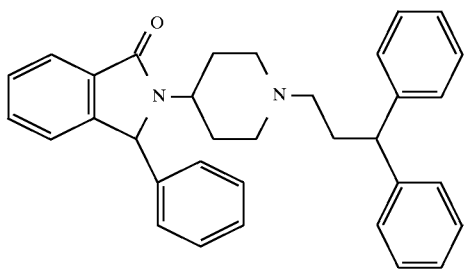

A. 2-[1-(3,3-Diphenylpropyl)-4-piperidinyl]-2,3-dihydro-3-hydroxy-3-phenyl-1H-isoindol-1-one

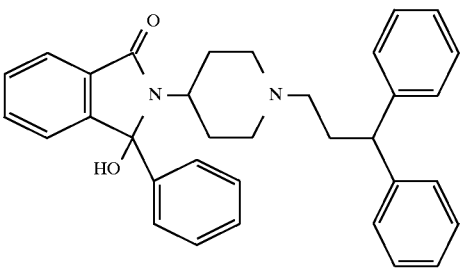

To a stirred solution of 1.06 g (2.88 mmol) of Example 1, Part E compound, 977 mg (4.30 mmol) of 2-benzoylbenzoic acid, 1.8 mL (12.9 mmol) of triethylamine in 1.8 mL (12.9 mmol) of methylene chloride at 0° C. under argon was added 1.01 mg (4.30 mmol) of bis(2-oxo-3-oxazolidinyl) phosphinic chloride. After the reaction was allowed to come to room temperature, it was stirred for 16 hours then quenched with water and 4M HCl, and diluted with methylene chloride. The aqueous layer was basified and extracted with methylene chloride. The combined organic layers were dried (sodium sulfate) and concentrated. The crude product was purified by flash chromatography on silica gel eluted with 97:3 methylene chloride/methanol to provide 1.15 mg (88%) of a white solid, which was combined with 261 mg from another reaction and further purified by recrystallization from ethyl acetate/hexanes to provide 700 mg (combined yield for both reactions 47%) of title compound, as a yellow solid.

m.p. 150°–153° C.

Anal. Calc. for $C_{33}H_{34}N_2O_2 \cdot 0.1\ C_2H_5O_2CCH_3$: C, 80.78; H, 6.86; N, 5.48

Found: C, 80,80; H, 6.87; N, 5.53.

B. 2-[1-(3,3-Diphenylpropyl)-4-piperidinyl]-2,3-dihydro-3-phenyl-1H-isoindol-1-one To a stirred solution of 475 mg (0.94 mmol) of Part A compound in 6 mL (excess) of trifluoroacetic acid under argon was added 386 mL (1.07 mmol) of triethylsilane. After 15 minutes, the bright yellow color dispersed and the reaction was concentrated under vacuum. The residue was dissolved in methylene chloride and washed with saturated sodium bicarbonate, dried (sodium sulfate) and concentrated to 400 mg of a yellow semisolid. The crude product was purified by flash chromatography on silica gel (125 g) eluted with 7:2:1 hexane/ethyl acetate/methanol to provide 343 mg (75%) of title compound as a white solid.

m.p.: 65°–69° C.

Analysis Calcd. for $C_{34}H_{34}N_2O \cdot 0.43\ H_2O$: C, 82.58; H, 7.11; N, 5.67

Found: C, 82.69; H, 7.05; N, 5.56.

EXAMPLE 293

2,3-Dihydro-2-[1-[4-[phenyl(phenylmethoxy)methyl]-phenyl]-4-piperidinyl]-1H-isoindol-1-one

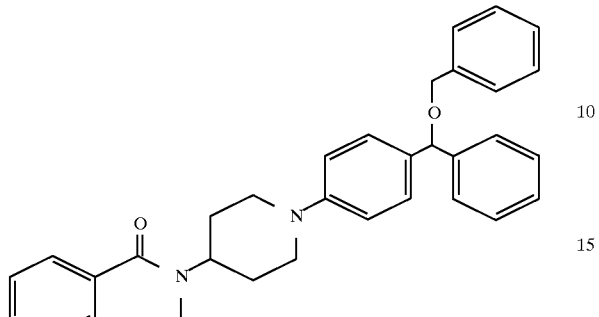

A.

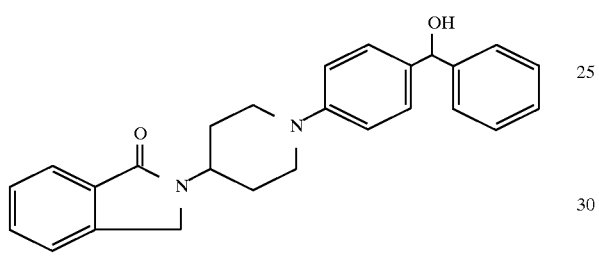

To a solution of Example 280 compound (500 mg, 1.26 mmol) in MeOH/THF (1:1)(30 mL) at 0° C. was added sodium borohydride (48 mg, 1.26 mmol). The reaction was stirred at 0° C. for 2 hours then warmed to RT overnight. Acetic acid was added to quench the reaction until the reaction was pH 6 by pH paper. The resulting mixture was evaporated to dryness. Ethyl ether (200 mL) was added to the residue, and the organic layer was washed with water (2×50 mL), saturated sodium bicarbonate solution (2×50 mL), brine (2×50 mL) and dried over MgSO$_4$. Evaporation gave title compound (355 mg, 71%) as a crude oil.

B. 2,3-Dihydro-2-[1-[4-[phenyl(phenylmethoxy)methyl] phenyl]-4-piperidinyl]-1H-isoindol-1-one To a suspension of potassium hydride (153 mg, 0.89 mmol) in DMF (5 mL) at 0° C. was added a solution of Part B compound (355 mg, 0.89 mmol) in DMF (1 mL). The reaction was stirred at 0° C. for 30 min. Benzyl bromide (0.13 mL, 1.07 mmol) was added to the reaction at 0° C. The reaction was stirred at 0° C. for 2 h then warmed to RT for 3 h. The reaction was quenched with saturated ammonium chloride solution (2 mL). Ethyl ether (200 mL) was added to the reaction, and the organic layer was washed with water (2×50 mL), brine (2×50 mL) and dried over MgSO$_4$. Purification was performed by flash chromatography on silica gel (100 g), loaded and eluted with 25% ethyl acetate in hexane. Pure fractions were combined and evaporated to give title compound (110 mg, 31%) as a white solid m.p. 112°–115° C.

Anal. Calc. for $C_{33}H_{32}N_2O_2 \cdot 0.4H_2O$: C, 79.94; H, 6.67; N, 5.65;
Found: C, 80.11; H, 6.74; N, 5.54.

EXAMPLE 294

2-[1-(3,3-Diphenylpropyl)-4-piperidinyl]-2,3-dihydro-4-hydroxy-1H-isoindol-1-one

A.

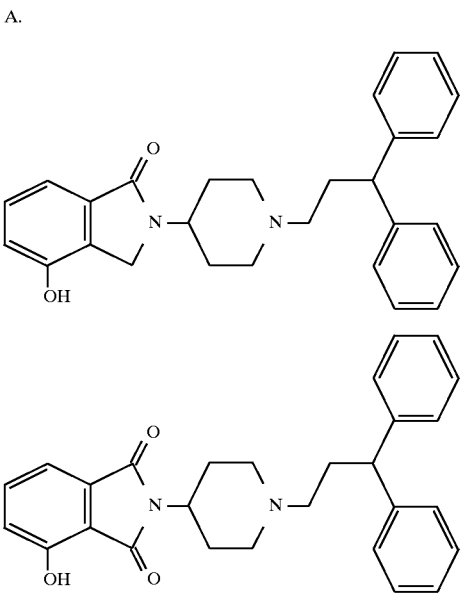

To a suspension of Example 1 Part E compound (4.48 g, 12.2 mmol) and 3-hydroxyphthalic anhydride (Aldrich) (2.0 g, 12.2 mmol) in toluene (10 mL) under argon was added N,N-diisopropylethylamine (4.7 mL, 26.8 mol). The bright yellow mixture was heated at reflux with azeotropic removal of water with a Dean-Stark trap for 18 h. The biphasic reaction was cooled to RT, diluted with CH$_2$Cl$_2$ (150 mL), and washed with 1M Na$_2$CO$_3$. The aqueous layer was adjusted to pH 7 with glacial acetic acid, and the organic layer was dried over Na$_2$SO$_4$. Evaporation gave a yellow foamy solid which was purified by flash chromatography on silica gel (300 g) eluting with a step gradient of 3:97 MeOH/CH$_2$Cl$_2$ to 5:95 MeOH/CH$_2$Cl$_2$ to afford title compound (4.21 g, 78%) as a yellow solid (mp 114°–118° C.).

B. 2-[1-(3,3-Diphenylpropyl)-4-piperidinyl]-2,3-dihydro-4-hydroxy-1H-isoindol-1-one Zinc dust (654 mg, 10 mmol) was added to a warm solution of Part A compound (440 mg, 1 mmol) in glacial acetic acid (3 mL). The reaction was refluxed under argon for 24 h, then cooled to RT. The reaction was filtered and the solids washed with glacial acetic acid (10 mL). The filtrate was concentrated in vacuo, and the resultant residue was azeotroped with toluene (10 mL). The residue was then dissolved in EtOAc (20 mL) and washed with saturated NaHCO$_3$ (5 mL) and brine (5 mL), then dried over Na$_2$SO$_4$. Evaporation gave 426 mg of a colorless glass, which was purified by flash chromatography on silica gel (40 g) to give title compound (128 mg, 30%) as a white solid, and the 7-hydroxy isomer (156 mg, 37%) as a colorless glass.

mp 223°–25° C.

Anal. Calcd. for $C_{28}H_{30}N_2O_2$: C, 78.84; H, 7.09; N, 6.57
Found: C, 78.53; H, 7.16; N, 6.95.

EXAMPLE 295

(Z)-2-[1-[4-(9H-Fluoren-9-yl)-2-butenyl]-4-piperidinyl]-2,3-dihydro-1H-isoindol-1-one

A.

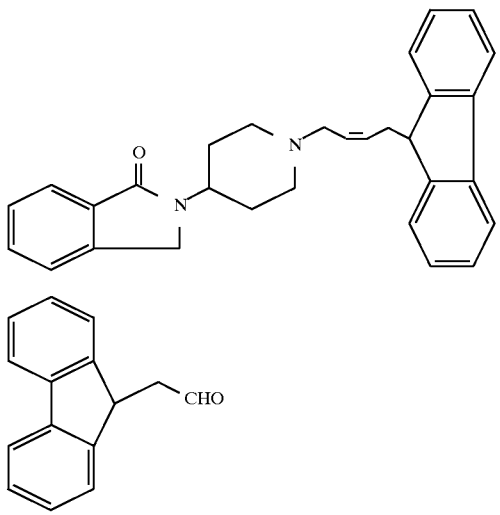

To a solution of oxalyl chloride (2.0M, 1.37 mL, 2.73 mmol) in dichloromethane (30 mL) at −74° C. was added dropwise a solution of DMSO (0.4 mL, 5.46 mmol) in dichloromethane (1 mL). The reaction was stirred at −74° C. for 1 h. A solution of Example 288, Part A compound (440 mg, 5.46 mmol) in dichloromethane (4 ml) was added dropwise. The reaction was stirred at −74° C. for 1.5 h. Triethylamine (1.5 g, 14.7 mmol) was added and the reaction was warmed to RT over 1 h. Ethyl ether (100 mL) was added and the organic layer was washed with 1N HCl solution (2×30 mL), water (2×30 mL), saturated sodium bicarbonate solution (2×30 mL), brine (2×30 mL) and dried over $MgSO_4$. Evaporation gave title compound (400 mg, 92%) as a crude oil.

B.

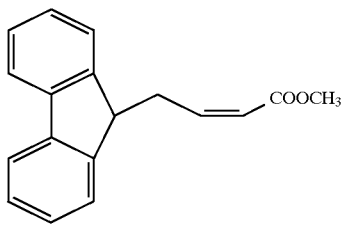

To a solution of bis(2,2,2-trifluoroethyl)-(methoxycarbonylmethyl)phosphonate (672 mg, 2.11 mmol) and 18-crown-6 (557 mg, 2.11 mmol) in THF (10 mL) at 0° C. was added a solution of potassium bis(trimethylsilyl)amide in toluene (0.5M, 4.22 mL, 2.11 mmol). The reaction was stirred at 0° C. for 30 min then cooled to −78° C. A solution of Part A compound (400 mg, 1.92 mmol) in THF (1 mL) was added. The reaction was stirred at −78° C. for 1 h. The reaction was quenched with saturated ammonium chloride solution (5 mL). Ethyl ether (200 mL) was added to the reaction, and the organic layer was washed with water (2×30 mL), brine (2×30 mL) and dried over $MgSO_4$. Purification was performed by flash chromatography on silica gel (200 g), loaded and eluted with 20% dichloromethane in hexane. Pure fractions were combined and evaporated to give title compound (390 mg, 77%) as a colorless oil.

C.

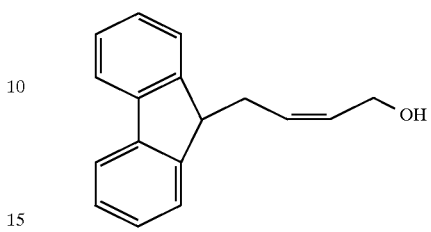

To a solution of Part B compound (390 mg, 1.48 mmol) in THF (20 mL) at 0° C. was added dropwise a solution of diisobutylaluminum hydride in hexane (1.0M, 3.26 mL, 3.26 mmol). The ice bath was removed and the reaction was stirred at RT for 15 min. The reaction was quenched by methanol (2 mL) followed by potassium sodium tartrate solution (1M, 100 mL). The mixture was stirred at RT overnight. Ethyl ether (150 mL) was added and the organic layer was washed with water (2×30 mL), brine (2×30 mL) and dried over $MgSO_4$. Purification was performed by flash chromatography on silica gel (100 g), loaded and eluted with 20% ethyl acetate in hexane. Pure fractions were combined and evaporated to give title compound (240 mg, 69%) as a colorless oil.

D.

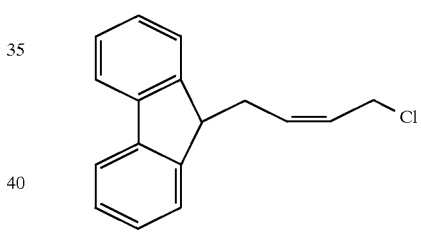

To a solution of N-chlorosuccinimide (155 mg, 1.17 mmol) in dichloromethane (5 mL) at −40° C. was added dropwise methyl sulfide (0.11 mL, 1.52 mmol). The reaction was stirred at −40° C. for 10 min then warmed to RT for 30 min. The reaction was recooled to −40° C., and a solution of Part C compound (230 mg, 0.97 mmol) in dichloromethane (2 mL) was added dropwise. The reaction was stirred at −40° C. for 2 h then warmed to RT for 30 min. Ethyl ether (120 mL) was added to dilute the reaction and the organic layer was washed with water (2×30 mL), brine (2×30 mL) and dried over $MgSO_4$. Evaporation gave title compound (210 mg, 85%) as a colorless oil.

E. (Z)-2-[1-[4-(9H-Fluoren-9-yl)-2-butenyl]-4-piperidinyl]-2,3-dihydro-1H-isoindol-1-one To a solution of Part D compound (216 mg, 0.85 mmol) in DMF (10 mL) was added Example 2 Part A compound (183 mg, 0.85 mmol) followed by anhydrous potassium carbonate (129 mg, 0.94 mmol). The reaction was stirred at RT overnight. Ethyl ether (100 mL) was added to dilute the reaction, and the solution was washed with water (2×30 mL), brine (2×30 mL) and dried over $MgSO_4$. Evaporation gave a crude oil. Purification was performed by flash chromatography on 100 g of silica gel, loaded and eluted with 2% methanol in dichloromethane. Pure fractions were combined and evaporated to give title compound (221 mg, 60%) as a white solid.

m.p. 112°–116° C.

Anal. Calc. for C$_{30}$H$_{30}$N$_2$O·0.2 H$_2$O: C, 82.23; H, 6.99; N, 6.39

Found: C, 81.92; H, 7.00; N, 6.59.

EXAMPLE 296

2-[1-(3,3-Diphenylpropyl)-4-piperidinyl]-2,3-dihydro-7-hydroxy-1H-isoindol-1-one

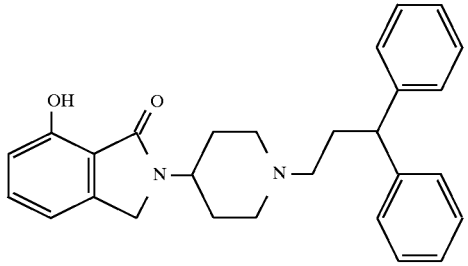

To a solution of Example 294 Part A compound (2.80 g, 6.36 mmol) in THF (30 mL) at −70° C. (internal temp) under argon was added lithium tri-sec-butylborohydride (L-Selectride®) (14.0 mL, 1.0M in THF, 14.0 mmol) dropwise over 45 min via syringe pump. The reaction was stirred at −70° C. for 10 min then allowed to warm to −40° C. over 1.5 h, at which time the reaction gelatinized to a yellow cake. The reaction was quenched with acetic acid (1 mL) and warmed to RT. The reaction was concentrated in vacuo and the residue was partitioned between CH$_2$Cl$_2$ (75 mL) and 1M sodium phosphate buffer (pH 7, 25 mL). The organic layer was washed with brine (30 mL) then dried over Na$_2$SO$_4$. Evaporation gave 3.3 g of a pale yellow solid.

To a suspension of the crude product above in toluene (50 mL) was added trimethylamine N-oxide dihydrate (5.65 g, 50.9 mmol). The reaction was refluxed under argon for 3 h, then cooled to RT. The reaction was diluted with CH$_2$Cl$_2$ (200 mL) and washed with brine (50 mL) then dried over Na$_2$SO$_4$. Evaporation gave 2.45 g of a light brown solid.

To a solution of the crude product above in trifluoroacetic acid (30 mL) was added triethylsilane (1.5 mL, 9.54 mmol). The reaction was stirred vigorously under argon (became slightly exothermic) for 10 min, then concentrated in vacuo. The residue was dissolved in CH$_2$Cl$_2$ (100 mL) and washed with saturated NaHCO$_3$ (2×30 mL) and brine (30 mL), then dried over Na$_2$SO$_4$. Evaporation gave 2.6 g of a brown foam, which was purified by flash chromatography on silica gel (150 g) eluting with 15:85 isopropanol/hexane to afford title compound (890 mg, 33%) as a pale yellow solid. Additional clean product (990 mg, 36%) was obtained upon flushing flash column with 10:90 MeOH/CH$_2$Cl$_2$ (1 L).

mp 118°–122° C.

Anal. Calcd. for C$_{28}$H$_{30}$N$_2$O$_2$: C, 78.84; H, 7.09; N, 6.57

Found: C, 78.57; H, 7.23; N, 6.46.

EXAMPLE 297

2-[1-(3,3-Diphenylpropyl)-4-piperidinyl]-2,3-dihydro-7-phenyl-1H-isoindol-1-one

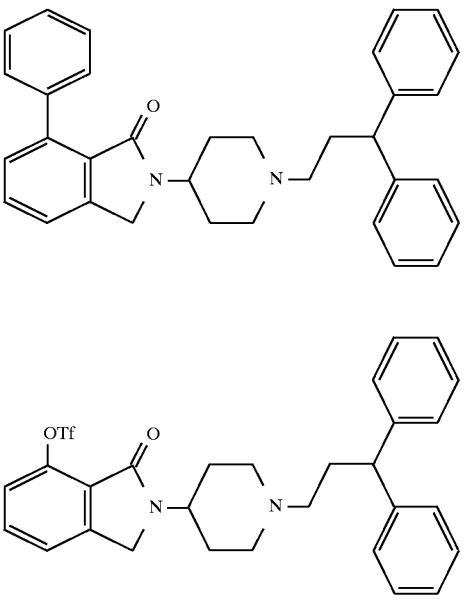

Trifluoromethanesulfonic anhydride (463 μL, 2.76 mmol) was added dropwise to a solution of Example 296 compound (980 mg, 2.30 mmol) in CH$_2$Cl$_2$ (10 mL) at −20° C. under argon. The reaction was stirred at −20° C. for 15 min, then washed with saturated NaHCO$_3$ (5 mL). The aqueous layer was extracted with CH$_2$Cl$_2$ (10 mL) and the combined organic layers were dried over Na$_2$SO$_4$. Evaporation gave title compound (1.38 g, 100%) as a crude brown foam.

B. 2-[1-(3,3-Diphenylpropyl)-4-piperidinyl]-2,3-dihydro-7-phenyl-1H-isoindol-1-one A mixture of Part A compound (439 mg, 0.787 mmol), phenylboric acid (192 mg, 1.57 mmol), and anhydrous potassium carbonate (163 mg, 1.18 mmol) in toluene (8 mL) at RT was degassed by bubbling argon through the reaction solution. Tetrakis(triphenylphosphine)palladium (45 mg, 0.039 mmol) was added and the reaction was refluxed for 1.5 h. The reaction was cooled to RT, diluted with EtOAc (20 mL), and washed with saturated NaHCO$_3$, water, and brine (5 mL each). The organic layer was dried over Na$_2$SO$_4$ and evaporated to give 460 mg of a brown foam, which was chromatographed on silica gel (50 g) eluting with 10:90 acetone/CH$_2$Cl$_2$ to give 250 mg of a brown foam containing the desired product and an unidentified compound. The contaminated product (209 mg) was dissolved in toluene (4 mL) and trimethylamine N-oxide (244 mg, 2.2 mmol) was added. The reaction was refluxed under argon for 3.5 h, then cooled to RT. The reaction mixture was diluted with EtOAc (10 mL) and washed with saturated NaHCO$_3$ (3 mL) and brine (3 mL), then dried over Na$_2$SO$_4$. Evaporation gave 200 mg of a brown oil, which was purified by flash chromatography on silica gel (50 g) eluting with 1:99 MeOH/EtOAc to give title compound (111 mg, 35%) as a white foam.

Anal. Calcd. for C$_{34}$H$_{34}$N$_2$O·0.4 H$_2$O: C, 82.69; H, 7.10; N, 5.67

Found: C, 82.97; H, 7.11; N, 5.47.

EXAMPLE 298

(z)-2,3-Dihydro-2-[1-[4-[9-(2-propenyl)-9H-fluoren-9-yl]-2-butenyl]-4-piperidinyl]-1H-isoindol-1-one

A.

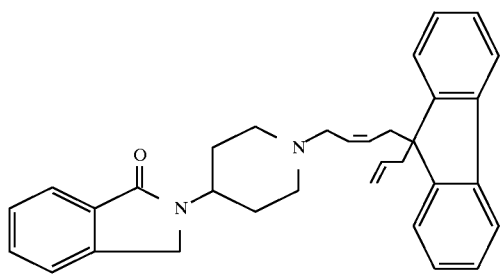

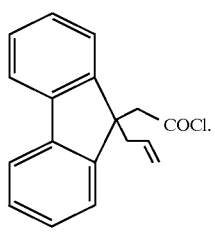

To a solution of Example 291 Part A compound (650 mg, 2.46 mmol) in dichloromethane (10 mL) at RT was added dropwise a solution of oxalyl chloride in dichloromethane (2.0M, 1.85 mL, 3.70 mmol) followed by DMF (3.69 mL, 0.05 mmol). The reaction was stirred at RT for 1 h. The reaction was evaporated to give title compound (650 mg, 100%) as a yellowish oil.

B.

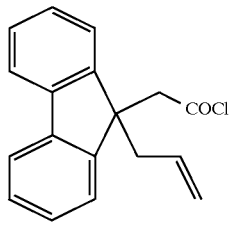

To a solution of Part A compound (650 mg, 2.46 mmol) in THF (10 mL) at −78° C. was added dropwise a solution of lithium tri-tert-butoxyaluminohydride (1.0M, 2.60 mL, 2.60 mmol) in THF over 2.5 h. The reaction was stirred at −78° C. overnight. The reaction was quenched with saturated ammonium chloride (5 mL) and warmed to RT. Ethyl ether (150 mL) was added and the organic layer was washed with 1N potassium hydrogen sulfate solution (30 mL), water (2×30 mL), saturated sodium bicarbonate solution (2×30 mL), brine (2×30 mL) and dried over MgSO$_4$. Evaporation gave title compound (400 mg, 65%) as a crude oil.

C.

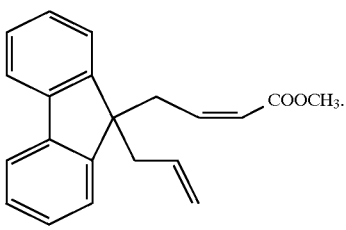

To a solution of bis(2,2,2-trifluoroethyl)-(methoxycarbonyl-methyl)phosphonate (560 mg, 1.76 mmol), 18-crown-6 (465 mg, 1.76 mmol) in THF (10 mL) at 0° C. was added a solution of potassium bis(trimethylsilyl)amide in toluene (0.5M, 3.52 mL, 1.76 mmol). The reaction was stirred at 0° C. for 30 min then cooled to −78° C. A solution of Part B compound (400 mg, 1.60 mmol) in THF (1 mL) was added. The reaction was stirred at −78° C. for 1 h. The reaction was quenched with saturated ammonium chloride solution (5 mL). Ethyl ether (120 mL) was added to the reaction, and the organic layer was washed with water (2×50 mL), brine (2×50 mL) and dried over MgSO$_4$. Purification was performed by flash chromatography on silica gel (100 g), loaded and eluted with 5% ethyl acetate in hexane. Pure fractions were combined and evaporated to give title compound (280 mg, 58%) as a colorless oil.

D.

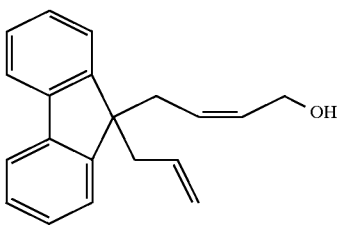

To a solution of Part C compound (280 mg, 0.92 mmol) in THF (8 mL) at 0° C. was added dropwise a solution of diisobutylaluminum hydride in toluene (1.0M, 2.03 mL, 3.26 mmol). The ice bath was removed and the reaction was stirred at RT for 15 min. The reaction was quenched by methanol (2 mL) followed by potassium sodium tartrate solution (1M, 100 mL). The mixture was stirred at RT overnight. Ethyl ether (150 mL) was added and the organic layer was washed with water (2×30 mL), brine (2×30 mL) and dried over MgSO$_4$. Purification was performed by flash chromatography on silica gel (100 g), loaded and eluted with 20% ethyl acetate in hexane. Pure fractions were combined and evaporated to give title compound (240 mg, 69%) as a colorless oil.

E.

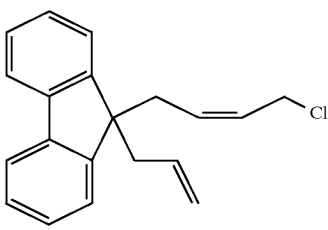

To a solution of N-chlorosuccinimide (122 mg, 0.91 mmol) in dichloromethane (5 mL) at −40° C. was added dropwise methyl sulfide (0.08 mL, 1.14 mmol). The reaction was stirred at −40° C. for 10 min then warmed to RT for 30 min. The reaction was recooled to −40° C., and a solution of Part D compound (210 mg, 0.76 mmol) in dichloromethane (2 mL) was added dropwise. The reaction was stirred at −40° C. for 2 h then warmed to RT for 30 min. Ethyl ether (120 mL) was added to dilute the reaction and the solution was washed with water (2×30 mL), brine (2×30 mL) and dried over MgSO$_4$. Evaporation gave title compound (210 mg, 94%) as a colorless oil.

F. (Z)-2,3-Dihydro-2-[1-[4-[9-(2-propenyl)-9H-fluoren-9-yl]-2-butenyl]-4-piperidinyl]-1H-isoindol-1-one To a solution of Part E compound (210 mg, 0.71 mmol) in DMF (8 mL) was added Example 2 Part A compound (154 mg, 0.71 mmol) followed by anhydrous potassium carbonate (108 mg, 0.78 mmol). The reaction was stirred at RT overnight. Ethyl ether (100 mL) was added to dilute the reaction, and the solution was washed with water (2×30 mL), brine (2×30 mL) and dried over MgSO$_4$. Evaporation gave a crude oil. Purification was performed by flash chromatography on 100 g of silica gel, loaded and eluted with 1% methanol in dichloromethane. Pure fractions were combined and evaporated to give title compound (219 mg, 65%) as a white solid.

m.p. 117°–120° C.

Anal. Calc. for $C_{33}H_{34}N_2O \cdot 0.6H_2O$: C, 81.65; H, 7.31; N, 5.77

Found: C, 81.69; H, 7.31; N, 5.64

EXAMPLE 299

2,3-Dihydro-2-[1-[4-[phenyl(3-phenylpropoxy)-methyl]phenyl]-4-piperidinyl]-1H-isoindo-1-one

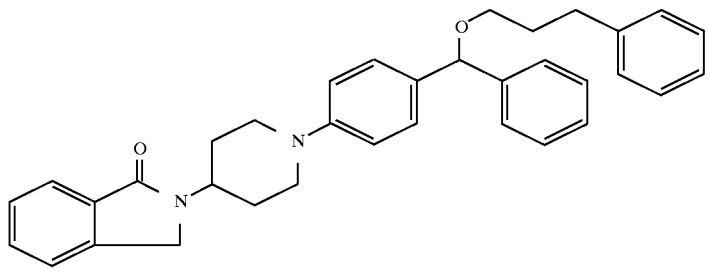

To a suspension of sodium hydride (44 mg, 1.1 mmol) in DMF (5 mL) at 0° C. was added dropwise a solution of Example 293 Part A compound (400 mg, 1.0 mmol) in DMF (1 mL). The reaction was stirred at 0° C. for 30 min. 1-Bromo-3-phenylpropane (219 mg, 1.1 mmol) was added dropwise to the reaction at 0° C. The reaction was stirred at 0° C. for 1 h then warmed to RT overnight. The reaction was quenched with saturated ammonium chloride solution (2 mL). Ethyl acetate (100 mL) was added to the reaction, and the organic layer was washed with water (2×30 mL), brine (2×30 mL) and dried over MgSO$_4$. Purification was performed by flash chromatography on silica gel (100 g), loaded and eluted with 50% ethyl acetate in hexane. Pure fractions were combined and evaporated to give title compound (335 mg, 65%) as a white solid.

m.p. 117°–120° C.

Anal. Calc. for $C_{35}H_{36}N_2O_2 \cdot 0.3 H_2O$: C, 80.52; H, 7.07; N, 5.37

Found: C, 80.64; H, 7.01; N, 5.11.

EXAMPLE 300

2,3-Dihydro-2-[1-[4-[(4-pyridinylmethoxy)phenylmethyl]phenyl]-4-piperidinyl]-1H-isoindol-1-one

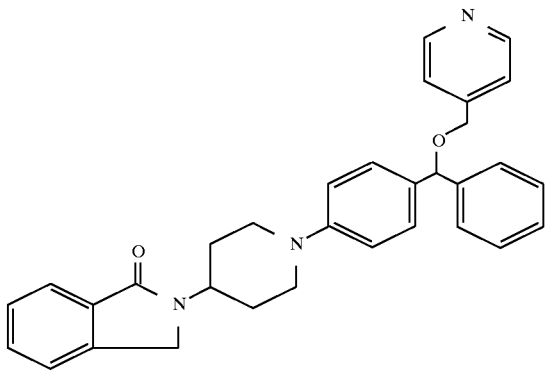

To a solution of 4-picolyl chloride hydrochloride (226 mg, 1.38 mmol) in water (4 mL) was added sodium hydroxide solution (1N, 1.5 mL, 1.50 mmol). The resulting solution was extracted with ethyl ether (3×5 mL). The organic layers were combined and evaporated to give 4-picolyl chloride (175 mg, 100%).

To a suspension of sodium hydride (55.3 mg, 1.38 mmol) in DMF (5 mL) at 0° C. was added dropwise a solution of Example 293 Part A compound (500 mg, 1.26 mmol) in DMF (8 mL). The reaction was stirred at 0° C. for 30 min. A solution of 4-picolyl chloride (175 mg, 1.38 mmol) in DMF (1 mL) was added dropwise to the reaction at 0° C. The reaction was stirred at 0° C. for 1 h then warmed to RT overnight. The reaction was quenched with saturated ammonium chloride solution (2 mL). Ethyl acetate (200 mL) was added to the reaction, and the organic layer was washed with water (2×100 mL), brine (2×100 mL) and dried over MgSO$_4$. Purification was performed by flash chromatography on silica gel (100 g), loaded and eluted with 70% EtOAc in hexane. Pure fractions were combined and evaporated to give title compound (320 mg, 52%) as a white solid.

m.p. 77°–81° C.

Anal. Calc. for C=H$_{31}$N$_3$O$_2$·0.2 H$_2$O: C, 77.93; H, 6.42; N, 8.52

Found: C, 77.69; H, 6.21; N, 8.71.

EXAMPLE 301

2,3-Dihydro-2-[1-[4-[(2-pyridinylmethoxy)phenylmethyl]phenyl]-4-piperidinyl]-1H-isoindol-1-one

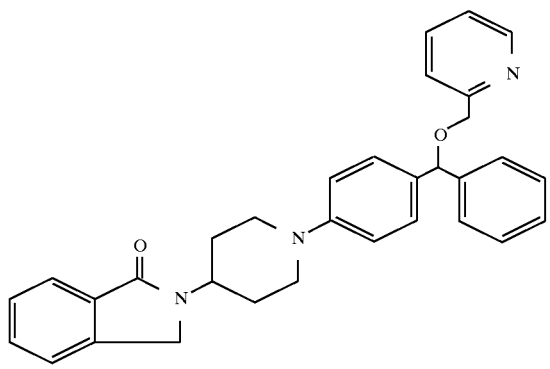

Following the procedure for the preparation of the compound of Example 300, reaction of Example 293 Part A compound (500 mg, 1.26 mmol) and 2-picolyl chloride hydrochloride (316 mg, 1.89 mmol) gave title compound (350 mg, 56%) as a white solid.

m.p. 149°–151° C.

Anal. Calc. for C$_{32}$H$_{31}$N$_3$O$_2$: C, 78.50; H, 6.38; N, 8.58

Found: C, 78.19; H, 6.32; N, 8.78.

EXAMPLES 302 to 308

Following the procedures set out in Examples 289 to 301, the following compounds of the invention were prepared.

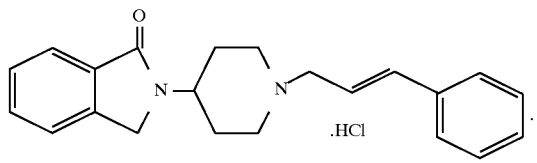
302 m.p.: 260°–264° C.

Elemental Anal. Calc. for C$_{22}$H$_{25}$ClN$_2$O·0.3 H$_2$O: C, 70.59; H, 6.89; N, 7.48; Cl, 9.47

Found: C, 70.77; H, 6.96; N, 7.47; Cl, 9.49.

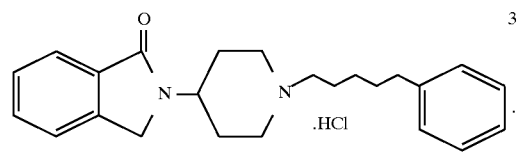
303 m.p.: 199°–201° C.

Elemental Anal. Calc. for C$_{24}$H$_{31}$ClN$_2$O·0.2 H$_2$O: C, 71.60; H, 7.86; N, 6.96; Cl, 8.81

Found: C, 71.60; H, 7.95; N, 6.93; Cl, 8.89.

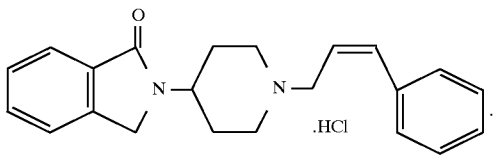
304 m.p.: 244°–247° C.

Elemental Anal. Calc. for C$_{22}$H$_{25}$ClN$_2$O: C, 71.63; H, 6.83; N, 7.59; Cl, 9.61

Found: C, 71.61; H, 6.84; N, 7.50; Cl, 9.75.

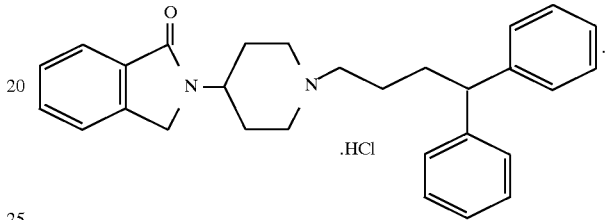
305 m.p. 212°–215° C.

Elemental Anal. Calc. for C$_{29}$H$_{33}$ClN$_2$O·0.4 H$_2$O: C, 74.39; H, 7.28; N, 5.98; Cl, 7.57

Found: C, 74.27; H, 7.28; N, 6.22; Cl, 7.66.

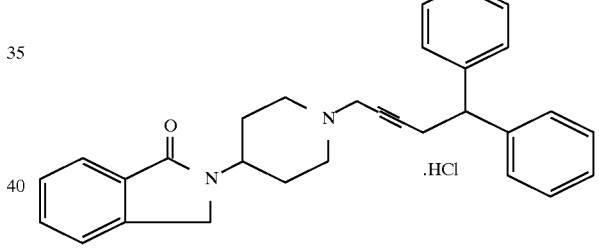
306 m.p.: 221°–225° C.

Elemental Anal. Calc. for C$_{30}$H$_{31}$ClN$_2$O·1.5 H$_2$O: C, 72.35; H, 6.88; N, 5.62; Cl, 7.12

Found: C, 72.35; H, 7.02; N, 5.51; Cl, 6.79.

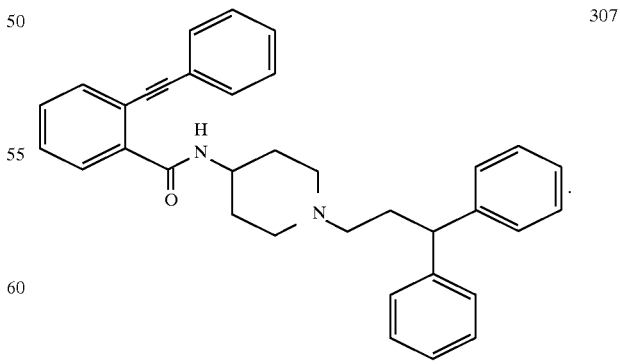
307

MS (CI, pos. ions) 497 (M+H)

Analysis Calcd for C$_{35}$H$_{34}$N$_2$O·0.99 H$_2$O: C, 81.38; H, 7.02; N, 5.42

Found: C, 81.35; H, 6.74; N, 5.45.

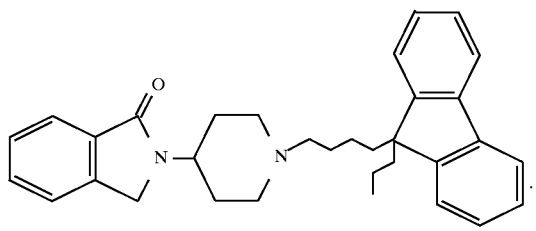

MS (ES) 479 (M+H)

Anal. Calcd. for $C_{33}H_{38}N_2O \cdot 0.6\ H_2O$: C, 80.97; H, 8.07; N, 5.72

Found: C, 80.95; H, 7.87; N, 5.65.

EXAMPLE 309

(Z) -2,3-Dihydro-2-[1-[4-[9-(3-phenylpropyl) -9H-fluoren-9-yl]-2-butenyl]-4-piperidinyl]-1H-isoindol-1-one

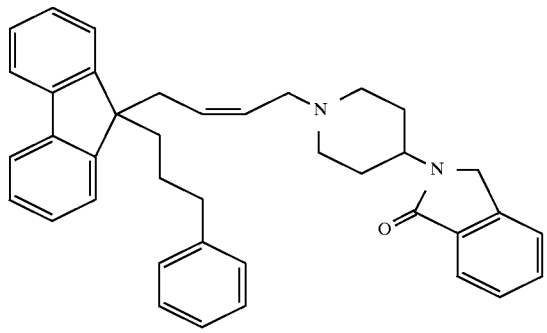

A.

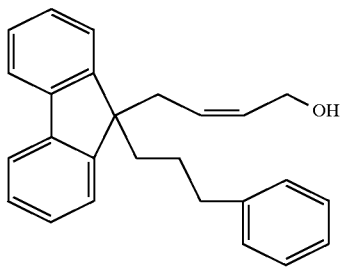

To a solution of the alcohol prepared in Example 295, Part C (330 mg, 1.40 mmol) in THF (8 mL) at −78° C. was added dropwise a solution of n-butyllithium in hexane (1.6M, 1.84 mL, 2.94 mmol) followed by a solution of 1-bromophenylpropane (0.26 mL, 1.68 mmol) in THF (1 mL). The reaction was stirred at −78° C. for 30 min, then warmed to −25° C. for 30 min. The reaction was quenched with saturated ammonium chloride solution (2 mL) and warmed to RT. Ethyl ether (100 mL) was added and the organic layer was washed with water (2×50 mL), brine (2×50 mL) and dried over $MgSO_4$ Purification was performed by flash chromatography on silica gel (200 g), loaded and eluted with 20% ethyl acetate in hexane. Pure fractions were combined and evaporated to give title compound (410 mg, 81%) as a colorless oil.

B.

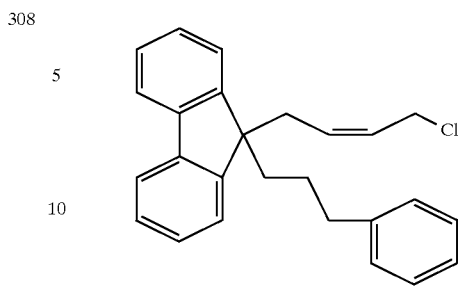

Following the procedure in Example 295, Part D, the above Part A compound (400 mg, 1.13 mmol) was reacted to give title compound (360 mg, 86%) as a colorless oil.

C. (Z)-2,3-Dihydro-2-[1-[4-[9-(3-phenylpropyl)-9H-fluoren-9-yl]-2-butenyl]-4-piperidinyl]-1H-isoindol-1-one To a solution of Part B compound (360 mg, 0.97 mmol) in DMF (10 mL) was added Example 2, Part A compound (209 mg, 0.97 mmol) followed by anhydrous potassium carbonate (160 mg, 1.16 mmol). The reaction was stirred at 50° C. overnight. Ethyl ether (70 mL) was added to dilute the reaction, and the solution was washed with water (2×50 mL), brine (2×50 mL) and dried over $MgSO_4$. Evaporation gave a crude oil. Purification was performed by flash chromatography on 100 g of silica gel, loaded and eluted with 2.5% methanol in dichloromethane. Pure fractions were combined and evaporated to give title compound (310 mg, 58%) as a white solid. m.p. 118°–122° C.

MS (Cl,+ion): 553 (M+H).

Anal. Calc. for $C_{39}H_{40}N_2O \cdot 1.2\ H_2O$: C, 81.55; H, 7.44; N, 4.88

Found: C, 81.63; H, 7.51;. N, 4.78.

EXAMPLE 310

9-[3-[4-(2,3-Dihydro-1-oxo-1H-isoindol-2-yl)-1-piperidinyl]propyl]-N-propyl-9H-fluorene-9-carboxamide

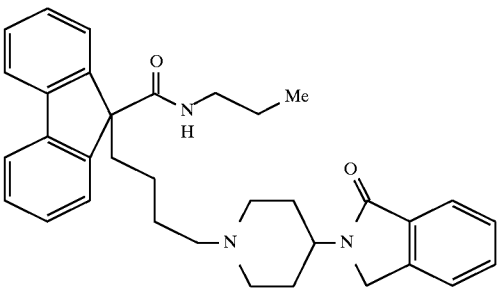

A.

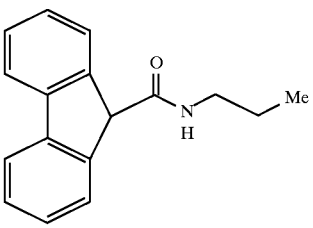

To a suspension of 10 g (47.57 mmol) of 9-fluorenecarboxylic acid (Aldrich) in 80 mL of $CH_2Cl_2$, under argon at 0° C., was added a catalytic amount of DMF (0.5 mL) followed by the dropwise addition of 36 mL (71.35 mmol) of oxalyl chloride (2M in $CH_2Cl_2$). The reaction was warmed to RT and was stirred for 45 min (the reaction becomes a clear yellow solution) at which time it was evaporated to dryness and pumped on under high vacuum for 0.5 h. The yellow residue was dissolved in 50 mL of $CH_2Cl_2$, cooled to 0° C., and treated dropwise with 7.8 mL (95.14 mmol) of propylamine(very exothermic) followed by 7 mL of pyridine to sponge up excess HCl. The reaction solidified and was treated with 1:1 $CH_2Cl_2$/water (200 mL) and allowed to stir until everything was in solution. The organics were washed with water (2×), dried ($NaSO_4$) and evaporated to provide a yellow solid. Purification by crystallization from hot methanol resulted in 4.0 g (33%) of title compound as a pale yellow solid.

mp 198°–200° C.

B.

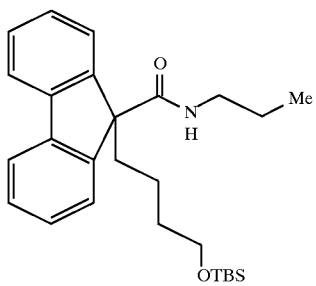

B(1).

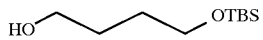

To a solution of 49 mL (0.55 mol) of 1,4-butanediol in 25 mL of DMF, under argon at 0° C., was added 10.5 g (0.15 mol) of imidazole followed by 20.7 g (0.14 mol) of t-butyldimethylsilyl chloride. The reaction was slowly warmed to RT and stirred for 18 h at which time the reaction was diluted with ether and washed with $NH_4Cl$, water, $Na_2CO_3$, brine and dried ($MgSO_4$). The resulting colorless title compound in the form of a liquid, 50 g, contained approximately 15% of the disilylated compound.

B(2).

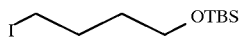

To a solution of 8.5 g (42 mmol) of Part B(1) compound in 50 mL of THF, under argon at 0° C., was added 7.3 g (108 mmol) of imidazole and 16.7 g (64 mmol) of triphenylphosphine. This mixture was stirred for 45 min (solution became homogeneous) at which time 16.2 g (64 mmol) of iodine in 50 mL of THF was added dropwise over 20 min. The reaction was stirred for 1 h, diluted with hexanes and washed with 1M sodium bisulfite, $Na_2CO_3$, brine and dried ($Na_2SO_4$). The resulting residue was triturated with ether (3×), filtered (to remove triphenylphosphine oxide) and evaporated to provided 10 g (61%) of title compound as a pale yellow oil.

B(3).

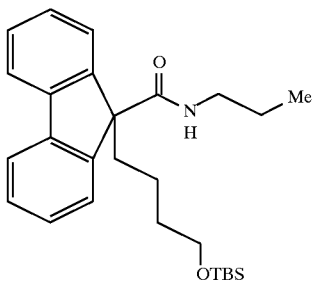

To a mixture of 300 mg (1.20 mmol) of Part A compound in 10 mL of THF, under argon at 0° C., was added dropwise 960 mL (2.40 mmol) of n-BuLi (2.5M in hexanes). The resulting orange dianion was stirred at 0° C. for 0.5 h at which time 452 mg (1.44 mmol) of Part B(2) compound was added dropwise. The reaction was warmed to RT and was stirred for 18 h at which time it was treated with a 1:1 mixture of ethyl acetate/water. The organics were dried ($Na_2SO_4$), evaporated and flash chromatographed on 50 g of silica gel eluting with 4:1 hexanes/ethyl acetate to provide 460 mg (87%) of title compound as a pale yellow solid.

C.

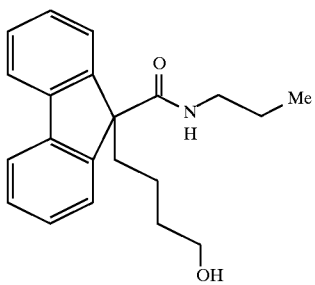

To 5.6 g (12.80 mmol) of Part B compound was added 14.1 mL (14.10 mmol) of 1M tetrabutylammonium fluoride in THF. The reaction was stirred, under argon at RT, for 18 h at which time it was diluted with ether and quenched with $NH_4Cl$. The organics were washed with water, brine, dried ($Na_2SO_4$) and evaporated. Flash chromatography was performed on 250 g of silica gel eluting with 95:5 dichloromethane/isopropanol to provide 4.09 g (99%) of title compound as a white solid.

mp 73°–75° C.

D.

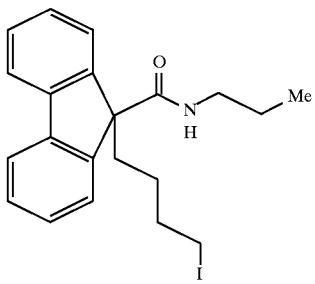

To a solution of 1 g (3.10 mmol) Part C compound in 20 mL of THF, under argon at 0° C., was added 463 mg (6.81 mmol) of imidazole followed by 1.0 g (4.03 mmol) of triphenylphosphine. The mixture became homogeneous after 15 min at which time 1.0 g ( 4.03 mmol) of iodine in 20 mL of THF was added dropwise over 20 min. The reaction was warmed to RT and was stirred for 1 h at which time it was diluted with hexanes and the organics were washed with sodium bisulfite, NaHCO$_3$, brine and dried (Na$_2$SO$_4$). Flash chromatography was performed on 100 g of silica gel eluting with 1:1 hexanes/ethyl acetate to provide 1.1 g (85%) of title compound as a colorless oil.

E. 9-[3-[4-(2,3-Dihydro-1-oxo-1H-isoindol-2-yl)-1-piperidinyl]propyl]-N-propyl-9H-fluorene-9-carboxamide To a solution of 330 mg (0.76 mmol) of Part D compound in 5 mL of DMF, under argon at RT, was added 210 mg (1.52 mmol) of K$_2$CO$_3$ followed by 198 mg (0.76 mmol) of Example 2 Part A compound. The mixture was stirred at RT for 72 h, at which time the reaction was diluted with ether and washed with water, brine, dried (Na$_2$SO$_4$) and evaporated. Recrystallization was attained from hot hexanes to provide 270 mg (68%) of title compound as a white solid. mp 136°–138° C.

Anal. Calcd. for C$_{34}$H$_{39}$N$_3$O$_2$: C, 78.28; H, 7.53; N, 8.05 Found: C, 78.11; H, 7.62; N, 8.09.

EXAMPLE 310A

Alternate synthesis of Example 310 hydrochloride salt

To a solution of Example 314 free amine (12 g, 23.1 mmol) in absolute EtOH (400 mL) was added 10% palladium on activated carbon (1.2 g). The mixture was hydrogenated on a Parr apparatus at 40 psi for 2 h, then filtered through Celite. The filtrate was concentrated in vacuo to provide a colorless oil. The product was dissolved in MeOH (100 mL) and 1.0M HCl in Et$_2$O (20 mL, 20 mmol) was added dropwise. The reaction was stirred for 10 min then concentrated in vacuo. The residue was taken up in CH$_3$CN (2 mL) and water (25 mL) was added. The slightly cloudy solution was lyophilized overnight to give title compound (11.1 g, 86%) as a white lyophilate.

Analysis Calcd. for C$_{34}$H$_{39}$N$_3$O$_2$·1.3HCl·1.6H$_2$O: C, 68.24; H, 7.33; N, 7.02; Cl, 7.76
Found: C, 68.27; H, 7.31; N, 6.99; Cl, 7.77.

EXAMPLE 311

2,3-Dihydro-2-[1-[4-oxo-4-(9-propyl-9H-fluoren-9-yl)butyl]-4-piper-idinyl]-1H-isoindol-1-one, monohydrochloride

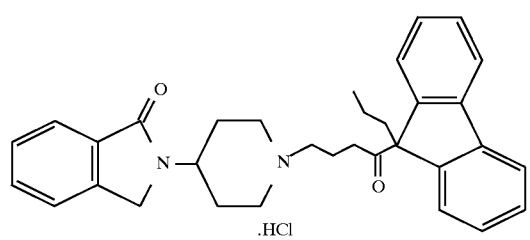

A.

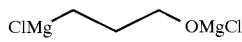

To a stirred solution of 28.55 g (301.9 mmol) of 3-chloro-1-propane (Aldrich) in 300 mL of THF at –20° C. under argon was added 101 mL (303 mmol) of 3.0M methyl magnesium chloride in THF dropwise over 20 min. After 0.5 h at –20° C., the reaction was allowed to warm to room temperature and 11.0 g (452.8 mmol) of magnesium turnings were added and the reaction was heated to reflux. At the start of reflux, 0.60 mL (6.94 mmol) of 1,2-dibromoethane was added and after 1 h at reflux another 0.60 mL was added. After 2 h at reflux the reaction was allowed to cool to room temperature.

B.

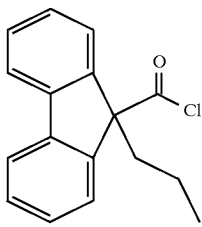

B(1). 9-Propyl-9H-fluorene-9-carboxylic acid

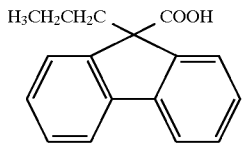

A solution of 9-fluorenecarboxylic acid (12 g, 57 mmol) in 250 ml of THF was cooled to 0° C. under an argon atmosphere and 2 equiv. (71.25 ml) of a 1.6M n-butyl lithium solution in hexane was added followed by the addition of n-propyl iodide (7.5 ml, 13.1 g, 77 mmol). The reaction mixture was stirred at 0° C. for 6 hrs. An additional 1 ml of n-propyl iodide was added and the reaction stirred for 4 hrs at 0° C. The reaction was quenched by adding 75 ml of water and the pH was adjusted to pH 1 with 3N HCl. The reaction mixture was extracted with hexane (3×200ml) and the hexane extract washed with water, brine and dried over anhy. sodium sulfate. The solvents were evaporated yielding the crude product as a yellow oil which was dissolved in ~250 ml of ethanol and heated at reflux with Darco G-60, filtered through Celite and concentrated to approximately one half of the original volume. Water was slowly added until the mixture became cloudy. The mixture was reheated and slowly allowed to cool to room temperature yielding 10.5 grams (73%) of title compound as colorless crystals.
m.p.120°–122° C.

B(2).

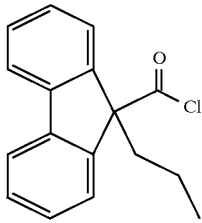

A solution of oxalyl chloride (4.5 mL, 8.93 mmol) was added over 5 min. to a solution of Part B(1) compound in CH$_2$Cl$_2$ (10 mL) containing 2 drops of DMF. The reaction was stirred at RT for 2 h, then concentrated in vacuo to give 1.6 g of the crude acid chloride as a dark yellow solid.

C.

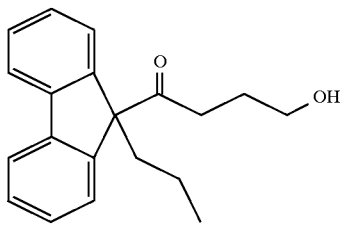

A solution of Part B compound (1.07 g, 3.97 mmol) in THF (10 mL) under argon was cooled to 0° C. Copper (I) iodide (38 mg, 0.20 mmol) was added followed by dropwise addition of Part A compound (14.5 mL, 0.3M in THF, 4.37 mmol) over 10 min. Upon addition, a deep red color appeared but quickly dissipated with stirring. The opaque yellow reaction was stirred at 0° C. for 45 min, then quenched by addition of saturated NH$_4$Cl (10 mL). The reaction was diluted with water (10 mL) and extracted with EtOAc (3×30 mL). The combined organic layers were washed with saturated NH$_4$Cl, water, and brine (10 mL each), then dried over MgSO$_4$. Evaporation gave 1.3 g of a yellow oil, which was purified by flash chromatography on silica gel (150 g), loading in 50% EtOAc/hexane, and eluting with 25% EtOAc/hexane to provide title compound (885 mg, 76%) as a colorless oil.

D.

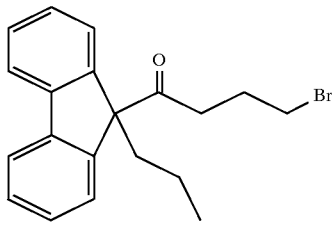

N-Bromosuccinimide (431 mg, 2.42 mmol) was added to a solution of Part C compound (647 mg, 2.20 mmol) and triphenylphosphine (634 mg, 2.42 mmol) in CH$_2$Cl$_2$ (7 mL) at 0° C. under argon. The reaction was stirred at 0° C. for 1 h, diluted with CH$_2$Cl$_2$ (20 mL), and washed with 10% aqueous potassium sulfite (5 mL), water (5 mL), and brine (5 mL), then dried over MgSO$_4$. The mixture was filtered, and to the filtrate was added silica gel (3 g). Evaporation gave a green powder, which was purified by flash chromatography on silica gel (50 g) eluting with 30% CH$_2$Cl$_2$/hexane to provide title compound (733 mg, 93%) as a colorless oil.

E. 2,3-Dihydro-2-[1-[4-oxo-4-(9-propyl-9H-fluoren-9-yl)butyl]-4-piperidinyl]-1H-isoindol-1-one, monohydrochloride A solution of Part D compound (336 mg, 0.941 mmol) and Example 2 Part A compound (225 mg, 1.04 mmol) in absolute ethanol (3 mL) was refluxed under argon overnight (20 h) and cooled to RT, at which time a white solid precipitated. The mixture was concentrated in vacuo, and the resulting residue was partitioned between EtOAc (20 mL) and saturated NaHCO$_3$ (10 mL). The organic layer was washed with water (5 mL) and brine (5 mL), then dried over Na$_2$SO$_4$. Evaporation gave 415 mg of a colorless oil, which was purified by flash chromatography on silica gel (50 g) eluting with 25% acetone/CH$_2$Cl$_2$ to give 205 mg of the desired free amine as a colorless oil.

To a solution of the amine prepared above in Et$_2$O (3 mL) was added 1N HCl/Et$_2$O (3 mL, 3 mmol). The mixture containing a gummy solid was concentrated in vacuo to give a gummy glass. The product was dissolved in isopropanol (2 mL) and hexane (15 mL) was added to precipitate the product. The mixture was concentrated in vacuo to give a foamy solid, which was dried at 60° C. overnight under high vacuum to give title compound (206 mg, 41%) as a white foam.

Anal. Calcd. for C$_{33}$H$_{37}$ClN$_2$O$_2$·H$_2$O: C, 72.27; H, 7.19; N, 5.11; Cl, 6.46

Found: C, 72.36; H, 7.21; N, 5.02; Cl, 6.59.

EXAMPLE 312

(E)-9-[4-[4-(1,3-Dihydro-1-oxo-2H-isoindol-2-yl)-1-piperidinyl]-2-butenyl-2,7-difluoro-N-(2,2,2-trifluoroethyl)-9H-fluorene-9-carboxamide

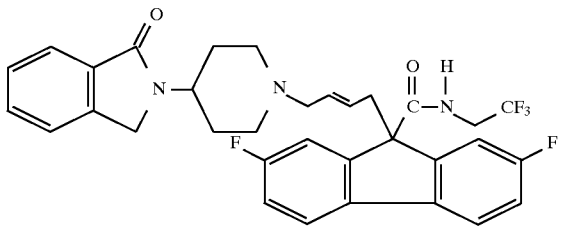

A.

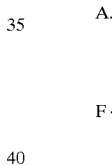

To a THF (25 ml) supension of 2,7-diaminofluorene (Aldrich) (7.17 g, 0.036 mol) at −10° C. under argon was added aqueous HBF$_4$ (71 mL, 1.13 mol, 48–50%). Near the end of addition stirring became difficult due to solid formation, although most of the solid went into solution upon complete addition of acid. A saturated aqueous solution of sodium nitrite (7.1 g in 11 mL, 0.103 mol) was added and after 1.5 h the mixture was filtered, washing with 5% aq. HBF$_4$, MeOH, then ether, and the collected solid dried briefly on the fliter flask. The resulting brown solid (9.7 g) was used in the subsequent reaction.

The above solid was suspended in xylenes (100 ml) and heated to 110° C. for 2 h, with gas evolution observed, then brought to reflux for an additional 2 h. The solution was decanted from a black tar in the reaction flask and the volatiles removed under high vacuum to give a dark tan solid (7.5 g). The solid was crystallized from hot EtOH to give title compound (1.4 g) as a colorless solid. An ether wash of the black tar was combined with the mother liquor and concentrated in vacuo. The oily-solid residue (4.3 g) was purified by flash column chromatography (SiO$_2$, 9 by 16 cm), eluting with hexanes then 2.5% EtOAc:hexanes, to give title compound (2.44 g, total 3.84 g, 52% yield) as a colorless solid.

B.

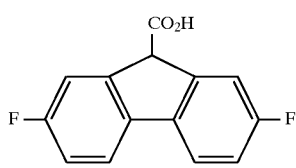

To a THF (15 ml) solution of Part A compound (1.38 g, 6.82 mmol) at −5° C. (ice/brine bath) under argon was added dropwise n-BuLi (3.4 ml, 8.50 mmol, 2.5M in hexanes). After 1.15 h, crushed solid $CO_2$ (excess) was added, followed by $Et_2O$ (~5 ml), and the reaction allowed to stir at room temperature for 19 h. The brown colored reaction mixture was cooled to 0° C., quenched with 2N HCl, and the aqueous layer extracted twice with EtOAc. The combined organics were dried over $Na_2SO_4$ and evaporated in vacuo to give crude title compound (1.64 g), as a colorless solid suitable for the next reaction. Trituration with hexanes can remove unreacted starting material Part A compound.

C.

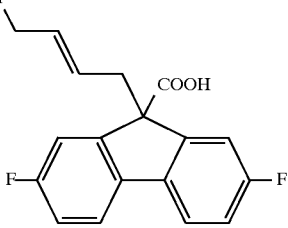

A solution of Part B compound (2,7-difluorofluorene-9-carboxylic acid) (500mg, 2.05 mmol) in 5 ml of THF was cooled to −30° C. under an argon atmosphere and 2 equiv. of a 2.5M solution of n-butyl lithium in hexane (1.64 ml, 4.1 mmol) was added. The mixture was stirred for 5 min. at −30° C. and was then added to a cold (−30° C.) solution of 1,4-dibromo-2-butene (2.14 g, 10 mmol) in 4 ml of THF. The reaction mixture was stirred at −30° C. for 30 min and was then quenched with 1N HCl and extracted with ethyl acetate (3×10 ml). The ethyl acetate extract was washed with water, brine and dried over anhy. sodium sulfate. The crude material was purified on a Merck EM silica column eluting with 5% isopropanol/dichloromethane yielding 480 mg (62%) of title compound as a colorless solid, m.p. 142°–146° C.

D.

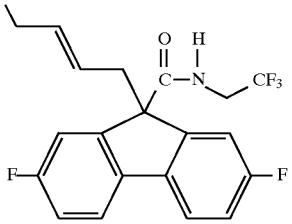

The Part C carboxylic acid (465 mg, 1.23 mmol) was dissolved in 10 ml of dichloromethane and DMF (50 ml) was added. The mixture was cooled to 0° C. under an argon atmosphere and oxalyl chloride (165 mg, 1.3 mmol) was added and the mixture allowed to warm to ambient temperature and stir for 2.5 hrs. The mixture was evaporated several times from dichloromethane yielding the crude acid chloride as a pale yellow solid.

The acid chloride was dissolved in 5 ml of THF and cooled to 0° C. under an argon atmosphere. Triethylamine (142 mg, 1.4 mmol) was added followed by the addition of 2,2,2-trifluoroethyl-amine (139 mg, 1.4 mmol). The reaction was allowed to warm to ambient temperature and stir overnight. The reaction was quenched by adding sat. sodium bicarbonate and extracted with ethyl acetate (3×20 ml). The crude product was purified on a Merck EM silica column eluting with 10% ethyl acetate/hexane yielding 230 mg (38%) of title compound as a pale yellow solid.

E.

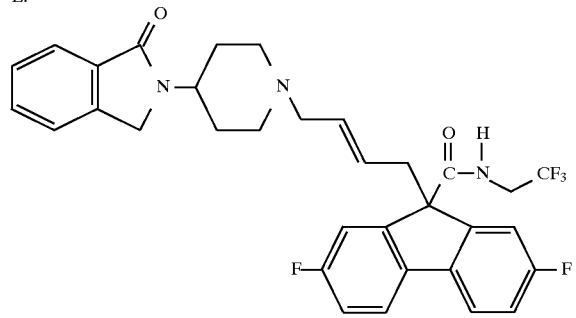

A solution of Part D compound (184 mg, 0.4 mmol) in dimethylformamide (3 ml) was stirred under an argon atmosphere and potassium carbonate (55 mg, 0.4 mmol) was added, followed by the addition of Example 2 Part A compound (95 mg, 0.44 mmol) and the resulting mixture was stirred overnight at ambient temperature. The reaction was diluted with ethyl acetate and washed with water, brine and dried over anhy. sodium sulfate. The solvents were evaporated and the crude residue was purified on a Merck EM silica column eluting with 5% isopropanol/dichloromethane yielding 230 mg (96%) of title compound as a colorless solid.

Anal Calc'd for $C_{33}H_{30}N_3F_5O_2$+1.7 $H_2O$: C, 63.35; H, 5.37; N, 6.72; F, 15.18

Found: C, 63.24; H, 5.34; N, 6.45; F, 15.14.

m.p. 168°–170° C.

EXAMPLE 313

9-[4-[4-(1,3-Dihydro-1-oxo-2H-isoindol-2-yl)-1-piperidinyl]butyl]-2,7-difluoro-N-(2,2,2-trifluoroethyl)-9H-fluorene-9-carboxamide

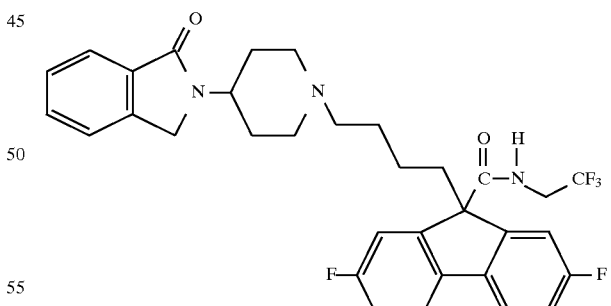

A solution of Example 312 compound (100 mg, 0.17 mmol) in 2 ml of DMF and 2 ml of methanol containing 30 mg of 10% palladium on carbon was stirred under a hydrogen atmosphere (balloon) for 18 hrs. The reaction was filtered through a 0.2 mm nylon filter to remove the catalyst and the solvent evaporated yielding the crude product as a colorless oil. The product was purified on a Merck EM silica column eluting 5% IPA/dichloromethane yielding 91 mg (90%) of title compound as a colorless solid.

m.p. 150°–152° C.

Anal Calc'd for $C_{33}H_{32}N_3F_5O_4+1.75\ H_2O$: C, 63.01; H, 5.69; N, 6.68; F, 15.10
Found: C, 63.05; H, 5.50; N, 6.48; F, 14.99.

EXAMPLE 314

(Z)-9-[4-[4-(2,3-Dihydro-1-oxo-1H-isoindol-2-yl)-1-piperidinyl]-2-butenyl]-N-propyl-9H-fluorene-9-carboxamide, monohydrochloride

A.

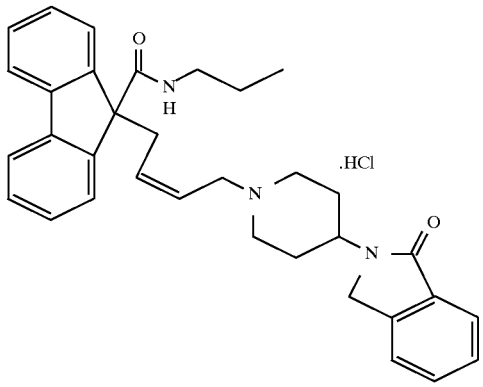

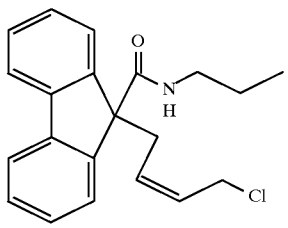

Butyllithium (8.4 mL, 2.5M in hexane, 21 mmol) was added dropwise over 10 min to a solution of fluorenecarboxylic acid (Aldrich Chemical Co.) (2.10 g, 10 mmol) in THF (50 mL) at 0° C. under argon. During addition of the first equivalent of BuLi, the reaction became thick with a white precipitate which became yellow and cleared after addition of the second equivalent. The reaction was stirred at 0° C. for 20 min, then cis-1,4-dichloro-2-butene (1.2 mL, 11 mmol) was added dropwise over 5 min. The reaction lightened in color during addition and was stirred at 0° C. for 3 h, then poured into 1N HCl (50 mL) and extracted with $CH_2Cl_2$ (3×50 mL). The combined organic layers were washed with brine (30 mL) then dried over $MgSO_4$. Evaporation provided 3.5 g of a yellow oil containing crystalline solid. The crude residue was triturated with hexane (20 mL). The supernatant was decanted, and the residue pumped under high vacuum to give 2.93 g of a tan solid.

To a suspension of the crude acid prepared above (1.42 g, 4.77 mmol) and N,N-dimethylformamide (5 drops) in $CH_2Cl_2$ (15 mL) at RT under argon was added oxalyl chloride (3.6 mL, 2.0M in $CH_2Cl_2$, 7.16 mmol). The reaction bubbled for 10 min, then the reaction was stirred at RT for 1.5 h, at which time all solids had dissolved. The reaction was concentrated in vacuo to give an orange oil. The crude acid chloride was dissolved in $CH_2Cl_2$ (15 mL) and cooled to 0° C. Propylamine (1.2 mL, 14.3 mmol) was added dropwise over 1 min, and the reaction was stirred at 0° C. for 10 min. The reaction was partitioned between EtOAc (50 mL) and water (20 mL). The organic layer was washed with 1N HCl (2×20 mL) and brine (20 mL), then dried over $MgSO_4$. Evaporation gave 1.7 g of an orange oil, which was purified by flash chromatography on silica gel (150 g) eluting with $CH_2Cl_2$ to give title compound (1.38 g, 84%) as a pale yellow oil.

B. 9-[4-[4-(2,3-Dihydro-1-oxo-1H-isoindol-2-yl)-1-piperidinyl]-2-butenyl]-N-propyl-9H-fluorene-9-carboxamide, monohydrochloride A mixture of Part A compound (440 mg, 1.30 mmol) and Example 2 Part A compound (337 mg, 1.56 mmol) in DMF (3 mL) under argon was heated at 50° C. overnight, cooled to RT, then the solvent was distilled off under high vacuum at RT. The residue was partitioned between $CH_2Cl_2$ (20 mL) and saturated $NaHCO_3$ (7 mL). The organic layer was washed with brine (5 mL) and dried over $Na_2SO_4$. Evaporation gave 900 mg of a pale yellow oil, which was purified by flash chromatography on silica gel (75 g) eluting with 3% $MeOH/CH_2Cl_2$ to afford 467 mg of the free base as a white foam.

The free amine prepared above was dissolved in MeOH (3 mL) and treated with 1N $HCl/Et_2O$ (3 mL), then concentrated in vacuo. The resulting foam was heated at 50° C. under high vacuum overnight then for 6 h further at 60° C. to give title compound (420 mg, 58%) as a white foamy solid.

Anal. Calcd. for $C_{34}H_{38}ClN_3O_2 \cdot 0.7H_2O$: C, 71.81; H, 6.98; N, 7.39; Cl, 6.23.
Found: C, 71.86; H, 7.34; N, 7.34.; Cl, 6.16.

Following the procedure of Examples 310 to 314, the following additional compounds were prepared.

315. 2,3-Dihydro-2-[1-[2-oxo-2-(9-propyl-9H-fluorene-9-yl)ethyl]-4-piperidinyl]-1H-isoindol-1-one, monohydrochloride

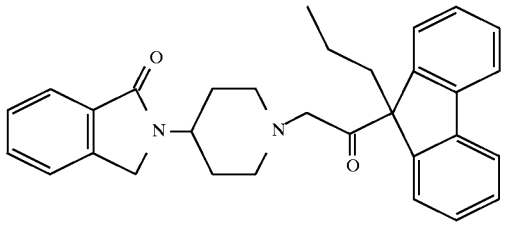

MS (ES) 465 (M+H)
mp 146°–149° C.
Anal. Calcd. for $C_{31}H_{33}ClN_2O_2 \cdot 0.95\ H_2O$:
Calcd: C, 71.85; H, 6.79; N, 5.41
Found: C, 72.29; H, 7.22; N, 5.37.

316. (E)-9-[4-[4-(2,3-Dihydro-1-oxo-1H-isoindol-2-yl)-1-piperidinyl]-2-butenyl]-N-propyl-9H-fluorene-9-carboxamide, monohydrochloride

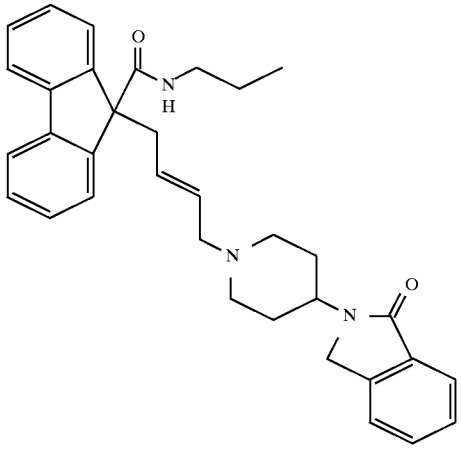

MS(CL) 520 (M+H)
mp 115°–116.5° C.
Anal. Calcd. for $C_{34}H_{37}N_3O_2$

Calcd: C, 78.58; H, 7.18; N, 8.09

Found: C, 78.49; H, 7.26; N, 8.06.

317. 9-[3-[4-(2,3-Dihydro-1-oxo-1H-isoindol-2-yl)-1-piperidinyl]propyl]-N-propyl-9H-fluorene-9-carboxamide

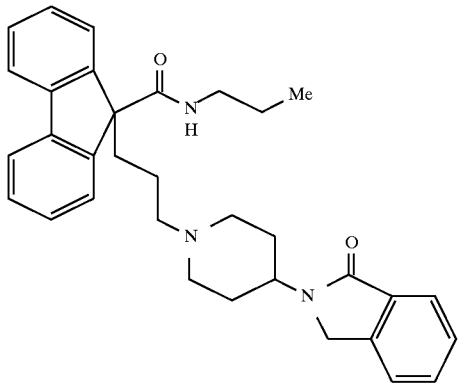

M.S. (ES,+ions) m/e 508 (M+H)

mp 172°–175° C.

Calcd: C, 78.07; H, 7.34; N, 8.28

Found: C, 77.80; H, 7.50; N, 8.10.

EXAMPLE 318

A.

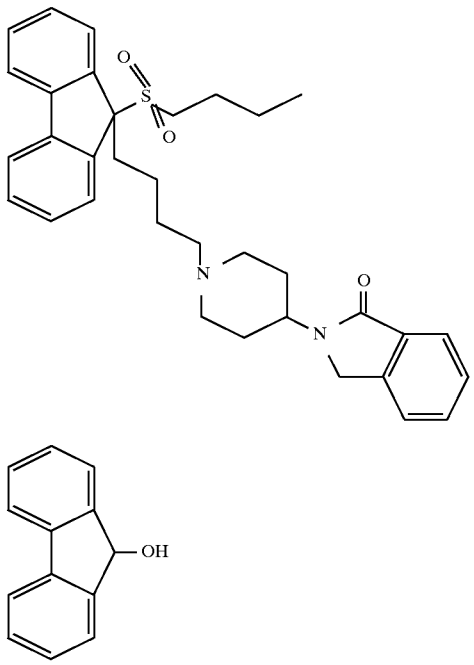

The title compound was purchased from Aldrich Chemical Co.

B.

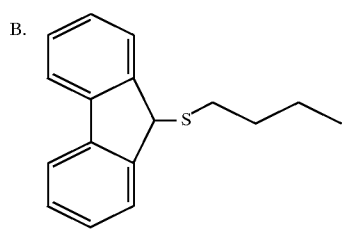

A solution of Part A alcohol (1.58 g, 10.0 mmol) and butanethiol (0.72 g, 8.00 mmol) in 10 mL of dichloromethane at −20° C. was treated with boron triflouride etherate (1.28 g, 9.00 mmol). The reaction was stirred for 1 h at −20° C. and warmed to room temperature. After stirring for 18 h the reaction was concentrated in vacuo, and the crude product was purified by column chromatography on silica gel (100 g) with hexanes followed by 1:9 dichloromethane/hexanes to give 1.54 g (75%) of title compound as a colorless oil.

C.

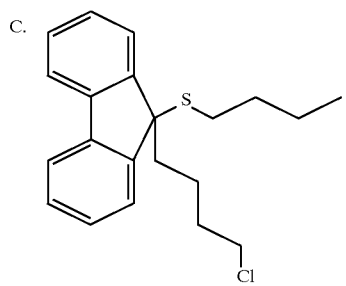

A solution of Part B compound (1.0 g, 3.93 mmol) in 10 mL of THF at −78° C. was treated with n-butyllithium in hexanes (1.75 mL, 4.40 mmol) followed by 1-chloro-4-bromo-butane (0.81 g, 4.70 mmol). The reaction was stirred for 0.5 h and warmed to room temperature for 18 h. The reaction was diluted with 30 mL of aqueous $NH_4Cl$ solution and 30 mL of ethyl acetate. The organic fraction was dried ($Na_2SO_4$) and concentrated. The crude product was purified by column chromatography on silica gel (50 g) with 2:98 acetone/dichloromethane (500 mL) followed by 15:85 dichloromethane/hexanes to give 1.00 (73%) of title compound as a colorless oil.

D.

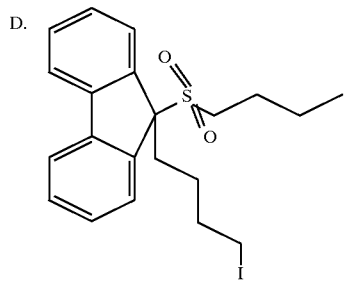

To a solution of Part C sulfide (0.30 g, 0.86 mmol) in dichloromethane (5 mL) at 0° C. was added 3-chloroperoxybenzoic acid (0.37 g, 80% by weight ≈0.1.72 mmol) in one portion. The mixture was stirred for 1 h then partitioned between 0.1M $K_2CO_3$ (20 mL) and ether (30 mL). The organic fraction was dried ($Na_2SO_4$) and concentrated. The crude product was purified by column chromatography on silica gel (50 g) with 15:85 ethyl acetate/hexanes to give 0.24 g of sulfone as a colorless oil.

To a solution of the sulfone chloride (0.24 g, 0.64 mmol) in 2-butanone (10 mL) at RT was added sodium iodide (1.00 g, 6.66 mmol) in one portion. The mixture was refluxed for 30 h when it was diluted with water (20 mL) and ether (30 mL). The organic fraction was dried (Na₂SO₄) and concentrated. The crude product was purified by column chromatography on silica gel (50 g) with 15:85 ethyl acetate/hexanes to give 0.24 g (81%) of title compound as a colorless oil.

E.

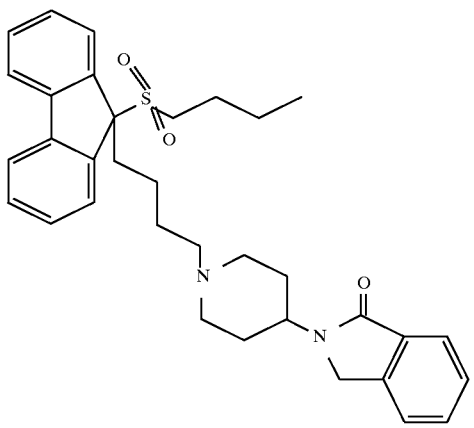

To a stirred solution of 0.70 g (1.49 mmol) of Part D compound in 6 mL of DMF at RT was added 0.38 g (1.80 mmol) of

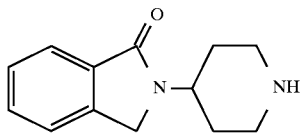

(prepared as described in Example 2). The reaction mixture was warmed to 55° and allowed to stir for 24 h. The mixture was diluted with NaHCO₃ solution (50 mL) and ethyl acetate (50 mL). The layers were separated, the organics dried (Na₂SO₄) and concentrated. The remainder was purified by flash column chromatography on silica gel (100 g) eluting with 5:95 methanol/dichloromethane (700 mL) followed by 5:95:0.5 methanol/dichloromethane/NH₃ (1 L). Pure fractions were pooled and concentrated to give 0.70 g (85%) of title compound as a thick oil which solidified after standing.

m.p. 128°–131° C.

Anal. calcd for C₃₄H₄₀N₂O₃S·0.45 H₂O: C, 72.29; H, 7.30; N, 4.96; S, 5.76

Found: C, 72.25; H, 7.15; N, 5.00; S, 5.69.

EXAMPLE 319

9-[4-[4-[[(1,1-Dimethylethoxy)carbonyl]amino]-1-piperidinyl]butyl]-N-propyl-9H-fluorene-9-carboxamide

A.

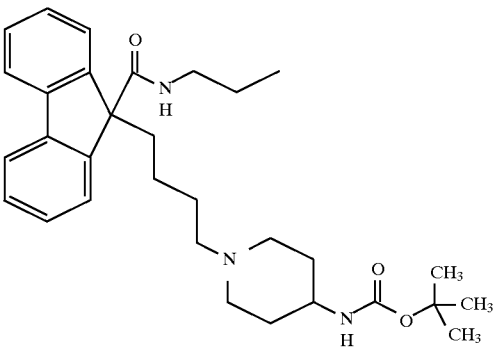

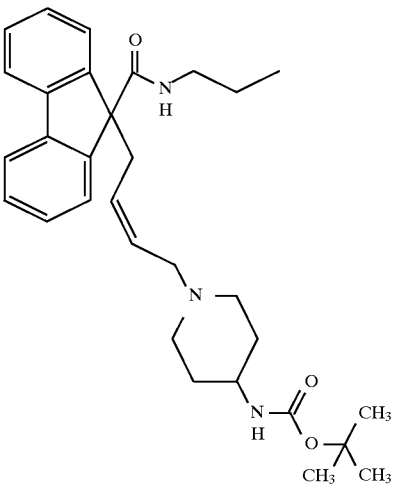

The solution of Example 314 Part A compound (6.0 g, 17.6 mmol) and Example 1 Part B compound (2.88 g, 16.0 mmol) in DMF (3mL) was stirred at 50° C. overnight. Ethyl acetate (150 mL) was added and the organic layer was washed with saturated sodium bicarbonate solution (2×30 mL), water (2×50 mL), brine (2×50 mL) and dried over MgSO₄. Purification was performed by flash chromatography on silica gel (300 g), loaded and eluted with 2.5% methanol in dichloromethane. Pure fractions were combined and evaporated to give title compound(3.0 g, 34%) as a colorless oil.

B. 9-[4-[4-[[(1,1-Dimethylethoxy)carbonyl]-amino]-1-piperidinyl]butyl]-N-propyl-9H-fluorene-9-carboxamide To a solution of Part A compound (3.0 g, 5.89 mmol) in methanol (10 mL) at RT was added palladium on activated carbon (10%, 300 mg). The reaction was hydrogenated (balloon) at RT for 18 h. The reaction was filtered and the filtrate was evaporated to give a white solid. The resulting solid was recrystallized from ethyl acetate/hexane to give title compound (2.90 g, 97%) as a white solid.

m.p. 118°–120° C.

Anal. Calc. for C₃₁H₄₃N₃O₃·2.4 H₂O: C, 67.83; H, 8.78; N, 7.65

Found: C, 67.45; H, 8.33; N, 7.52

EXAMPLE 320

N-[2-[4-(1,3-Dihydro-1-oxo-2H-isoindol-2-yl)-1-piperidinyl]ethyl]-9-propyl-9H-fluorene-9-carboxamide

A.

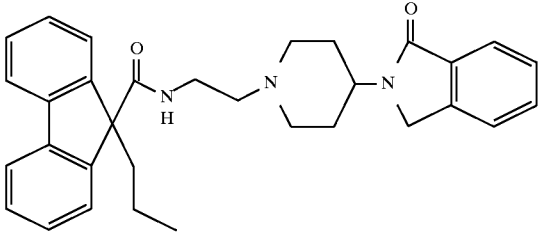

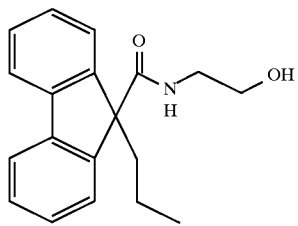

To a CH₂Cl₂ (30 ml) solution of Example 311 Part B(1) compound (2 g, 7.93 mmol) under nitrogen was added 1,1'-carbonyldiimidazole (1.35 g, 8.32 mmol). After 1 h, ethanolamine (0.486 g, 7.95 mmol) was added, followed by DMF (1.5 mL) to aid solubility of the amine, and the reaction allowed to stir at room temperature overnight. After 24 h, the reaction mixture was diluted with saturated NaHCO₃ and the aqueous layer extracted twice with CH₂Cl₂. The combined organics were washed with H₂O, dried over Na₂SO₄ and evaporated in vacuo to give an oily residue (2.55 g). The residue was purified by flash column chromatography (SiO₂, 350 mL), eluting with 30% EtOAc:CH₂Cl₂, to give title compound (1.73 g, 74% yield) as a colorless solid.

B.

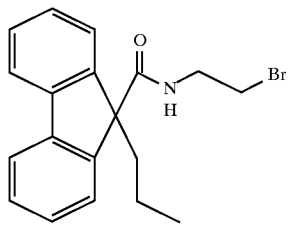

To a CH₂Cl₂ (30 ml) solution of Part A compound (1.4 g, 4.74 mmol) at 0° C. under argon was added triphenylphosphine (1.39 g, 5.30 mmol) and N-bromosuccinimide (0.930 g, 5.22 mmol) and the reaction allowed to stir for 2 h. The reaction mixture was diluted with CH₂Cl₂ and the poured into 10% aqueous sodium bisulfite. The aqueous layer was extracted 4 times with CH₂Cl₂, the combined organics dried over Na₂SO₄, and evaporated in vacuo to give an oily brown colored residue (3.4 g). The residue was purified by flash column chromatography (SiO₂, 5 by 18.5 cm), eluting with 4:1 CH₂Cl₂:hexanes to give title compound (1.52 g, 89.5% yield) as a colorless solid.

C. N-[2-[4-(1,3-Dihydro-1-oxo-2H-isoindol-2-yl)-1-piperidinyl]ethyl]-9-propyl-9H-fluorene-9-carboxamide A DMF (1.5 ml) solution of Part B compound (520 mg, 1.45 mmol) and Example 2 Part A compound (315 mg, 1.45 mmol) under argon was stirred for 1 h, followed by the addition of K₂CO₃ (200 mg, 1.45 mmol) and DMF (0.5 ml). After 24 h, the reaction was partitioned between saturated NaHCO₃ and EtOAc. The aqueous layer was extracted with EtOAc, CHCl₃, and twice with CH₂Cl₂. The combined organics were dried over Na₂SO₄ and the volatiles were removed in vacuo to give an oily-solid residue (720 mg). The residue was purified by flash column chromatography (SiO₂, 5 by 8 cm), eluting with 1% MeOH:CH₂Cl₂ then 5% MeOH:CH₂Cl₂, to give title compound (184 mg, 25% yield) as a colorless solid. mp 219°–221° C.

Anal. Calc. for C₃₂H₃₅N₃O₂·0.32 H₂O:
C, 76.97 H, 7.19; N 8.42
Found: C, 76.88; H, 7.16; N, 8.51.

EXAMPLE 321

9-[4-[4-[[2-(Phenoxyphenyl)carbonyl]amino]-1-piperidinyl]butyl]-N-propyl-9H-fluorene-9-carboxamide

A.

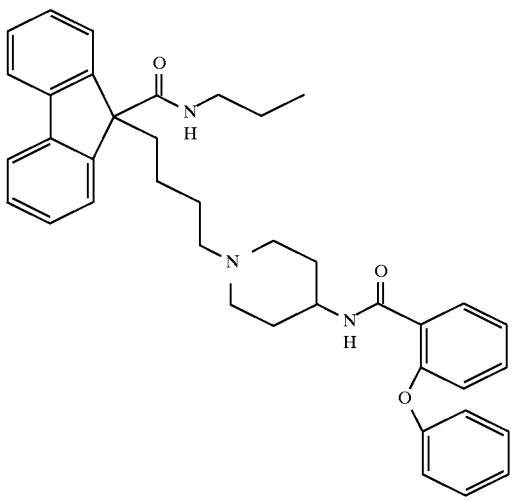

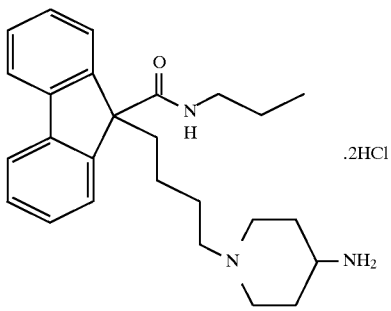

To a solution of Example 319 Part A compound (2.65 g, 5.20 mmol) in dioxane (10 mL) at RT was added a solution of hydrochloric acid in dioxane (4N, 10 mL, 40 mmol). The reaction was stirred at RT for 3.5 h. The reaction was evaporated to give a white solid. The resulting solid was recrystallized from methanol/water to give title compound (2.4 g, 97%) as a white solid.

m.p. 156°–160° C.

Anal. Calc. for C₂₆H₃₇Cl₂N₃O·1.1 H₂O: C, 62.67; H, 7.93; N, 8.43

Found: C, 62.63; H, 7.87; N, 8.46.

B. 9-[4-[4-[[2-(Phenoxyphenyl) carbonyl]-amino]-1-piperidinyl]butyl]-N-propyl-9H-fluorene-9-carboxamide To a solution of 2-phenoxybenzoic acid (purchased from Aldrich) (500 mg, 2.33 mmol) and DMF (1 drop) in dichloromethane (10 mL) at RT was added dropwise a solution of oxalyl chloride in dichloromethane (2.0M, 1.28 mL, 2.56 mmol). Bubbling of escaping gasses continued for 10 min after addition. The reaction was stirred at RT for 60 min, then concentrated in vacuo to give a crude oil. To a solution of crude acid chloride and triethylamine (1.14 mL, 8.16 mmol) in dichloromethane (10 mL) at 0° C. under argon was added dropwise a solution of Part A compound (1.12 g, 2.33 mmol) in dichloromethane (2 mL). The reaction was stirred at 0° C. for 30 min. Ethyl acetate (100 mL) was added to dilute the reaction and the resulting solution was washed with H$_2$O (2×30 mL), brine (2×30 mL) and dried over MgSO$_4$. Evaporation gave a crude gum. Purification was performed by flash chromatography on silica gel (100 g), loaded and eluted with 2.5% methanol in dichloromethane. Pure fractions were combined and evaporated to give a coloress gum. The resulting product was triturated with ethyl ether to give title compound (720 mg, 51%) as a white solid.

m.p. 149°–152° C.

Anal. Calc. for C$_{39}$H$_{43}$N$_3$O$_3$·0.2 H$_2$O: C, 77.38; H, 7.23; N, 6.94

Found: C, 77.37; H, 7.39; N, 6.89.

EXAMPLES 322 to 329

Following the procedures set out in Examples 309 to 321, the following compounds of the invention were prepared.

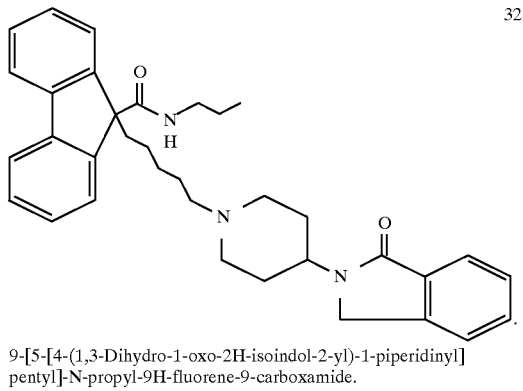

322

9-[5-[4-(1,3-Dihydro-1-oxo-2H-isoindol-2-yl)-1-piperidinyl]pentyl]-N-propyl-9H-fluorene-9-carboxamide.

m.p. 146°–148° C.

MS (ES, +ION): 536 (M+H)

Anal. Calcd. for C$_{35}$H$_{42}$ClN$_3$O$_2$·1.8 H$_2$O: C, 69.76; H, 7.29; N, 6.97; Cl, 5.88

Found: C, 69,70; H, 7.39; N, 7.00; Cl, 5.74.

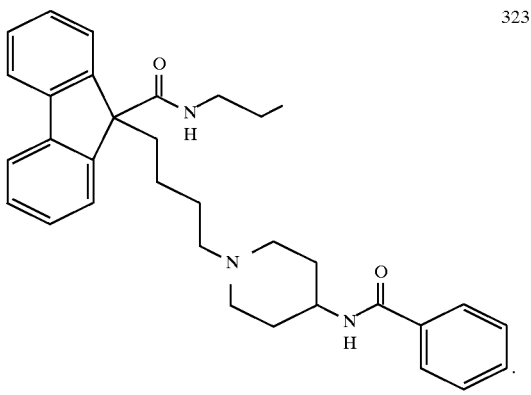

323

9-[4-[4-(Benzoylamino)-1-piperidinyl]butyl]-N-propyl-9H-fluorene-9-carboxamide.

m.p. 157°–160° C.

MS (Cl, +ion) (M+H) 510

Anal. Calcd. for C$_{33}$H$_{39}$N$_3$O$_2$·0.5 H$_2$O: C, 76.41; H, 7.77; N, 8.10

Found: C, 76.37; H, 7.70; N, 8.02.

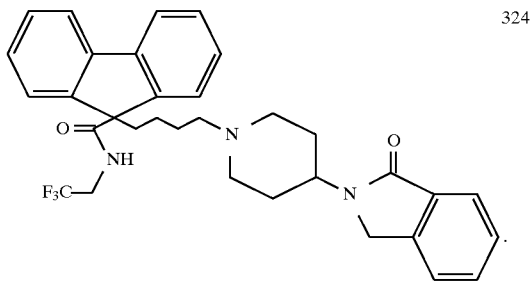

324

9-[4-[4-(2,3-Dihydro-1-oxo-1H-isoindol-2-yl)-1-piperidinyl]butyl]-N-(2,2,2-trifluoroethyl)-9H-fluorene-9-carboxamide m.p. 143°–146° C.

MS (ES, +ions) m/z 562 (M+H)

Anal. Calcd. for C$_{33}$H$_{34}$N$_3$F$_3$O$_2$: C, 70.57; H, 6.10; N, 7.48; F, 10.15

Found: C, 70.04; H, 6.18; N, 7.34; F, 9.87.

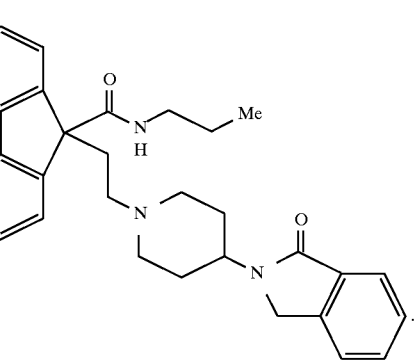

325

9-[2-[4-(2,3-Dihydro-1-oxo-1H-isoindol-2-yl)-1-piperidinyl]ethyl]-N-propyl-9H-fluorene-9-carboxamide, monohyrochloride.

-continued

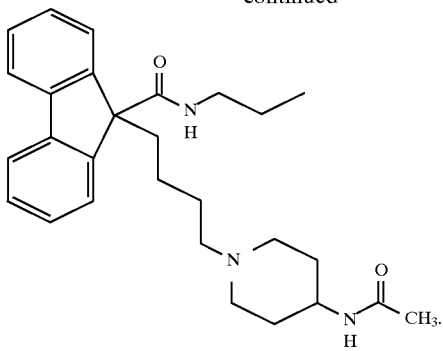

9-[4-[4-(Acetylamino)-1-piperidinyl]butyl]-N-propyl-9H-fluorene-9-carboxamide.

m.p. 133°–135° C.
MS (Cl, +ion) (M+H) 448
Anal. Calcd. for $C_{28}H_{37}N_3O_2 \cdot 1.0$ $H_2O$: C, 72.23; H, 8.44; N, 9.02
Found: C, 71.94; H, 7.90; N, 8.88.

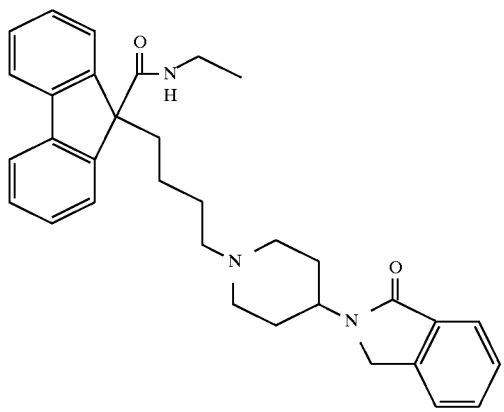

N-Ethyl-9-[4-[4-(2,3-dihydro-1-oxo-1H-isoindol-2-yl)-1-piperidinyl]butyl]-9H-fluorene-9-carboxamide m.p. 137°–140° C.
MS (Cl, M+H$^+$) m/z 508$^+$
Anal. Calcd. for $C_{33}H_{37}N_3O_2 \cdot 0.29$ $H_2O$: C, 77.27; H, 7.39; N, 8.19
Found: C, 77.05; N, 7.38; N, 8.41.

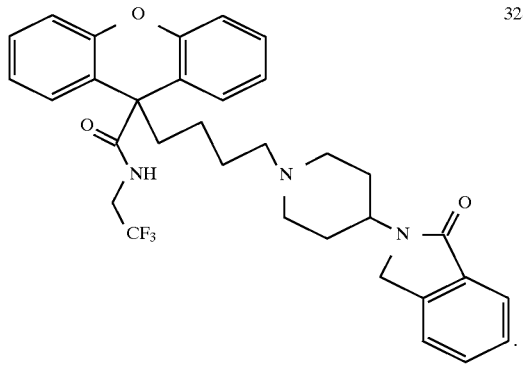

9-[4-[4-(2,3-Dihydro-1-oxo-1H-isoindol-2-yl)-1-piperidinyl]butyl]-N-2,2,2-trifluoroethyl-9H-xanthene-9-carboxamide.

m.p. 164°–166° C. (dec)

M.S. (FAB) m/z 578 (M+H)

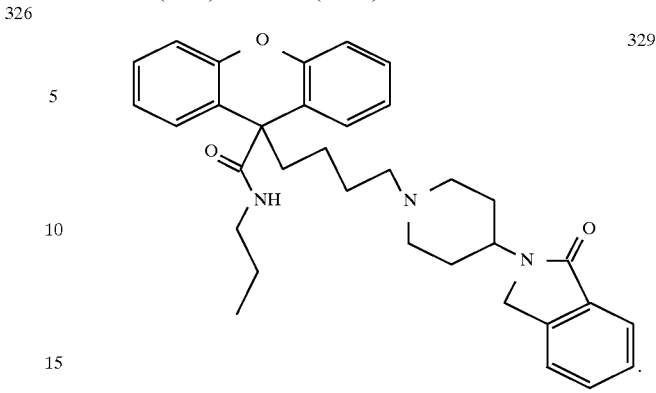

9-[4-[4-(2,3-Dihydro-1-oxo-1H-isoindol-2-yl)-1-piperidinyl]butyl]-propyl-9H-xanthene-9-carboxamide.

m.p. 62°–65° C.

Anal. Calcd. for $C_{34}H_{39}O_3N_3+0.5$ $H_2O$: C, 74.70; H, 7.37; N, 7.69

Found: C, 74.45; H, 7.32; N, 7.56

EXAMPLE 330

2-[1-(3,3-Diphenylpropyl)-4-piperidinyl]-1H-isoindol-1,3(2H)-dione, monohydrochloride

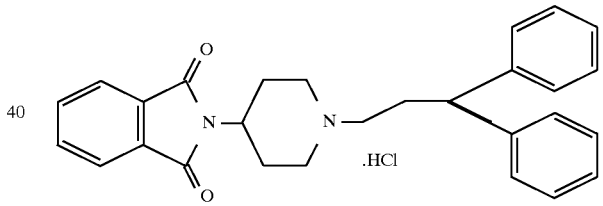

A solution of Example 1 Part E compound (320 mg, 1.08 mg) in $CH_2Cl_2$ (5 mL) was washed with saturated $NaHCO_3$ (2×2 mL) then dried over $Na_2SO_4$. Evaporation gave the free amine which was combined with phthalic anhydride (160 mg, 1.08 mmol) and heated at 125° C. for 30 min. The reaction was allowed to cool to RT, and the resultant glass was purified by flash chromatography on silica gel (50 g) eluting with 2.5% MeOH/$CH_2Cl_2$ to provide the free base as a white solid. A solution of the free base in MeOH (0.5 mL) was treated with 1N HCl in $Et_2O$ (1 mL) then concentrated in vacuo. The product was pumped under high vacuum to give the title compound (85 mg, 17%) as a white solid.

m.p. 218°–222° C.

Anal. Calc. for $C_{28}H_{29}ClN_2O_2 \cdot 1.2$ $H_2O$: C, 69.98; H, 6.56; N, 5.80; Cl, 7.35

Found: C, 69.83; H, 6.50; N, 5.71; Cl, 7.42.

EXAMPLE 331

9-[4-[4-(2,3-Dihydro-1,3-dioxo-1H-isoindol-2-yl)-1-piperidinyl]butyl]-N-propyl-9H-fluorene-9-carboxamide, monohydrochloride.

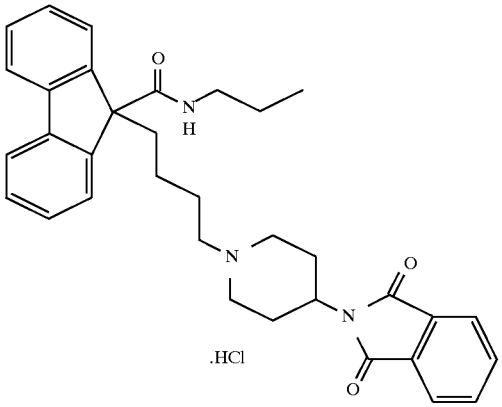

A solution of Example 321 Part A compound (500 mg, 1.05 mmol), diisopropylethylamine (0.4 mL, 2.31 mmol) and phthalic anhydride (170 mg, 1.15 mmol) in toluene (3 mL) was refluxed for 5 h, then cooled to RT. Dichloromethane (80 mL) was added and the solution was washed with water (2×30 mL), brine (2×30 mL) and dried over MgSO$_4$. Purification was performed by flash chromatography on silica gel (50 g), loaded and eluted with 2.5% methanol in dichloromethane. Pure fractions were combined and evaporated to give a white solid. The resulting product was dissolved in ethyl ether (5 mL) and a solution of hydrochloric acid in ethyl ether (0.77M, 2.0 mL) was added. The reaction was stirred at RT for 10 min, then evaporated to dryness. The product was dried in a vacuum oven (50° C., 18 h) to give title compound (440 mg, 73%) as a white solid.

m.p. 125°–130° C.

Anal. Calc. for $C_{34}H_{38}ClN_3O_3 \cdot 1.3$ H$_2$O: C, 68.57; H, 6.87; N, 7.06; Cl, 5.95

Found: C, 68.71; H, 6.66; N, 7.01; Cl, 5.82.

EXAMPLE 332

9-[4-[4-(2,3-Dihydro-1-oxo-1H-isoindol-2-yl)-1-piperidinyl]butyl]-N-propyl-9H-indeno[2,1-b]-pyridine-9-carboxamide

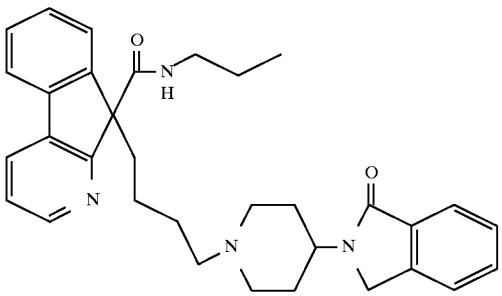

A.
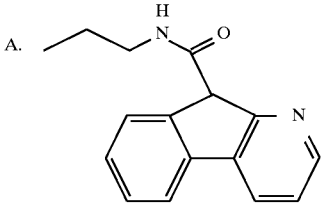

A THF (5 ml) solution of 1-aza-fluorene (233 mg, 1.39 mmol; prepared from benzo(f)quinoline by known procedures, Kloc, K. *Journal f. prakt. Chemie,* 319, 959–967 (1977) and Kloc, K. *Heterocycles,* 9, 849–852 (1978)) and n-propylisocyanate (0.13 ml, 1.39 mmol) was degassed three times by cooling to −78° C., evacuating, and allowing to warm to room temperature, and finally purging with argon. To the degassed solution at −10° C. was added dropwise sodium bis(trimethylsilyl)amide (1.4 ml, 1M in THF). After 5 min, a second portion of n-propylisocyanate (0.13 ml, 1.39 mmol) was added to the red solution. The now green colored reaction mixture was quenched after a further 15 min with saturated NH$_4$Cl. The aqueous layer was extracted with EtOAc, the organics washed with brine, dried over Na$_2$SO$_4$ and evaporated in vacuo to give a red colored oily-solid residue (535 mg). The residue was purified by flash column chromatography (SilicAR" buffered silica gel, 5 by 7 cm), eluting with 20% EtOAc:CH$_2$Cl$_2$, and flushing with 5% MeOH:CH$_2$Cl$_2$ to give title compound (202 mg, 58% yield) as an orange colored solid. mp 131°–133° C.

B. 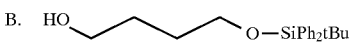

To a THF (100 ml) suspension of sodium hydride (4 g, 60% oil dispersion, 0.10 mol) at 18° C. (cool water bath) under argon is added 1,4-butanediol. After stirring at room temperature for 14 h, t-butylchlorodiphenylsilane (26 mL, 0.1 mol) was added in rapid drops. The reaction was quenched after 30 min with H$_2$O and the aqueous layer was extracted with hexanes. The organic layer was dried over Na$_2$SO$_4$ and evaporated to an oil (33 g). The residue was purified by flash column chromatography (silica gel, 10 by 26 cm), eluting with CH$_2$Cl$_2$, 5, 7.5, and then 10% EtOAc:CH$_2$Cl$_2$ to give title compound (24.5 g, 74%) as a colorless oil.

C. 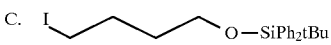

To a THF (70 ml) solution of Part B compound (5.48 g, 0.0167 mol), triphenylphosphine (4.3 g, 0.0164 mol), and imidazole (2.49 g, 0.0366 mol) at 0° C. was added a THF (15 ml) solution of iodine (4.23 g, 0.0167 mol) over 10 min. After 1 h at room temperature, the reaction was cooled to 0° C. and quenched with 5% aqueous sodium bisulfite. The mixture was diluted with H$_2$O and hexanes, the organic layer washed with H$_2$O, saturated NaHCO$_3$, and brine. The organic layer was dried over Na$_2$SO$_4$ and evaporated to an oily-solid. The residue was triturated with hexanes, cooled to 0° C., filtered and the volatiles removed in vacuo to give an oil (7.35 g). This residue was purified by flash column chromatography (SilicAR buffered silica gel, 5 by 10 cm), eluting with 30% CH$_2$Cl$_2$: hexanes to give title compound (6.2 g, 84%) as a colorless oil.

D.

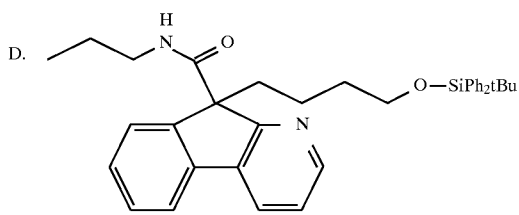

A THF (9 ml) solution of Part A compound (400 mg, 1.58 mmol) was degassed three times by cooling to −78° C., evacuating, and allowing to warm to room temperature, and finally purging with argon. To the degassed solution at 0° C. was added dropwise n-BuLi (1.3 ml, 2.5M in hexanes). After several minutes, Part C compound (0.63 ml, 1.82 mmol) was added to the red solution. The now brown colored reaction mixture was quenched after a further 1 h with saturated NH$_4$Cl. The aqueous layer was extracted twice with EtOAc, the organics dried over Na$_2$SO$_4$, and evaporated in vacuo to give an orange colored oil (1.07 g). The residue was purified by flash column chromatography (SilicAR" buffered silica gel, 5 by 8.5 cm), eluting with 8% EtOAc:CH$_2$Cl$_2$ to give title compound (817 mg, 92%) as a colorless oil.

E.

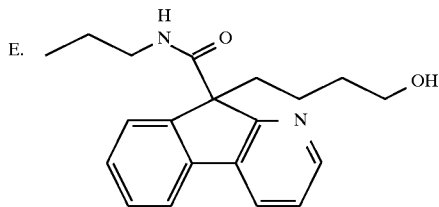

To a THF (3.5 ml) solution under argon of Part D compound (800 mg, 1.42 mmol) was added dropwise tetrabutylammonium fluoride (1.5 ml, 1M in THF). After 2 h, a second portion of tetrabutylammonium fluoride (0.15 ml, 1M in THF) was added and the reaction mixture was allowed to stir a further 1 h. The reaction mixture was partitioned between H$_2$O and EtOAc. The aqueous layer was extracted 3 times with EtOAc, and the organics washed with brine. The first organic layer contained less ammonium salts and was dried over Na$_2$SO$_4$, and evaporated in vacuo to give an oil (885 mg). The residue was purified by flash column chromatography (SilicAR" buffered silica gel, 90 g), eluting with 4.5% MeOH:CH$_2$Cl$_2$ to give title compound (437 mg, 95%) as a colorless oil.

F.

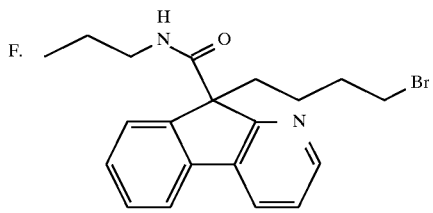

To a CH$_2$Cl$_2$ (5 ml) solution of Part E compound (231 mg, 0.712 mmol) and triphenylphosphine (285 mg, 1.09 mmol) at 0° C. under argon was added N-bromosuccinimide (153 mg, 0.860 mmol). After 2.15 h, a second portion of N-bromosuccinimide (18 mg, 0.101 mmol) was added and the reaction stirred 45 min at 0° C. and 15 min at room temperature. The reaction mixture was then quenched with 10% sodium bisulfite and the aqueous layer extracted twice with CH$_2$Cl$_2$. The combined organics were washed with brine, dried over Na$_2$SO$_4$, and evaporated in vacuo to give an oily-solid residue (653 mg). The residue was purified by flash column chromatography (SilicAR" buffered silica gel, 68 g), eluting with 10.5% EtOAc:CH$_2$Cl$_2$ to give the unstable title compound (217 mg, 78%) as a colorless oil.

G.

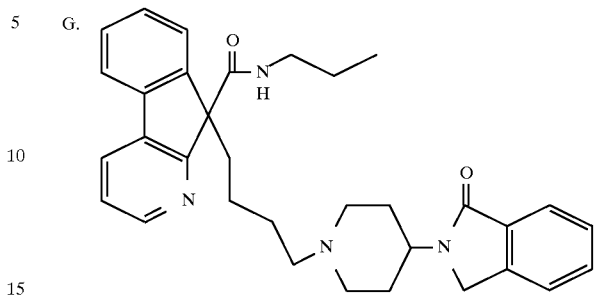

To a DMF (1.6 ml) solution of Part F compound (180 mg, 0.465 mmol) and Example 2 Part A compound (135 mg, 0.624 mmol) under argon was added K$_2$CO$_3$ (65 mg, 0.47 mmol). After 18.15 h, the purple colored reaction was partitioned between dilute NaHCO$_3$ and EtOAc. The aqueous layer was extracted twice with EtOAc, the combined organics were washed with H$_2$O, brine, dried over Na$_2$SO$_4$, and the volatiles were removed in vacuo to give a purple colored oil (230 mg). The residue was purified by flash column chromatography (SilicAR" buffered silica gel, 26.5 g), eluting with 5 then 6% MeOH:CH$_2$Cl$_2$, to give title compound (83 mg, 34% yield) as a colorless foam. Additional title compound was obtained as a mixture (96 mg, 92% pure by HPLC, 72% yield)

mp 52°–54° C.

MS: (electrospray, M+H$^+$): m/z 523$^+$.

EXAMPLE 333

2,3-Dihydro-2-[1-[4-hydroxy-4-(9-propyl-9H-fluoren9-yl)butyl]-4-piperidinyl]-1H-isoindol-1-one

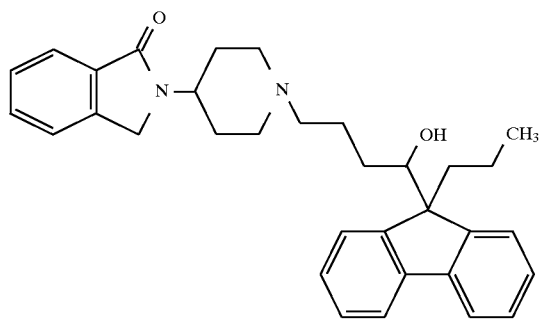

A solution of Example 311 Part D free amine (300 mg, 0.61 mmol) in 12 ml of methanol was cooled to 0° C. under an argon atmosphere and 2 equiv. of sodium borohydride (48.5 mg, 1.28 mmol) was added. The reaction mixture was stirred at 0° C. for 45 min. The reaction was quenched with 1N hydrochloric acid and extracted with ethyl acetate (3×20 ml). The extract was washed with brine and dried over sodium sulfate. Evaporation yielded an oily residue which was dissolved in dichloromethane, dried over sodium sulfate and evaporated to yield 550 mg of a colorless solid. The crude product was purified on a Merck EM silica column eluting with 5% methanol/dichloromethane yielding 290mg (96%) of title compound as colorless solid.

m.p. 75°–78° C.

MS(CI) m/z 495 (M+H).

EXAMPLE 334

2,3-Dihydro-2-[1-[3-[(9-propyl-9H-fluoren-9-yl)-thio]propyl]-4-piperidinyl]-1H-isoindol-1-one

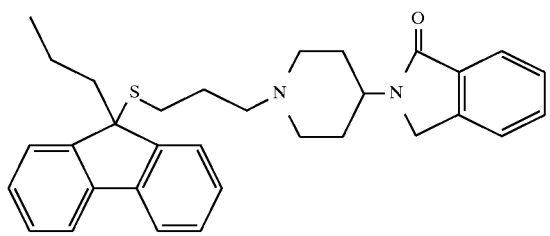

A.

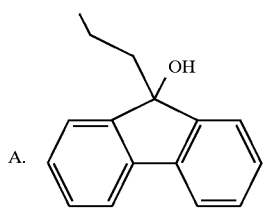

To a THF (100 ml) solution of fluoren-9-one (9.12 g, 0.051 mol) at −10° C. under argon was added dropwise n-propylmagnesium chloride (25.4 ml, 2M in ether). After 1.15 h, the orange colored reaction mixture was quenched with saturated $NH_4Cl$. The aqueous layer was extracted twice with EtOAc, the organics washed with brine, dried over $Na_2SO_4$ and evaporated in vacuo to give an oily-solid residue (11.1 g). The residue was purified by crystallization from EtOH:$H_2O$ to give title compound contaminated with 14% by weight 9-hydroxyfluorene (4 g, 30% yield) as a colorless solid. Material was sufficiently pure for the subsequent reaction.

B.

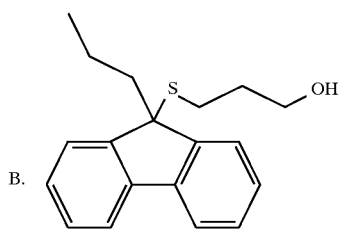

To an AcOH (25 ml) solution of Part A compound (3.64 g, 0.014 mol) and methyl 3-mercaptopropionate (1.62 ml, 0.015 mol) under argon is added concentrated $H_2SO_4$ (7 drops). After stirring at room temperature for 24 h, the reaction was concentrated to ⅓ the original volume and diluted with $H_2O$. The aqueous layer was extracted with EtOAc and the organic layer washed with 1N NaOH. The basic wash was extracted 3 times with EtOAc, the combined organics extracted with brine, dried over $Na_2SO_4$ and evaporated to an oily-solid of the structure (B1)

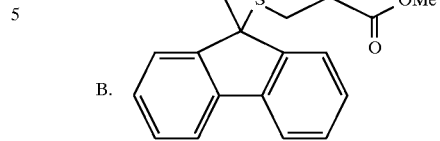

B.

(5.55 g). (Compound B(1) was sufficiently pure for the subsequent reaction. Rf=0.49 (25% EtOAc:hexanes).

To an EtOH (15 ml) solution of compound B(1) (385 mg, 0.956 mmol) was added $NaBH_4$ (470 mg, 0.012 mol). After stirring overnight, the reaction mixture was cooled to 0° C. and quenched with saturated $NH_4Cl$. The aqueous layer was extracted with EtOAc, the organic layer washed with brine, dried over $Na_2SO_4$ and evaporated to an oily residue (390 mg). This residue was purified by flash column chromatography (silica gel, 3 by 10 cm), eluting with 3% EtOAc:$CH_2Cl_2$ to give title compound (110 mg, 38% yield from Part A compound) as a colorless oil.

C.

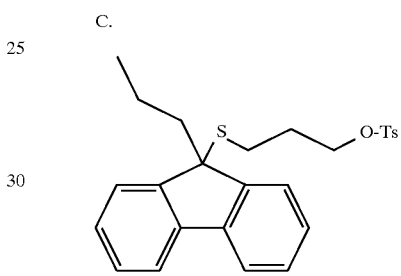

To a pyridine (0.75 ml) solution of Part B compound (110 mg, 0.369 mmol) at 0° C. was added p-toluenesulfonyl chloride (80 mg, 0.42 mmol) and the reaction slowly allowed to come to room temperature. After 4 h and 7.5 h, more p-toluenesulfonyl chloride (60 and then 40 mg, 0.52 mmol) was added at room temperature and the reaction was stirred at 5° C. overnight. A final portion of p-toluenesulfonyl chloride (40 mg, total 1.15 mmol) was then added and the reaction stirred at room temperature for 8 h. The reaction mixture was partitioned between EtOAc and saturated $NaHCO_3$. The aqueous layer was extracted 3 times with EtOAc, the organic layer washed with brine, dried over $Na_2SO_4$ and evaporated to an oily-solid (200 mg). This residue was preabsorbed onto Celite and purified by flash column chromatography (silica gel, 3 by 8 cm), eluting with 15% EtOAc:hexanes to give title compound (110 mg, 66% yield) as a colorless oil.

D.

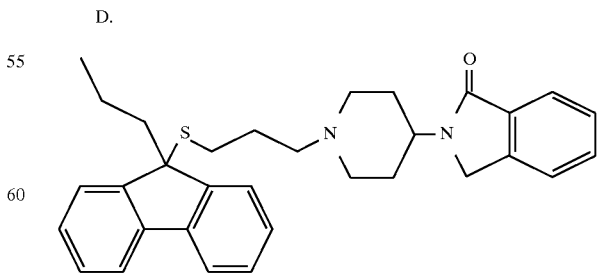

A mixture of Part C compound (102 mg, 0.227 mmol), Example 2 Part A compound (64 mg, 0.296 mmol), and $K_2CO_3$ (34 mg, 0.246 mmol) in isopropanol (1.5 ml) under argon was refluxed for 6 h. After cooling, the reaction was partitioned between saturated NaHCO$_3$ and EtOAc. The aqueous layer was extracted twice with EtOAc, the combined organics were dried over Na$_2$SO$_4$ and the volatiles were removed in vacuo to give an oil (126 mg). The residue was combined with another crude residue from an identical reaction using 48.6 mmol of Part C compound (146 mg total). The mixture was purified by flash column chromatography (silica gel, 3 by 5.5 cm), eluting with 4% MeOH:CH$_2$Cl$_2$ to give impure title compound (108 mg). The mixture was further purified by flash column chromatography (silica gel, 12 g), eluting with 4% MeOH:CH$_2$Cl$_2$ to give title compound (101 mg, 74% yield) as an oily foam.

MS: (electrospray, M+H$^+$): m/z 497$^+$.

Anal. Calcd. for C$_{32}$H$_{36}$N$_2$OS·0.26 H$_2$O: C, 76.64; H, 7.34; N, 5.59

Found: C, 76.73; H, 7.27; N, 5.51.

EXAMPLE 335

2,3-Dihydro-2-[1-[3-[(9-propyl-9H-fluoren-9-yl)-sulfonyl]propyl]-4-piperidinyl]-1H-isoindol-1-one

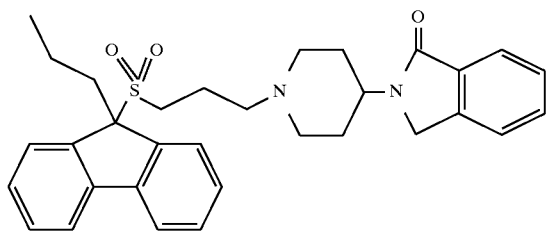

A.

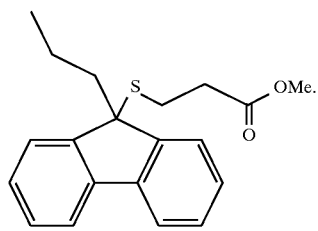

To an AcOH (25 ml) solution of Example 334 Part A compound (3.64 g, 0.014 mol) and methyl 3-mercaptopropionate (1.62 ml, 0.015 mol) under argon is added concentrated H$_2$SO$_4$ (7 drops). After stirring at room temperature for 24 h, the reaction was concentrated to ⅓ the original volume and diluted with H$_2$O. The aqueous layer was extracted with EtOAc and the organic layer washed with 1N NaOH. The basic wash was extracted 3 times with EtOAc, the combined organics extracted with brine, dried over Na$_2$SO$_4$ and evaporated to an oily-solid (5.55 g, >100% recovery).

To a CH$_2$Cl$_2$ (25 ml) solution of crude compound prepared above (1 g, 2.63 mmol) at 0° C. under argon was added 3-chloroperoxybenzoic acid (1.41 g, 6.13 mmol, 75%) and the reaction brought to room temperature. After 1.45, 4.1, and 6 h, more 3-chloroperoxybenzoic acid (0.25, 0.3, and 0.2 g, total 9.39 mmol) was added. The reaction was stored at −80° C. after 8 h. After warming, the reaction mixture was partitioned between 1N NaOH and EtOAc. The aqueous layer was extracted twice with EtOAc, the organic layer washed with brine, dried over Na$_2$SO$_4$ and evaporated to an oily-solid residue. This residue was purified by flash column chromatography (silica gel, 5 by 9 cm), eluting with 18% EtOAc:hexanes to give title compound (630 mg, 67% yield from Example 334 Part A compound) as a colorless solid. mp 74°–77° C.

Anal. Calc. for C$_{20}$H$_{22}$SO$_4$·0.29 H$_2$O: C, 66.04; H, 6.26; S, 8.81

Found: C, 66.04; H, 6.11; S, 8.45.

B.

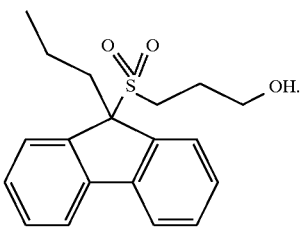

To an EtOH (14 ml) suspension of Part A compound (559 mg, 1.56 mmol) at 0° C. under argon was added NaBH$_4$ (80 mg, 3.36 mmol) and the mixture brought to room temperature. After 1 h, the reaction mixture was cooled to 0° C. and a second portion of NaBH$_4$ (80 mg, 3.36 mmol) was added. After 5 h at room temperature, the reaction mixture was quenched at 0° C. with saturated NH$_4$Cl and the mixture stirred at room temperature for 30 min. The aqueous layer was extracted twice with EtOAc and the combined organic layers were evaporated to an oily residue. This residue was co-evaporated 3 times with MeOH to give 500 mg of oily-solid. After pre-absorbing onto Celite, the residue was purified by flash column chromatography (silica gel, 5 by 7 cm), eluting with 3% MeOH:CH$_2$Cl$_2$ to give title compound (328 mg, 64% yield) as a colorless solid. mp 111.5°–112.5° C.

C.

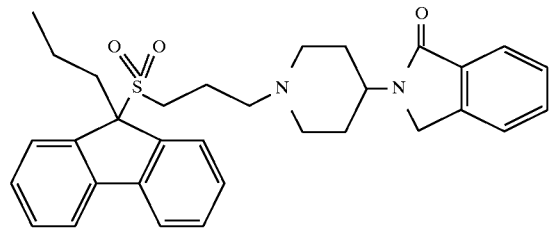

To a CH$_2$Cl$_2$ (5 ml) solution of Part B compound (308 mg, 0.933 mmol) and triphenylphosphine (490 mg, 1.87 mmol) at 0° C. under argon was added N-bromosuccinimide (210 mg, 1.18 mmol). After 2 h, a second portion of N-bromosuccinimide (40 mg, 0.34 mmol) was added and the reaction stirred an additional 1 h. The reaction mixture was then quenched with 10% sodium bisulfite and the aqueous layer extracted twice with EtOAc. The combined organics were washed with H$_2$O, brine, dried over Na$_2$SO$_4$, and evaporated in vacuo to give an oily-solid residue. The residue was purified by flash column chromatography (SilicAR" buffered silica gel, 5 by 9 cm), eluting with 6.7% hexanes:CH$_2$Cl$_2$, then CH$_2$Cl$_2$ to give the unstable Compound C(1) of the structure

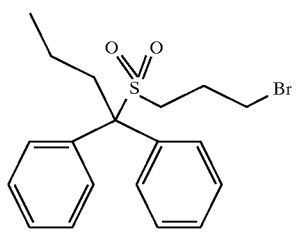

(283 mg, 77% yield) as a colorless solid. mp 83°–86° C.

A DMF (2 ml) solution of Compound C(1) (234 mg, 0.595 mmol) and Example 2 Part A compound (155 mg, 0.717 mmol) under argon was stirred for 15 h. A second portion of Example 2 Part A compound (17 mg, 0.078 mmol) was then added, followed in 4 h by $K_2CO_3$ (33 mg, 0.239 mmol). After 24 h, the cooled reaction mixture was partitioned between saturated $NaHCO_3$ and EtOAc. The aqueous layer was extracted with EtOAc, the organics were washed with brine, dried over $Na_2SO_4$ and the volatiles were removed in vacuo to give an oil (357 mg). The mixture was purified by flash column chromatography (silica gel, 3 by 12.5 cm), eluting with 5% $MeOH:CH_2Cl_2$ to give impure title compound (222 mg), as well as pure title compound (76 mg, contaminated with 10% DMF). The pure title compound was crystallized from EtOAc:hexanes to give title compound (39 mg) as a colorless solid. The impure title compound was further purified by flash column chromatography (silica gel, 24 g), eluting with 5% $MeOH:CH_2Cl_2$ to give title compound (153 mg, 192 mg total, 61% yield). mp dec. 138°–141° C. MS: (electrospray, M+H$^+$) : m/z 529$^+$.

Anal. Calcd. for $C_{32}H_{36}N_2O_3S \cdot 1.01\ H_2O$: C, 70.29; H, 7.01; N, 5.12

Found: C, 70.45; H, 6.60; N, 4.96.

EXAMPLE 336

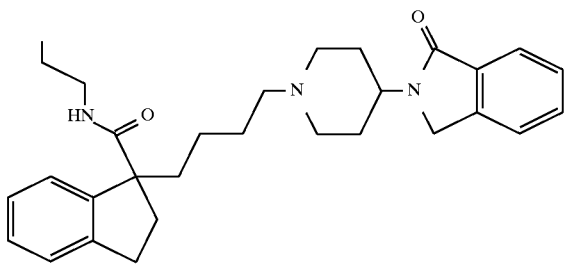

2,3-Dihydro-1-[4-[4-(2,3-dihydro-1-oxo-1H-isoindol-2-yl)-1-piperidinyl]butyl]-N-propyl-1H-indene-1-carboxamide

A.

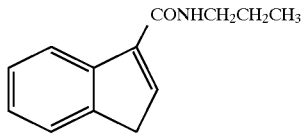

To a stirred slurry of

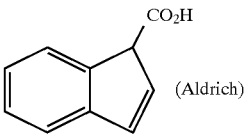

(Aldrich)

(3.20 g, 20.0 mmol) in 20 mL of dichloromethane at room temperature under argon was added 15.0 mL of oxalyl chloride solution (30.0 mmol, 2M in dichloromethane) and then 0.1 mL of DMF. Vigorous gas evolution results in a light yellow solution. After 1 h, the reaction mixture was evaporated at less than 25° C. and the residue was dissolved in 10 mL of THF.

This solution was then added dropwise over 15 minutes to a solution of 3.5 mL of n-propylamine (46 mmol) in 25 mL of THF at –10° C. under argon. After one hour, the reaction mixture was partitioned between ethyl acetate and 10% citric acid solution. The organic extract was dried ($MgSO_4$) and evaporated. Purification by flash chromatography on silica gel (5×20 cm column, 1:2 ethyl acetate/hexanes as elutant) provided title compound as a yellow solid, 2.36 g, 59% yield, mp 123°–125° C.

B.

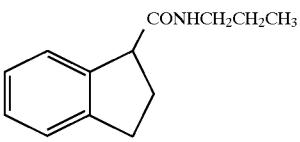

A degassed slurry of Part A compound (1.10 g, 5.47 mmol) and 330 mg of 10% palladium-on-carbon in 25 mL of ethyl acetate at room temperature was stirred under atmospheric pressure hydrogen for 16 h. The reaction was filtered through Celite and evaporated to give title compound as a white solid, 894 mg, 81% mp 61°–63° C.

C.

To a solution of 49 mL (0.55 mol) of 1,4-butanediol in 25 mL of DMF, under argon at 0° C., was added 10.5 g (0.15 mol) of imidazole followed by 20.7 g (0.14 mol) of t-butyldimethylsilyl chloride. The reaction was slowly warmed to RT and stirred for 18 h at which time the reaction was diluted with ether and washed with $NH_4Cl$, water, $Na_2CO_3$, brine and dried ($MgSO_4$). The resulting colorless liquid

50 g, contained approximately 15% of the disilylated compound.

To a solution of 8.5 g (42 mmol) of the above alcohol in 50 mL of THF, under argon at 0° C., was added 7.3 g (108 mmol) of imidazole and 16.7 g (64 mmol) of triphenylphosphine. This mixture was stirred for 45 min (solution became homogeneous) at which time 16.2 g (64 mmol) of iodine in 50 mL of THF was added dropwise over 20 min. The reaction was stirred for 1 h, diluted with hexanes and washed with 1M sodium bisulfite, $Na_2CO_3$, brine and dried ($Na_2SO_4$). The resulting residue was 5 triturated with ether (3×), filtered (to remove triphenylphosphine oxide) and evaporated to provided 10 g (61%) of title iodobutane as a pale yellow oil.

D.

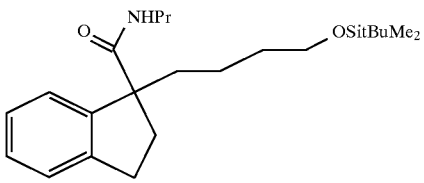

To a stirred solution of diisopropylamine (0.95 mL, 6.8 mmol) in 10 mL of THF at −5° C. under argon was added n-butyllithium solution (2.70 mL, 6.75 mmol, 2.5M in hexane) and stirred for 15 min. A solution of Part B compound (593 mg, 3.38 mmol) in 5 mL of THF was added over 10 min. The resulting deep orange solution was stirred for 30 min and a solution of Part C 1-t-butyldimethyl-silyloxy-4-iodobutane (1.03 g, 3.31 mmol) in 5 mL of THF was added. A light yellow solution forms within 1 hour. The reaction mixture was quenched with saturated sodium bicarbonate solution and extracted twice with ethyl acetate. The organic extracts were combined, dried ($Na_2SO_4$) and evaporated. Purification by flash chromatography on silica gel gave title compound as a colorless oil, 680 mg, 58%.

E.

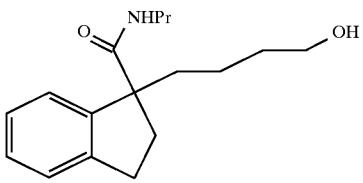

To a solution of Part D compound (675 mg, 1.73 mmol) in 5 mL of THF at room temperature under argon was added a solution of tetrabutylammonium fluoride (3 mL, 3 mmol, 1M in THF). After 1 h, the reaction mixture was partitioned between ethyl acetate and 10% citric acid solution. The organic extract was dried ($MgSO_4$) and evaporated. Purification by flash chromatography on silica gel (2.5×15 cm column, 1:4 hexanes/ethyl acetate) provided title compound as a colorless oil, 380 mg, 80%.

F.

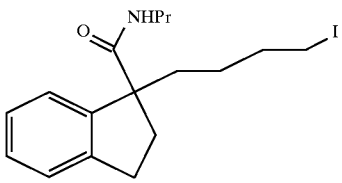

To a solution of Part E compound (380 mg, 1.38 mmol) in 5 mL of THF under argon at room temperature was added triphenylphosphine (365 mg, 1.39 mmol) and imidazole (210 mg, 3.0 mmol) and then iodine (360 mg, 1.39 mmol) in 5 mL of THF. After 15 min, the reaction was quenched with 5% $NaHSO_3$ solution and extracted with ether. The organic extract was dried ($MgSO_4$) and evaporated. Purification by flash chromatography on silica gel (5×15 cm column, 5:7 ethyl acetate/hexanes) gave title compound as a colorless oil, 442 mg, 83%.

G. 2,3-Dihydro-1-[4-[4-(2,3-dihydro-1-oxo-1H-isoindol-2-yl)-1-piperidinyl]butyl]-N-propyl-1H-indene-1-carboxamide To a stirred solution of Part F compound (430 mg, 1.12 mmol) in 5 mL of DMF at room temperature under argon was added Example 2 Part A compound (265 mg, 1.23 mmol). The reaction was heated to 50° C. After 14 h, the reaction was quenched with 10% $NaHSO_3$ solution and extracted with ethyl acetate. The organic extract was dried ($MgSO_4$), evaporated and re-evaporated twice from toluene. Purification by flash chromatography on silica gel (2.5×15 cm column, 1:9 methanol/ethyl acetate) gave title compound as a colorless amorphous solid, 425 mg, 88%.

IR (thin film) 3470, 2940, 1680, 1660, 1530, 1510, 1470, 1455, 740 $cm^{-1}$.

Calculated for $C_{30}H_{39}N_3O_2 \cdot 0.94\ H_2O$:

C, 73.45; H, 8.30; N 8.57

Found: C, 73.44; H, 8.11; N 8.47.

MS (electrospray, +ions) m/e 474 (M+H).

$^1$H NMR (CDCl$_3$, 300 MHz)

δ 7.83 (d, 1H; J=7.3 Hz)

7.52-7.44 (m, 3H)

7.30-7.23 (m, 4H)

5.53 (t, 1H, J=5.5 Hz)

4.35 (s, 2H)

4.30 (5-plet, 1H, J=5.3 Hz)

4.01 (dd, 1H, J=7.2, 7.8 Hz)

3.13 (m, 2H)

3.04 (d, 2H, J=9.8 Hz)

2.92 (t, 2H, J=6.7 Hz)

2.50 (5-plet, 1H, J=5.5 Hz)

2.38 (t, 4H, J=7.7 Hz)

2.18-1.84 (m, 9H)

1.56-1.35 (m, 6H)

EXAMPLE 337

0.81 (t, 3H, J=7.4 Hz) ppm.

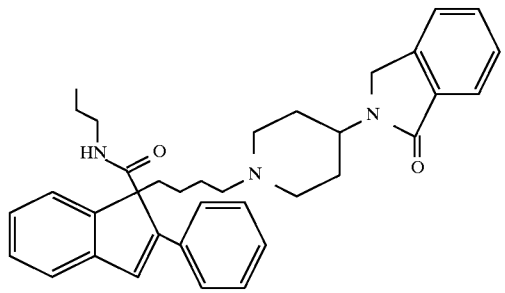

1-[4-[4-(2,3-Dihydro-1-oxo-1H-isoindol-2-yl)-1-piperidinyl]butyl]-2-phenyl-N-propyl-1H-indene-1-carboxamide

A.

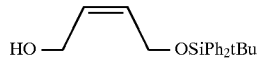

To a slurry of sodium hydride (6.975 g, 60% mineral oil dispersion, 0.174 mol) in 200 mL of THF at room temperature under argon was added 2-butene-1,4-diol (15.36 g, 0.174 mol) over 20 minutes. Gas evolved and a thick precipitate formed. The slurry was stirred for 16 h and then was rapidly treated with t-butyl diphenylchlorosilane (47.82 g, 0.174 mol). The reaction warms to 40° C. autogenously and a clear solution formed. After 15 min, the reaction was quenched with water and extracted twice with hexanes. The organic layers were combined, dried (Na₂SO₄) and evaporated.

Purification by flash chromatography on silica gel (12×30 cm column, dichloromethane) gave title compound as a colorless oil, 46.6 g, 82%.

B.

To a stirred solution of Part A compound (6.53 g, 20.0 mmol) and triethylamine (3.53 mL, 25.3 mmol) in 50 mL of dichloromethane at room temperature under argon was added acetic anhydride (2.4 mL, 22.5 mmol) and DMAP (20 mg, 0.16 mmol). The reaction was evaporated at less than 30° C. and the residue partitioned between 10% citric acid and hexanes. The organic layer was washed with water and saturated sodium bicarbonate solution, dried (Na₂SO₄) and evaporated. The isolated colorless oil, (7.02 g, 95%), was used without further purification in Part F.

C.

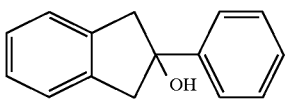

Anhydrous cerium chloride (16.00 g, 64.9 mmol) was stirred in an evacuated flask heated in an oil bath to 145° C. for 2 h. The flask is flooded with argon, cooled to room temperature and then to 0° C. in an ice bath. To this powder was added 150 mL of THF. The stirred slurry was warmed to room temperature. After 14 h, the flask was again cooled to 0° C. and phenylmagnesium chloride solution (21.2 mL, 63.6 mmol, 3M in ether) was added. The resulting yellow slurry was stirred for 1.5 h and then a solution of 2-indanone (5.45 g, 41.2 mmol, freshly chromatographed) was added. After 30 min, the reaction mixture was quenched with 10% citric acid and extracted twice with ether. The organic extracts were dried (MgSO₄) and evaporated. Purification by flash chromatography on silica gel (5×20 cm column, 17:3 dichloro-methane/hexanes) gave title compound as a colorless oil, 6.66 g, 77%.

D.

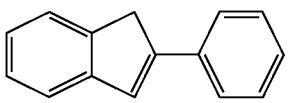

To neat Part C compound (6.40 g, 30.4 mmol) was added potassium bisulfate (6.4 g, 47 mmol). The mixture was stirred under argon and placed in an oil bath heated to 160° C. for 20 min. The resulting solid mass was cooled, partitioned between dichloromethane and water. The organic layer was dried (MgSO₄) and evaporated to provide title compound (5.84 g, 100%) as a white solid, mp 163°–164° C.

E.

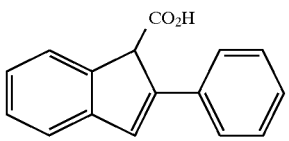

To a solution of Part D compound (1.481 g, 7.70 mmol) in 20 mL of THF at 0° C. under argon was added n-butyllithium (3.0 mL, 7.50 mmol, 2.5M in hexanes) over 10 min. The resulting deep orange solution was stirred for 1 h. The reaction was quenched with several small pieces of THF-washed dry ice. The resulting thick yellow slurry was stirred for 1 h and then treated with 20 mL of 2M potassium hydroxide solution. This solution was extracted twice with ether and the aqueous residue was brought to pH 2 with 3N sulfuric acid. The mixture was extracted three times with ethyl acetate, the extracts combined, dried (MgSO₄) and evaporated to give title compound as a light yellow powder (1.50 g, 82%), mp 212°–215° C.

F.

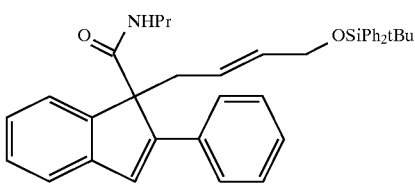

A mixture of Part E compound (890 mg, 3.77 mmol), Part B compound (2.55 g, 3.77 mmol) and triphenylphosphine (190 mg, 0.724 mmol) was evaporated twice from toluene. The mixture was dissolved in 20 mL of THF, stirred under argon and treated with bis(trimethylsilyl)acetamide (BSA) (3.7 mL, 15 mmol). After 30 min, tetrakis(triphenylphosphine)palladium(0) (430 mg, 0.39 mmol) was added and the reaction set to reflux. After 16 h, the orange solution was cooled, evaporated and re-evaporated twice from methanol. The gummy residue was dissolved in ether and washed once with 10% citric acid. The organic extract was dried (MgSO₄), evaporated and re-evaporated once from toluene.

To a stirred solution of this product in 10 mL of dichloromethane under argon at room temperature was added oxalyl chloride (0.9 mL, 7.0 mmol) and then DMF (0.05 mL). After 1 h, the reaction was evaporated to give an orange oil which was dissolved in 10 mL of THF.

This solution was added to a stirred solution of n-propylamine (1.4 mmol, 16 mmol) in 10 mL of THF at 0° C. over 10 min. After 1 h, the reaction mixture was diluted with ether and washed once with 10% citric acid. The organic extract was dried (MgSO₄) and evaporated. Purification by flash chromatography on silica gel (5×20 cm column, dichloromethane) gave title compound as an orange oil, 1.50 g, 77%.

G.

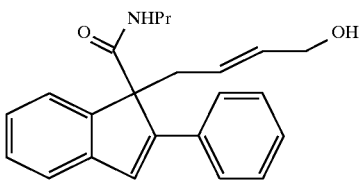

To a stirred solution of Part F compound (2.15 g, 4.18 mmol) in 15 mL of THF at room temperature under argon was added tetrabutyl-ammonium fluoride (10 mL, 10 mmol, 1M in THF). After 1 h, the reaction was quenched with brine and extracted three times with ethyl acetate. The organic extract was dried (MgSO$_4$) and evaporated. Purification by flash chromatography on silica gel (5×15 cm column, 3:2 hexanes/ethyl acetate) gave title compound as a colorless glass, 1.09 g, 75%.

H.

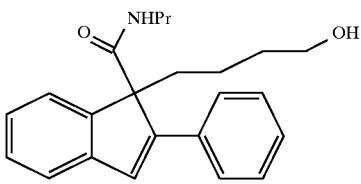

To a solution of Part G compound (209 mg, 0.60 mmol) in 10 mL of ethanol at room temperature purged with argon was added 5% Pd—C (45 mg). The flask is evacuated and purged with argon twice and with hydrogen from a baloon and stirred under a hydrogen atmosphere for 30 min. The reaction was filtered through Celite and the filtrate evaporated. Purification by flash chromatography (2.5×15 cm column, 1:1 hexanes/ethyl acetate) gave title compound as a white foam, 92 mg, 44%.

I.

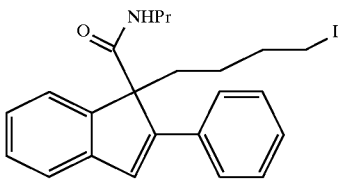

To a stirred solution of Part H compound (90 mg, 0.26 mmol) in 2 mL of THF at room temperature under argon was added triphenylphosphine (68 mg, 0.26 mmol) and imidazole (40 mg, 0.57 mmol) and then iodine (65 mg, 0.26 mmol) in 2 mL of THF. After 10 min, the reaction was quenched with 10% NaHSO$_3$ solution and extracted with ether. The organic extract was dried (MgSO$_4$) and evaporated. Purification by flash chromatography on silica gel (2.5×15 cm column, dichloromethane) gave title compound as a white solid, 87 mg, 73%, mp 125°–127° C.

J. 1-[4-[4-(2,3-Dihydro-1-oxo-1H-isoindol-2-yl)-1-piperidinyl]butyl]-2-phenyl-N-propyl-1H-indene-1-carboxamide To a stirred solution of Part I compound (74 mg, 0.161 mmol) in 2 mL of DMF at room temperature under argon was added Example 2 Part A compound (40 mg, 0.181 mmol). The reaction was heated to 50° C,. After 14 h, the reaction was quenched with 10% NaHSO$_3$ solution and extracted with ethyl acetate. The organic extract was dried (MgSO$_4$), evaporated and re-evaporated twice from toluene. Purification by flash chromatography on silica gel (2.5×15 cm column, 1:12 methanol/ethylacetate) gave title compound as a white solid, 80 mg, 91%, mp 156°–57° C.

IR (KBr pellet) 3326, 2942, 2863, 1678, 1622, 1512, 1454, 1302, 737 cm$^{-1}$.

MICROANALYSIS Calculated for C$_{36}$H$_{41}$N$_3$O$_2$.1.17 H$_2$O:
C, 76.02; H, 7.68; N 7.39
Found: C, 76.02; H, 7.43; N 7.30.
MS (electrospray, +ions) m/e 548 (M+H).
$^1$H NMR (CDCl$_3$, 300 MHz)
δ 7.83 (d, 1H, J=7.6 Hz)
7.56 (d, 2H, J=7.6 Hz)
7.40 (s, 1H)
7.54-7.2 (m, 9H)
5.32 (t, 1H, J=5.8 Hz)
4.30 (d, 1H, J=7.3 Hz)
3.05 (m, 2H)
2.85 (d, 2H)
2.62 (dt, 1H, J=4.2, 9.2 Hz)
2.31 (dt, 1H, J=4.5, 9.2 Hz)
2.06 (m, 2H)
1.94 (m, 2H)
1.71 (m, 4H)
1.26 (m, 4H)
0.59 (t, 3H, J=7.3 Hz)
0.6 (m, 1H)
0.43 (m, 1H) ppm.

EXAMPLE 338

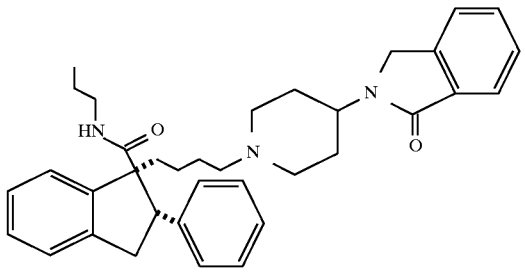

trans-2,3-Dihydro-1-[4-[4-(2,3-dihydro-1-oxo-1H-isoindol-2-yl)-1-piperidinyl]butyl]-2-phenyl-N-propyl-1H-indene-1-carboxamide

A.

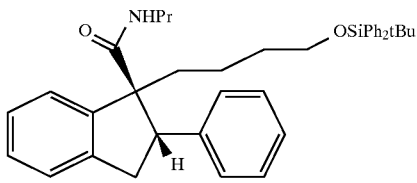

To a solution of 682 mg (1.34 mmol) of compound Example 337 Part F in 10 mL of ethanol at room temperature was added 2 g (32 mmol) of ammonium formate. The slurry was stirred and purged with nitrogen for 20 min. After adding 10% palladium-on-carbon (1 g), the reaction was stirred under argon for 16 h. The reaction mixture was filtered through Celite®, washing with ethyl acetate. The filtrate was washed twice with water and once with brine, dried (MgSO$_4$) and evaporated. Purification by flash chromatography on silica gel (5×15 cm column, 1:99 ether/dichloromethane) gave title compound as a colorless oil, 354 mg, 52%.

B.

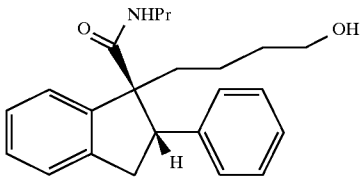

To a stirred solution of Part A compound (315 mg, 0.534 mmol) in 3 mL of THF at room temperature under argon was added tetrabutyl-ammonium fluoride (1.0 mL, 1.0 mmol, 1M in THF). After 1 h, the reaction was quenched with brine and extracted three times with ethyl acetate. The organic extract was dried (MgSO$_4$) and evaporated. Purification by flash chromatography (2.5×15 cm column, 3:5 hexanes/ethyl acetate) gave title compound as a white foam, 135 mg, 72%.

C.

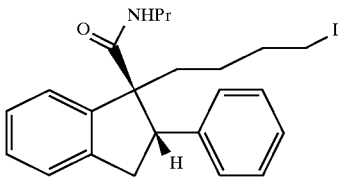

To a stirred solution of Part B compound (127 mg, 0.361 mmol) in 2 mL of THF at room temperature under argon was added triphenylphosphine (95 mg, 0.36 mmol) and imidazole (60 mg, 0.86 mmol) and then iodine (92 mg, 0.36 mmol) in 1 mL of THF. After 15 min, the reaction was quenched with 5% NaHSO$_3$ solution and extracted with ether. The organic extract was dried (MgSO$_4$) and evaporated. Purification by flash chromatography (2.5×15 cm column, dichloromethane) gave title compound as a colorless glass, 101 mg, 61%.

D. trans-2,3-Dihydro-1-[4-[4-(2,3-dihydro-1-oxo-1H-isoindol-2-yl)-1-piperidinyl]-butyl]-2-phenyl-N-propyl-1H-indene-1-carboxamide To a stirred solution of Part C compound (100 mg, 0.217 mmol) in 3 mL of DMF at room temperature under argon was added Example 2 Part A compound (54 mg, 0.244 mmol). The reaction was heated to 50° C. After 14 h, the reaction was quenched with 10% NaHSO$_3$ solution and extracted with ethyl acetate. The organic extract was dried (MgSO$_4$), evaporated and re-evaporated twice from toluene. Purification by flash chromatography on silica gel (2.5×15 cm column, 1:9 hexane/ethyl-acetate) gave title compound as a light yellow amorphous glass, 105 mg, 88%.
IR (KBr pellet) 3432, 2934, 2872, 1676, 1516, 1470, 1454, 766, 737 cm$^{-1}$.
MICROANALYSIS Calculated for $C_{36}H_{43}N_3O_2 \cdot 1.54\ H_2O$:
C, 74.87; H, 8.04; N 7.64
Found: C, 74.88; H, 7.82; N 7.33.
MS (electrospray, +ions) m/e 550.5 (M+H).
$^1$H NMR (CDCl$_3$, 300 MHz)
δ 7.82 (d, 1H, J=7.3 Hz)
7.51-7.14 (m, 12H)
5.66 (t, 1H, J=5.2 Hz)
4.33 (m, 2H)
4.26 (dd, 1H, J=0.7, 3.6 Hz)
4.01 (dd, 1H, J=7.2, 7.8 Hz)
3.28 (m, 4H)
2.95 (d, 2H, J=10.7 Hz)
2.24 (m, 2H)
2.12 (t, 2H, J=11.1 Hz)
1.80 (m, 4H)
1.53-1.16 (m, 8H)
0.88 (t, 3H, J=7.3 Hz) ppm.

Additional compounds falling within the scope of the present invention are described by the following structures. Substituents for each example are identified in the table following each structure.

TABLE B

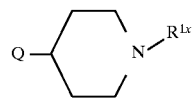

where $R^{1x}$ is (a), (b), (c), (d) or (e) as in Table A

Examples of Q

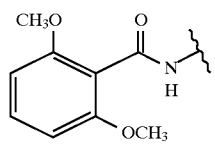 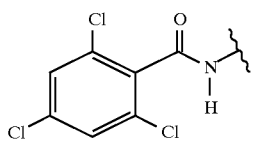 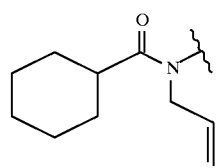

TABLE B-continued
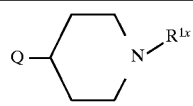
where $R^{1x}$ is (a), (b), (c), (d) or (e) as in Table A
Examples of Q
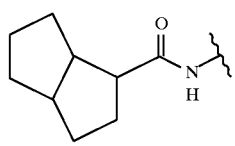 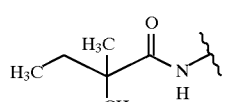 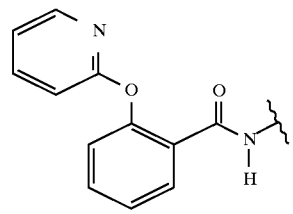
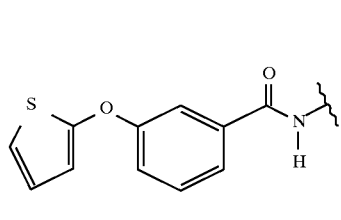 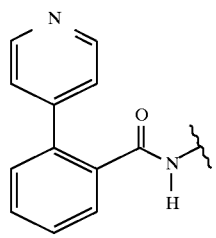 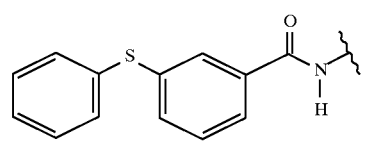
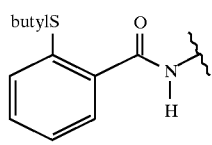 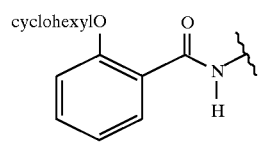 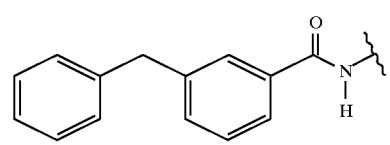
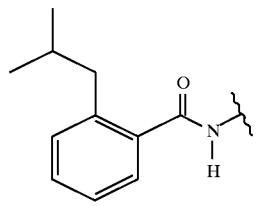 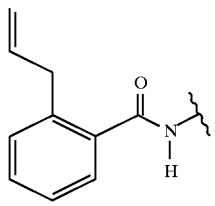 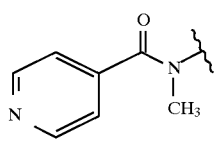
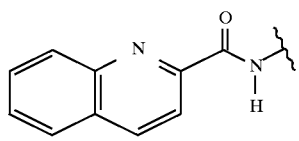 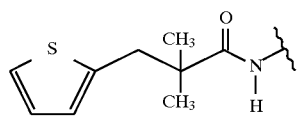 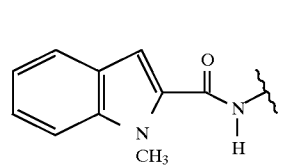
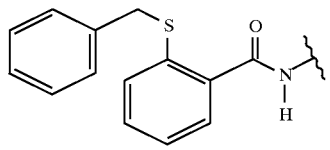 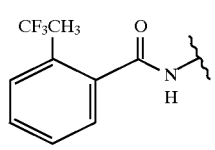 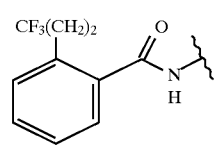
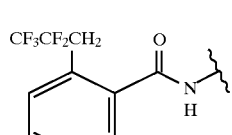 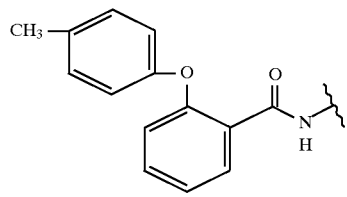 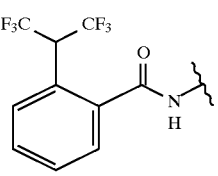

TABLE C
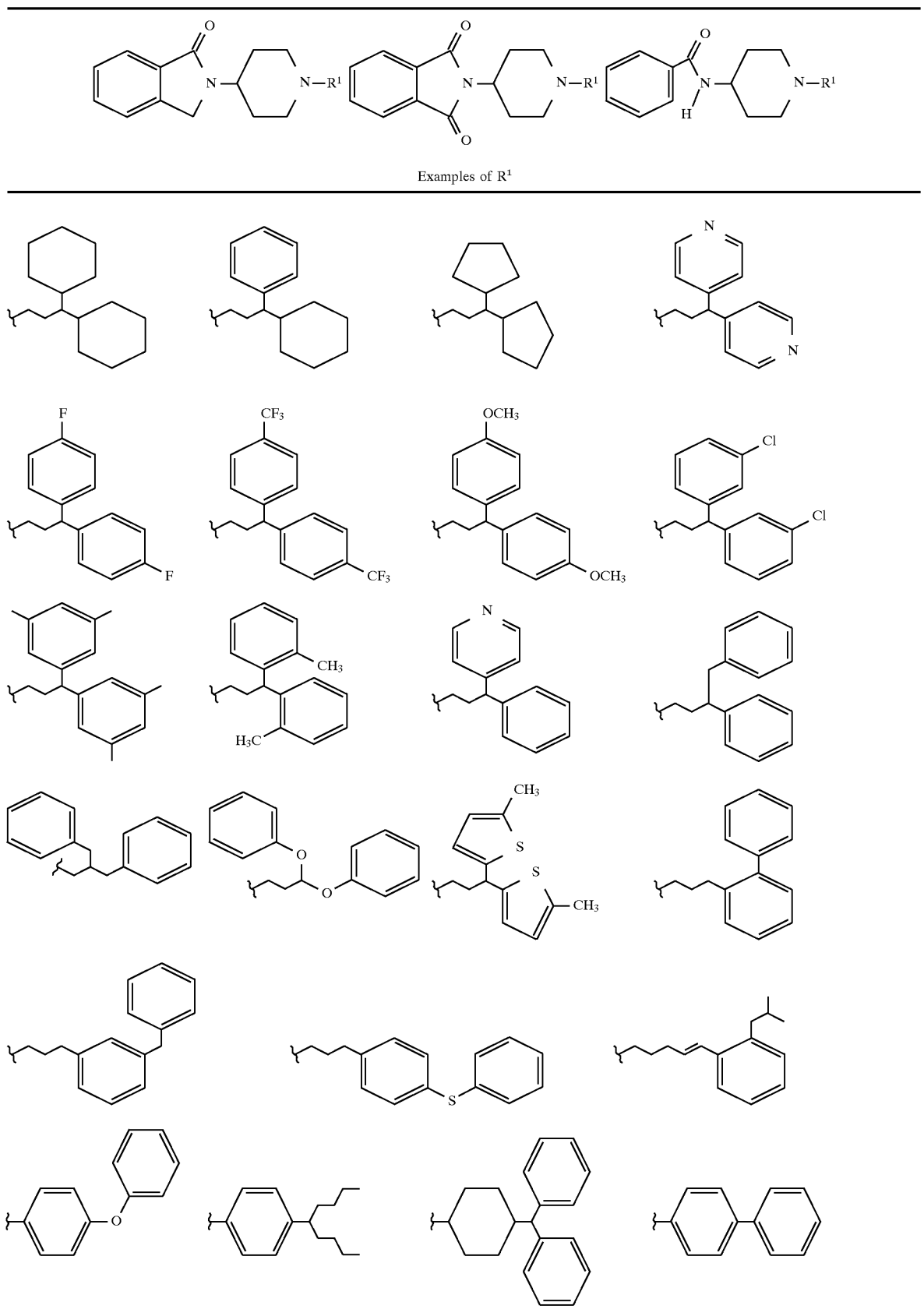
Examples of $R^1$

TABLE C-continued
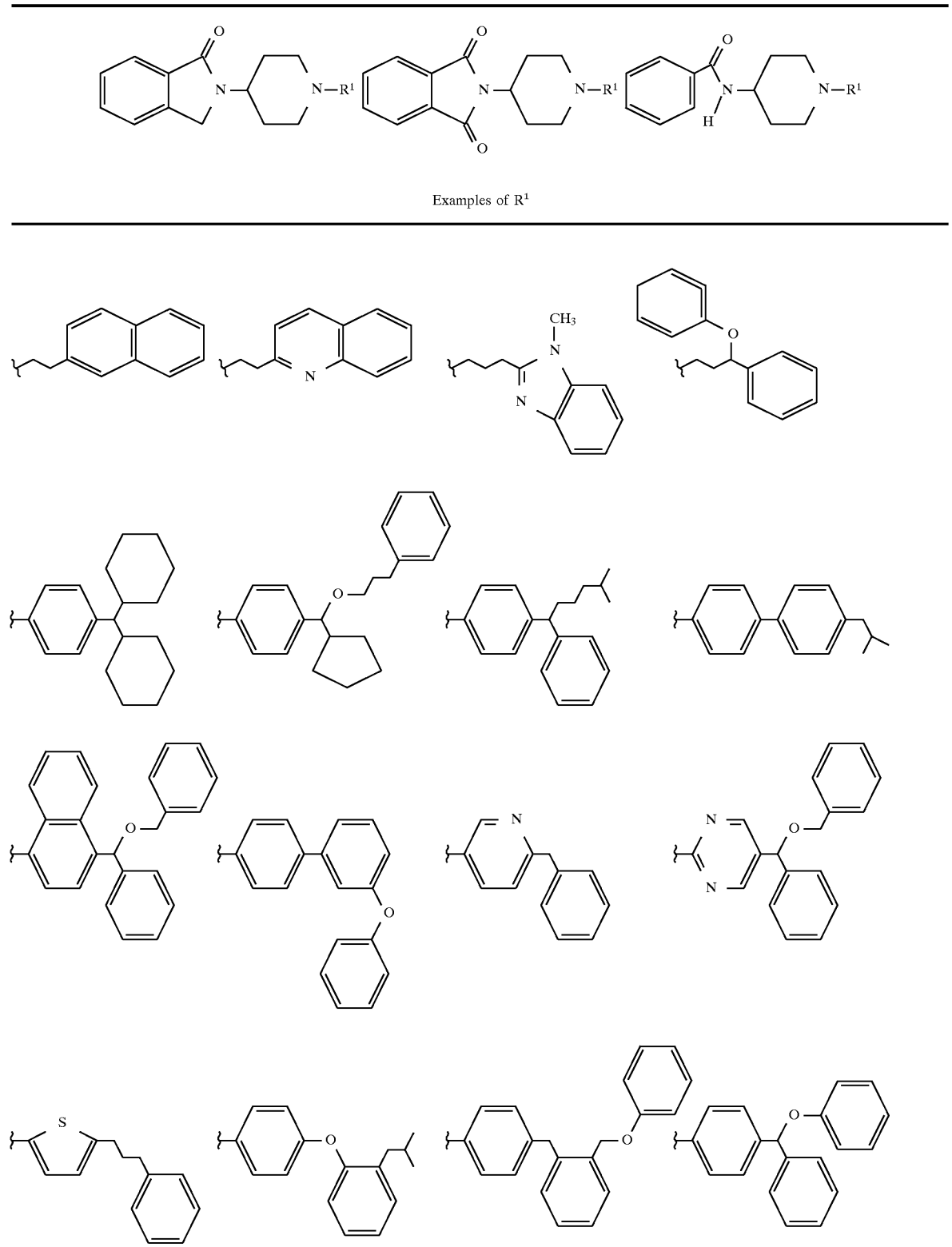
Examples of R¹

TABLE C-continued
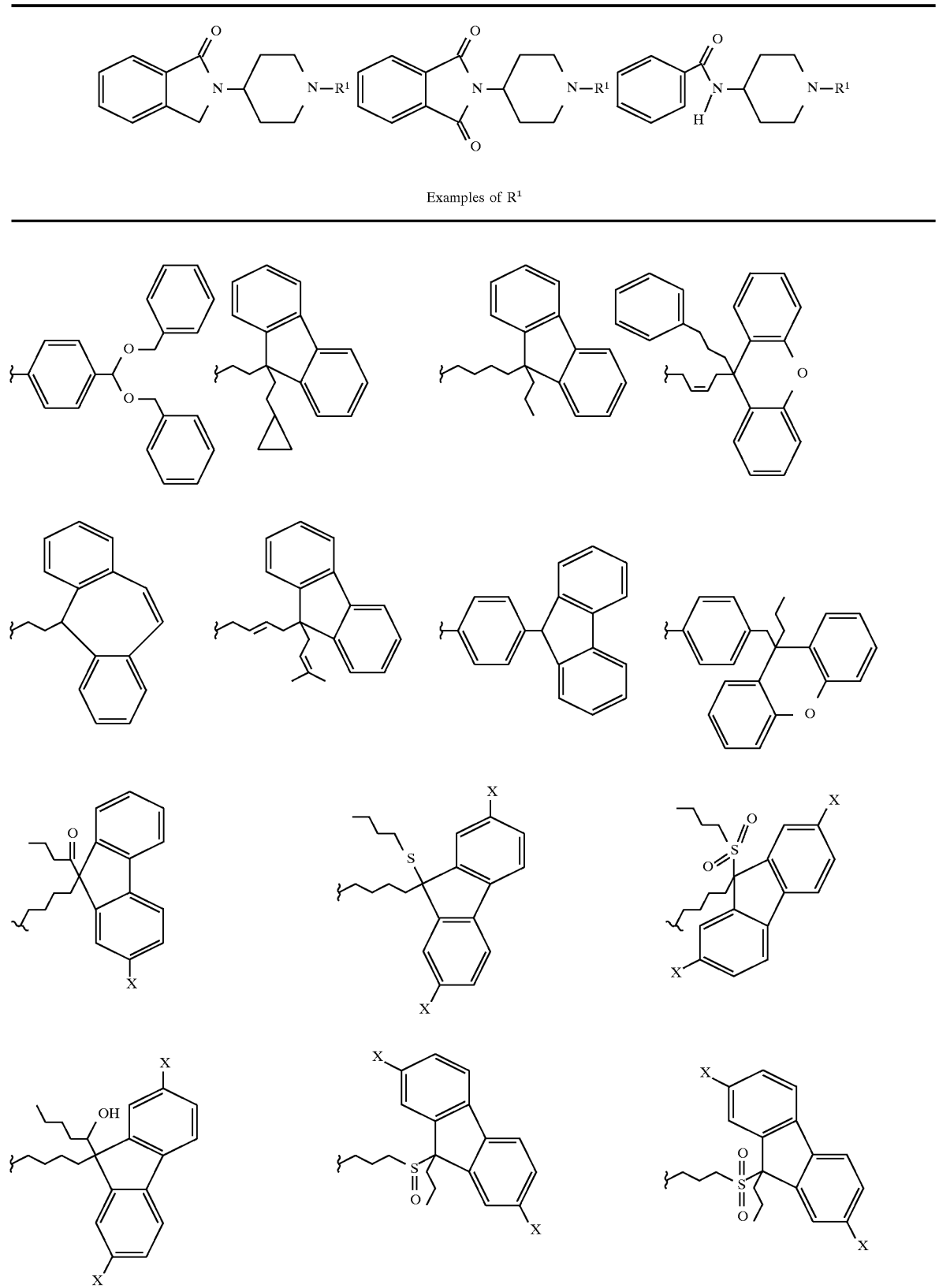
Examples of R¹

TABLE C-continued
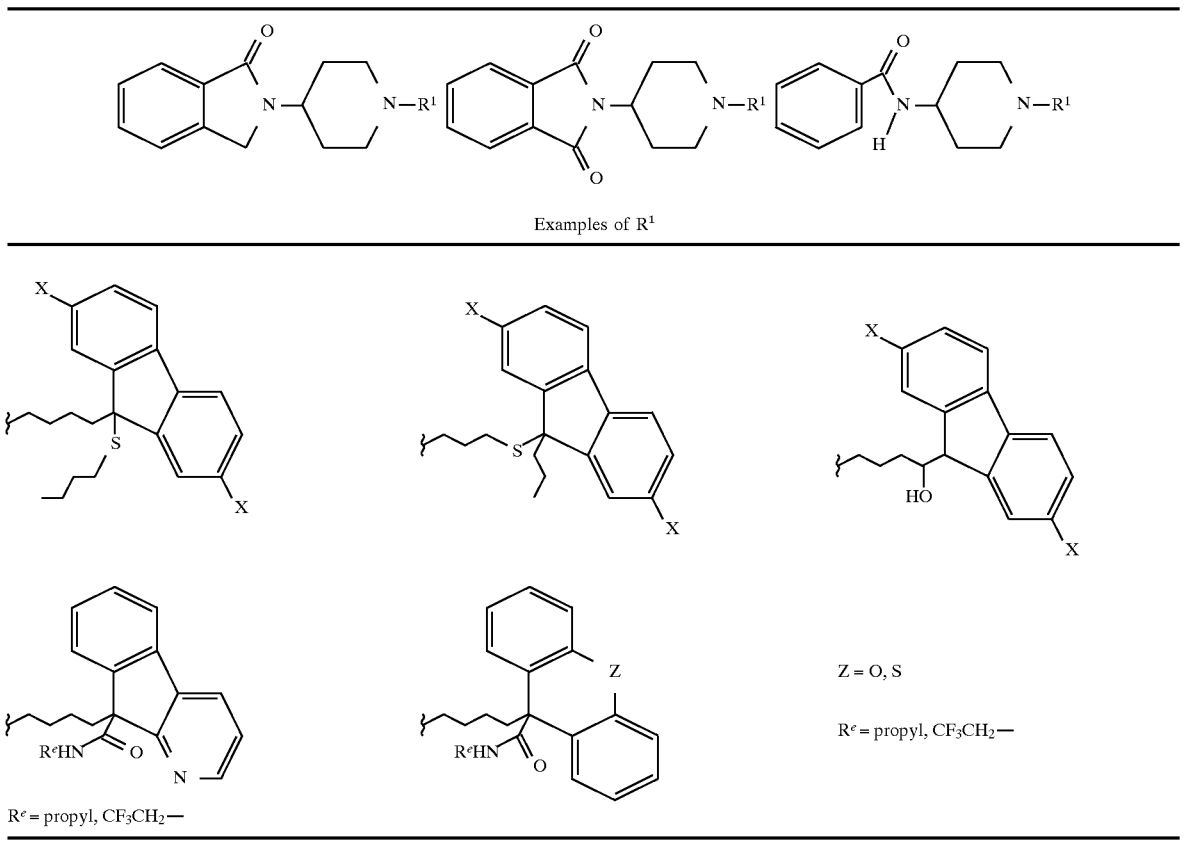
Examples of R[1]
X for Table C = H or F
TABLE D
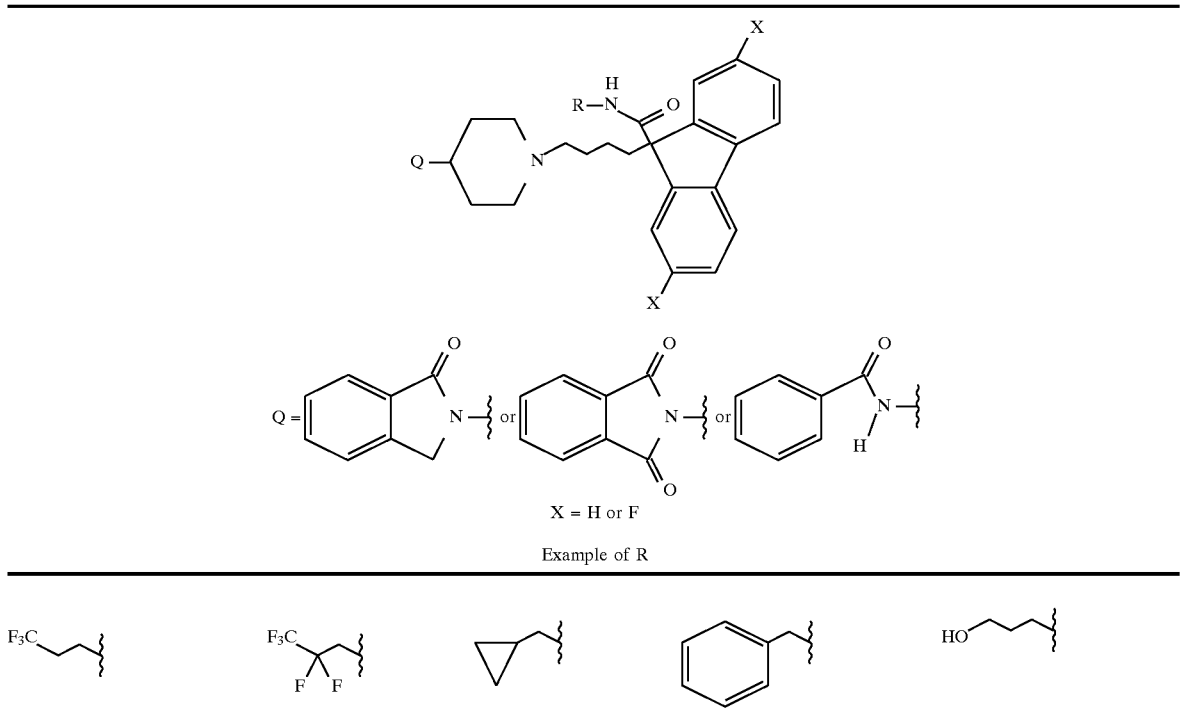
X = H or F
Example of R TABLE D-continued
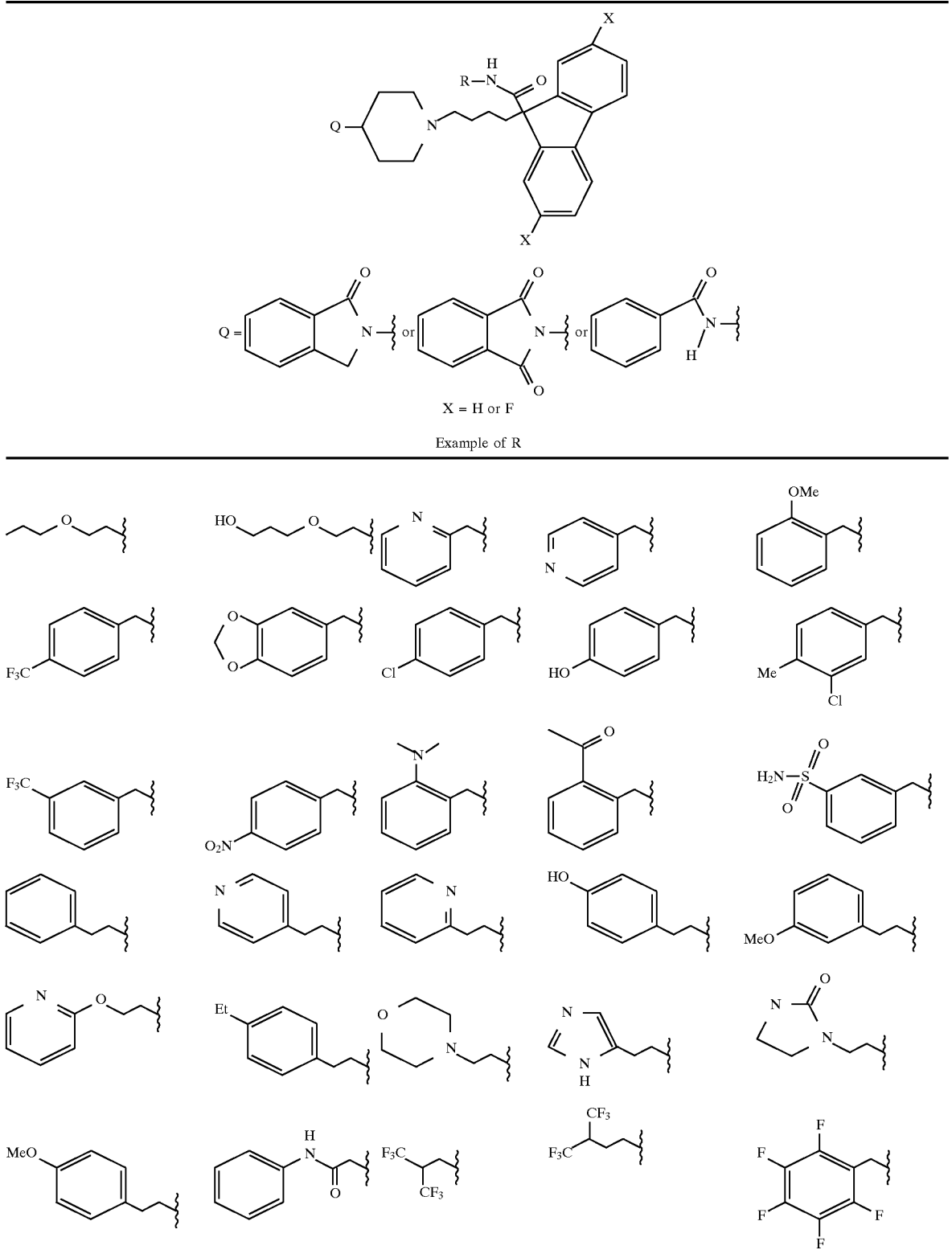

TABLE E
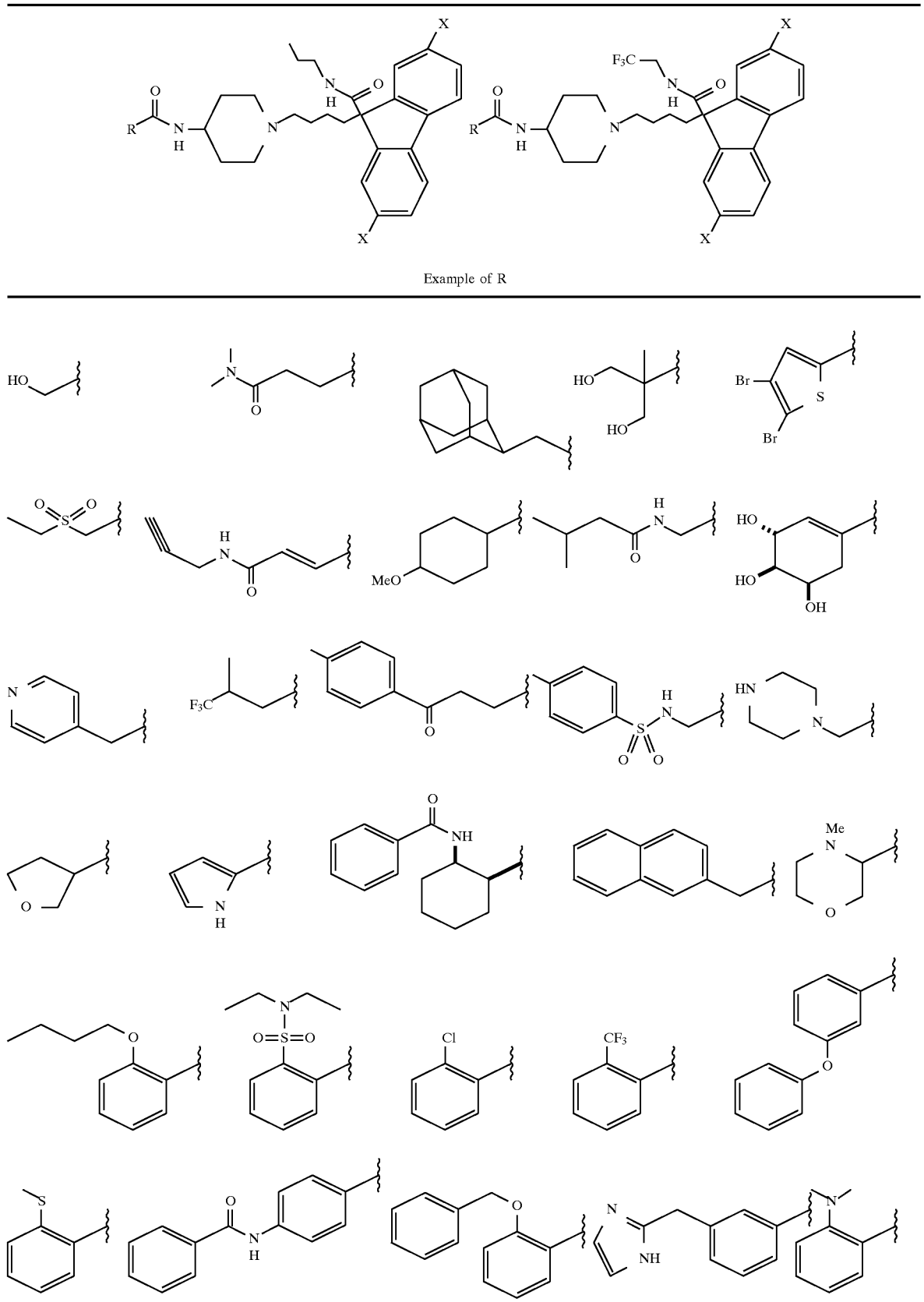
Example of R

TABLE E-continued
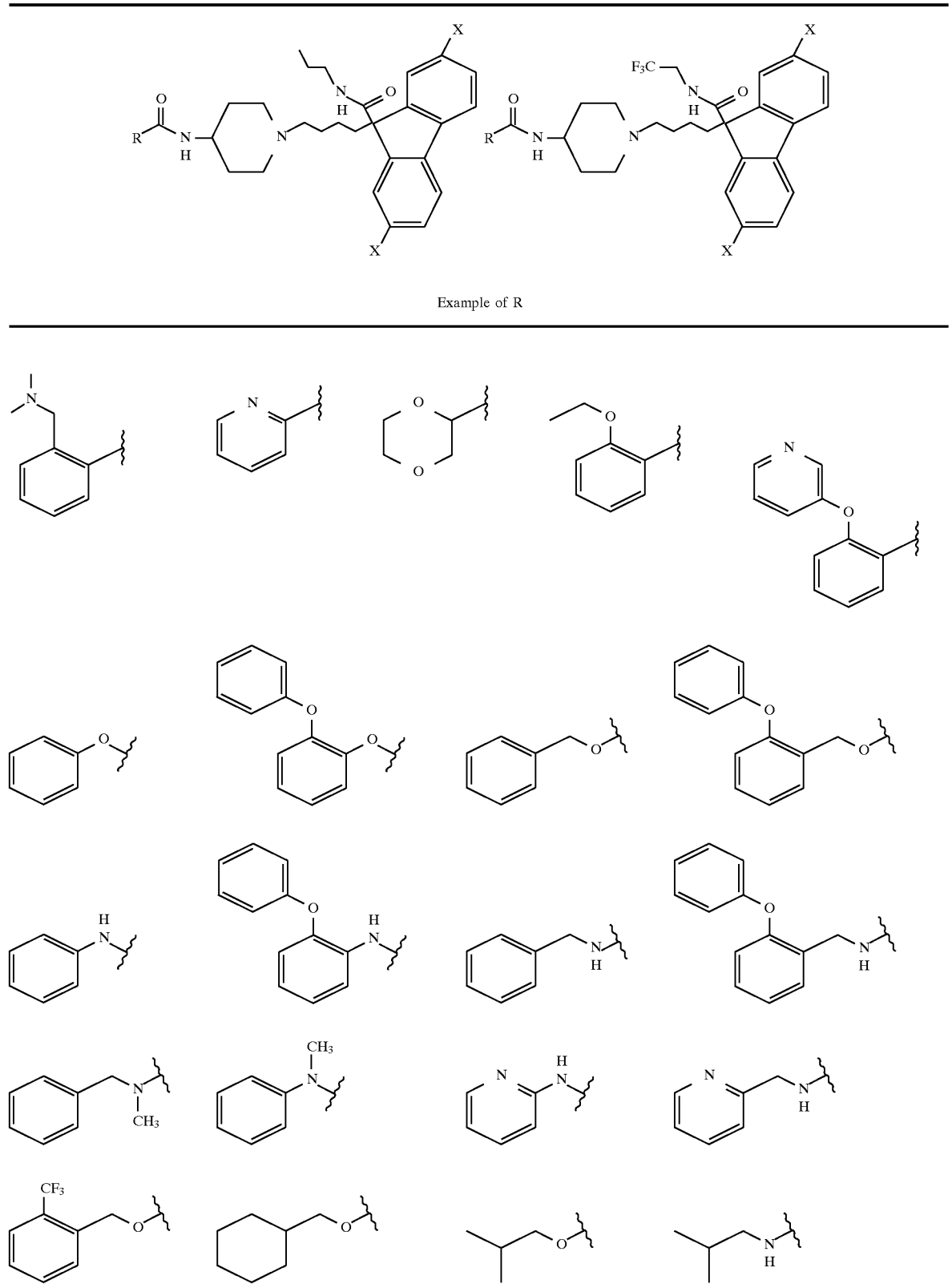
Example of R

TABLE E-continued
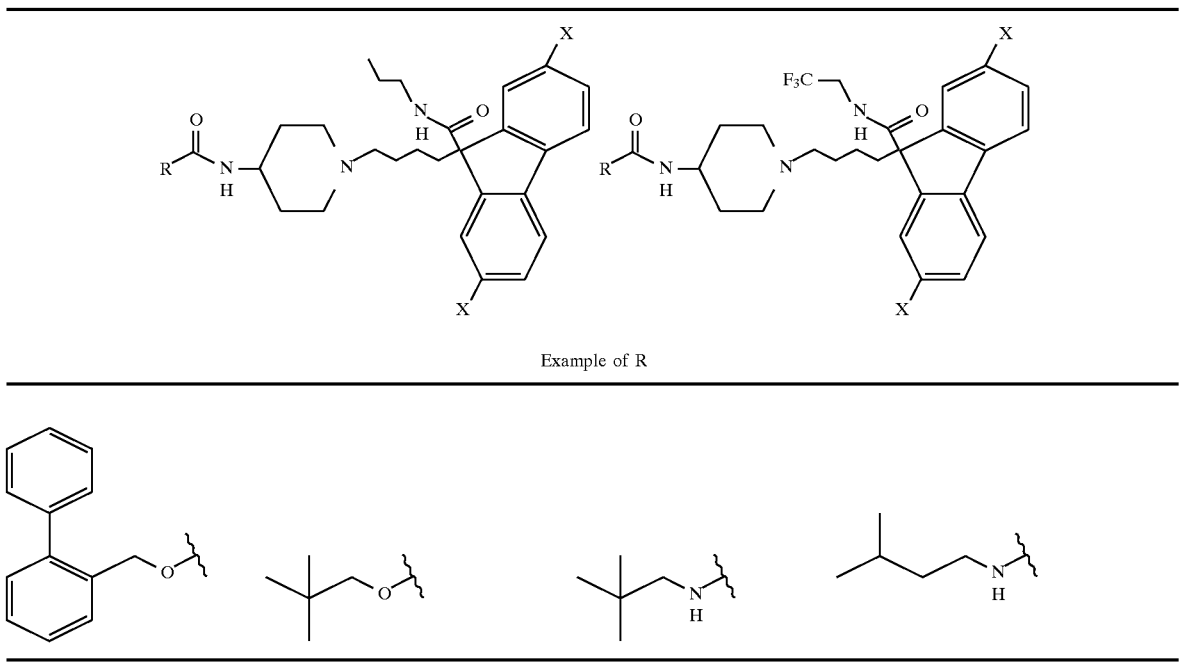
Example of R
TABLE F
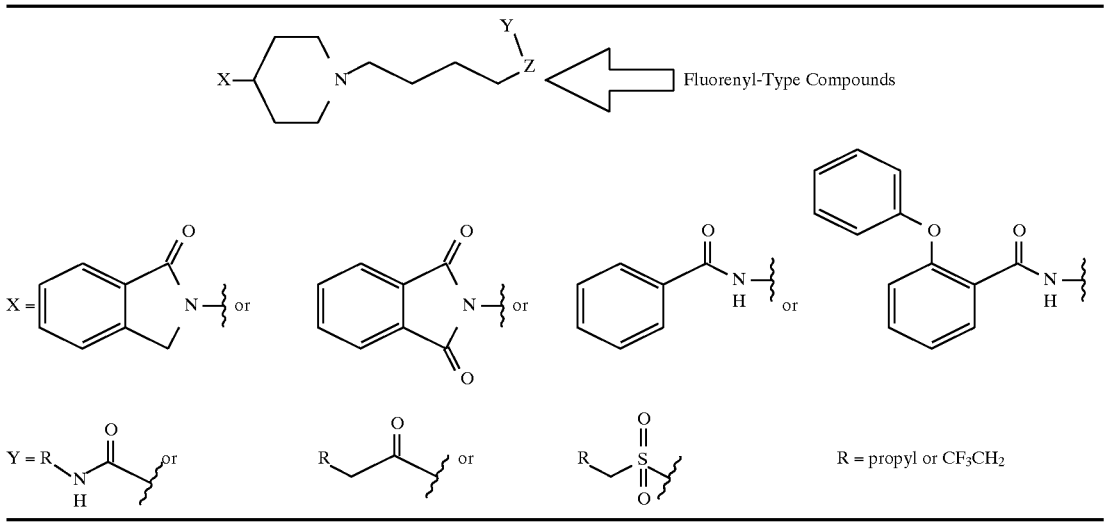
Fluorenyl-Type Rings: Z =
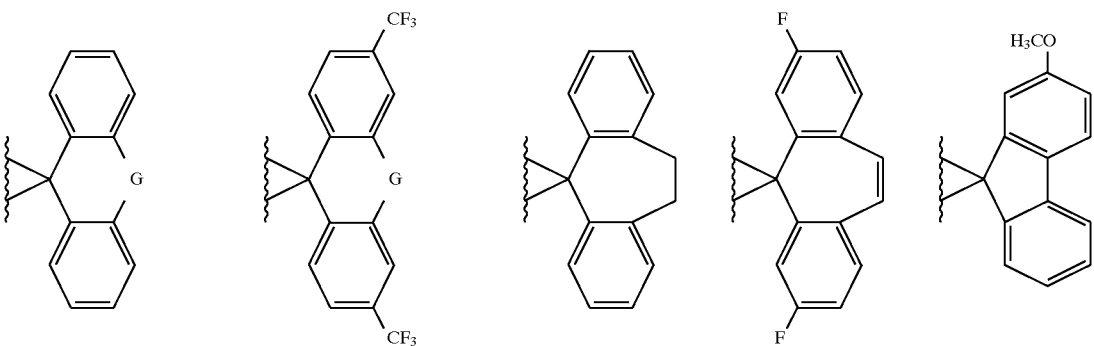

TABLE F-continued
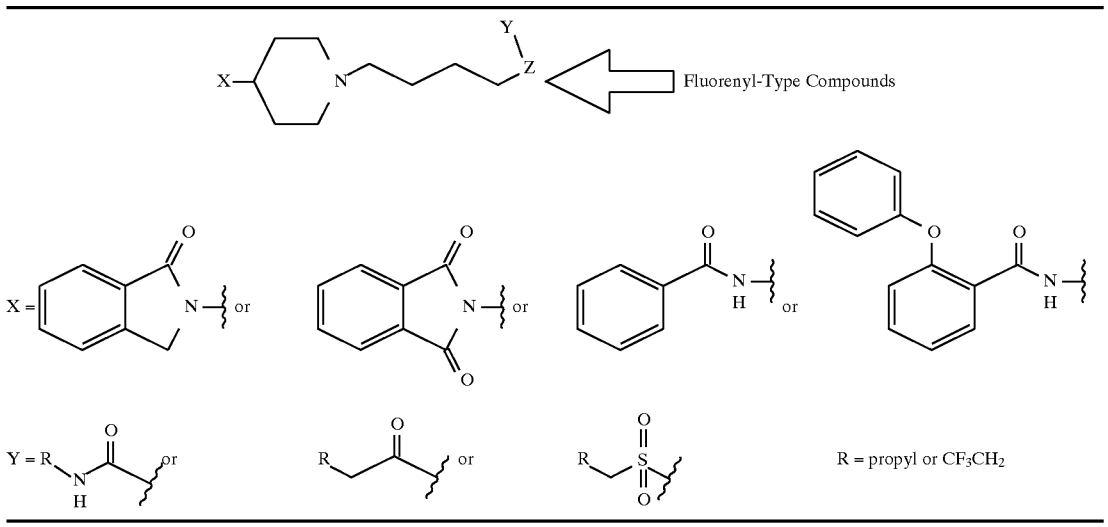
Fluorenyl-Type Compounds
R = propyl or CF₃CH₂
Fluorenyl-Type Rings: Z =
G = CH₂, O, S, SO, SO₂
G = CH₂, O, S, SO, SO₂
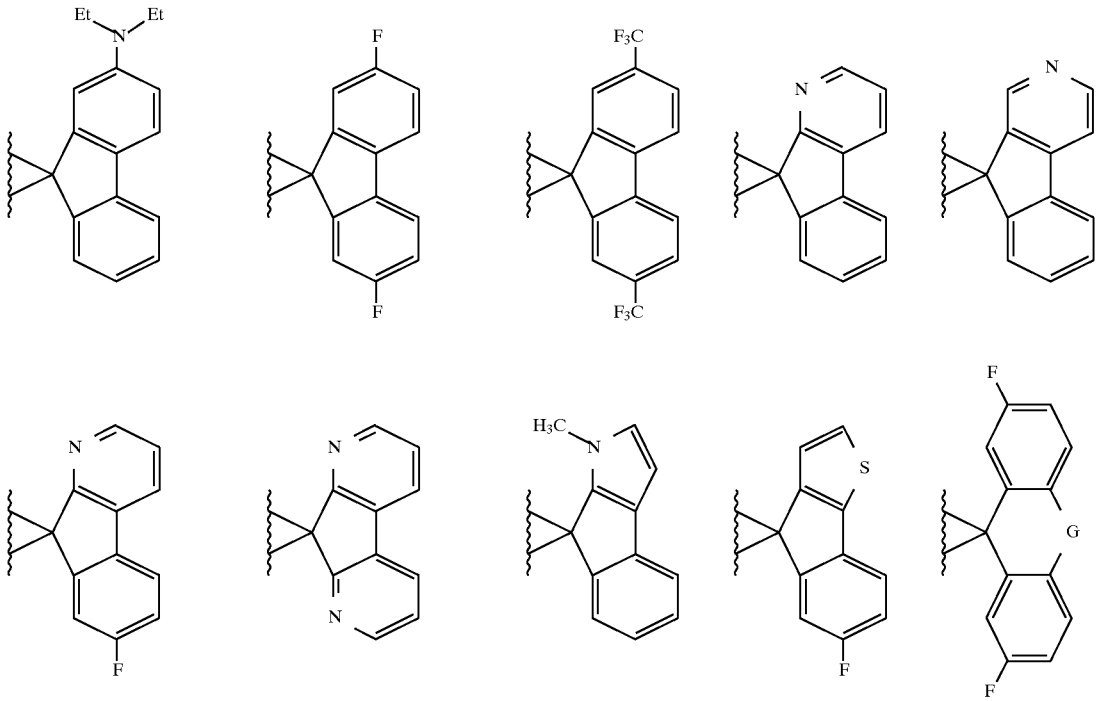
G = CH₂, O, S, SO, SO₂

TABLE G
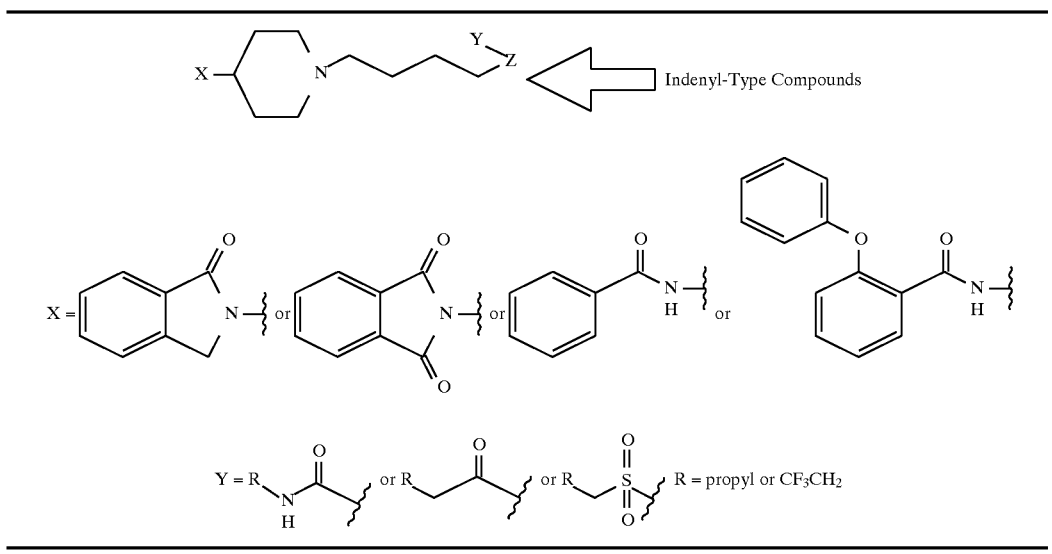
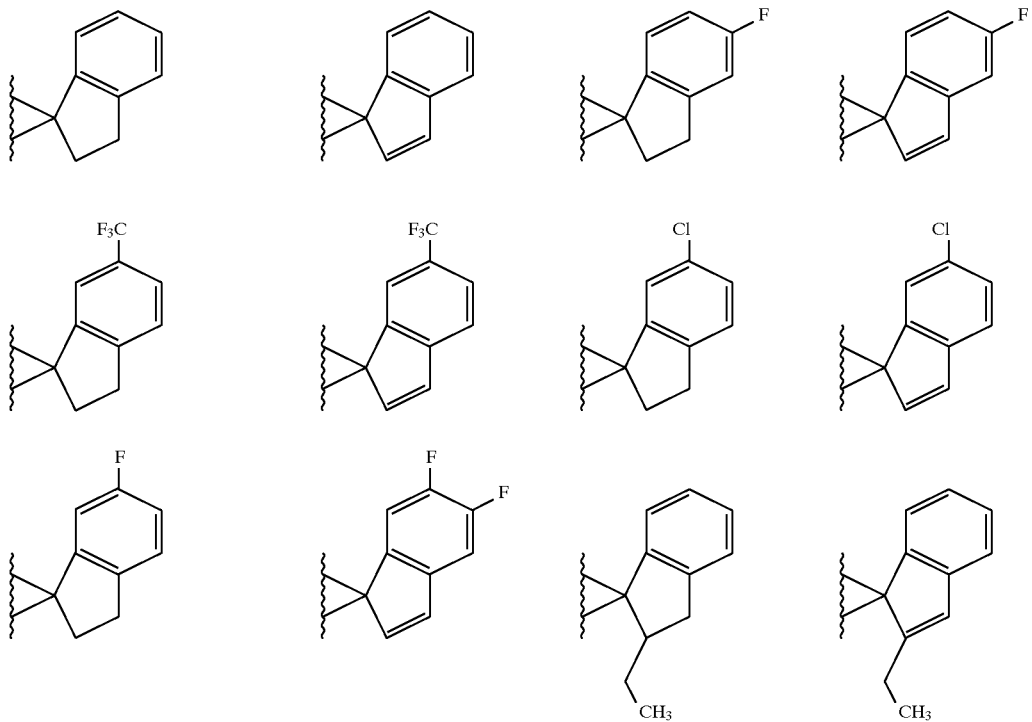
Indenyl-Type Rings: Z =
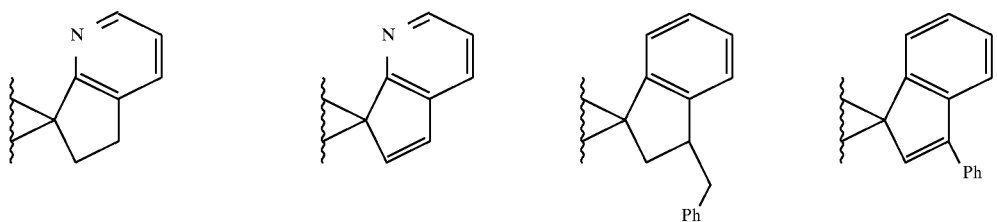
Indenyl-Type Rings: Z =

TABLE G-continued
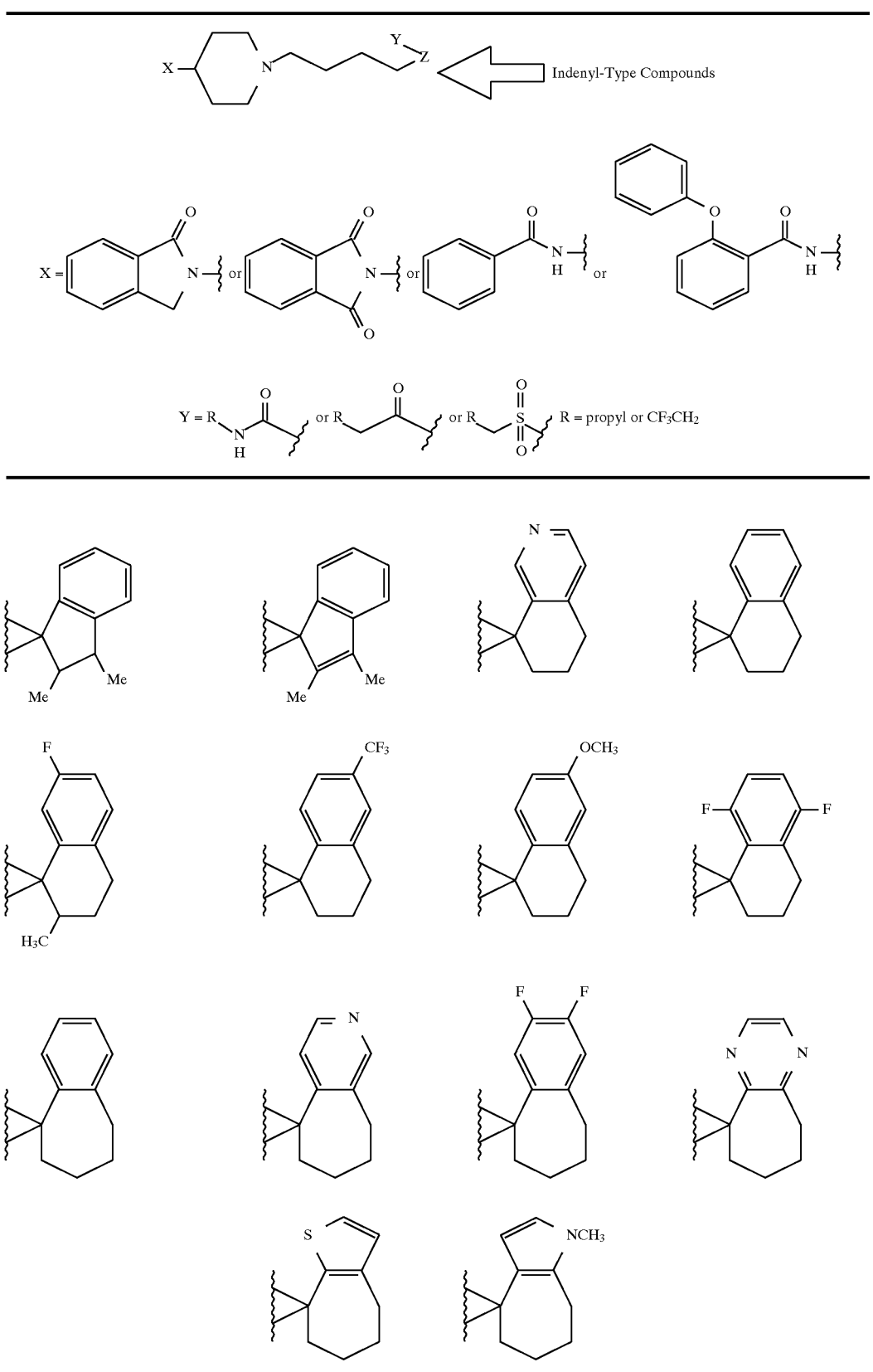

TABLE H

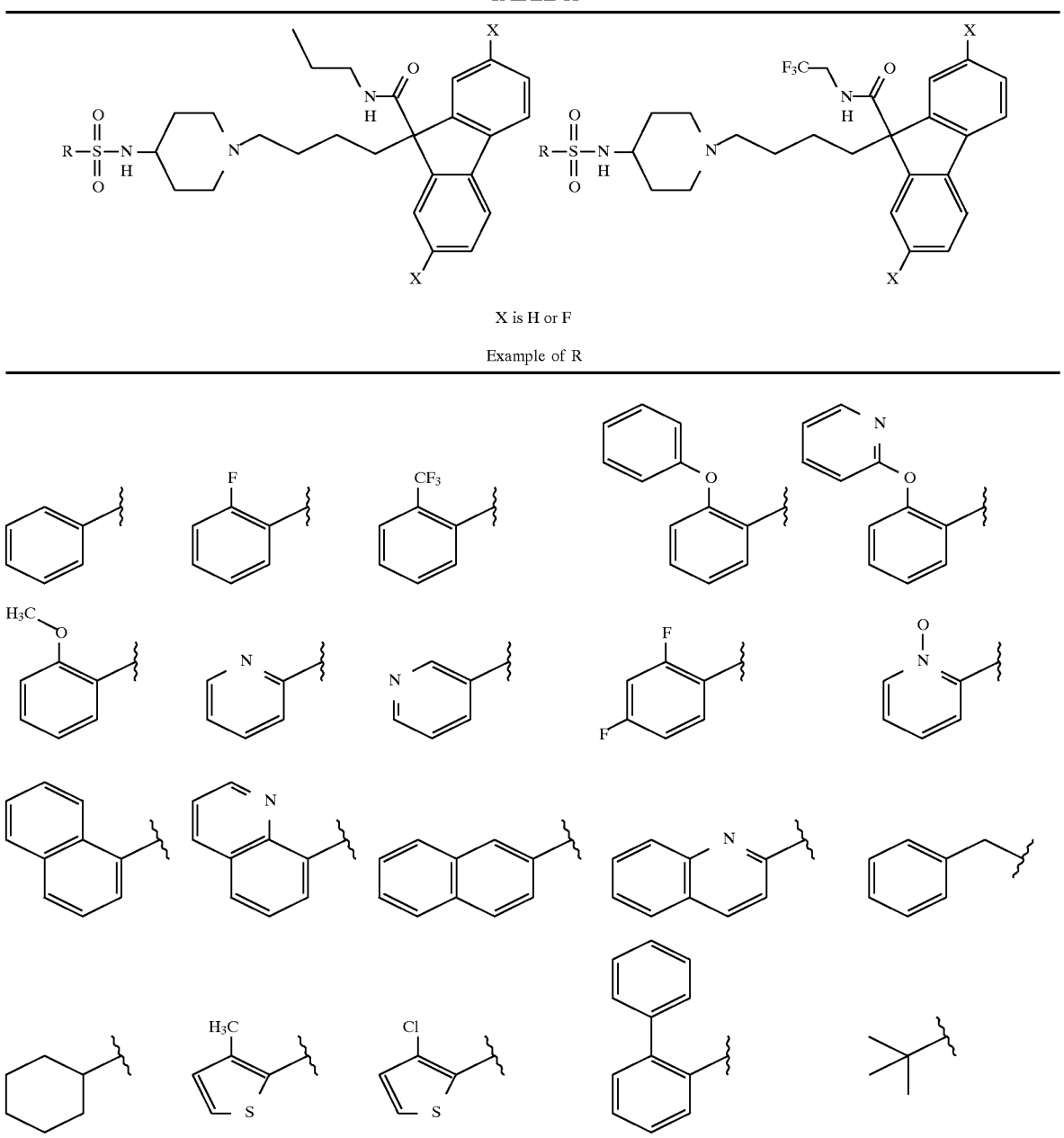

X is H or F

Example of R

EXAMPLE 339
cis-9-[4-[4-(2,3-Dihydro-1H-isoindol-2-yl)-1-piperidinyl]butyl]-N-propyl-9H-fluorene-9-carboxamide, N-oxide A slurry of 3-chloroperoxybenzoic acid (approx. 50%) (341 mg, 0.99 mmol) in $CH_2Cl_2$ (1 mL) was added dropwise to a solution of Example 310 compound (524 mg, 0.99 mmol) in $CH_2Cl_2$ (1 mL) at 0° C. under argon. The reaction was stirred at 0° C. for 20 min, diluted with $CH_2Cl_2$ (15 mL), washed with saturated $NaHCO_3$ (5 mL) and brine (5 mL), then dried over $MgSO_4$. Evaporation gave 612 mg of a white foam, which was purified by flash chromatography on silica gel (75 g) eluting with a step gradient of 4% to 5% to 7% to 10% $MeOH/CH_2Cl_2$ to give title compound (308 mg, 58%) as a white foam.

MS (ES): 538 [M+H]

Anal. Calcd. for $C_{34}H_{39}N_3O_3 \cdot 1.5\ H_2O$:

C, 72.29; H, 7.50; N, 7.44

Found: C, 72.32; H, 7.28; N, 7.41.

EXAMPLE 340
2-[1-[4-[9-(Butylsulfonyl)-9H-fluoren-9-yl]butyl]-4-piperidinyl]-2.3-dihydro-1H-isoindol-1-one In the foregoing Tables which set out compounds of the invention of formulae I and II, that is compounds which include the 4-substituted piperidine isomers, it will be understood that the formulae I and II compounds may be substituted with compounds of the invention of formulae Ii and IIi, that is compounds which include the 3-substituted piperidine isomers.

A.

A solution of 9-hydroxy-(9H)-flourene (1.58 g, 10.0 mmol) and butanethiol (0.72 g, 8.00 mmol) in 10 mL of dichloromethane at −20° C. was treated with borontrifluoride etherate (1.28 g, 9.00 mmol). The reaction was stirred for 1 h at −20° C. and warmed to room temperature. After stirring for 18 h the contents of the flask were purified by column chromatography on silica gel (100 g) with hexanes followed by 1:9 dichloromethane/hexanes to give 1.54 g (75%) of title compound as a colorless oil.
TLC Silica gel (1:9 dichloromethane/hexanes) $R_f$=0.5.

B.

A solution of Part A compound (1.0 g, 3.93 mmol) in 10 mL of THF at −78° C. was treated with n-butyllithium in hexanes (1.75 mL, 4.40 mmol) followed by 1-chloro-4-bromo-butane (0.81 g, 4.70 mmol). The reaction was stirred for 0.5 h and warmed to room temperature for 18 h. The contents of the flask were diluted with 30 mL of aqueous $NH_4Cl$ solution and 30 mL of ethyl acetate. The organic fraction was dried ($Na_2SO_4$) and concentrated. The remainder was purified by column chromatography on silica gel (50 g) with 2:98 acetone/ dichloromethane (500 mL) followed by 15:85 dichloromethane/hexanes to give 1.00 (73%) of title compound as a colorless oil.
TLC Silica gel (2:8 dichloromethane/hexanes) $R_f$=0.4.
Mass Spec. (ES, +ions) ml/e 255 (M-$SC_4H_9$).

C.

To a solution of Part B compound (0.30 g, 0.86 mmol) in dichloromethane (5 mL) at 0° C. was added 3-chloroperoxybenzoic acid (m-CPBA) (0.37 g, 80% by weight~0.1.72 mmol) in one portion. The mixture was stirred for 1 h when it was diluted with 0.1M $K_2CO_3$ (20 mL) and ether (30 mL). The organic fraction was dried ($Na_2SO_4$) and concentrated. The remainder was purified by column chromatography on silica gel (50 g) with 15:85 ethyl acetate/hexanes to give 0.24 g (75%) of title compound as a colorless oil.

TLC Silica gel (2:8 dichloromethane/hexanes) $R_f$=0.07.

D.

To a solution of Part C compound (0.24 g, 0.64 mmol) in 2-butanone (10 mL) at RT was added NaI (1.00 g, 6.66 mmol) in one portion. The mixture was refluxed for 30 h when it was diluted with water (20 mL) and ether (30 mL). The organic fraction was dried ($Na_2SO_4$) and concentrated. The remainder was purified by column chromatography on silica gel (50 g) with 15:85 ethyl acetate/hexanes to give 0.24 g (81%) of title compound as a colorless oil.

E. 2-[1-[4-[9-(Butylsulfonyl)-9H-fluoren-9-yl]butyl]-4-piperidinyl]-2,3-dihydro-1H-isoindol-1-one To a stirred solution of 0.70 g (1.49 mmol) of Part D compound in 6 mL of DMF at RT was added 0.38 g (1.80 mmol) of Example 2 Part A compound. The reaction mixture was warmed to 55° C. and allowed to stir for 24 h. The mixture was diluted with $NaHCO_3$ solution (50 mL) and ethyl acetate (50 mL). The layers were separated, the organics dried ($Na_2SO_4$) and concentrated. The remainder was purified by flash column chromatography on silica gel (100 g) eluting with 5:95 methanol/dichloromethane (700 mL) followed by 5:95:0.5 methanol/dichloromethane/$NH_3$ (1 L). Pure fractions were pooled and concentrated to give 0.70 g (85%) of title compound as a thick oil which solidified after standing.
mp: 130°–132° C.
TLC Silica gel (5:95:1 methanol/dichloromethane/$NH_3$) $R_f$=0.35.
Anal. Calcd. for $C_{34}H_{40}N_2SO_3$+0.5 $H_2O$:
C, 72.79; H, 7.30; N, 4.96; S, 5.68
Found: C, 72.25; H, 7.15; N, 5.00; S, 5.69.

EXAMPLE 341

9-[4-[[4-[(1,1-Dimethylethoxy)carbonyl]amino]-1-piperidinyl]butyl]-2,7-difluoro-N-(2,2,2-trifluoroethyl)-9H-fluorene-9-carboxamide

A.

A Solution of Example 312 Part B compound (8.00 g, 32.5 mmol) in 100 mL of THF at room temperature was carefully evacuated and then purged with argon four times. The stirred solution was cooled to −25° C. and a solution of n-butyllithium (26.5 mL, 2.5M in hexanes, 66.3 mmol) was added over 15 min. The resulting slurry was stirred for 1 h and cooled to −78° C. Neat dibromobutane (6.0 mL, 50.0 mmol) was added in one portion and the reaction was allowed to warm to room temperature over the course of 6 h. After an additional 14 h, the reaction mixture was poured into 1M hydrochloric acid (70 mL) and extracted twice with ethyl acetate. The combined organic extracts were dried ($Na_2SO_4$) and evaporated. The semi-solid residue was triturated with hexanes and filtered to give 11.32 g of an off-white solid.

To a slurry of the above solid (11.0 g) in 25 mL of dichloromethane at room temperature under argon was added a solution of oxalyl chloride (25 mL, 2.0M in dichloromethane, 50 mmol) followed by 0.5 mL (6.0 mmol) of DMF. After 1 h, the reaction was evaporated at less than 25° C. and the residue redissolved in 30 mL of THF. This solution was added over 20 min to a solution of 2,2,2-trifluoro-ethyl amine (6.10 g, 61.5 mmol) in 25 mL of THF at −10° C. under argon. After 2 h, the reaction was quenched with 10% citric acid solution and extracted twice with ethyl acetate. The organic extract was dried ($Na_2SO_4$) and evaporated. Purfication by flash chromatography (12×20 cm column, 7:3 dichloromethane/hexanes as elutant) on silica gel provided title compound as a white solid, 9.03 g, 60% yield from Example 312 Part B compound, mp 147°–148° C.

B. 9-[4-[[4-[(1,1-Dimethylethoxy)carbonyl]-amino]-1-piperidinyl]butyl]-2,7-difluoro-N-(2,2,2-trifluoroethyl)-9H-fluorene-9-carboxamide To a stirred solution of Part A compound (5.48 g, 11.9 mmol) in 20 mL of DMF at room temperature under argon was added Example 1 Part B compound (2.85 g, 14.2 mmol). The reaction was heated to 50° C. After 14 h, the reaction was quenched with 10% $NaHSO_3$ solution and extracted with ethyl acetate. The organic extract was dried ($MgSO_4$), evaporated and re-evaporated twice from toluene. Purification by flash chromatography on silica gel (2.5×15 cm column, ethyl acetate elutant) gave title compound, as a white solid, 6.23 g, 90%, mp 152°–154° C.

EXAMPLE 342

9-[4-[4-[(2-Phenoxybenzoyl)amino]-1-piperidinyl]-butyl]-N-(2,2,2-trifluoroethyl)-9H-fluorene-9-carboxamide, monohydrochloride Following the procedure in Example 321 Part B, 2-phenoxybenzoic acid (2.0 g, 9.34 mmol) was transformed into the acid chloride then reacted with Example 346 Part D compound (4.84 g, 9.34 mmol) to give a white solid (5.0 g). The product was dissolved in MeOH (5 mL), then 0.77M HCl in ethyl ether (15 mL) was added. The solution was evaporated and heated in a vacuum oven (55° C.) overnight to give title compound (5.1 g, 82%) as a white solid. m.p. 123°–127° C.

MS (ES, +ion): 656 (M+H).

Anal. Calc. for $C_{38}H_{39}ClF_3N_3O_2 \cdot 0.7\ H_2O$:

C, 66.07; H, 5.90; N, 6.08; F, 8.25

Found: C, 66.05; H, 5.97; N, 5.96; F, 8.21.

EXAMPLE 343

9-[4-[[4-(Benzoylamino)-1-piperidinyl]butyl]-2,7-difluoro-N-(2,2,2-trifluoroethyl)-9H-fluorene-9-carboxamide A solution of Example 341 compound (2.07 g, 3.56 mmol) in 10 mL of 4N hydrogen chloride in dioxane was stirred, protected by a calcium chloride drying tube, for 3 h. The solution was evaporated at 30° C. and the resulting solid was re-dissolved in 20 mL of THF. To this stirred solution, cooled to −10° C. under argon, was added triethylamine (1.24 mL, 8.9 mmol) and then benzoyl chloride (0.46 mmol, 4.0 mmol) over 10 min. After 1 h, the reaction was quenched with saturated sodium bicarbonate solution and extracted twice with ethyl acetate. The organic extract was dried ($Na_2SO_4$) and evaporated. Purfication by flash chromatography on silica gel (5×20 cm column, 1:19 methanol/ethylacetate as elutant) provided, after recrystallization from ethyl acetate/hexanes, title compound as a white solid, 1.83 g, 87% yield, mp 177°–179° C.

Anal. Calc'd for $C_{32}H_{32}F_5N_3O_2 \cdot 0.25\ H_2O$:

C, 65.13; H, 5.55; F, 16.10; N, 7.12

Found: C, 65.10; H, 5.49; F, 15.85; N, 7.12.

MA (electrospray, +ions) m/e 586 (M+H).

EXAMPLE 344

9-[4-[[4-(1,3-Dihydro-1,3-dioxo-2H-isoindol-2-yl)-1-piperidinyl]butyl]-2,7-difluoro-N-(2,2,2-tri-fluoroethyl)-9H-fluorene-9-carboxamide A solution of Example 341 compound (2.02 g, 3.47 mmol) in 10 mL of 4N hydrogen chloride in dioxane was stirred, protected by a calcium chloride drying tube, for 3 h. The solution was evaporated at 30° C. and partitioned between saturated sodium bicarbonate solution and dichloromethane. The organic layer was separated, dried ($Na_2SO_4$) and evaporated to give a white solid. To this residue was added 550 mg (3.71 mmol) of phthalic anhydride under an argon atmosphere. The solids were melted together at 150° C. for 6 h. On cooling, the resulting solid was recrystallized from ethyl acetate/hexanes to give title compound as a white solid, 1.71 g, 80% yield, mp 186°–188° C.

Anal. Calc'd for $C_{38}H_{36}F_5N_3O_3 \cdot 0.13\ H_2O$:

C, 64.56; H, 4.94; N 6.87

Found: C, 64.56; H, 5.03; N 6.81.

MS (electrospray, +ions) m/e 612.2 (M+H).

EXAMPLE 345

2,7-Difluoro-9-[4-[[4-[(2-phenoxybenzoyl)amino]-1-piperidinyl]butyl]-N-(2,2,2-trifluoroethyl)-9H-fluorene-9-carboxamide To a solution of 565 mg (2.64 mmol) of 2-phenoxybenzoic acid (Aldrich) in 10 mL of dichloromethane under argon, was added 2 mL of oxalyl chloride (2.0M in dichloromethane, 4.0 mmol) and then 0.1 mL of DMF. After 1 h, the reaction was evaporated and the residue, 2-phenoxybenzoyl chloride, was redissolved in 10 mL of THF.

A solution of Example 341 compound (1.00 g, 1.76 mmol) in 10 mL of 4N hydrogen chloride in dioxane was stirred, protected by a calcium chloride drying tube, for 3 h. The solution was evaporated at 30° C. and the resulting solid was re-dissolved in 10 mL of THF. To this stirred solution, cooled to −10° C. under argon was added triethylamine (0.95 mL, 6.5 mmol) and then the 2-phenoxybenzoyl chloride solution prepared above over 10 min. After 1 h, the reaction was quenched with saturated sodium bicarbonate solution and extracted twice with ethyl acetate. The organic extract was dried ($Na_2SO_4$) and evaporated. Purfication by flash chromatography on silica gel (5×20 cm column, 1:19 methanol/ethylacetate as elutant) provided, after recrystallization from ethyl acetate/hexanes, title compound as a white solid, 1.01 g, 85% yield, mp 168°–69° C.

Anal. Calc'd for $C_{38}H_{36}F_5N_3O_3$:

C, 67.35; H, 5.35; F, 14.02; N 6.20

Found: C, 67.20; H, 5.35; F, 14.33; N 6.08.

MS (electrospray, −ions) m/e 676.3 (M−H).

EXAMPLE 346

9-[4-[4-(Benzoylamino)-1-piperidinyl]butyl]-N-(2,2,2-trifluoroethyl)-9H-fluorene-9-carboxamide, monohydrochloride

A.

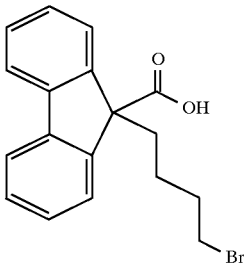

To a solution of 9-fluorenecarboxylic acid (50 g, 240 mmol) in THF (1200 mL) at 0° C. was added dropwise a solution of n-butyllithium (2.5M, 211 mL, 530 mmol) in THF. The yellow reaction was stirred at 0° C. for 1 h, then 1,4-dibromobutane (31.3 mL, 260 mmol) was added dropwise over 30 min. The reaction was stirred at 0° C. for 30 min, then the reaction was warmed to RT for 30 h. The reaction was extracted with water (3×750 mL). The combined aqueous layers were extracted with ethyl ether (800 mL). The aqueous layer was made acidic with HCl solution (1N, 500 mL), then extracted with dichloromethane (3×750 mL). The combined organic layers were dried over MgSO$_4$. Evaporation gave title compound (71 g, 85%) as a white solid.

B.

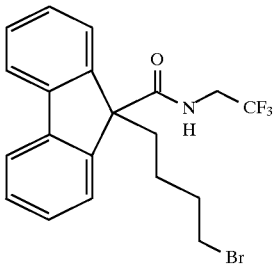

To a solution of Part A acid (60 g, 173 mmol) and DMF (100 μL) in CH$_2$Cl$_2$ (600 mL) under argon at 0° C. was added oxalyl chloride (104 mL, 2.0M in CH$_2$Cl$_2$, 208 mmol) dropwise. The reaction was stirred at 0° C. for 10 min, then warmed to RT and stirred for 1.5 h. The reaction was concentrated in vacuo to give the crude acid chloride as a yellow oil. To a suspension of 2,2,2-trifluoroethylamine hydrochloride (25.9 g, 191 mmol) in CH$_2$Cl$_2$ (500 mL) at 0° C. under argon was added triethylamine (73 mL, 521 mmol) followed by dropwise addition of a solution of the crude acid chloride in CH$_2$Cl$_2$ (15 mL). The reaction was stirred at 0° C. for 1 h, diluted with CH$_2$Cl$_2$ (500 mL), and washed with water (2×300 mL), 1N HCl (2×300 mL), saturated NaHCO$_3$ (2×300 mL), and brine (2×300 mL), then dried over MgSO$_4$. Evaporation gave 80 g of a oil which was purified by flash chromatography on silica gel (2.5 kg). The crude product was loaded in a mixture of CH$_2$Cl$_2$ and hexane, and eluted with a step gradient of 10% EtOAc/hexane (4 L) to 15% EtOAc/hexane (2 L) to 20% EtOAc/hexane (4 L). Pure fractions were combined and evaporated to give title compound (52.5 g, 71%) as a white solid (mp 88°–92° C.).

C.

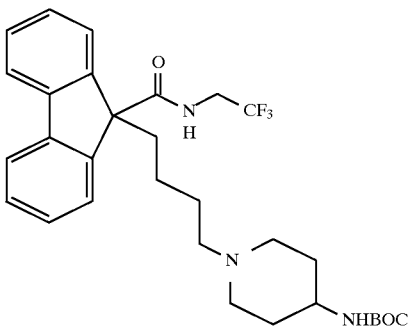

A mixture of Part B compound (29.5 g, 69.2 mmol), Example 1 Part B compound (14.5 g, 72.7 mmol), and anhydrous potassium carbonate (11.5 g, 83.0 mmol) in DMF (100 mL) was stirred at 50° C. for 48 h, concentrated to dryness, and taken up in CH$_2$Cl$_2$ (500 mL). The solution was washed with saturated NaHCO$_3$ (3×80 mL) and brine (2×80 mL), then dried over MgSO$_4$. Evaporation gave a yellow oil which was purified by flash chromatography on silica gel (600 g), loaded in CH$_2$Cl$_2$, and eluted with a step gradient of 2% MeOH/CH$_2$Cl$_2$ (3 L) to 3% MeOH/CH$_2$Cl$_2$ (4 L). Pure fractions were combined and evaporated to give title compound (30 g, 86%) as a white foamy gum.

D.

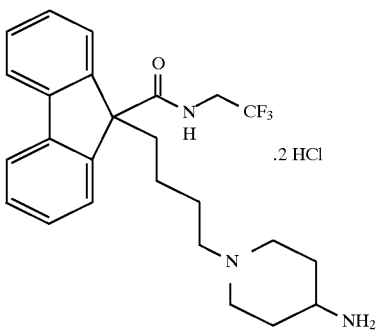

To a solution of Part C compound (30.5 g, 60.4 mmol) in dioxane (120 mL) was added 4N HCl in dioxane (121 mL, 483 mmol). The reaction was stirred at RT for 4 h, then concentrated in vacuo to provide title compound (30 g) as a white foamy solid, containing a residual amount of dioxane.

E. 9-[4-[4-(Benzoylamino)-1-piperidinyl]-butyl]-N-(2,2,2-trifluoroethyl)-9H-fluorene-9-carboxamnide, monohydrochloride To a solution of Part D compound (1.6 g, 3.08 mmol) and triethylamine (1.5 mL, 10.8 mmol) in dichloromethane (10 mL) at 0° C. was added dropwise benzoyl chloride (0.4 mL, 3.40 mmol). The reaction was stirred at 0° C. for 30 min. Dichloromethane (200 mL) was added and the solution was washed with water (2×50 mL), brine (2×50 mL) and dried over MgSO$_4$. Purification was performed by flash chromatography on silica gel (100 g), loaded and eluted with 2.5% methanol in dichloromethane. Pure fractions were combined and evaporated to give a white solid. The product was dissolved in methanol (5 mL) and a solution of HCl in ethyl ether (0.77N, 5.19 mL) was added. The reaction was stirred at RT for 10 min, then evaporated to dryness. After drying in a vacuum oven (65° C., 72 h), title compound was obtained (1.3 g, 72%) as a white solid.

m.p. 132°–137° C.
MS (Cl, +ion): 550 (M+H).
Anal. Calc. for $C_{32}H_{35}ClF_3N_3O_2 \cdot 0.2\ H_2O$:
C, 65.18; H, 6.05; N, 7.13; Cl, 6.01;
F, 9.66
Found: C, 65.45; H, 6.06; N, 6.88; Cl, 5.16;
F, 9.30.

EXAMPLE 347

2,3-Dihydro-2-[1-[4-[9-(1-oxopentyl)-9H-fluoren-9-yl]butyl]-4-piperidinyl]-1H-isoindol-1-one, monohydrochloride

A.

A(1).

HO~~~~~OTBS (TBS is Si(CH₃)₂t-Bu)

To a solution of 49 mL (0.55 mol) of 1,4-butanediol in 25 mL of DMF, under argon at 0° C., was added 10.5 g (0.15 mol) of imidazole followed by 20.7 g (0.14 mol) of t-butyldimethylsilyl chloride. The reaction was slowly warmed to RT and stirred for 18 h at which time the reaction was diluted with ether and washed with NH₄Cl, water, Na₂CO₃, brine and dried (MgSO₄). The resulting title compound in the form of a colorless liquid, 50 g, contained approximately 15% of the disilylated compound.

A(2).

To a solution of 8.5 g (42 mmol) of Part A(1) compound in 50 mL of THF, under argon at 0° C., was added 7.3 g (108 mmol) of imidazole and 16.7 g (64 mmol) of triphenylphosphine. This mixture was stirred for 45 min (solution became homogeneous) at which time 16.2 g (64 mmol) of iodine in 50 mL of THF was added dropwise over 20 min. The reaction was stirred for 1 h, diluted with hexanes and washed with 1M sodium bisulfite, Na₂CO₃, brine and dried (Na₂SO₄). The resulting residue was triturated with ether (3 ×), filtered (to remove triphenylphosphine oxide) and evaporated to provided 10 g (61%) of title compound as a pale yellow oil.
TLC Silica gel (4:1 hexanes/ethyl acetate)
$R_f=0.60$.

B.

To a solution of 5 g (23.78 mmol) of 9-fluorenecarboxylic acid (Aldrich) in 20 mL of THF, under argon at 0° C., was added 20.6 mL (52.32 mmol) of n-butyllithium (2.5M in hexanes) dropwise. The orange-red anion was stirred for 0.5 h, at which time 7.5 g (23.78 mmol) of

I~~~~~OTBS (prepared as described in Part A) was added dropwise. The reaction gradually warmed to RT and was stirred for 36 h, at which time it was diluted with a 1:1 mixture of ethyl acetate/H₂O (250 mL). The organics were washed with NaHCO₃, brine, dried (Na₂SO₄) and evaporated. Flash chromatography was performed on 250 g of silica gel eluting with 9:1 dichloromethane/isopropanol to provide 4.9 g (52%) of title compound as a yellow oil.
TLC: Silica gel (9:1 dichloromethane/isopropanol)
$R_f=0.50$.

C.

To 550 mg (1.38 mmol) of Part B compound was added 5 mL of DMSO. The reaction was stirred for 18 h, under argon at RT, at which time it was diluted with ether and washed with water (3 ×). Flash chromatography was performed on 100 g of silica gel eluting with 95:5 hexanes/ethyl acetate to provide 340 mg (70%) of title compound as a pale yellow oil.
TLC: Silica gel (95:5 hexanes/ethylacetate)
$R_f=0.31$.

D.

To a solution of 340 mg (0.96 mmol) of Part C compound in 3 mL of THF, under argon at 0° C., was added dropwise 462 mL (1.16 mmol) of n-butyllithium (2.5M in hexanes). The resulting anion was stirred for 0.5 h, at which time 140 mL (1.16 mmol) of freshly distilled valeryl chloride (Aldrich) was added dropwise. The reaction was stirred for 2 h, at which time it was diluted with ether and quenched with NaHCO₃. The organics were washed with water, brine, dried (NaSO₄) and evaporated. Flash chromatography was performed on 100 g of silica gel eluting with 95:5 hexanes/dichloromethane to provide 290 mg (69%) of title compound as a pale yellow oil.
TLC: Silica gel (95:5 hexanes/ethyl acetate)

$R_f$=0.36.
MS (CI—NH$_3$, +ions) m/e 397 (M+H).
Anal. Calcd. for C$_{24}$H$_{32}$O$_3$Si+0.15 mol H$_2$O:
C, 72.20; H, 8.15
Found: C, 72.20; H, 7.88.

E.

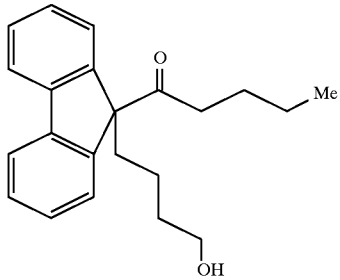

To 200 mg (0.46 mmol) of Part D compound was added 1 mL of 5:95 aqueous HF/acetonitrile. The reaction was stirred under argon at RT, for 3 h, at which time it was diluted with ether and washed with NaHCO$_3$, water (3 ×), brine, dried (MgSO$_4$) and evaporated. Flash chromatography was performed on 50 g of silica gel eluting with 7:3 hexanes/ethyl acetate to provide 120 mg (81%) of title compound as a pale yellow oil.
TLC: Silica gel (8:2 hexanes/ethyl acetate)
$R_f$=0.15.

F.

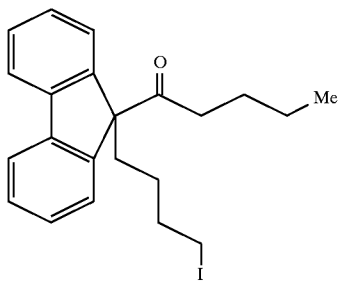

To a solution of 120 mg (0.37 mmol) of Part E compound in 1.5 mL of THF, under argon at 0° C., was added 55 mg (0.81 mmol) of imidazole followed by 126 mg (0.48 mmol) of triphenylphosphine. The mixture was stirred for 0.5 h, at which time 122 mg (0.48 mmol) of iodine in 1 mL of THF was added dropwise. The reaction was stirred for 1 h at 0° C., 1 h at RT, then diluted with hexanes and washed with fresh sodium bisulfite solution, NaHCO$_3$, water, brine, dried (MgSO$_4$) and evaporated. Flash chromatography was performed on 25 g of silica gel eluting with 9:1 hexanes/ethyl acetate to provide 130 mg (81%) of title compound as a colorless oil.
TLC: Silica gel (9:1 hexanes/ethyl acetate)
$R_f$=0.40.

G. 2,3-Dihydro-2-[1-[4-[9-(1-oxopentyl)-9H-fluoren-9-yl]butyl]-4-piperidinyl]-1H-isoindol-1-one, monohydrochloride To a solution of 130 mg (0.30 mmol) of Part F compound in 1.5 mL of DMF, under argon at RT, was added 20 mg (0.15 mmol) of K$_2$CO$_3$ and 84 mg (0.39 mmol) of Example 2 Part A compound. The reaction was stirred for 18 h, at which time it was poured into water. The precipitate was collected, dissolved into ether, dried (Na$_2$SO$_4$) and evaporated to provide a pale yellow solid. The solid was dissolved in ether and treated with 305 mL (0.30 mmol) of HCl (1M in ether). The ether was decanted off, the solids collected and dried for 18 h (50° C. under vacuum) to provide 115 mg (74%) of title compound as a pale yellow solid.
mp 96°–100° C.
TLC: Silica gel (95:5 dichloromethane/isopropanol+1% NH$_4$OH) $R_f$=0.46.
MS (ES; NH$_{40}$OH, +ions) m/e 521 (M+H).
Anal. Calcd. for C$_{35}$H$_{40}$N$_2$O$_2$HCl+0.5 mol H$_2$O:
C, 74.25; H, 7.48; N, 4.95
Found: C, 74.24; H, 7.45; N, 4.98.

EXAMPLE 348
2,3-Dihydro-2-[1-(1-oxo-3,3-diphenylpropyl)-4-piperidinyl]-1H-isoindol-1-one To a solution of 3,3-diphenylpropionic acid (500 mg, 2.21 mmol) and DMF (1 drop) in dichloromethane (5 mL) at RT was added dropwise a solution of oxalyl chloride in dichloromethane (2.0M, 1.66 mL, 3.32 mmol). Bubbling of escaping gasses continued for 10 min after addition. The reaction was stirred at RT for 60 min, then concentrated in vacuo to give a crude oil. To a solution of crude acid chloride and triethylamine (1.4 mL, 10.0 mmol) in dichloromethane (10 mL) at 0° C. under argon was added dropwise a solution of Example 2 Part A compound (434 mg, 2.00 mmol) in dichloromethane (2 mL). The reaction was stirred at 0° C. for 10 min. Dichloromethane (100 mL) was added to dilute the reaction and the resulting solution was washed with H$_2$O (40 mL), saturated sodium bicarbonate solution (40 mL), brine (40 mL) and dried over MgSO$_4$. Evaporation gave a crude gum. Purification was performed by flash chromatography on silica gel (100 g), loaded and eluted with 2.5% methanol in dichloromethane. Pure fractions were combined and evaporated to give title compound (610 mg, 72%) as a off-white solid.
m.p. 166°–169° C.
MS (FAB, +ion): 425 (M+H)
Anal. Calc. for C$_{28}$H$_{28}$N$_2$O$_2$.1.1 H$_2$O:
C, 75.68; H, 6.85; N, 6.30
Found: C, 75.50; H, 6.45; N, 6.24.

EXAMPLE 349
[1-[4-[9-[(Propylamino)carbonyl]-9H-fluoren-9-yl]-butyl]-3-piperidinyl]carbamic acid, phenylmethyl ester, monohydrochloride

A.

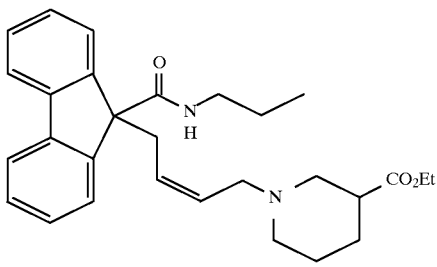

A mixture of Example 314 Part A compound (2.34 g, 6.90 mmol) and ethyl nipecotate (1.3 mL, 8.28 mmol) in DMF (3.5 mL) under argon was heated at 60° C. for 22 h, then cooled to RT. The solvent was removed under reduced pressure. The resulting orange residue was dissolved in CH$_2$Cl$_2$ (50 mL), washed with saturated NaHCO$_3$ (2×15 mL) and brine (20 mL), then dried over Na$_2$SO$_4$. Evaporation gave 3.6 g of an orange gum, which was dissolved in a minimal amount of CH$_2$Cl$_2$ and purified by flash chromatography on silica gel (175 g) eluting with 2% MeOH/CH$_2$Cl$_2$ to provide 2.65 g of product contaminated with approximately 20 mol % DMF. The product was dissolved in EtOAc (60 mL), washed with water (3×20 mL) and brine (20 mL), then dried over Na$_2$SO$_4$. Evaporation gave title compound (2.38 g, 75%) as an amber oil.

B.

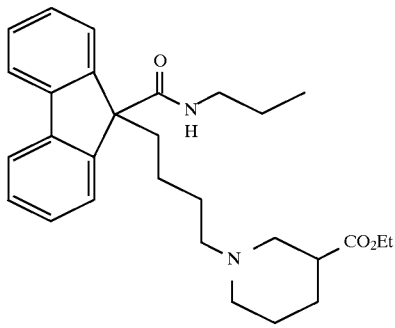

Palladium on carbon (10%) (273 mg, 0.258 mmol) was added to a solution of Part A compound (2.37 g, 5.15 mmol) in a mixture of EtOAc (10 mL) and EtOH (15 mL). The mixture was hydrogenated (balloon) at RT for 1.5 h, filtered through Celite, and washed with EtOAc (3×20 mL). The filtrate was concentrated in vacuo to give title compound (2.42 g, 100%) as a pale yellow oil.

C.

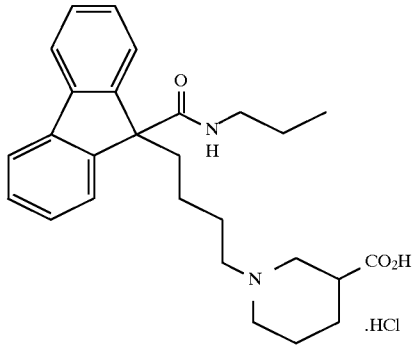

Aqueous KOH (5.6 mL, 1N, 5.6 mmol) was added to a solution of Part B compound (2.17 g, 4.70 mmol) in THF (10 mL) under argon. The biphasic mixture was stirred at RT for 4 h, then heated at 50° C. for 48 h. The reaction was cooled to RT and acidified to pH 1.5 with 1N HCl. The cloudy reaction was diluted with water (30 mL) and extracted with CHCl$_3$ (3×100 mL), then dried over Na$_2$SO$_4$. Evaporation afforded title compound (2.2 g, 100% crude) as a foamy white solid.

D. [1-[4-[9-[(Propylamino)carbonyl]-9H-fluoren-9-yl]-butyl]-3-piperidinyl]carbamic acid, phenylmethyl ester, monohydrochloride To a cloudy suspension of Part C compound (336 mg, 0.714 mmol) and triethylamine (238 μL, 1.71 mmol) in dioxane under argon was added diphenylphosphoryl azide (184 μL, 0.857 mmol). The mixture was heated at 80° C. for 2 h (N$_2$ evolution observed soon after heating commenced). Benzyl alcohol (367 μL, 3.57 mmol) was added, and the reaction was heated at 80° C. overnight. The reaction was cooled to RT and the solvent was distilled off under reduced pressure. The resulting residue was partitioned between CH$_2$Cl$_2$ (20 mL) and saturated NaHCO$_3$ (5 mL). The organic layer was washed with brine (5 mL) and dried over Na$_2$SO$_4$. Evaporation gave 760 mg of a yellow oil, which was purified by flash chromatography on silica gel (50 g) eluting with 3% MeOH/CH$_2$Cl$_2$ to give 215 mg of a colorless oil.

The free amine was dissolved in Et$_2$O (3 mL) and treated with 0.77N HCl in Et$_2$O (3 mL). The white precipitate was filtered, washed with Et$_2$O (2×3 mL), then dried under high vacuum at 50° C. overnight to give title compound (173 mg, 42%) as a white foamy solid.

MS (ES) 540 [M+H]

Anal. Calcd. for C$_{34}$H$_{42}$ClN$_3$O$_3$.0.3 H$_2$O:

C, 70.22; H, 7.38; N, 7.23.

Found: C, 70.11; H, 7.24; N, 7.09.

EXAMPLE 350

9-[4-[4-(2,3-Dihydro-1-oxo-1H-isoindol-2-yl)-1-piperidinyl]butyl]-N-(2,2,2-trifluoroethyl)-9H-fluorene-9-carboxamide, hydrochloride salt

A.

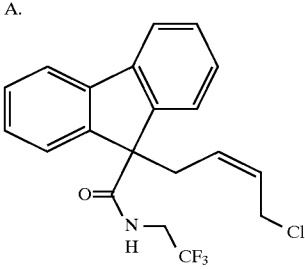

To a stirred solution of 10.0 g (33.5 mmol) of compound prepared in Example 314 Part A first paragraph in 100 mL of dichloromethane at RT was added 20.0 mL (40 mmol) of 2M oxalyl chloride in dichloromethane followed by 30 mL of DMF. The reaction was allowed to stir at RT for 2 h when the solvent was evaporated and the semisolid residue pumped (~1 mm pressure) for 0.5 h. The residue was dissolved by adding 300 mL of ether and cooled to 0° C. The mixture was treated with 7.30 g (67 mmol) of 2,2,2-trifluoroethylamine and warmed to room temperature. The mixture was diluted with 150 mL of ethyl acetate and 100 mL of 0.5M HCL. The layers were separated, the organics dried (Na$_2$SO$_4$) and concentrated. The remainder was purified by flash column chromatography on silica gel (250 g) eluting with 1:9 ethyl acetate/hexanes (800 mL) followed by 1:5 ethyl acetate/hexanes (1 L). Pure fractions were pooled and concentrated to give 9.25 g (73%) of title compound as a white solid.

mp: 87°–89° C.

B.

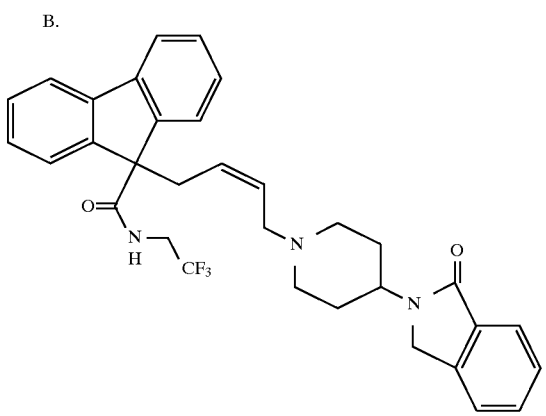

To a stirred solution of 6.54 g (17.22 mmol) of Part A compound in 6 mL of DMF at RT was added 4.00 g (18.51 mmol) of Example 2 Part A compound and 2.41 g (17.50 mmol) of $K_2CO_3$. The reaction mixture was warmed to 40° and allowed to stir for 20 h. The mixture was diluted with 200 mL of water and 2 mL of 1M NaOH solution (pH=11). The white solids were collected by filtration and dried to give 10.0 g (100%) of title compound.
TLC Silica gel (5:95:1 methanol/dichloromethane/$NH_3$) $R_f$=0.35.

C. 9-[4-[4-(2,3-Dihydro-1-oxo-1H-isoindol-2-yl)-1-piperidinyl]butyl]-N-(2,2,2-tri-fluoroethyl)-9H-fluorene-9-carboxamide A suspension of 10.00 g (~17 mmol) of Part B compound in 80 mL of ethanol was treated with 0.5 g of 10% Pd/carbon and placed under an atmosphere of $H_2$ (balloon pressure). The reaction mixture was stirred for 25 h when it was filtered through a pad of Celite and concentrated. The remainder was triturated with warm water to give 9.0 g (93%) of title compound as a white solid.
mp: 143°–146° C.
TLC Silica gel (5:95:1 methanol/dichloromethane/$NH_3$) $R_f$=0.35.

D. 9-[4-[4-(2,3-Dihydro-1-oxo-1H-isoindol-2-yl)-1-piperidinyl]butyl]-N-(2,2,2-triflu-oroethyl)-9H-fluorene-9-carboxamide, hydrochloride salt A suspension of 9.00 g (~16 mmol) of Part B compound in 200 mL of ethyl ether was treated with 8 mL (32 mmol) of 4M HCl in dioxane and the reaction mixture stirred for 1 h under an atmmosphere of $N_2$. The reaction mixture was filtered and the white solid collected. The solid was dried at 40° C. under vaccuum to give 9.0 g (93%) of title compound as a white solid.
mp: 139°–141° C.
TLC Silica gel (5:95:1 methanol/dichloromethane/$NH_3$) $R_f$=0.35.
MS (ES, +ions) m/z 562 (M+H).
Anal. Calcd. for $C_{33}H_{35}N_3O_2F_3Cl$:

C, 66.27; H, 5.90; N, 7.03; F, 9.53
Found: C, 66.53; H, 5.82; N, 6.78, F, 8.99.

EXAMPLE 351

9-[4-[4-(2,3-Dihydro-1-oxo-1H-isoindol-2-yl)-1-piperidinyl]butyl]-N-(2,2,2-trifluoroethyl)-9H-fluorene-9-carboxamide, hydrochloride salt

A.

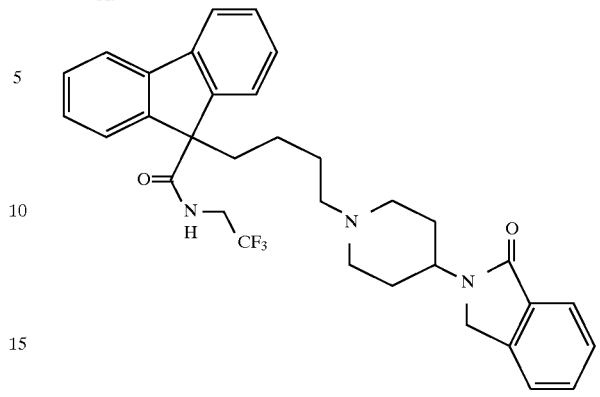

To a stirred solution of 4.00 g (9.38 mmol) of Example 346 Part B compound in 6 mL of DMF at RT was added 2.44 g (18.51 mmol) of Example 2 Part A compound and 1.59 g (11.30 mmol) of $K_2CO_3$. The reaction mixture was warmed to 50° C. and allowed to stir for 18 h. The mixture was diluted with 200 mL of water and 2 mL of 1M NaOH solution (pH=11). The white solids were collected by filtration and dried to give 4.50 g of title compound.

B. 9-[4-[4-(2,3-Dihydro-1-oxo-1H-isoindol-2-yl)-1-piperidinyl]butyl]-N-(2,2,2-trifluoroethyl)-9H-fluorene-9-carboxamide, hydrochloride salt A suspension of 4.00 g (~9.00 mmol) of Part A compound in 200 mL of ethyl ether was treated with 8 mL (32 mmol) of 4M HCl in dioxane and the reaction mixture stirred for 1 h under an atmosphere of $N_2$. The reaction mixture was filtered and the cream colored solid collected. The solid was dried at 40° C. under vacuum to give 3.8 g (73%) of title compound.
mp: 139°–141° C.
MS (ES, +ions) m/z 562 (M+H).
Anal. Calcd. for $C_{33}H_{35}N_3O_2F_3Cl$:

C, 66.27; H, 5.90; N, 7.03
Found: C, 65.87; H, 6.14; N, 6.71.

EXAMPLES 352–360

Following the procedures set out herein, the following compounds were prepared.

EXAMPLE 352

9-[4-[3-(Benzoylamino)-1-piperidinyl]butyl]-N-propyl-9H4fluorene-9-carboxamide.
MS (ES) 510 (M+H)
Anal. Calcd. for $C_{33}H_{39}N_3O_2$.0.2 $H_2O$:

C, 77.22; H, 7.74; N, 8.19
Found: C, 77.12; H. 7.58; N. 8.16.

EXAMPLE 353

9-[4-[3-(1,3-Dihydro-1,3-dioxo-2H-isoindol-2-yl)-1-piperidinyl]butyl]-N-propyl-9H-fluorene-9-carboxamide.
MS (ES) 536 (M+H)
Anal. Calcd. for $C_{34}H_{37}N_3O_3$.0.2 $H_2O$:

C, 75.72; H, 6.99; N. 7.79
Found: C, 75.68; H, 6.78; N, 7.68.

EXAMPLE 354

9-[4-[4-(2,3-Dihydro-1-oxo-1H-isoindol-2-yl)-1-piperidinyl]butyl]-N-(2,2,3,3,4,4,4-heptafluorobutyl)-9H-fluorene-9-carboxamide, monohydrochloride.
mp: 122°–132° C.

MS (ES, +ions) m/z 662 (M+H)
Anal. Calcd. for $C_{35}H_{35}O_2N_3F_7Cl.0.8\ H_2O$:
 C, 59.04; H, 5.17; N, 5.90
Found: C, 59.04; H, 5.04; N, 5.90.

EXAMPLE 355

9-[4-[[4-[(1,1-Dimethylethoxy)carbonyl]amino]-1-piperidinyl]butyl]-3,6-difluoro-N-(2,2,2-trifluoroethyl)-9H-fluorene-9-carboxamide.
mp: 59°–64° C.
MS (FAB, M+H)$^+$=m/z 582$^+$
Anal. Calcd. for $C_{30}H_{36}F_5N_3O_3$.0.2 equiv. hexane:
 C, 62.58; H, 6.53; N, 7.02
Found: C, 62.41; H, 6.55; N, 6.84.

EXAMPLE 356

1-[4-[4-(1,3-Dihydro-1-oxo-2H-isoindol-2-yl)-1-piperidinyl]butyl]-2-methyl-N-(2,2,2-trifluoroethyl)-1H-indene-1-carboxamide.
mp: 124°–126° C.
MS m/z (ES, +ions) 526.3 (M+H)
Anal. Calcd. for $C_{30}H_{34}F_3N_3O_2$:
 C, 67.55; H, 6.52; N, 7.99; F, 10.84
Found: C, 67.80; H, 6.53; N, 7.89; F, 10.75.

EXAMPLE 357

9-[4-[4-(1,3-Dihydro-1-oxo-2H-isoindol-2-yl)-1-piperidinyl]butyl]-N-(2,2,3,3,3-pentafluoropropyl)-9H-fluorene-9-carboxamide, monohydrochloride.
mp: 130°–144° C.
MS (ES, +ions) m/z 578 (M+H)
Anal. Calcd. for $C_{34}H_{35}N_3O_2F_5Cl+1.2\ H_2O$:
 C, 60.98; H, 5.63; N, 6.27; F, 14.18
Found: C, 61.34; H, 5.48; N, 6.08; F, 13.69.

EXAMPLE 358

1-[4-[4(1,3-Dihydro-1-oxo-2H-isoindol-2-yl)-1-piperidinyl]butyl]-N-(2,2,2-trifluoroethyl)-1H-indene-1-carboxamide.
mp: 62°–65° C.
MS m/z (ES, −ions) 510 (M−H), 556 (M+HCO$_2$-)
Anal. Calcd. for $C_{29}H32F_3N_3O_2$.0.16 $H_2O$:
 C, 67.70; H, 6.33; N, 8.17; F, 11.08
Found: C, 67.70; H, 6.26; N, 7.94; F, 10.62.

EXAMPLE 359

9-[4-[4-(Benzoylamino)-1-piperidinyl]butyl-]3,6difluoro-N-(2,2,2-trifluoroethyl)-9H-fluorene-9-carboxamide.
MS (FAB, M+H)+m/z 586$^+$
Anal. Calcd. for $C_{32}H_{32}F_5N_3O_2.H_2O0.15\ CH_2Cl_2$:
 C, 62.65; H, 5.61; N, 6.82
Found: C, 62.52; H, 5.56; N, 6.67.

EXAMPLE 360

3,6-Difluoro-9-[4-[4-[(2-phenoxybenzoyl)amino]-1-piperidinyl]butyl]-N-(2,2,2-trifluoroethyl)-9H-fluorene-9carboxamide.
mp: 124°–26° C.
MS (FAB, M+H) m/z 678$^+$
Anal. Calcd. for $C_{38}H_{36}F_5N_3O_3$:
 C, 67.35; H, 5.35; N, 6.20
Found: C, 67.38; H, 5.62; N, 5.92.

EXAMPLES 361 to 477

The following compounds were prepared by robotics procedures as described below.

Robotic Method for the Preparation of Amides

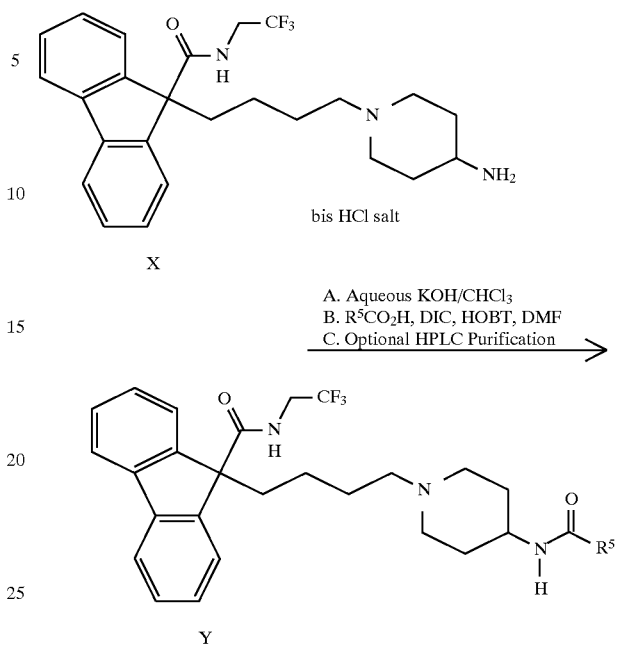

A. Preparation of the diamine starting material:

A solution of the diamine bishydrochloride salt (compound X) (10 g, 19.3 mmol) in chloroform (400 mL) was washed with 1N KOH solution (3×100 mL). The organic layer was washed $H_2O$ (2×100 mL), brine (2×100 mL) and dried over $MgSO_4$.

Evaporation gave the free diamine (8.8 g, 100%) as a colorless oil.

B. General Experimental for Robotics Compounds

The following is a general procedure for the synthesis of amides according to the above equation via the coupling of carboxylic acids with the diamine. These acid-amine couplings and subsequent purifications were carried out using a Zymark Benchmate® Robotic system using an IBM PC to run the operating program and to write the Benchmate procedures.

A 16 mm×100 mm tube was charged with 1.6 mmol, 4 eq $R^5CO_2H$ acid and capped loosely with a plastic cap/column holder. The Benchmate® then carried out the following steps on, the tube:

1) Added 1 mL (81 mg, 0.6 mmol, 1.5 eq) of a 81 mg/mL solution of 1-hydroxybenzotriazole hydrate in DMF.
2) Added 1 mL (75 mg, 0.6 mmol, 1.5 eq) of a 75 mg/mL solution of diisopropylcarbodiimide in $CH_2Cl_2$.
3) Added 1 mL (178 mg, 0.4 mmol, 1 eq) of a 178 mg/mL solution of diamine in $CH_2Cl_2$.
4) Washed syringe with 3 mL of $CH_2Cl_2$
5) Mixed tube contents by vortexing at speed 3 for 15 sec. After 12–48 h the reaction was complete (no starting amine remained as determined by TLC; 10% MeOH+1% $NH_4OH$ in $CH_2Cl_2$, $I_2$).

The reaction mixture contents were then purified by ion exchange chromatography mediated by the Benchmate® Robot. The following is the standard procedure developed for purification of the coupled products by the Benchmate®:

1) Condition a Varian solid phase extraction column (1.5 g, SCX cation exchange) with 10 mL of MeOH at 0.25 ml/sec
2) Load reaction contents onto column at 0.05 mL/sec
3) Wash column with 2×10 mL of MeOH at 0.1 ml/sec
4) Wash column with 10 mL of 0.1M ammonia in MeOH at 0.1 ml/sec
5) Elute column with 4 mL of 2M ammonia in MeOH and collect into a tared receiving tube at 0.1 ml/sec
6) Elute column with 1 mL of 2M ammonia in MeOH and collect into same tared receiving tube at 0.1 ml/sec
7) Rinse syringe with 5 mL of MeOH All solution/solvent deliveries were followed by 1.8 mL of air and 10 sec push delay was used after loading reaction contents onto the ion exchange column.

The product solution was concentrated on a Savant Speed Vac (approx. 2 mm Hg for 5 h) and final solvent remnants were removed by further exposure to high vac (0.015 mm Hg, 14 h) to afford product Y, which was characterized by HPLC and MS.

MS (ES, +ions) m/z 619 (M+H)

C. Preparative HPLC Purification

In cases where the coupling reaction is carried out with carboxylic acids bearing basic substituents (for example, pyridyl or amino), the product Y isolated as above in Part B, is contaminated with the starting acid. These materials were further purified by preparative HPLC.

The samples after elution from the SCX column and speed vac concentration were reconstituted in MeOH and a small amount of trifluoroacetic acid (1 drop) was added to each. The products Y were purified by preparative chromatography using the following conditions:

Solvent A: 10% MeOH, 90% $H_2O$, 0.1% TFA
Solvent B: 90% MeOH, 10% $H_2O$, 0.1% TFA
Column: YMC ODS-A, SH-363-5,30×250 mm I.D. S-5 $\mu$m, 120 A, No. 3025356A.
Starting % B: 0%
Final % B: 100%
Gradient time: 30 min
Flow rate: 25 mL/min
Wavelength: 220 nm
Attenuation: 9(1.28 AUFS)

Pure fractions were combined and concentrated to afford purified product Y, which was characterized by HPLC+MS.

Please note that in the Examples 361 to 477, for structures bearing only two single bonded substituents to nitrogen, the third substituent is always hydrogen, but it is not shown explicitly in the structures. Also, please note that in the Examples 361 to 477 for structures bearing oxygens and sulfurs with only one single bonded substituent, the second substituent is always hydrogen, but is not shown explicitly in the structures.

| Example No. | Molecular Structure | Analytical Data |
|---|---|---|
| 361 | 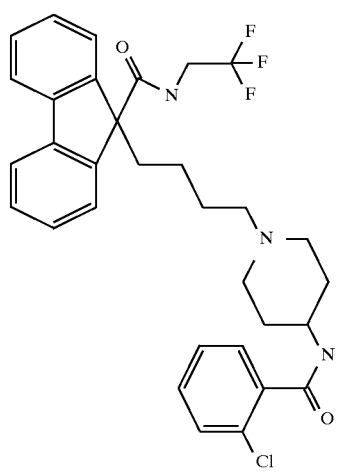 | m/z 585 (M+H) |

| Example No. | Molecular Structure | Analytical Data |
|---|---|---|
| 362 | 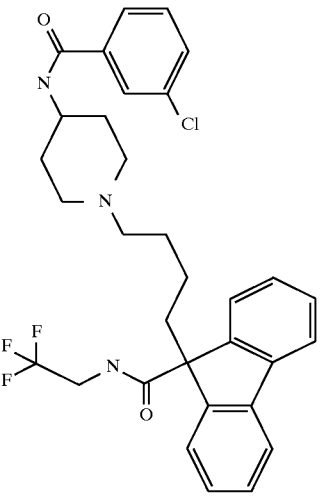 | m/z 585 (M+H) |
| 363 | 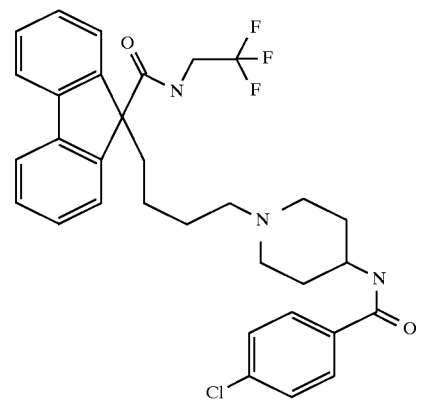 | m/z 585 (M+H) |
| 364 | 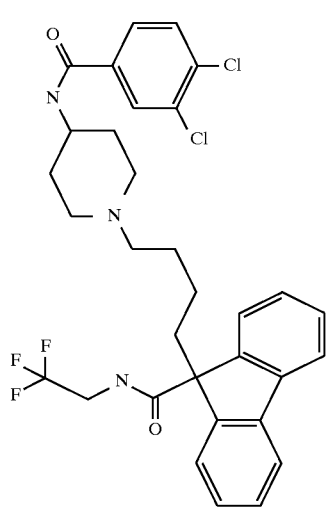 | m/z 619 (M+H) |

| Example No. | Molecular Structure | Analytical Data |
|---|---|---|
| 365 | 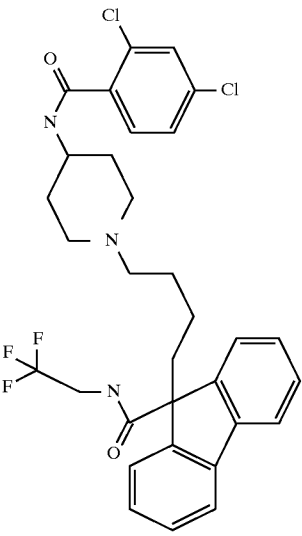 | m/z 619 (M+H) |
| 366 | 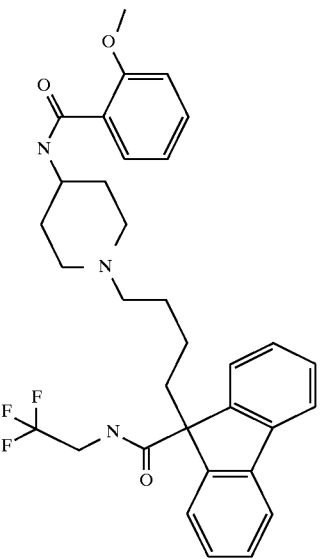 | m/z 580 (M+H) |
| 367 | 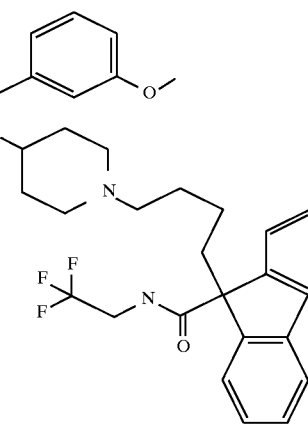 | m/z 580 (M+H) |

| Example No. | Molecular Structure | Analytical Data |
|---|---|---|
| 368 | 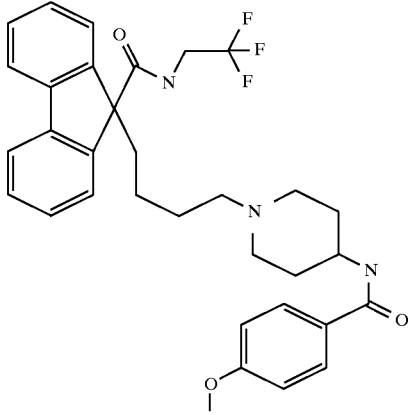 | m/z 580 (M+H) |
| 369 | 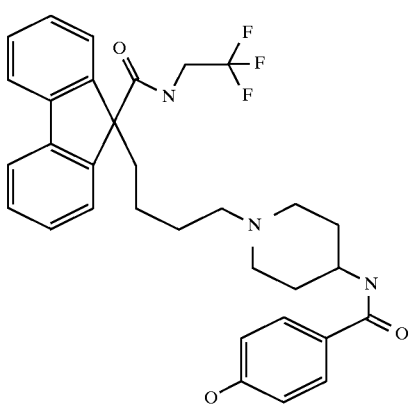 | m/z 563 (M−H) |
| 370 | 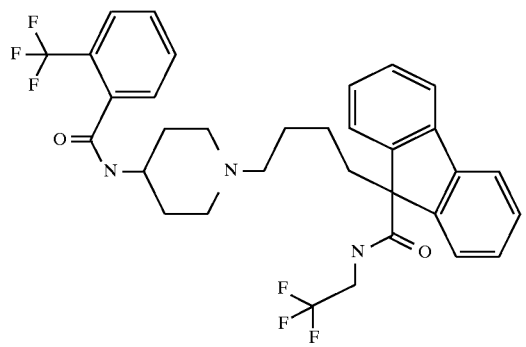 | m/z 618 (M+H) |
| 371 | 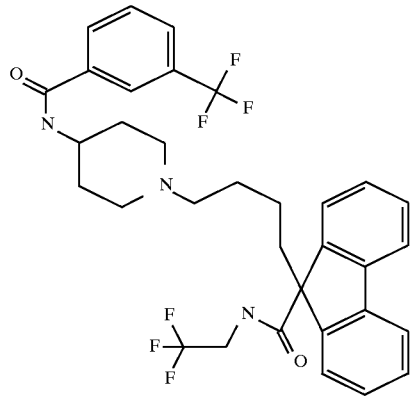 | m/z 618 (M+H) |

| Example No. | Molecular Structure | Analytical Data |
|---|---|---|
| 372 | 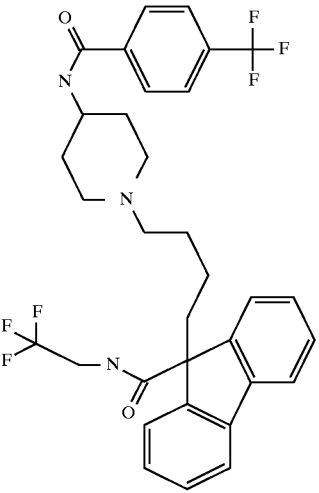 | m/z 618 (M+H) |
| 373 | 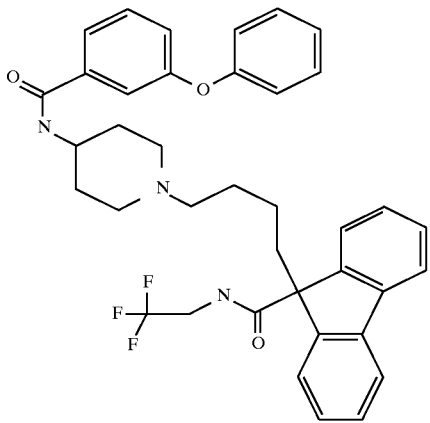 | m/z 642 (M+H) |
| 374 | 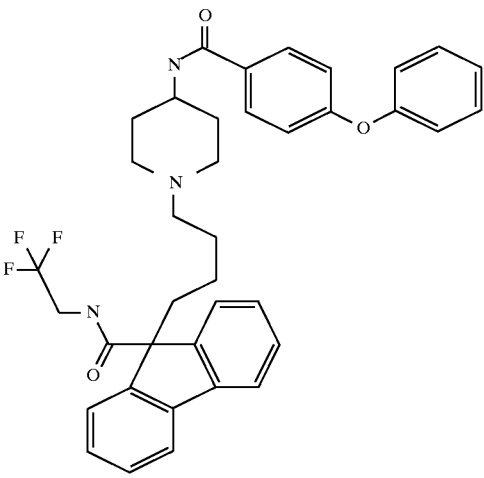 | m/z 642 (M+H) |

| Example No. | Molecular Structure | Analytical Data |
|---|---|---|
| 375 | 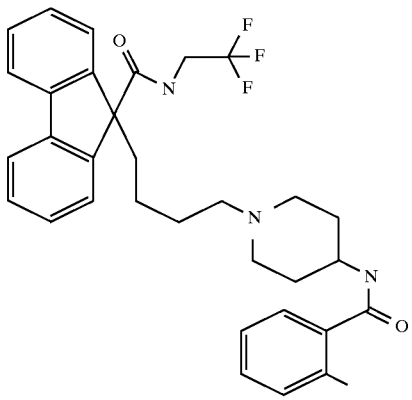 | m/z 564 (M+H) |
| 376 | 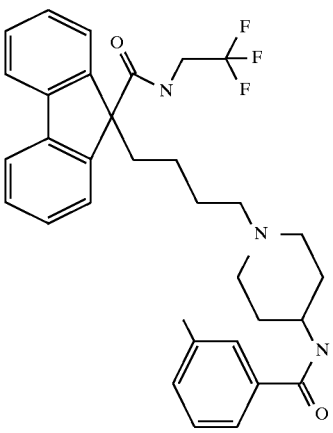 | m/z 564 (M+H) |
| 377 | 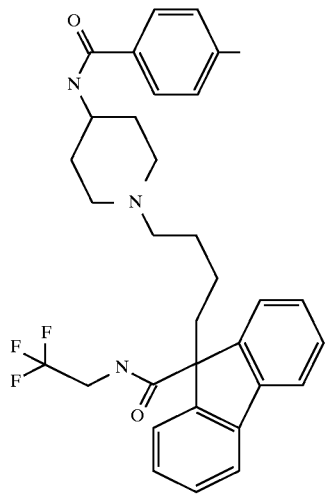 | m/z 564 (M+H) |

-continued

| Example No. | Molecular Structure | Analytical Data |
|---|---|---|
| 378 | 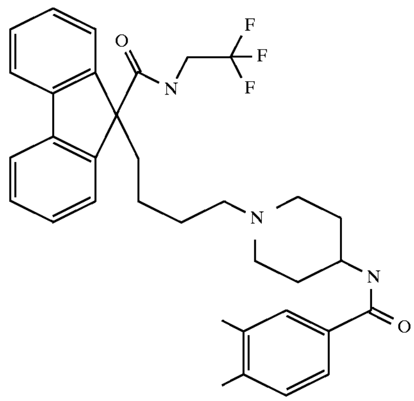 | m/z 578 (M+H) |
| 379 | 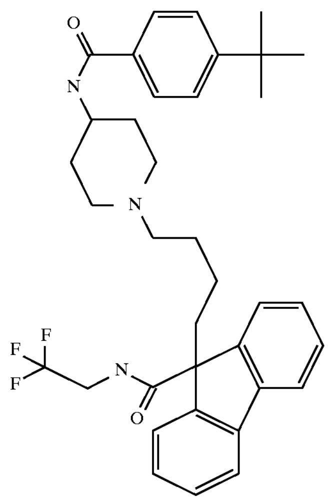 | m/z 606 (M+H) |
| 380 | 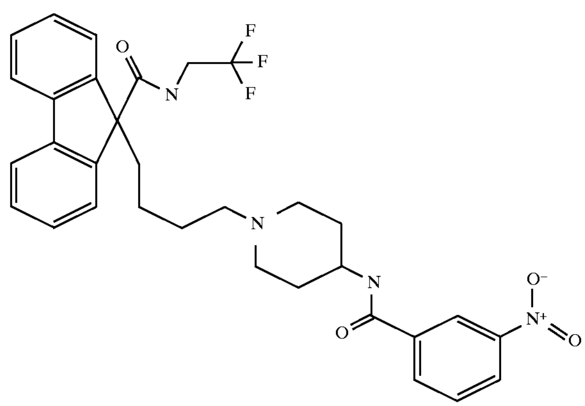 | m/z 595 (M+H) |

-continued

| Example No. | Molecular Structure | Analytical Data |
|---|---|---|
| 381 | 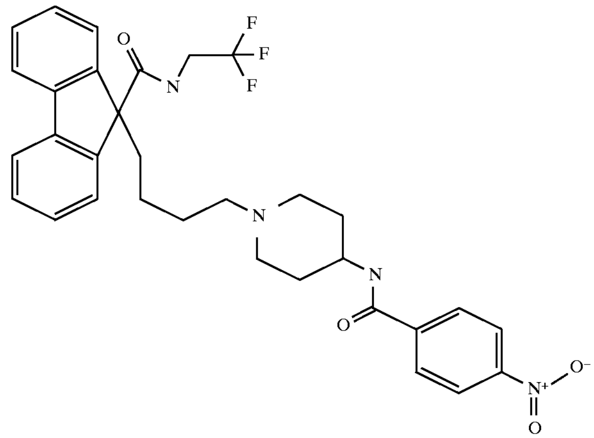 | m/z 595 (M+H) |
| 382 | 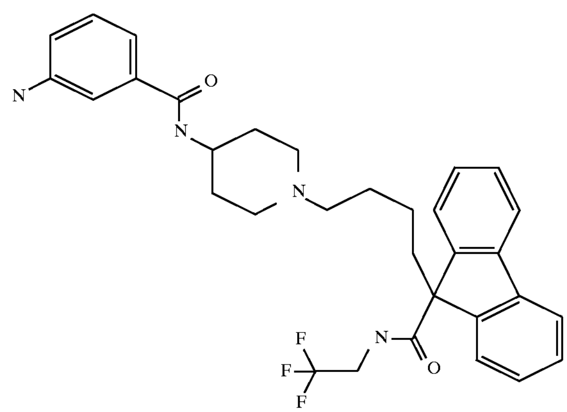 | m/z 563 (M−H) |
| 383 | 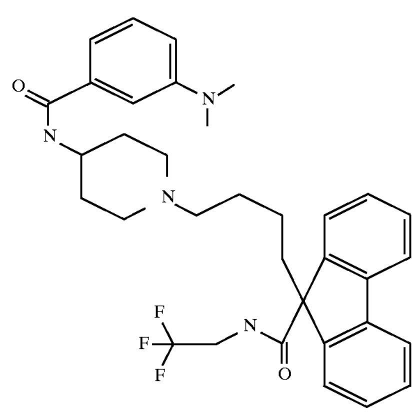 | m/z 591 (M−H) |
| 384 | 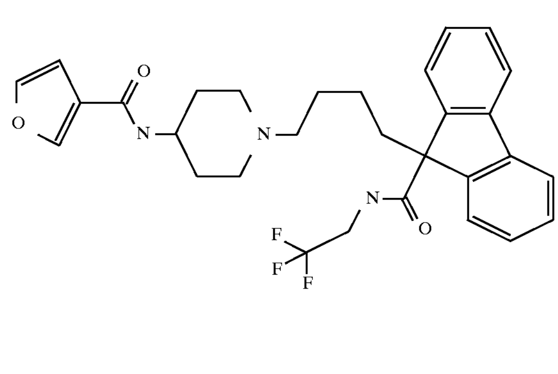 | m/z 540 (M+H) |

| Example No. | Molecular Structure | Analytical Data |
|---|---|---|
| 385 | 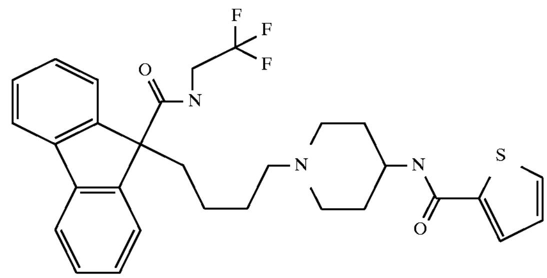 | m/z 556 (M+H) |
| 386 | 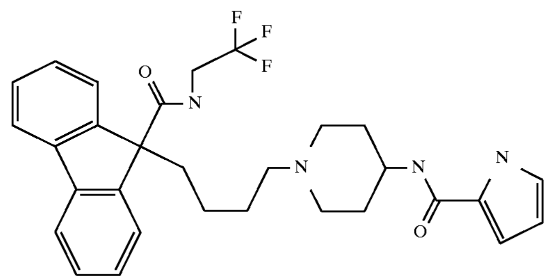 | m/z 539 (M+H) |
| 387 | 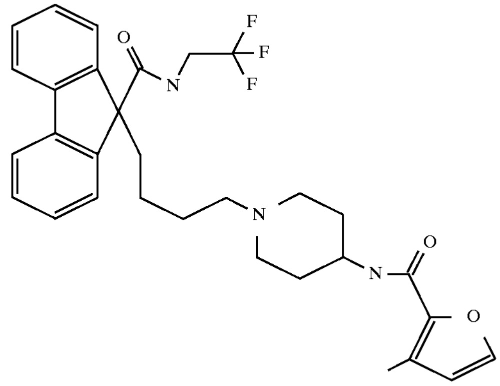 | m/z 554 (M+H) |
| 388 | 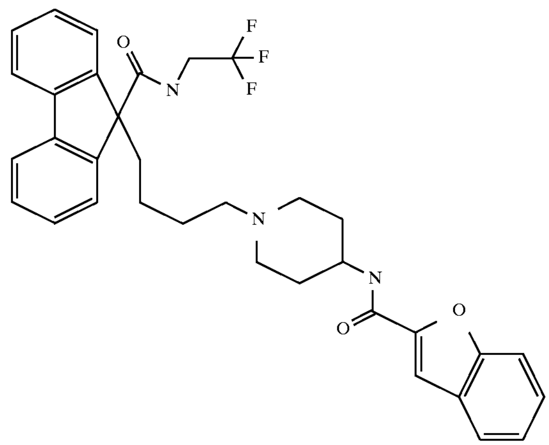 | m/z 590 (M+H) |

| Example No. | Molecular Structure | Analytical Data |
|---|---|---|
| 389 | 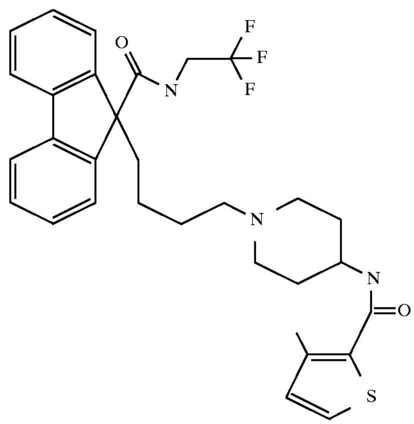 | m/z 570 (M+H) |
| 390 | 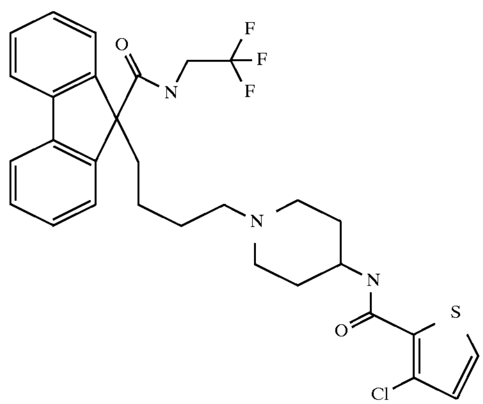 | m/z 591 (M+H) |
| 391 | 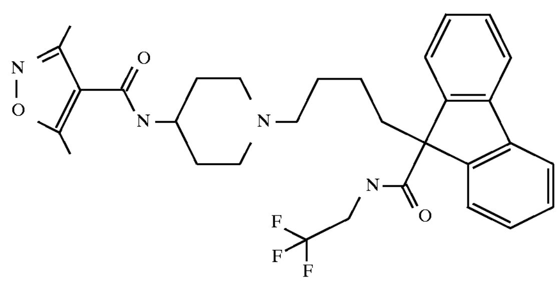 | m/z 569 (M+H) |
| 392 | 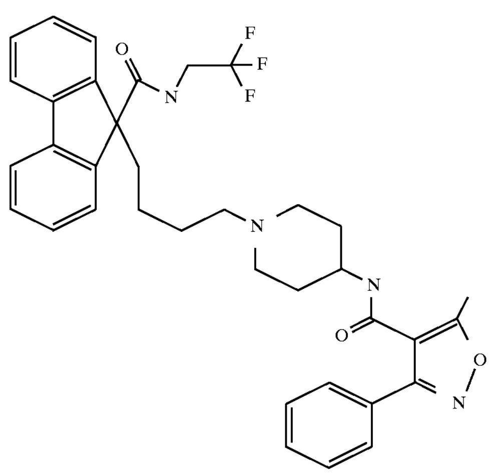 | m/z 631 (M+H) |

-continued

| Example No. | Molecular Structure | Analytical Data |
|---|---|---|
| 393 | 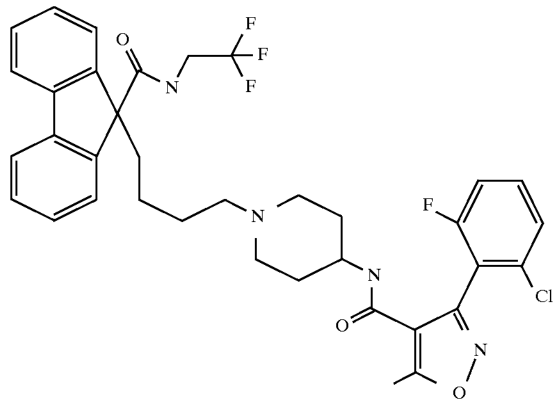 | m/z 684 (M+H) |
| 394 | 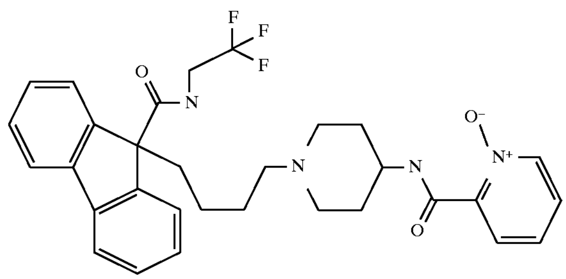 | m/z 567 (M+H) |
| 395 | 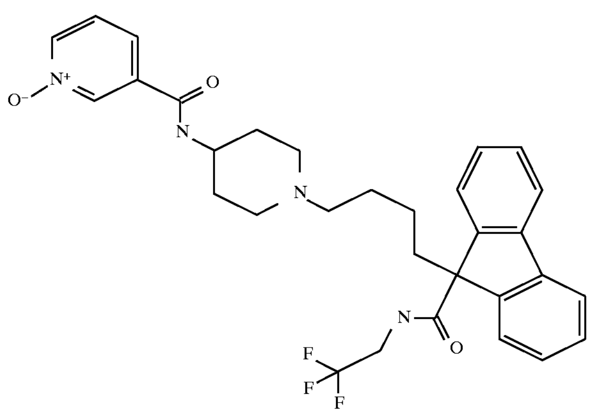 | m/z 565 (M−H) |
| 396 | 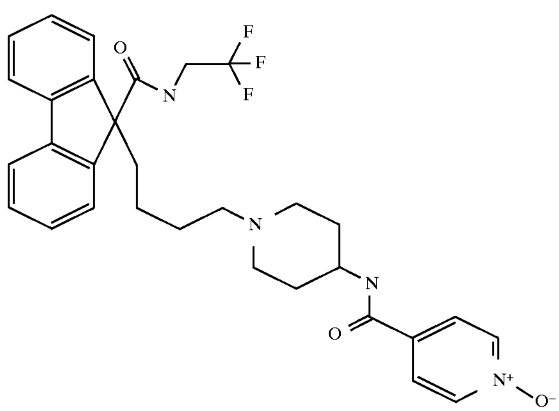 | m/z 565 (M−H) |

| Example No. | Molecular Structure | Analytical Data |
|---|---|---|
| 397 | 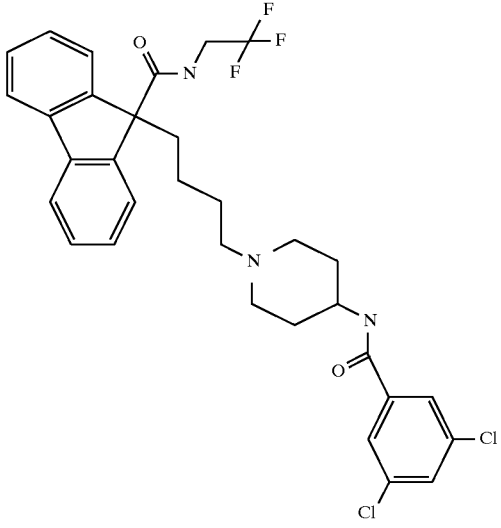 | m/z 619 (M+H) |
| 398 | 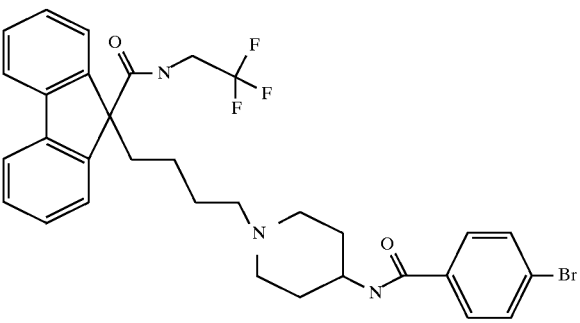 | m/z 629 (M+H) |
| 399 | 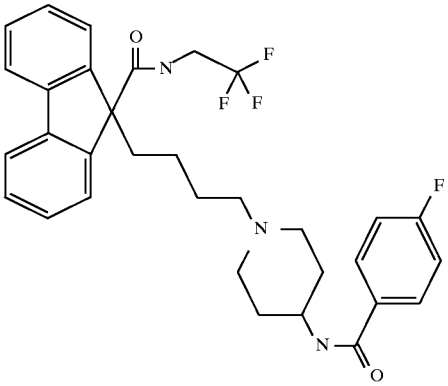 | m/z 568 (M+H) |
| 400 | 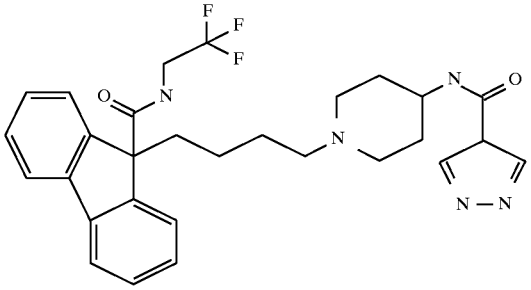 | m/z 540 (M+H) |

| Example No. | Molecular Structure | Analytical Data |
|---|---|---|
| 401 | 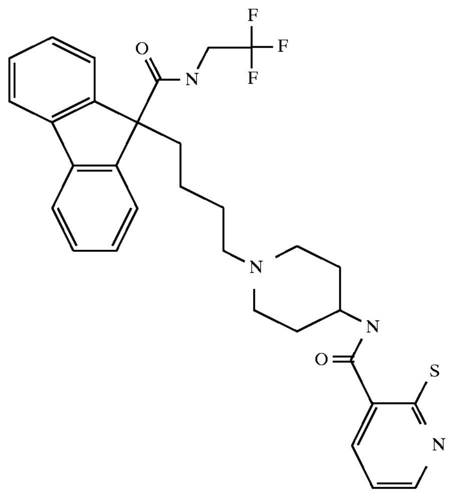 | m/z 583 (M+H) |
| 402 | 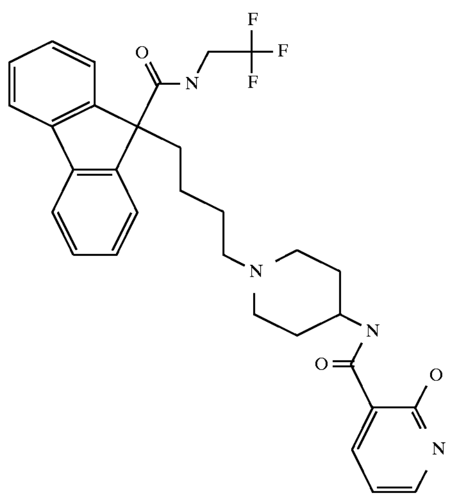 | m/z 567 (M+H) |
| 403 | 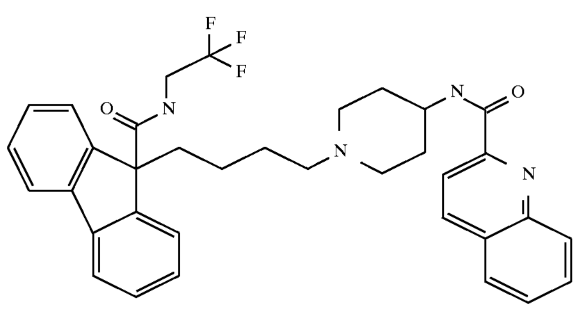 | m/z 601 (M+H) |

| Example No. | Molecular Structure | Analytical Data |
|---|---|---|
| 404 | 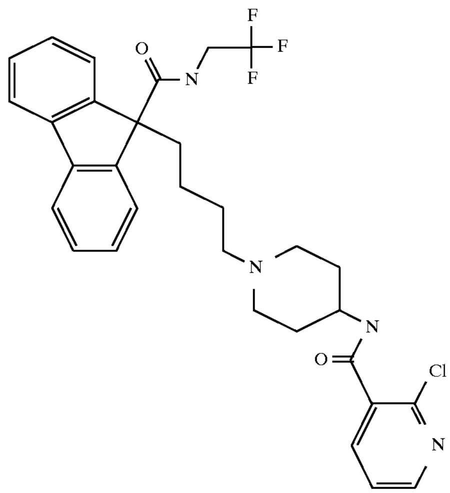 | m/z 586 (M+H) |
| 405 | 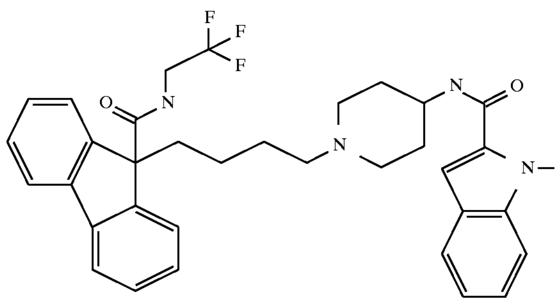 | m/z 603 (M+H) |
| 406 | 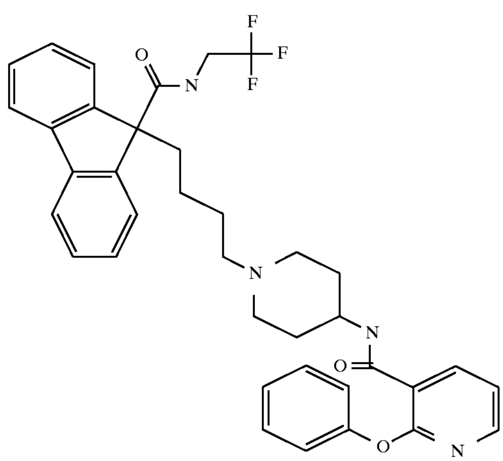 | m/z 643 (M+H) |

5,883,099
237
238
-continued
| Example No. | Molecular Structure | Analytical Data |
|---|---|---|
| 407 | 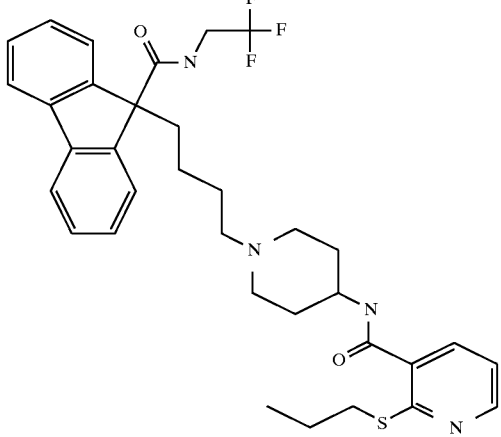 | m/z 625 (M+H) |
| 408 | 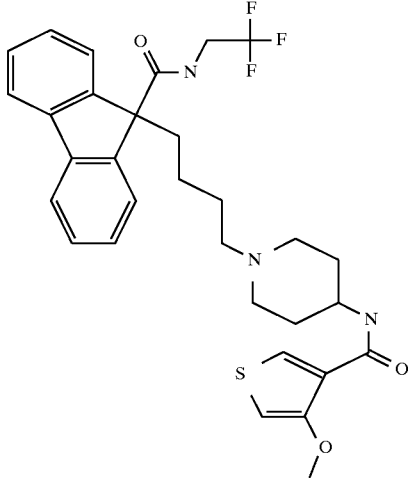 | m/z 587 (M+H) |
| 409 | 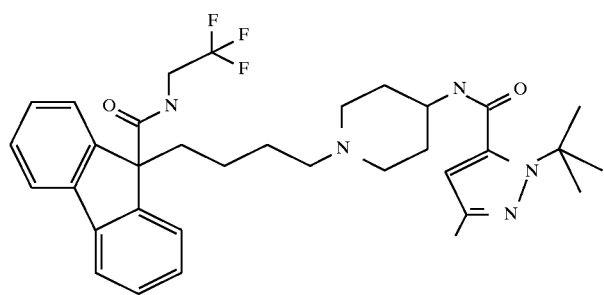 | m/z 610 (M+H) |

-continued

| Example No. | Molecular Structure | Analytical Data |
| --- | --- | --- |
| 410 | 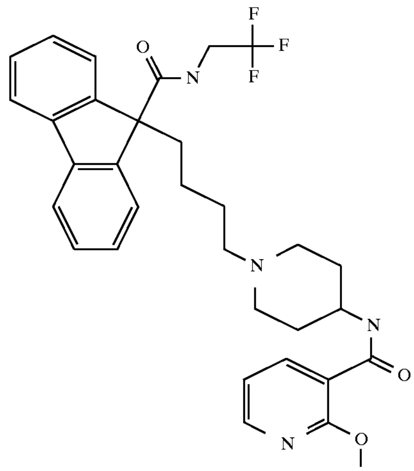 | m/z 581 (M+H) |
| 411 | 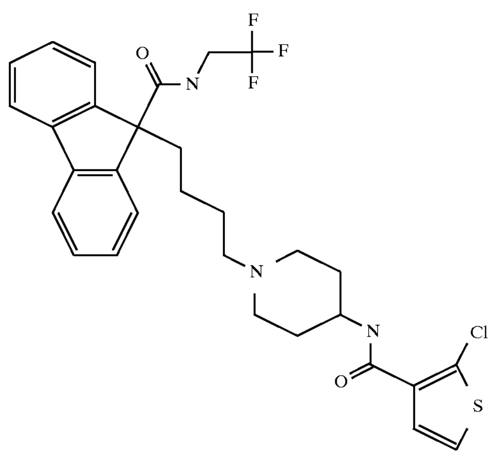 | m/z 591 (M+H) |
| 412 | 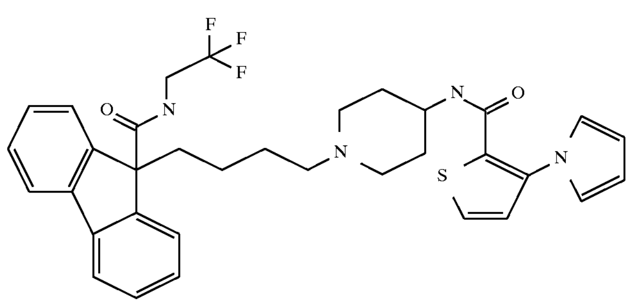 | m/z 621 (M+H) |
| 413 | 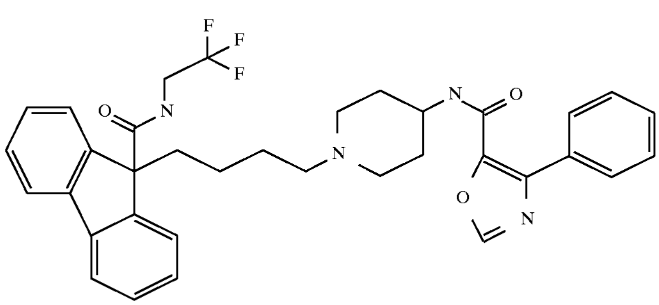 | m/z 617 (M+H) |

| Example No. | Molecular Structure | Analytical Data |
|---|---|---|
| 414 | 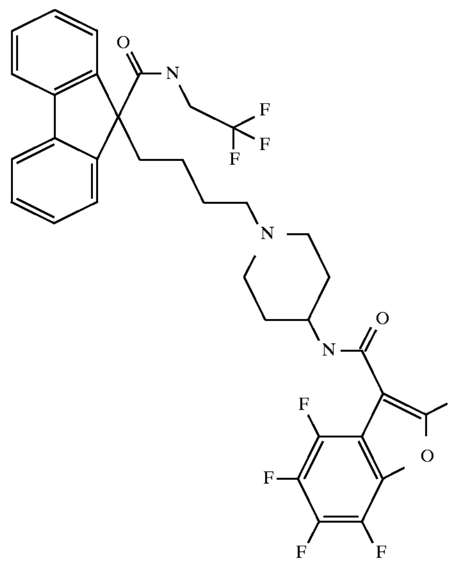 | m/z 676 (M+H) |
| 415 | 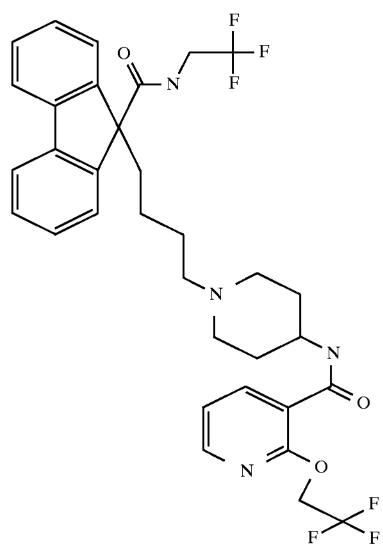 | m/z 676 (M+H) |
| 416 | 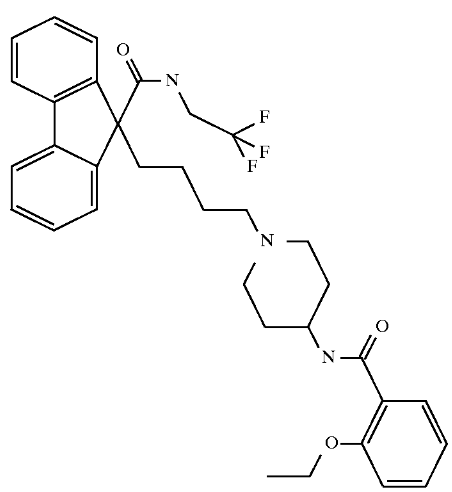 | m/z 594 (M+H) |

-continued
| Example No. | Molecular Structure | Analytical Data |
|---|---|---|
| 417 | 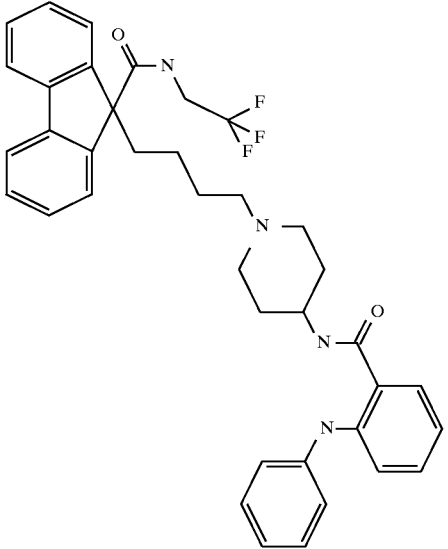 | m/z 641 (M+H) |
| 418 | 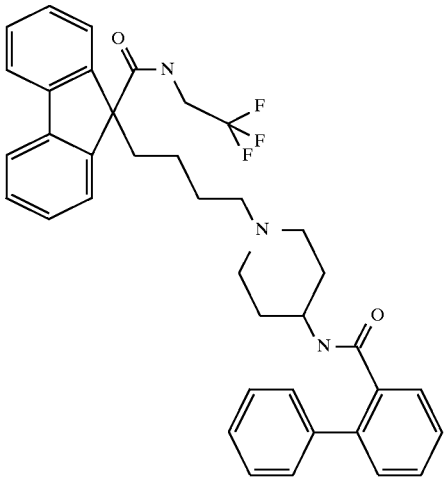 | m/z 626 (M+H) |
| 419 | 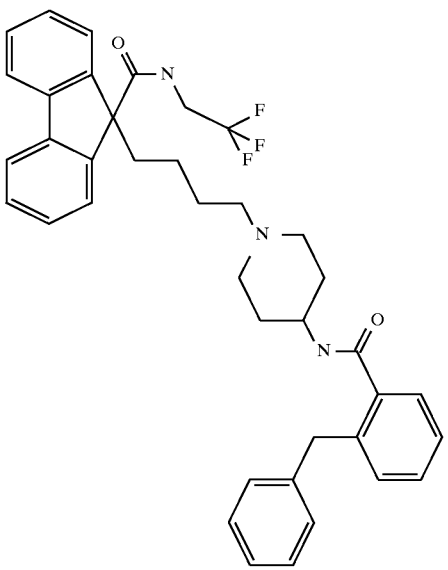 | m/z 640 (M+H) |

| Example No. | Molecular Structure | Analytical Data |
|---|---|---|
| 420 | 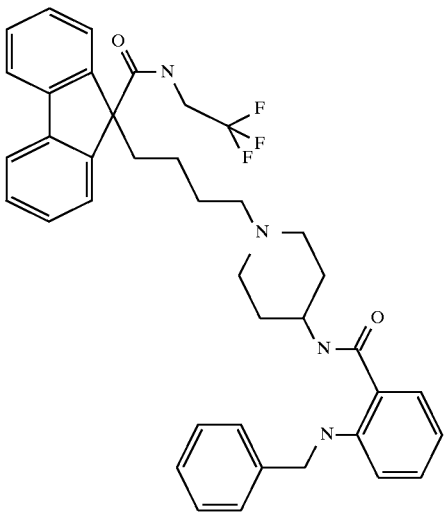 | m/z 655 (M+H) |
| 421 | 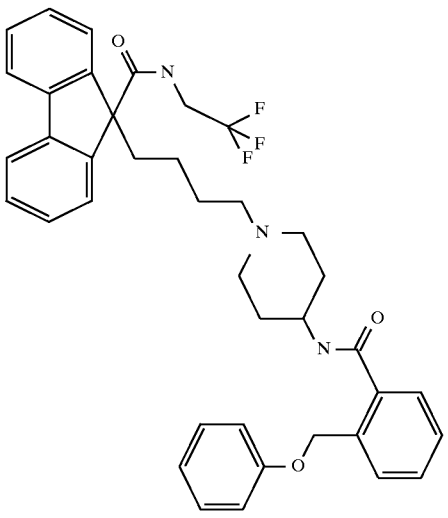 | m/z 565 (M+H) |
| 422 | 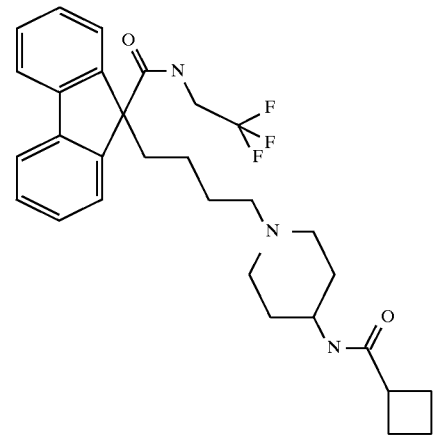 | m/z 528 (M+H) |

-continued
| Example No. | Molecular Structure | Analytical Data |
|---|---|---|
| 423 | 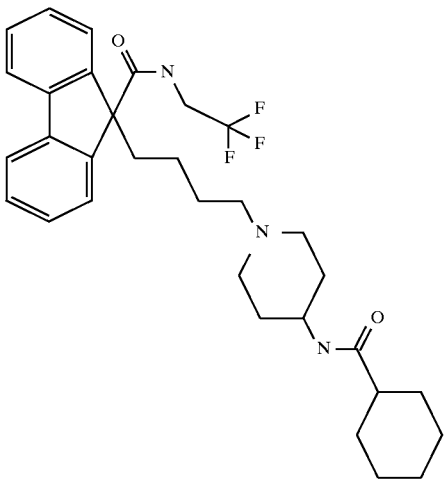 | m/z 556 (M+H) |
| 424 | 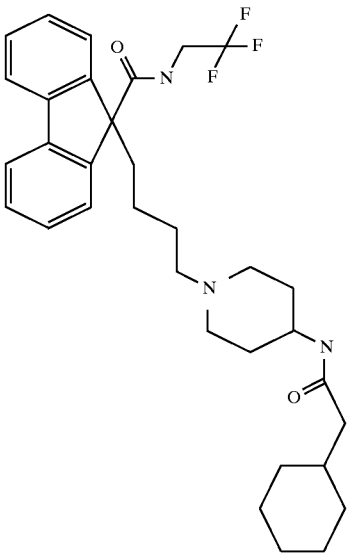 | m/z 570 (M+H) |
| 425 | 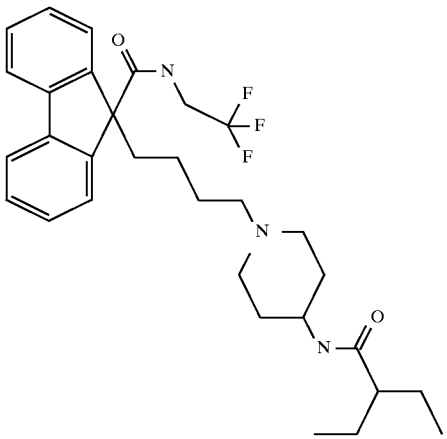 | m/z 544 (M+H) |

| Example No. | Molecular Structure | Analytical Data |
|---|---|---|
| 426 | 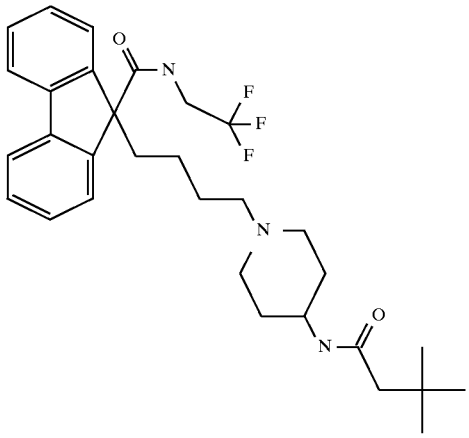 | m/z 544 (M+H) |
| 427 | 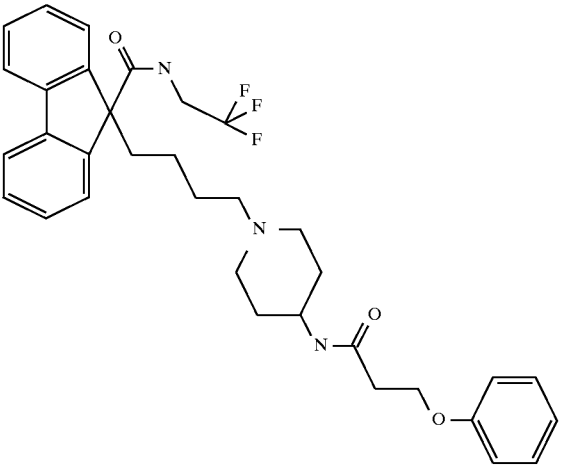 | m/z 594 (M+H) |
| 428 | 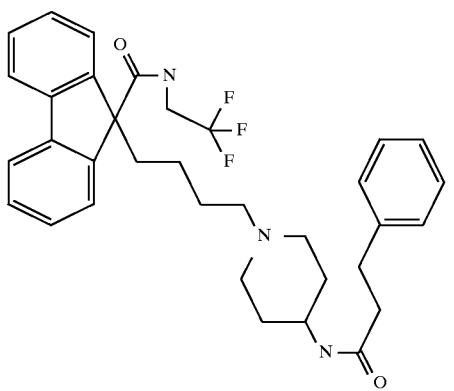 | m/z 578 (M+H) |

| Example No. | Molecular Structure | Analytical Data |
|---|---|---|
| 429 | 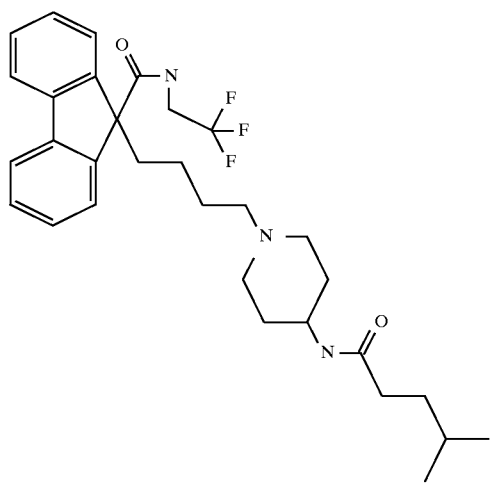 | m/z 544 (M+H) |
| 430 | 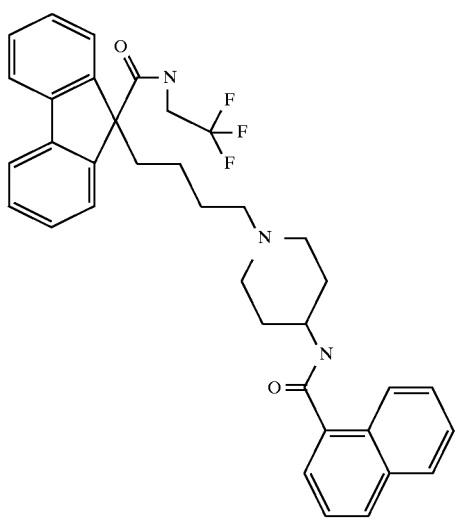 | m/z 600 (M+H) |
| 431 | 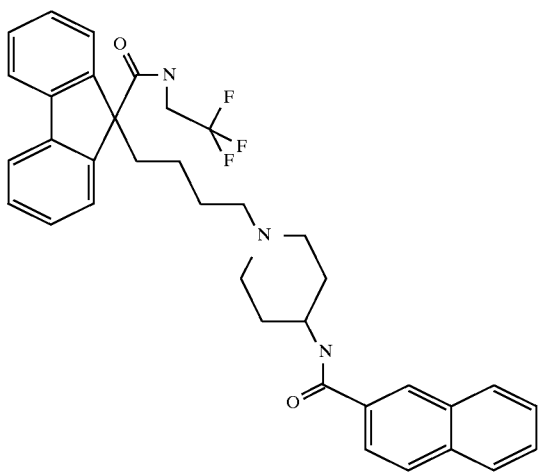 | m/z 600 (M+H) |

-continued
| Example No. | Molecular Structure | Analytical Data |
|---|---|---|
| 432 | 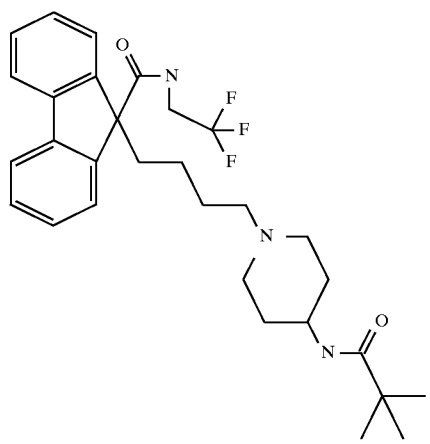 | m/z 530 (M+H) |
| 433 | 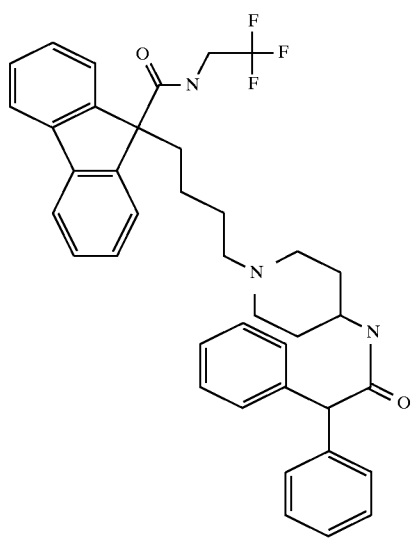 | m/z 640 (M+H) |
| 434 | 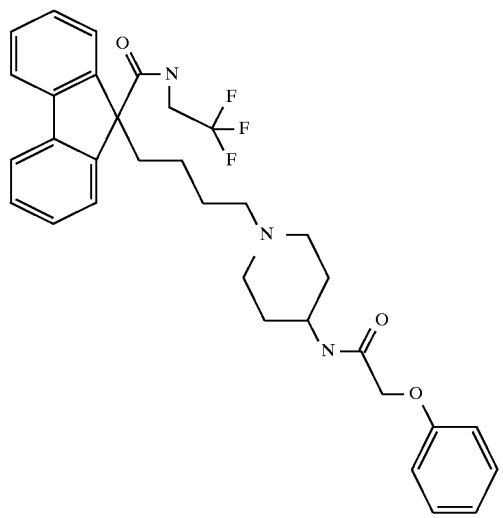 | m/z 580 (M+H) |

| Example No. | Molecular Structure | Analytical Data |
|---|---|---|
| 435 | 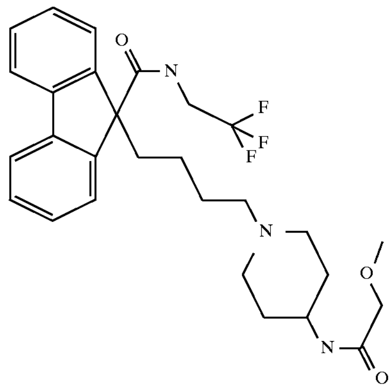 | m/z 518 (M+H) |
| 436 | 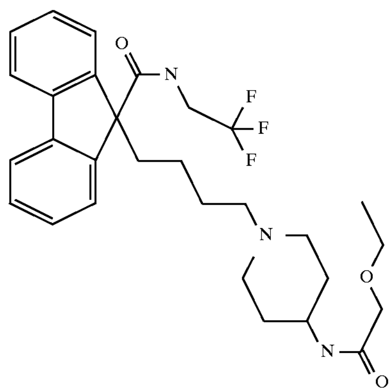 | m/z 532 (M+H) |
| 437 | 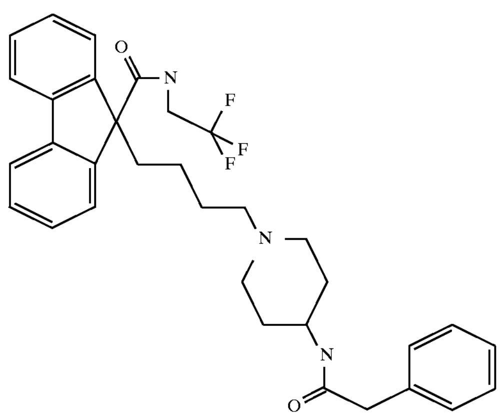 | m/z 564 (M+H) |
| 438 | 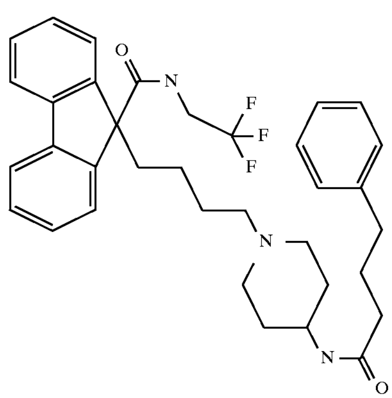 | m/z 592 (M+H) |

| Example No. | Molecular Structure | Analytical Data |
|---|---|---|
| 439 | 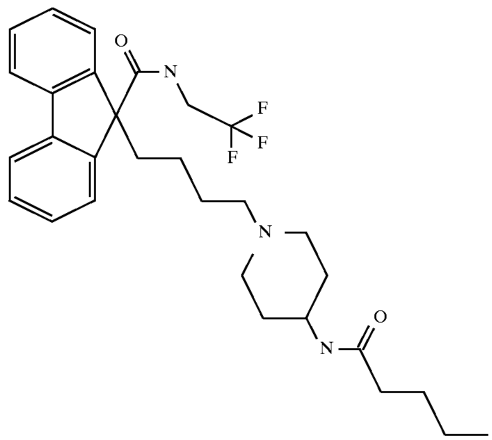 | m/z 530 (M+H) |
| 440 | 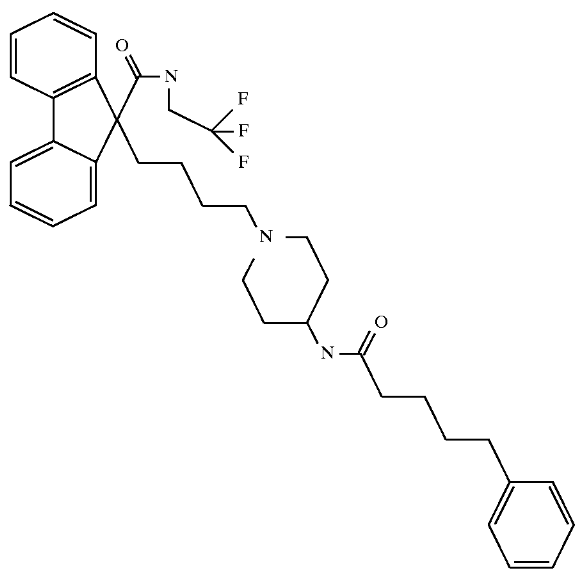 | m/z 606 (M+H) |
| 441 | 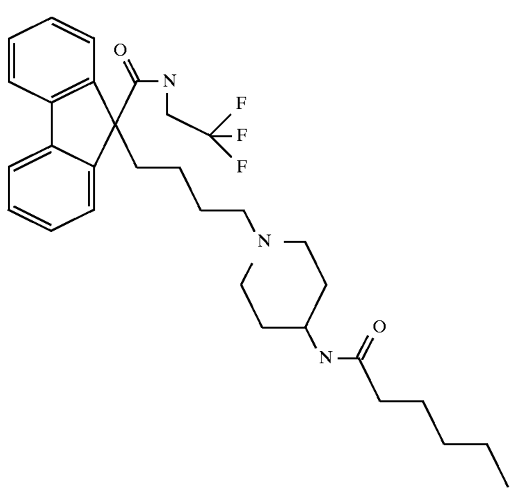 | m/z 544 (M+H) |

-continued

| Example No. | Molecular Structure | Analytical Data |
|---|---|---|
| 442 | 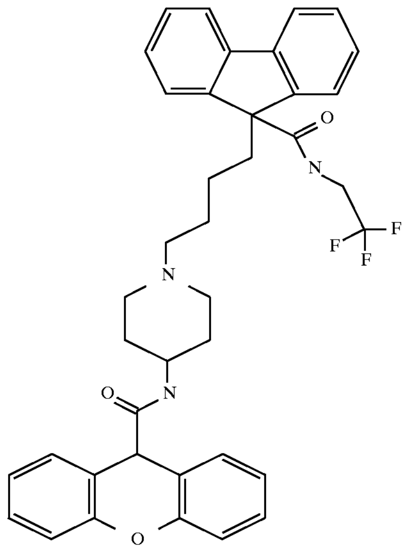 | m/z 654 (M+H) |
| 443 | 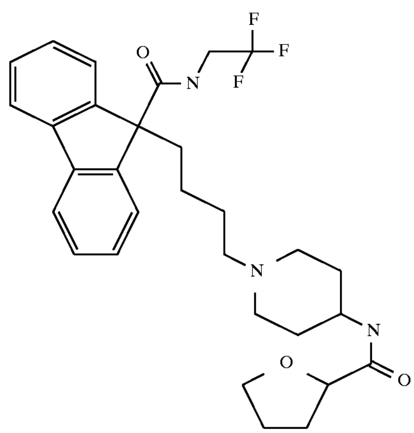 | m/z 545 (M+H) |
| 444 | 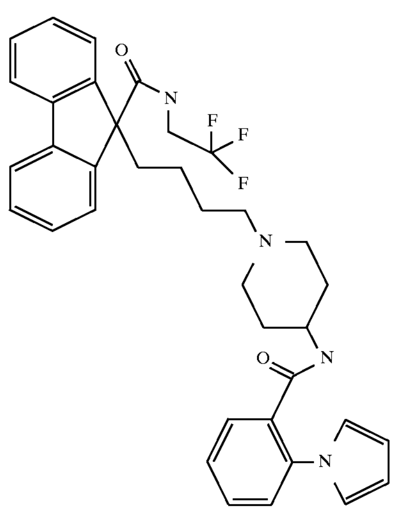 | m/z 615 (M+H) |

| Example No. | Molecular Structure | Analytical Data |
|---|---|---|
| 445 | 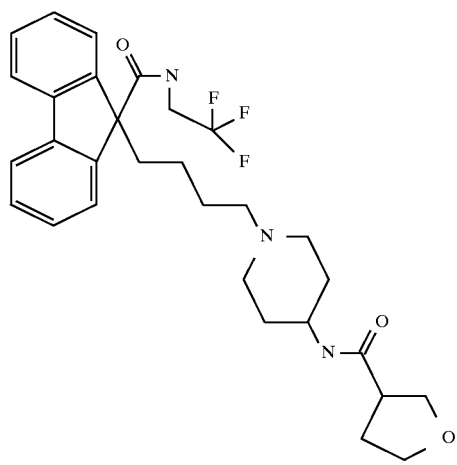 | m/z 544 (M+H) |
| 446 | 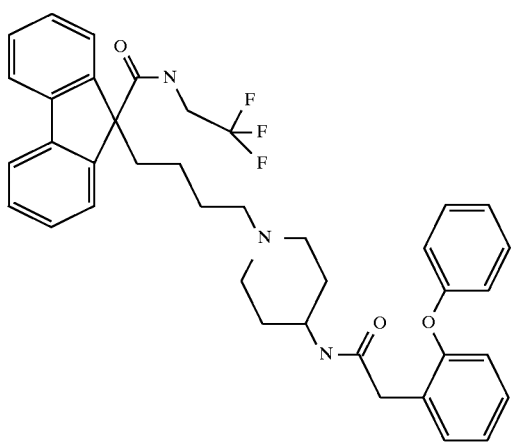 | m/z 656 (M+H) |
| 447 | 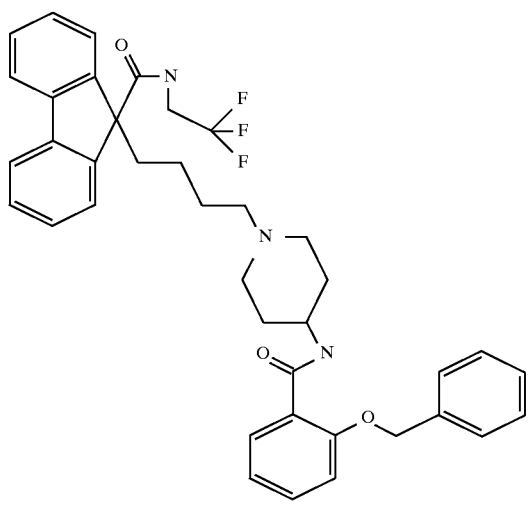 | m/z 658 (M+H) |

| Example No. | Molecular Structure | Analytical Data |
|---|---|---|
| 448 | 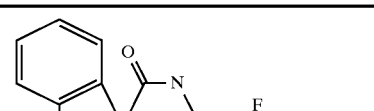 | m/z 532 (M+H) |
EXAMPLES 449 to 477
In the following Examples, the compounds prepared were purified by preparative HPLC (Method C) and isolated as trifluoroacetic acid salts.
| | | |
|---|---|---|
| 449 | 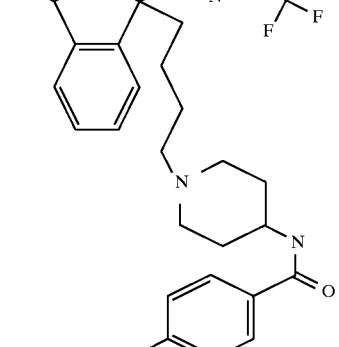 | m/z 565 (M + H) |
| 450 | 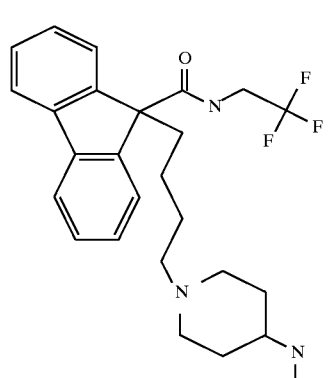 | m/z 593 (M + H) |

| | | |
|---|---|---|
| 451 | 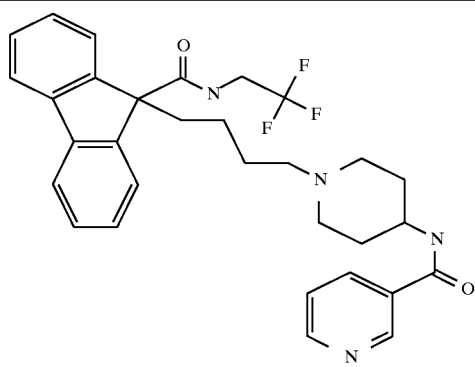 | m/z 551 (M + H) |
| 452 | 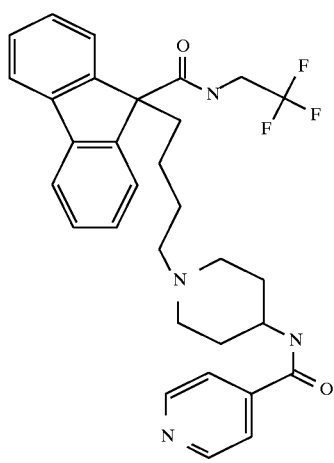 | m/z 551 (M + H) |
| 453 | 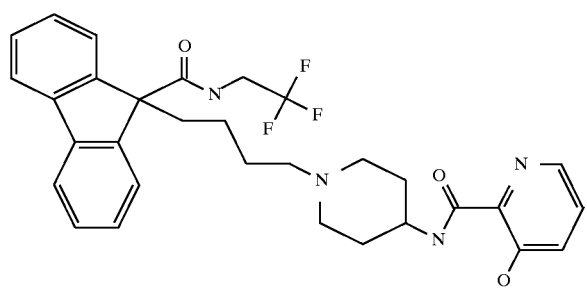 | m/z 567 (M + H) |
| 454 | 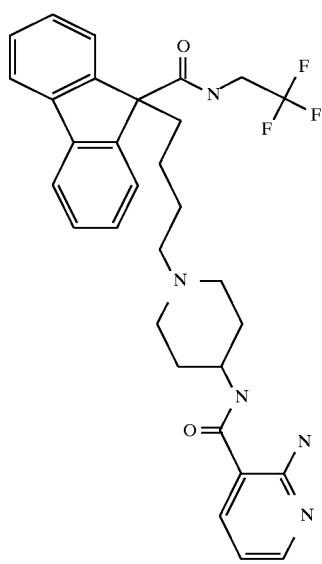 | m/z 566 (M + H) |

455 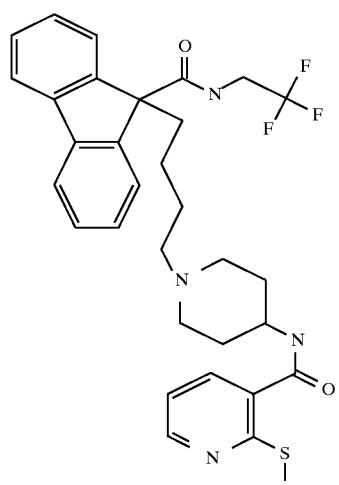 m/z 597 (M + H)
456 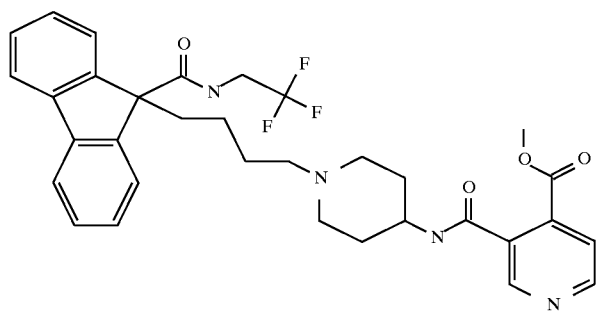 m/z 609 (M + H)
457 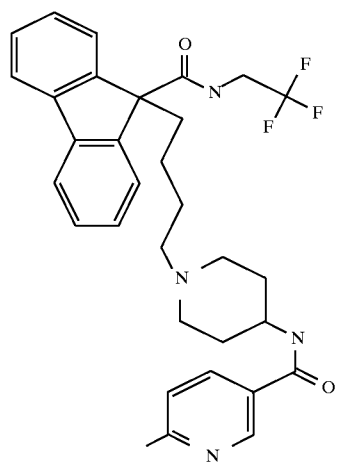 m/z 565 (M + H)

| 458 | 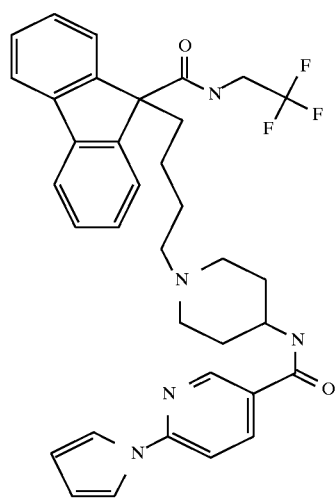 | m/z 616 (M + H) |
| 459 | 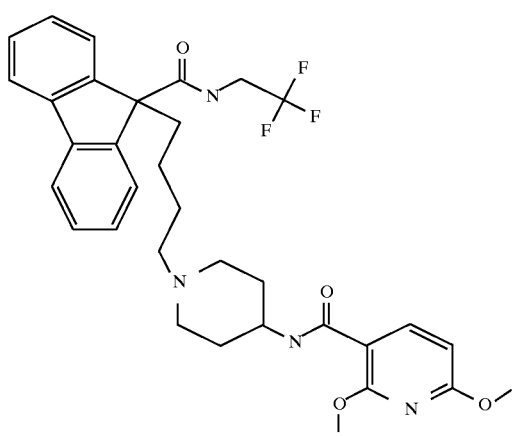 | m/z 611 (M + H) |
| 460 | 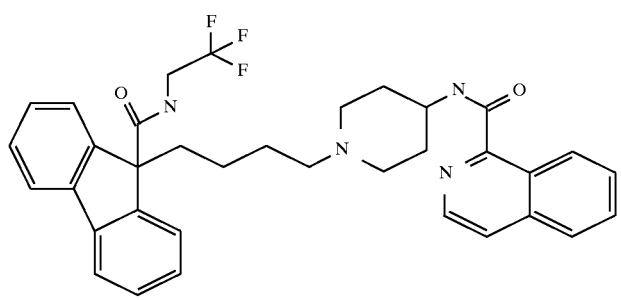 | m/z 601 (M + H) |
| 461 | 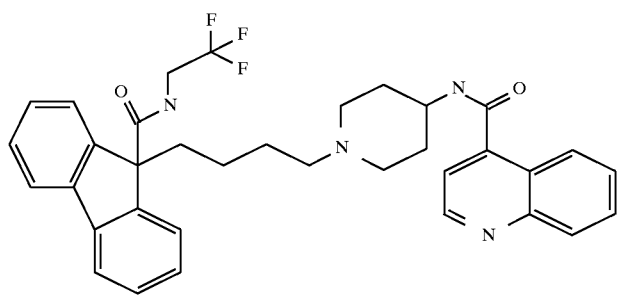 | m/z 601 (M + H) |

| | | |
|---|---|---|
| 462 | 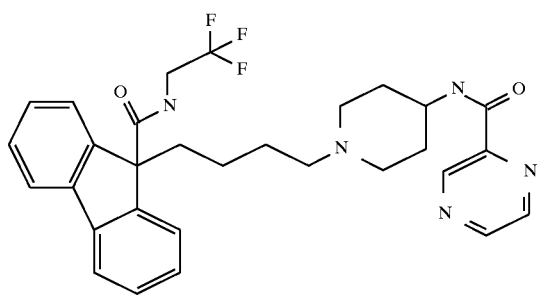 | m/z 552 (M + H) |
| 463 | 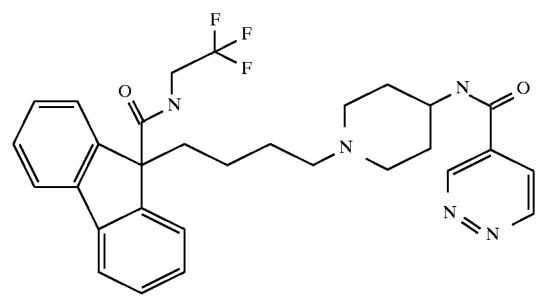 | m/z 552 (M + H) |
| 464 | 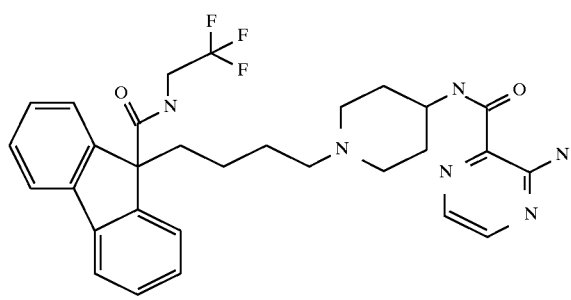 | m/z 567 (M + H) |
| 465 | 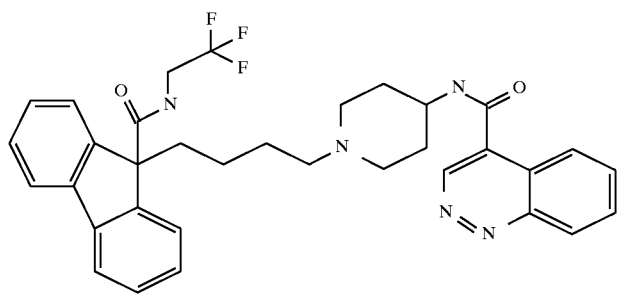 | m/z 602 (M + H) |
| 466 | 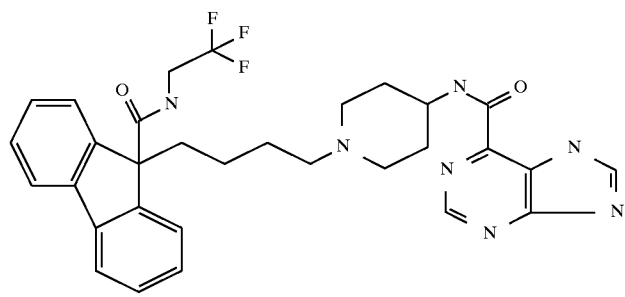 | m/z 592 (M + H) |

467 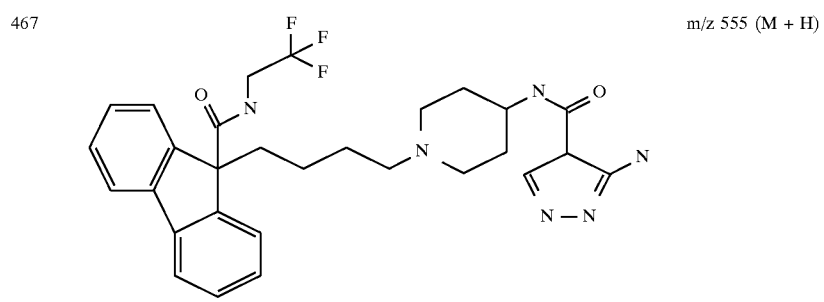 m/z 555 (M + H)
468 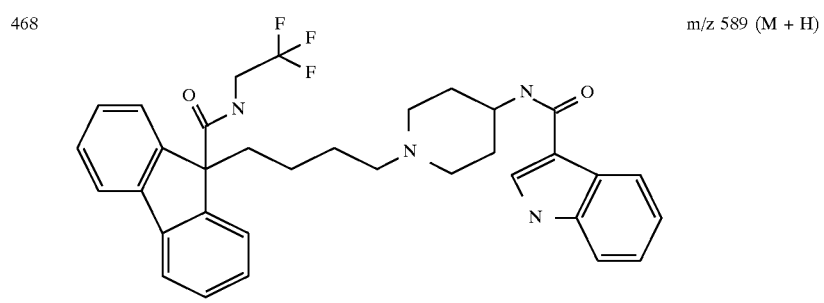 m/z 589 (M + H)
469 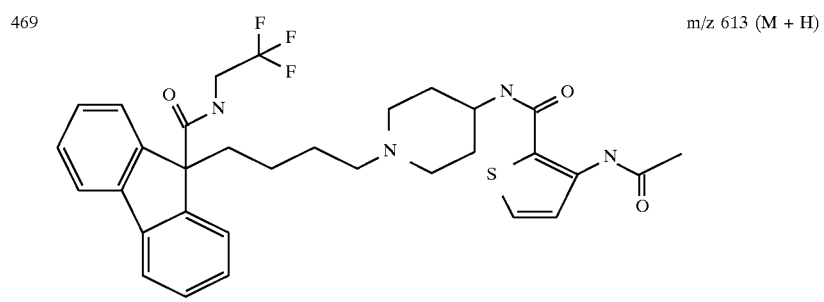 m/z 613 (M + H)
470 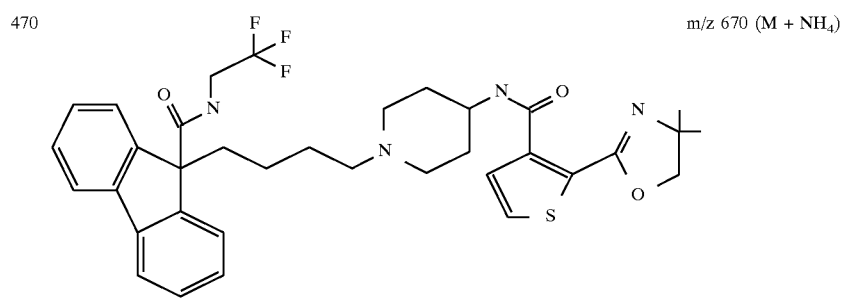 m/z 670 (M + NH$_4$)
471 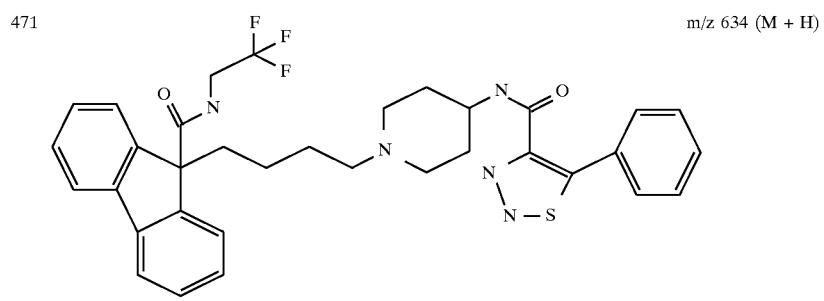 m/z 634 (M + H)

| 472 | 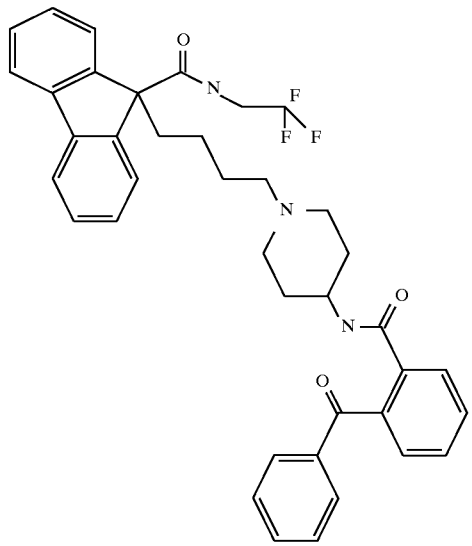 | m/z 654 (M + H) |
| 473 | 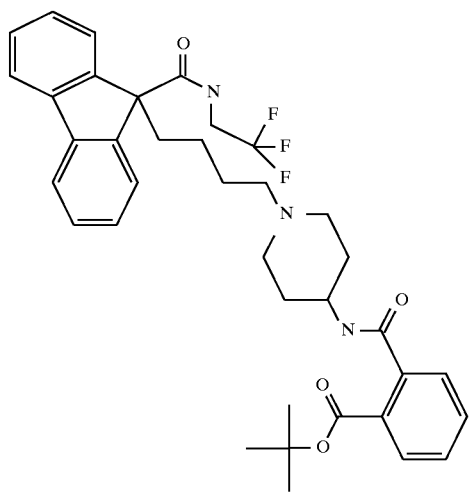 | m/z 650 (M + H) |
| 474 | 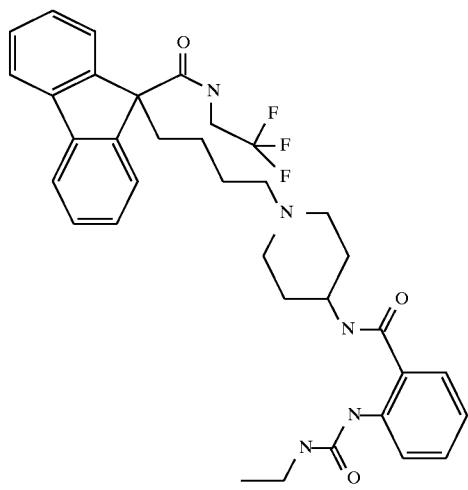 | m/z 636 (M + H) |

475 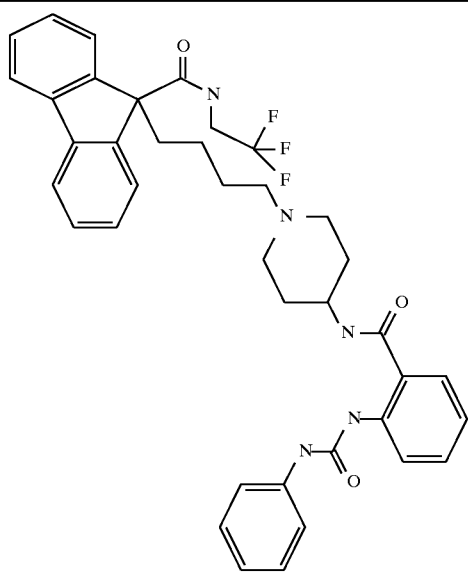 m/z 684 (M + H)

476 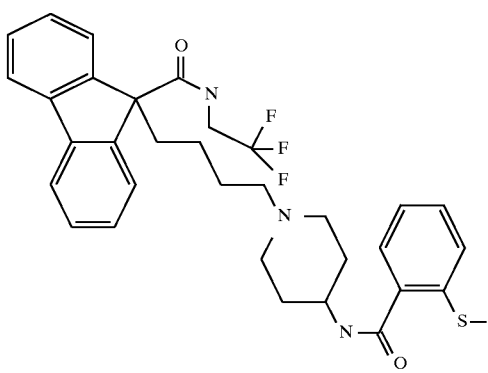 m/z 596 (M + H)

Chiral

477 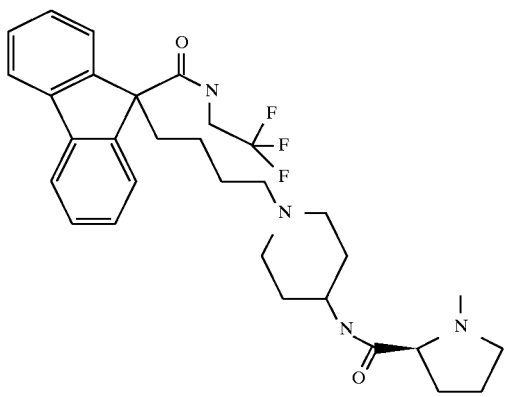 m/z 557 (M + H)

EXAMPLE 478

9-[4-[4-[(Phenoxycarbonyl)amino]-1-piperidinyl]-butyl]-N-(2,2,2-trifluoroethyl)-9H-fluorene-9-carboxamide, monohydrochloride To a solution of Example 346 Part D amine (500 mng, 0.96 mmol) and triethylamine (0.33 mL, 2.4 mmol) in dichloromethane (5 mL) at 0° C. was added dropwise phenyl chloroformate (0.14 mL, 1.06 mmol). The reaction was warmed to RT and stirring was continued for 1 h. Dichloromethane (100 mL) was added and the solution was washed with saturated sodium bicarbonate (2×30 mL), water (2×30 mL), brine (2×30 mL) and dried over MgSO$_4$. Evaporation gave a yellow oil. Purification was performed by flash chromatography on silica gel (100 g), loaded and eluted with 5% methanol in dichloromethane. Pure fractions were combined and evaporated to give a colorless oil. The resulting product was dissolved in methanol (1 mL) and a solution of hydrochloric acid in ethyl ether (1.1M, 1.1 mL) was added. The reaction was stirred at RT for 10 min, then evaporated to dryness. The product was dried in a vacuum oven (50° C., 24 h) to give title compound (300 mg, 53%) as a white solid.
m.p. 197°–200° C.
MS (ES, +ion): 566 (M+H)
Anal. Calc. for $C_{32}H_{35}ClF_3N_3O_3 \cdot 0.6\ H_2O$:
  C, 62.71; H, 5.95; N, 6.86; F, 9.30
Found: C, 62.79; H, 5.88; N, 6.50; F, 9.10

EXAMPLE 479

9-[4-[4-[[(Phenylamino)carbonyl]amino]-1-piper-idinyl]butyl]-N-(2,2,2-trifluoroethyl)-9H-fluorene-9-carboxamide, monohydrochloride To a solution of Example 346 Part D amine (500 mg, 0.96 mmol) and triethylamine (0.33 mL, 2.4 mmol) in dichloromethane (5 mL) at 0° C. was added dropwise phenyl isocyanate (0.10 mL, 1.06 mmol).

The reaction was warmed to RT and stirring was continued for 1 h. Dichloromethane (100 mL) was added and the solution was washed with saturated sodium bicarbonate (2×30 mL), water (2×30 mL), brine (2×30 mL) and dried over $MgSO_4$. Evaporation gave a yellow oil. Purification was performed by flash chromatography on silica gel (100 g), loaded and eluted with 5% methanol in dichloromethane. Pure fractions were combined and evaporated to give a colorless oil. The resulting product was dissolved in methanol (2 mL) and a solution of hydrochloric acid in ethyl ether (1.1M, 1.1 mL) was added. The reaction was stirred at RT for 10 min, then evaporated to dryness. The product was dried in a vacuum oven (55° C., 24 h) to give title compound (200 mg, 40%) as a white solid.
m.p. 145°–150° C.
MS (CI, +ion): 565 (M+H)
Anal. Calc. for $C_{32}H_{36}ClF_3N_4O_2 \cdot 0.6\ H_2O$:
  C, 62.81; H, 6.13; N, 9.16; F, 9.31
Found: C, 62.83; H, 6.05; N, 9.20; F, 9.27

EXAMPLE 480

9-[4-[4-[(Phenylsulfonyl)amino]-1-piperidinyl]-butyl]-N-(2,2,2-trifluoroethyl)-9H-fluorene-9-carboxamide, monohydrochloride To a solution of Example 346 Part D amine (500 mg, 0.96 mmol) and triethylamine (0.46 mL, 3.36 mmol) in dichloromethane (5 mL) at 0° C. was added dropwise benzenesulfonyl chloride (0.13 mL, 1.06 mmol). The reaction was warmed to RT and stirring was continued for 1 h. Dichloromethane (100 mL) was added and the solution was washed with saturated sodium bicarbonate (2×30 mL), water (2×30 mL), brine (2×30 mL) and dried over $MgSO_4$. Evaporation gave a yellow oil. Purification was performed by flash chromatography on silica gel (100 g), loaded and eluted with 5% methanol in dichloromethane. Pure fractions were combined and evaporated to give a colorless oil. The resulting product was dissolved in methanol (2 mL) and a solution of hydrochloric acid in ethyl ether (1.1M, 1.1 mL) was added. The reaction was stirred at RT for 10 min, then evaporated to dryness. The product was dried in a vacuum oven (55° C., 24 h) to give title compound (400 mg, 71%) as a white solid.
m.p. 130°–134° C.
MS (ES, +ion): 586 (M+H)
Anal. Calc. for $C_{31}H_{35}ClF_3N_3SO_3 \cdot 0.8\ H_2O$:
  C, 58.59; H, 5.65; N, 6.61; Cl, 5.58; F, 8.97
Found: C, 58.77; H, 5.66; N, 6.40; Cl, 5.95; F, 9.03.

EXAMPLE 481

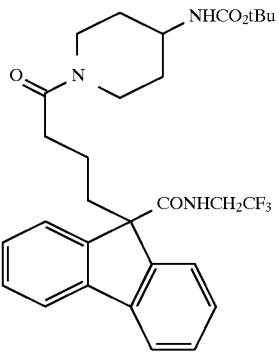

A.

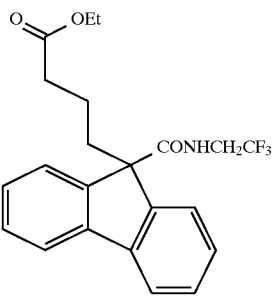

To a solution of 1.05 g (5.00 mmol) of 9-fluorenecarboxylic acid in 15 mL of THF under argon (evacuated and purged with argon three times) at −10° C., was added 4.0 mL of n-butyllithium (10.0 mmol, 2.5M in hexanes) over 10 min. A thick slurry formed initially followed by a yellow solution. After 30 min, 0.75 mL (7.0 mmol) of ethyl bromobutyrate was added. The reaction was allowed to warm to room temperature. After 24 h, the reaction was quenched with 10% citric acid solution and extracted twice with ethyl acetate. The organic extract was dried ($Na_2SO_4$) and evaporated. The residue was dissolved in 15 mL of dichloromethane and stirred at room temperature under argon while 7.5 mL of oxalyl chloride solution (2M in dichloromethane, 15 mmol) was added, followed by DMF (100 μL). After 1 h, the resulting solution was evaporated at less than 30° C. and the residue was then redissolved in 15 mL of THF. This solution was added to a solution of 2,2,2-trifluoroethylamine (1.1 g, 11 mmol) in 10 mL of THF under argon at 0° C. After 1 h, the reaction was quenched with 10% citric acid solution and extracted twice with ethyl acetate. The extracts were combined, dried ($MgSO_4$) and evaporated. Purfication by flash chromatography on silica gel (5×15 cm column, 3:97 ether/dichloromethane as elutant) provided title compound as a white solid, 956 mg, 47% yield, mp 108°–110° C.

B.

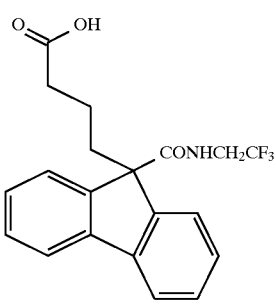

To a solution of Part A compound (580 mg, 1.43 mmol) in 5 mL of methanol at room temperature under argon was added a solution of lithium hydroxide hydrate (130 mg, 3.0 mmol) in 5 mL of water. The reaction mixture was stirred for 14 h and then partially evaporated to remove methanol. The reaction was quenched with 10% citric acid solution and extracted twice with ethyl acetate. The extracts were combined, dried ($MgSO_4$) and evaporated to give title compound as a white solid, 540 mg. It was used in the next step without further purification.

C.

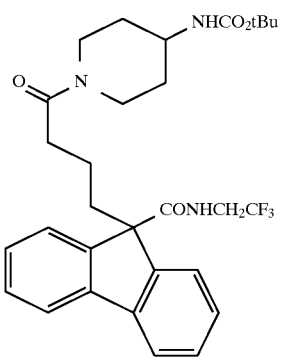

To a solution of Part B compound (530 mg, 1.41 mmol), Example 1 Part B amine (280 mg, 1.41 mmol) and HOAt (210 mg, 1.5 mmol) in 5 mL of THF at room temperature under argon, was added DCC (295 mg, 1.43 mmol). After 15 h, the reaction was quenched with 10% citric acid and extracted twice with ethyl acetate. The extracts were combined, washed once with water, once with saturated sodium bicarbonate solution, dried ($Na_2SO_4$) and evaporated. Purification by flash chromatography on silica gel (5×15 cm column, 1:2 ethyl acetate/dichloromethane as elutant) provided title compound as a white solid, 625 mg, 79% yield, mp 90°–92° C.
Anal. Calc. for $C_{30}H_{36}F_3N_3O_4 \cdot H_2O$:
C, 62.38; H, 6.63; F, 9.87; N 7.27.
Found: C, 62.41; H, 6.24; F, 9.78; N 7.14.
MS (electrospray, −ions) m/e 558 (M−H).

EXAMPLE 482
cis-9-[4-[4[(2-Phenoxybenzoyl)amino]-1-piperidinyl]butyl]-N-(2,2,2-trifluoroethyl)-9H-fluorene-9-carboxamide, N-oxide To a solution of Example 342 free amine (290 mg, 0.452 mmol) in $CH_2Cl_2$ (5 mL) at 0° C. under argon was added a solution of 3-chloroperoxybenzoic acid (80–85%) (82 mg, 0.407 mmol) in $CH_2Cl_2$ (1.5 mL) slowly over 5 min. The reaction mixture was stirred at 0° C. for 10 min, then saturated aqueous $NaHCO_3$ (1 mL) was added. The reaction mixture was stirred at 0° C. vigorously for 1 h, diluted with $CH_2Cl_2$ (10 mL), washed with brine (5 mL), and then dried over $Na_2SO_4$. Evaporation gave 320 mg of a white foam, which was purified by flash chromatography on silica gel (50 g) eluting with step gradient of 3% to 5% MeOH/$CH_2Cl_2$ to provide title compound (74 mg, 25%) as a white foamy solid.
MS (ES, +ions) m/z 658 (M+H)
Anal. Calcd for $C_{38}H_{38}F_3N_3O_4 + H_2O$:
C, 67.54; H, 5.97; N, 6.22; F, 8.43
Found: C, 67.61; H, 5.65; N. 6.18; F, 8.21.

EXAMPLE 483
9-[4-[4-[(2-Phenoxybenzoyl)amino]-1-piperidinyl]-4-oxobutyl]-N-(2,2,2-trifluoroethyl)-9H-fluorene-9-carboxamide A solution of Example 481 compound (2.00 g, 3.59 mmol) in 10 mL of 4N hydrogen chloride in dioxane was stirred, protected by a calcium chloride drying tube, for 3 h. The solution was evaporated at 30° C. and the resulting solid was re-dissolved in 10 mL of dichloromethane. To one-half of this solution (by weight), cooled to −10° C. under argon, was added triethylamine (0.75 mL, 5.4 mmol) and then 500 mg of 2-phenoxybenzoyl chloride (2.15 mmol) over 10 min. After 1 h, the reaction was quenched with saturated sodium bicarbonate solution and extracted twice with ethyl acetate. The organic extract was dried ($Na_2SO_4$) and evaporated. Purfication by flash chromatography on silica gel (5×15 cm column, 1:9 hexanes/ethyl acetate as elutant) provided, after recrystallization from ethyl acetate/hexanes, title compound as a white solid, 745 mg, 63% yield, mp 96°–98° C.
Anal. Calcd for $C_{38}H_{36}F_3N_3O_4 + H_2O$:
C, 67.74; H, 5.69; F, 8.46; N, 6.24.
Found: C, 67.84; H, 5.61; F, 8.63; N, 6.00.
MS (electrospray, +ions) m/z 656.3 (M+H), 673.3 (M+$NH_4$).

EXAMPLE 484

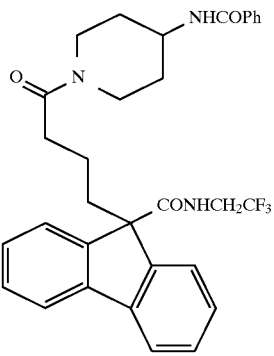

A solution of Example 481 compound (2.00 g, 3.59 mmol) in 10 mL of 4N hydrogen chloride in dioxane was stirred, protected by a calcium chloride drying tube, for 3 h. The solution was evaporated at 30° C. and the resulting solid was re-dissolved in 10 mL of dichloromethane. To one-half of this solution (by weight), cooled to −10° C. under argon, was added triethylamine (0.75 mL, 5.4 mmol) and then 0.25 mL of benzoyl chloride (2.2 mmol) over 10 min. After 1 h, the reaction was quenched with saturated sodium bicarbonate solution and extracted twice with ethyl acetate. The organic extract was dried ($Na_2SO_4$) and evaporated. Purfication by flash chromatography on silica gel (5×15 cm column, 1:9 hexanes/ethyl acetate as elutant) provided, after recrystallization from ethyl acetate/hexanes, title compound as a white solid, 725 mg, 71% yield, mp 204°–206° C.
Anal. Calcd for $C_{32}H_{32}F_3N_3O_3$:
 C, 68.19; H, 5.72; F. 10.11; N, 7.46.
Found: C, 68.14; H, 5.73; F, 10.33; N, 7.40.
MS (electrospray, −ions) m/z 437 (M-CF$_3$CH$_2$NHCO), 562 (M-H).

EXAMPLE 485
9-[4-[4-[[(1,1-Dimethylethoxy)carbonyl]amino]-1-piperidinyl]pentyl]-N-(2,2,2-trifluoroethyl)-9H-fluorene-9-carboxamide

A.

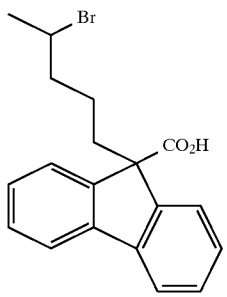

To a solution of 2.50 g (11.9 mmol) of 9-fluorenecarboxylic acid in 25 mL of THF under argon (evacuated and purged with argon three times) at −10° C., was added 10.0 mL of n-butyllithium (25.0 mmol, 2.5M in hexanes) over 10 min. A thick slurry formed initially followed by a yellow solution. After 40 min, 2.05 mL (15.0 mmol) of 1,4-dibromopentane was added. The reaction was allowed to warm to room temperature. After 60 h, the reaction was quenched with 10% citric acid solution and extracted twice with ethyl acetate. The organic extract was dried (MgSO$_4$) and evaporated. Trituration of the residue in ethyl acetate/hexanes gave title compound as a white solid, 3.72 g, 87%.

B.

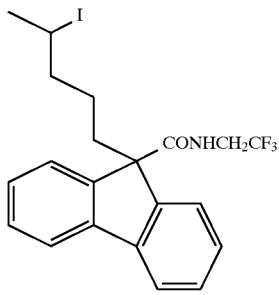

To a stirred solution of 1.80 g (ca. 5.0 mmol) of Part A compound in 10 mL of dichloromethane at room temperature under argon was added 0.65 mL of oxalyl chloride (7.5 mmol) followed by DMF (100μL). After 1 h, the resulting solution was evaporated at less than 30° C. and the residue was then redissolved in 15 mL of dichloromethane. This solution was added to a solution of 2,2,2-trifluoroethylamine hydrochloride (820 mg, 6.0 mmol) and 2.1 mL of triethylamine (15 mmol) in 20 mL of dichloromethane under argon at 0° C. After 1 h, the reaction was quenched with 10% citric acid solution and extracted twice with ethyl acetate. The extracts were combined, dried (MgSO$_4$) and evaporated. The crude product was dissolved in 25 mL of 2-butanone, 7.7 g (52 mmol) of sodium iodide was added and the reaction mixture was set to reflux for 48 h under argon. The solution was cooled, evaporated and the residue partitioned between ethyl acetate and 10% sodium bisulfite solution. The organic extract was dried (MgSO$_4$) and evaporated. Purfication by flash chromatography on silica gel (5×15 cm column, 3:7 hexanes/dichloromethane as elutant) provided title compound as a white solid, 1.42 g, 58% yield, mp 102°–106° C.

C.

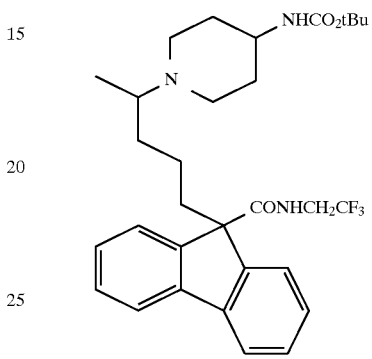

A solution of Part B compound (1.27 g, 2.60 mmol), Example 1 Part B amine (680 mg, 3.38 mmol) and potassium carbonate (420 mg, 3.0 mmol) in 5 mL of DMF at room temperature under argon was heated to 50° C. After 15 h, the reaction was quenched with water, decanted and the oily residue extracted twice with ethyl acetate. The extracts were combined, washed once with water, once with saturated sodium bicarbonate solution, dried (Na$_2$SO$_4$) and evaporated. Purification by flash chromatography on silica gel (5×15 cm column, 1:99 methanol/ethyl acetate as elutant) provided title compound as a white solid, 1.20 g, 82% yield, mp 58°–60° C.
Anal. Calcd for $C_{31}H_{40}F_3N_3O_3$+0.25 H$_2$O:
 C, 66.00; H, 7.24; F, 10.18; N, 7.45.
Found: C, 66.00; H, 7.14; F, 10.39; N, 7.60.
MS (electrospray, +ions) m/e 560.3 (M+H).

EXAMPLE 486
9-[4-[4-[[(2-Phenoxyphenyl)sulfonyl]amino]-1-piperidinyl] butyl]-N-(2,2,2-trifluoroethyl)-9H-fluorene-9-carboxamide, monohydrochloride To a solution of 2-phenoxyaniline (5.0 g, 27.0 mmol) in conc. hydrochloric acid (20 mL) and glacial acetic acid (6 mL) at −10° C., a solution of sodium nitrite (2.01 g, 29.2 mmol) in water (3.5 mL) was added dropwise at such a rate that the reaction temperature did not exceed −5° C. The reaction was stirred at −5° C. for 1 h. While the diazotization was being completed, sulfur dioxide was bubbled through glacial acetic acid (15 mL) until it was saturated. Cuprous chloride (0.75 g) was then added and the introduction of sulfur dioxide was continued until the yellow-green suspension became blue-green (30 min). The mixture was then cooled to 10° C. and the solution containing the diazonium salt was added dropwise over 15 min. The green reaction mixture was warmed to RT and stirred for an additional 30 min, then poured into ice water (300 mL). Ethyl ether (200 mL) was added and the organic layer was washed with water (2×100 mL), saturated sodium bicarbonate solution (6×100 mL), brine (2×100 mL) and dried over MgSO$_4$.

Evaporation gave a mixture containing

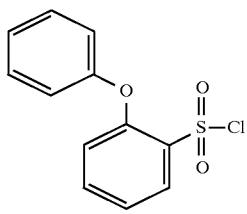

(2.5 g, 36%) as a brown oil.

Following the procedure in Example 480 the above sulfonyl chloride (2.5 g, 9.3 mmol) was reacted with Example 346 Part D amine (0.62 g, 1.2 mmol) followed by treatment with HCl to give title compound (210 mg, 26%) as a white solid.

m.p. 142°–146° C.

MS (ES, +ions ): 678 (M+H)

Anal. Calc. for $C_{37}H_{39}ClF_3N_3SO_4+0.4\ H_2O$:

C, 61.60; H, 5.56; N, 5.82; Cl, 4.91;

S, 4.44; F, 7.90.

Found: C, 61.67; H, 5.55; N. 5.62; Cl, 4.66;

S, 4.31; F, 7.95.

EXAMPLE 487

[1-[[[2-[9-[[(2,2,2-Trifluoroethyl)amino)carbonyl]-9H-fluoren-9-yl]ethyl]amino]carbonyl]-4-piperidinyl]carbamic acid, 1,1-dimethylethyl ester

A.

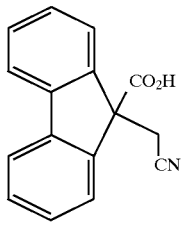

To a solution of 9-fluorenecarboxylic acid (10.5 g, 50 mmol) in THF (500 mL) at 0° C. was added dropwise a solution of n-butyllithium (44 mL of a 2.5M solution in hexanes, 110 mmol,) over 15 min under argon. The dark yellow solution was stirred at 0° C. for 30 min, and then chloroacetonitrile (3.8 mL, 60 mmol) was added dropwise over 3 min. The dark orange reaction mixture was stirred at 0° C. for 10 min, warmed to room temperature and stirred for 3h. The reaction mixture was diluted with $H_2O$ (250 mL) and $Et_2O$ (250 mL), and concentrated in vacuo to 300 mL. Water (200 mL) and $CH_2Cl_2$ (500 mL) were added. The mixture was acidified to pH 1.85 with 1N HCl and extracted with $CH_2Cl_2$ (6×250 mL). The combined organic extracts were dried over $MgSO_4$, filtered, and concentrated in vacuo to give crude solid title compound (10.45 g, 76.7%).

B.

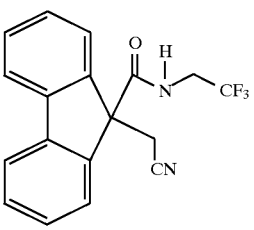

To a solution of Part A compound (6.7 g, 26.9 mmol, dried by concentration with THF/toluene) and DMF (102 µl, 1.36 mmol) in $CH_2Cl_2$ (80 mL) under $N_2$ was added oxalyl chloride (20.5 mL of a 2.0M solution in $CH_2Cl_2$, 40.6 mmol). The reaction was stirred at room temperature for 1.5 h and concentrated in vacuo and then dried under high vacuum to give the crude acid chloride. Triethylamine (11.3 mL, 81.0 mmol) was added to a suspension of 2,2,2-trifluoroethylamine hydrochloride (4.38 g, 32.4 mmol) in $CH_2Cl_2$ (50 mL) at 0° C. under $N_2$. The resulting thick slurry was stirred at 0° C. for 5 min and then a solution of the crude acid chloride in $CH_2Cl_2$ (30 mL) was added dropwise over 5 min. The reaction mixture was stirred at 0° C. for 10 min. Dichloromethane (100 mL) was added and the solution was washed with 1N HCl (2×80 mL) and saturated $NaHCO_3$ (80 mL), dried over $Na_2SO_4$, filtered and concentrated in vacuo to give foamy solid 8.3 g. This material was combined with another batch of crude solid (4.4 g) and the combined mixture was purified by flash chromatography on silica gel (1200 mL), eluting with $CH_2Cl_2$, to give title compound (10.5 g, 83.3%) as a solid.

C.

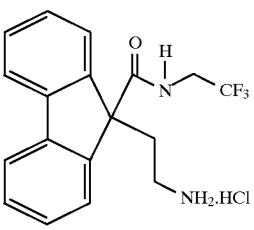

A solution of Part B compound (4.5 g, 13.6 mmol) in absolute ethanol (400 mL/$CHCl_3$ (7 mL) was hydrogenated at 50 psi over 10% Pd/C (2.1 g) for 3 days. The catalyst was removed by filtration through a nylon 66 filter, and the filtrate was concentrated in vacuo to give crude solid title compound (4.8 g).

D.

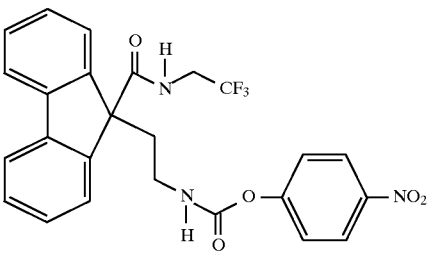

To a solution of the crude Part C compound (4.0 g) in THF (80 µL) and pyridine (3.5 mL, 43.4 mmol) at room temperature was added a solution of 4-nitrophenyl chloroformate (1.46 g, 7.22 mmol) in THF (25 mL). The mixture was stirred at room temperature overnight, concentrated in vacuo to remove THF, and diluted with EtOAc (700 mL). The EtOAc was washed with 5% NaHCO$_3$ (4×50 mL), H$_2$O (4×50 mL), 0.2N HCl (5×50 mL), H$_2$O (2×40 mL), and brine (40 mL) and then dried over Na$_2$SO$_4$. Evaporation gave 3.1 g of a foam, which was purified by flash chromatography on silica gel (500 mL), eluting with EtOAc/hexane (20:80 to 35:75) to give title compound (1.59 g, 41.6 %) as pale yellow solid (mp 138°–140° C.).

E. [1-[[[2-[9-[[(2,2,2-Trifluoroethyl)-amino)carbonyl]-9H-fluoren-9-yl]ethyl]-amino]carbonyl]-4-piperidinyl] carbamic acid, 1,1-dimethylethyl ester To a solution of Part D compound (1.59 g, 3.18 mmol) in CH$_2$Cl$_2$ (30 mL) under N$_2$ was added a solution of Example 1 Part B ester (1.27 g, 6.36 mmol) in CH$_2$Cl$_2$ (20 mL), followed by 4-dimethylaminopyridine (56 mg, 0.46 mmol). After stirring overnight at room temperature, the reaction mixture was diluted with CH$_2$Cl$_2$ (50 mL), washed with 0.1N NaOH (3×40 ml), H$_2$O (2×40 mL), 1% KHSO$_4$ (2×40 ml), H$_2$O (40 mL), 5% NaHCO$_3$ (2×40 mL), H$_2$O (40 mL) and brine 40 mL) and then dried over Na$_2$SO$_4$. Evaporation of the CH$_2$Cl$_2$ gave 1.8 g of a foam, which was purified by flash chromatography on silica gel (100 mL), eluting with EtOAc/hexane (60:40 to 100:0), to give title compound (1.43 g, 80.1% ) as a white solid. mp 77°–80° C.
MS (ESI, +ions) m/z 561 (M+H), 1121 (2M+H); (–ion) 559 (M–H).
Anal. Calcd for C$_{29}$H$_{35}$N$_4$O$_4$F$_3$+0.15CH$_2$Cl$_2$+0.4CH$_3$CO$_2$C$_2$H$_5$:
C, 60.69; H, 6.38; N, 9.21; F, 9.36
Found C, 60.83; H, 6.36; N, 9.29; F, 9.61.

EXAMPLE 488
9-[2-[[[4-(Benzoylamino)-1-piperidinyl]carbonyl]-amino] ethyl]-N-(2,2,2-trifluoroethyl)-9H-fluorene-9-carboxamide

A.

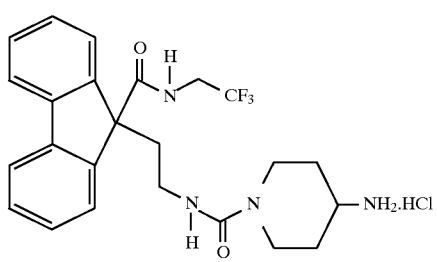

To a solution of Example 487 compound (1.1 g, 1.97 mmol) in THF (4 mL) was added 4N HCl in dioxane (9 mL, 36.4 mmol). The reaction mixture was stirred at room temperature for 3 h and concentrated in vacuo and then from dioxane (3×10 mL) to give crude title compound (1.46 g) as a white foamy solid.

B. 9-[2-[[[4-(Benzoylamino)-1-piperidinyl]-carbonyl] amino]ethyl]-N-(2,2,2-trifluoroethyl)-9H-fluorene-9-carboxamide To a solution of crude Part A compound (730 mg, 0.98 mmol) and triethylamine (615 μL, 4.41 mmol) in CH$_2$Cl$_2$ (10 mL) at 0° C. was added dropwise benzoyl chloride (172 μL, 1.47 mmol). The reaction was stirred at 0° C. for 30 minutes and diluted with CH$_2$Cl$_2$ (30 mL). The solution was washed with 0.1N NaOH (2×40 mL), H$_2$O (40 mL), 0.2N HCl (2×40 mL), H$_2$O (40 mL) and brine (40 ml),then dried over MgSO$_4$ and concentrated to a white solid (1.6 g).

Purification of this solid over silica gel (100 mL) by eluting with 5% methanol in dichloromethane gave title compound (427 mg, 77.2%) as white solid.
m.p. 220°–222° C.
MS (ESI, +ions) m/z 565 (M+H), 582 (M+NH$_4$); (–ion) 563 (M–H).
Anal. Calcd For C$_{31}$H$_{31}$N$_4$O$_3$F$_3$:
C, 65.95; H, 5.53; N. 9.92; F, 10.09.
Found: C, 65.80; H, 5.41; N, 9.84; F, 9.98.

EXAMPLE 489
4-[[(1,1-Dimethylethoxy)carbonyl]amino]-1-piperidinecarboxylic acid, 2-[9-[[(2,2,2-trifluoroethyl) amino]carbonyl]-9H-fluoren-9-yl]ethyl ester

A.

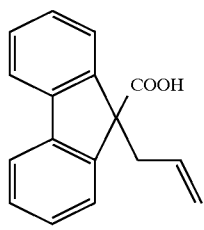

To a stirred solution of 8.41 g (40 mmol) of 9-fluorenecarboxylic acid in 400 mL of dry THF at 0° C. under argon was added, over 15 min, 35.2 mL of 2.5M n-butyllithium in hexane (88 mmol). The reaction was stirred at 0° C. for 30 min and then 4.2 mL (48.5 mmol) of allyl bromide was added over 15 min. The reaction was stirred at 0° C. for 15 min and at room temperature for 1 h and then quenched by addition of water (80 mL). The THF was removed in vacuo and the aqueous mixture was extracted with ether (2×100 mL). The aqueous layer was layered with CH$_2$Cl$_2$ (150 mL) and then acidified with 1N HCl (pH<2). After extraction, the aqueous was extracted with additional CH$_2$Cl$_2$ (2×100 mL), and the combined CH$_2$Cl$_2$ extracts were washed with water, dried (MgSO$_4$) and concentrated to give 9.41 g (94%) of title compound as an amorphous solid.

B.

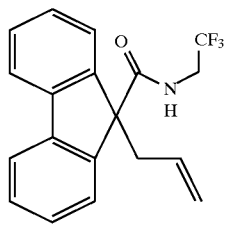

Part A compound (9.30 g) was dried by concentration in vacuo from a mixture of dry THF and dry toluene (2×). To a stirred solution of this acid in 100 mL of dry CH$_2$Cl$_2$ and 143 mL of DMF under nitrogen was added cautiously 28 mL of 2.0M oxalyl chloride in CH$_2$Cl$_2$ (55.8 mmol). The reaction was stirred at room temperature for 1.5 h and concentrated in vacuo and then dried at 0.5 mm for 1 h to give the crude acid chloride of Part A acid. Triethylamine (15.6 mL, 112 mmol) was added to a stirred suspension of 6.04 g (44.6 mmol) of 2,2,2-trifluoroethylamine hydrochloride in 75 mL of dry CH$_2$Cl$_2$ at 0° C. under argon. The slurry was stirred at 0° C. for 10 min and then a solution of the crude acid chloride in 35 mL of CH$_2$Cl$_2$ was added over 10 min keeping the internal temperature <12° C. The reaction was stirred at 0° C. for 15 min and at room temperature for 1 h and then diluted with 150 mL of $CH_2Cl_2$. The $CH_2Cl_2$ was washed with 1N HCl (2×75 mL), water (180 mL), 5% $NaHCO_3$ (120 mL), and water (2×180 mL), dried ($Na_2SO_4$), and concentrated to a residue (12.67 g). Chromatography of this residue over 500 g of silica gel provided 10.74 g (87%) of title compound as an amorphous white solid, mp 84°–86° C.

C.

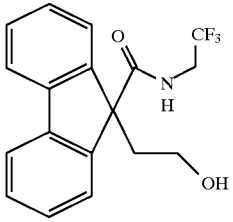

Ozone (in oxygen) was passed into a stirred solution of 5.30 g of Part B compound in 80 mL of dry $CH_3OH$ at −55° C. for 1 h. Nitrogen was bubbled through the reaction for 10 min at −55° C. and then the reaction was warmed to −30° C. A solution of $NaBH_4$ (908 mg, 24 mmol) in 20 mL of 50% aqueous $CH_3OH$ cooled to 0° C. was added and the reaction was stirred at −30° C. for 70 min. The cooling bath was removed, the pH was adjusted to <pH 2 (3N HCl), and the reaction was concentrated to remove $CH_3OH$. The residue was partitioned between EtOAc and water, and the EtOAc was washed with water (4×), dried ($Na_2SO_4$), and concentrated to a residue (6.67 g). Chromatography of this residue over 475 g of silica gel using hexane-EtOAc (6:4) and then hexane-EtOAc (1:1) afforded 2.77 g (49%) of title compound as an amorphous solid. An earlier eluting fraction provided 1.97 g of compound

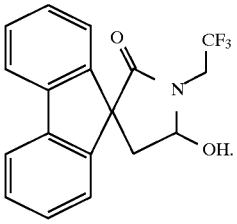

D.

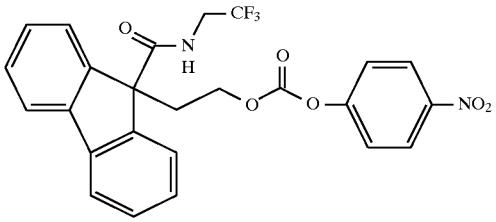

4-Nitrophenyl chloroformate (1.2 g, 6 mmol) was added to a stirred solution of 1.34 g. (4 mmol) of Part C compound and 0.97 mL (12 mmol) of dry pyridine in 15 mL of dry $CH_2Cl_2$ at room temperature under argon. The reaction was stirred for 20 min at room temperature and then diluted with $CH_2Cl_2$. The $CH_2Cl_2$ solution was washed with 5% $NaHCO_3$ (4×), water, dilute HCl (2×), and water (3×), dried ($Na_2SO_4$), and concentrated to give crude title compound in the form of a foamy residue (2.30 g).

E. 4-[[(1,1-Dimethylethoxy)carbonyl]amino]-1-piperidinecarboxylic acid, 2-[9-[[(2,2,2-trifluoroethyl)amino]carbonyl]-9H-fluoren-9-yl]ethyl ester 4-Boc-aminopiperidine (1.58 g, 7.90 mmoL) was added to a stirred solution of 2.29 g of the above preparation of Part D compound in 30 mL of dry $CH_2Cl_2$ at room temperature under argon. The reaction was stirred at room temperature for 2 h and then diluted with $CH_2Cl_2$. The $CH_2Cl_2$ solution was washed with dilute NaOH (2×), water (2×), dilute $KHSO_4$ (2×), and water (3×), dried ($Na_2SO_4$), and concentrated to give 2.63 g of an oily residue. Chromatography of this residue over 230 g of silica gel using hexane-EtOAc (6:4) and subsequent crystallization from EtOAc-hexane provided 2.07 g (94%) of title compound as a white solid having mp 120°–122° C.

Anal. Calcd for $C_{29}H_{34}F_3N_3O_5+0.5\ CH_3CO_2C_2H_5$:
C, 61.48; H, 6.32; N, 6.94; F, 9.41
Found: C, 61.25; H, 6.39; N, 6.85; F, 9.42.
MS (ESI-$NH_3$, +ions) 562 (M+H), 579 (M+$NH_4$); (−ions) 560.

EXAMPLE 490

4-[(2-Phenoxybenzoyl)amino]-1-piperidinecarboxylic acid, 2-[9-[[(2,2,2-trifluoroethyl)amino]carbonyl]-9H-fluoren-9-yl]ethyl ester

A.

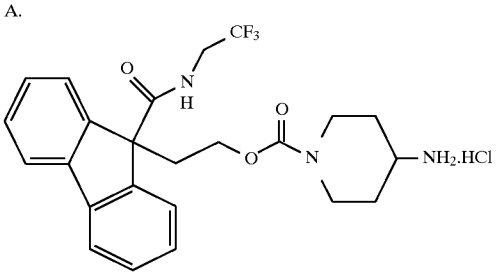

To a solution of 898 mg (1.6 mmol) of Example 489 compound in 3 mL of dry THF under argon at room temperature was added 6 mL of 4N HCl in dioxane (24 mmol). The reaction was stirred at room temperature for 2 h and then stored overnight at 5° C. The reaction was concentrated in vacuo and then concentrated from dry dioxane (2×5 mL) and then dried at 0.5 mm for 2 h to afford crude title compound as an amorphous residue.

B.

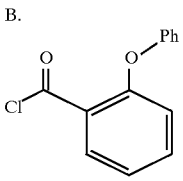

To 428 mg (2.0 mmol) of 2-phenoxybenzoic acid and 10 μL of DMF in 4 mL of dry $CH_2Cl_2$ at 0° C. under nitrogen was added 1.5 mL of 2.0M oxalyl chloride in $CH_2Cl_2$ (3.0 mmoL). The reaction was stirred at room temperature for 1.5 h and concentrated in vacuo and then dried at 0.5 mm for 1 h to give the crude title acid chloride as a pale yellow oil. This oil was dissolved in 3.2 mL of $CH_2Cl_2$.

C. 4-[(2-Phenoxybenzoyl)amino]-1-piperidinecarboxylic acid, 2-[9-[[(2,2,2-trifluoroethyl)amino]carbonyl]-9H-fluoren-9-yl]ethyl ester To a stirred solution of one-half of the crude preparation of Part A compound above (ca. 0.8 mmoL) in 4 mL of dry $CH_2Cl_2$ at 0° C. under argon was added 0.46 mL (4 mmol)

of triethylamine. The solution was stirred at 0° C. for 5 min and then a 2.0 mL aliquot of the above solution of Part B compound in 3.2 mL of $CH_2Cl_2$ (ca. 1.2 mmoL of crude Part B compound) was added. The reaction was stirred at 0° C. for 2.5 h and then diluted with $CH_2Cl_2$. The $CH_2Cl_2$ was washed with dilute NaOH (2x), water (2x), dilute HCl (2x), and water (3x), dried ($Na_2SO_4$), and concentrated to a thick oil (577 mg). Chromatography of this oil over 45 g of silica gel using hexane-EtOAc (1:1) provided 414 mg of title compound (79%) as a foam having mp 68°–73° C.
Anal. Calcd for $C_{37}H_{34}F_3N_3O_5+0.2$ $CH_3CO_2C_2H_5$:
  C, 67.23; H, 5.31; N, 6.22; F, 8.44
Found: C, 67.04; H, 5.20; N, 6.18; F, 8.70.
MS (ESI-$NH_3$, +ions) 658 (M+H), 675 (M+$NH_4$)

EXAMPLE 491
9-[4-[4-[(2-Phenoxybenzoyl)amino]-1-piperidinyl]-pentyl]-N-(2,2,2-trifluoroethyl)-9H-fluorene-9-carboxamide, monohydrochloride A solution of Example 485 compound (1.25 g, 2.23 mmol) in 10 mL of 4N hydrogen chloride in dioxane was stirred, protected by a calcium chloride drying tube, for 3 h. The solution was evaporated at 30° C. and the resulting solid was re-dissolved to a total volume of 20.0 mL with dichloromethane. To 10.0 mL of this stirred solution (ca. 1.12 mmol), cooled to –10° C. under argon, was added triethylamine (0.4 mL, 2.9 mmol) and then the 2-phenoxybenzoyl chloride (320 mg, 1.38 mmol) solution in 10 mL of dichloromethane over 10 min. After 1 h, the reaction was quenched with saturated sodium bicarbonate solution and extracted twice with ethyl acetate. The organic extract was dried ($Na_2SO_4$) and evaporated. Purfication by flash chromatography (5x20 cm column, ethyl acetate as elutant) provided a colorless oil, 603 mg, 77%. The oil was dissolved in 5 mL of ethyl acetate and then 0.25 mL of 4N HCl in dioxane was added. Ether was added until a gummy precipitate formed. Decanting and drying in vacuo gave title compound as a white solid, 650 mg, mp 136°–138° C.
Anal. Calcd for $C_{39}H_{40}F_3N_3O_3+HCl+H_2O$:
  C, 65.95; H, 6.10; Cl, 4.99; F, 8.02;
  N, 5.92
Found: C, 65.87; H, 6.08; Cl, 5.13; F, 7.96;
  N, 5.92.
MS (electrospray, +ions) m/e 654 (M+H).

EXAMPLES 492 to 497

Following the procedures set out herein-before and in the working Examples, the following additional compounds were prepared.

EXAMPLE 492
9-[2-[[[4-[(2-Phenoxybenzoyl)amino]-1-piperldinyl]carbonyl]amino]ethyl]-N-(2,2,2-trifluoroethyl)-9H-fluorene-9-carboxamide.
MS (ESI, +ion): 657 (M+H)
Anal. Calcd for $C_{37}H_{35}N_4O_4F_3+0.2$ $CH_2Cl_2+0.1$ $CH_3CO_2C_2H_5$.
  C, 66.17; H, 5.35; N, 8.21; F, 8.35
Found: C, 66.14; H, 5.29; N, 8.13; F, 8.47.
mp 84°–87° C.

EXAMPLE 493
4-(Benzoylamino)-1-piperidinecarboxylic acid, 2-[9-[[(2,2,2-trifluoroethyl)amino]carbonyl]-9H-fluoren-9-yl]ethyl ester.
MS (ESI-$NH_3$, +ions) 566 (M+H)
Anal. Calcd for $C_{31}H_{30}F_3N_3O_4+0.2$ $CH_3CO_2C_2H_5+0.25$ $H_2O$:
  C, 64.99; H, 5.51; N, 7.04; F, 9.70
Found: C, 64.77; H, 5.45; N, 7.15; F, 10.10.
75°–85° C.

EXAMPLE 494
9-[4-[4-(Benzoylamino)-1-piperidinyl]pentyl]-N-(2,2,2-trifluoroethyl)-9H-fluorene-9-carboxamide, monohydrochloride.
MS (electrospray, +ions) m/z 564 (M+H)
Anal. Calcd for $C_{33}H_{36}F_3N_3O_2+HCl+H_2O$:
  C, 64.12; H, 6.36; Cl, 5.74; F, 9.22;
  N, 6,80
Found: C, 64.17; H, 6.27; Cl, 5.65; F, 9.65;
  N, 6.60.
mp 130°–132° C.

EXAMPLE 495
9-[4-[4-[[(1,1-Dimethylethoxy)carbonyl]amino]-1-piperidinyl]butyl]-N-(2,2,2-trifluoroethyl)-9H-thioxanthene-9-carboxamide.
mp 76°–79° C.
MS (ES, +ions, $NH_3$) m/z 578 (M+H).

EXAMPLE 496
9-[4-[4-(Benzoylamino)-1-piperidinyl]butyl]-N-(2,2,2-trifluoroethyl)-9H-thioxanthene-9-carboxamide.
mp 167°–169° C.
MS (ES, +ions, $NH_3$) m/z 582 (M+H).

EXAMPLE 497
9-[4-[4-[[(2-Phenoxyphenyl)carbonyl]amino]-1-piperidinyl]butyl]-N-(2,2,2-trifluoroethyl)-9H-thioxanthene-9-carboxamide.
mp 164°–166° C.
MS (ES, +ions, $NH_3$) m/z 674 (M+H).

What is claimed is:
1. A compound which has the stricture

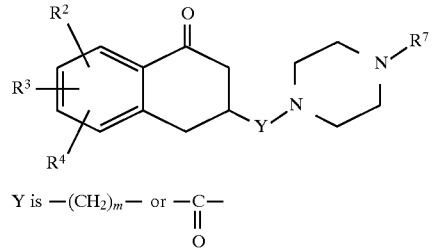

Y is $-(CH_2)_m-$ or 

wherein m is 2 or:3;
$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxyl or haloalkyl;
$R^7$ is alkyl, aryl or arylalkyl wherein alkyl by itself or as part of arylalky is optionally substituted with oxo $\begin{pmatrix} O \\ \parallel \end{pmatrix}$;

or a
pharmaceutically acceptable salt thereof;
with the provisos that
(1) where $R^2$, $R^3$ and $R^4$ are each H or where one of $R^2$, $R^3$ and $R^4$ is 6-fluoro, and the others are H, $R^7$ will be other then 4-(2-methoxyphenyl); and (2) where $R^2$, $R^3$ and $R^4$ are each H or where one of $R^2$, $R^3$ and $R^4$, is 6-fluoro, and the others are H, then where $R^7$ is alkyl or arylalkyl, the alkyl by itself or as part of arylalkyl will not be substituted with oxo $$\left(\begin{matrix} O \\ \| \end{matrix}\right).$$

2. The compound as defined in claim 1 wherein:
   $R^2$, $R^3$, $R^4$ are independently hydrogen, halo, alkyl, alkenyl, alkoxy, aryloxy, aryl, arylalkyl, alkylmercapto, arylmercapto.

3. A method for treating atherosclerosis; pancreatitis obesity or hyperglycemia, responsive to a decrease in MTP activity, in a patient, which comprises administering to a patient in need of treatment an MTP activity decreasing amount of a compound of the structure

[structure with $R^2$, $R^3$, $R^4$, Y, $R^7$]

Y is $-(CH_2)_m-$ or $-\underset{\underset{O}{\|}}{C}-$;

wherein
   m is 2 or 3;
   $R^2$, $R^{3,}$ $R^4$ are independently hydrogen, halo, alkyl, alkenyl, alkoxy, aryloxy, axyl, arylalkyl, alkylmercapto, arylmercapto, cyoloalkyl, cycloalkylalkyl, heteroaryl, heteroarylalkyl, hydroxy or haloalkyl;
   $R^7$ is alkyl, aryl or arylalkyl wherein alkyl by itself or as part of arylalkyl is optionally substituted with oxo $$\left(\begin{matrix} O \\ \| \end{matrix}\right);$$

or a pharmaceutically acceptable salt thereof.

4. A method of lowering serum lipid levels, cholesterol or triglycerides, or treatins hyperlipemia, hyperlipidemia, hyperlipoproteinemia, hyplrcholesterolemia or hypertriglyceridemia, responsive to a decrease in MTP activity, in a patient, which comprises administering to a patient in need of treatment an MTP activity decreasing amount of a compound of the structure

[structure with $R^2$, $R^3$, $R^4$, Y, $R^7$]

Y is $-(CH_2)_m-$ or $-\underset{\underset{O}{\|}}{C}-$;

wherein
   m is 2 or 3;
   $R^2$, $R^3$, $R^4$ are independently hydrogen, halo, alkyl, alkenyl, alkoxy, aryloxy, aryl, arylalkyl, alkylmercapto, arylmercapto, cycloalkyl cycloalkylalkyl, heteroaryl, heteroarylalkyl, hydroxy or haloalkyl;
   $R^7$ is alkyl, aryl or arylalkyl wherein alkyl by itself or as part of arylalkyl is optionally substituted with oxo $$\left(\begin{matrix} O \\ \| \end{matrix}\right);$$

or a pharmaceutically acceptable salt thereof.

5. The compound as defined in claim 1 wherein Y is $$-\underset{\underset{O}{\|}}{C}-.$$

6. The compound as defined in claim 1 wherein $R^7$ is aryl.

7. The compound as defined in claim 1 wherein $R^7$ is phenyl or phenyl substituted with alkoxy.

8. The compound as defined in claim 1 wherein $R^7$ is phenyl or 2-methoxyphenyl.

9. A compound which is 3,4-dihydro-3-[[4-phenyl-1-piperazinyl]methyl]-1(2H)-naphthalenone; or
   3,4-dihydro-3-[[4-(2-methoxyphenyl)-1-piperazinyl]-carbonyl]-1(2H)-naphthalenone.

* * * * *